US011702700B2

(12) United States Patent
Xin et al.

(10) Patent No.: US 11,702,700 B2
(45) Date of Patent: *Jul. 18, 2023

(54) INHIBITION OF HSD17B13 IN THE TREATMENT OF LIVER DISEASE IN PATIENTS EXPRESSING THE PNPLA3 I148M VARIATION

(71) Applicant: Regeneron Pharmaceuticals, Inc., Tarrytown, NY (US)

(72) Inventors: Yurong Xin, Tarrytown, NY (US); Jesper Gromada, Tarrytown, NY (US); Xiping Cheng, Tarrytown, NY (US); Frederick Dewey, Tarrytown, NY (US); Tanya Teslovich Dostal, Tarrytown, NY (US); Claudia Schurmann, Tarrytown, NY (US); Aris Baras, Tarrytown, NY (US); Noura Abul-Husn, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/178,420

(22) Filed: Feb. 18, 2021

(65) Prior Publication Data

US 2021/0246508 A1    Aug. 12, 2021

Related U.S. Application Data

(63) Continuation of application No. 16/157,503, filed on Oct. 11, 2018, now Pat. No. 10,961,583.

(60) Provisional application No. 62/570,985, filed on Oct. 11, 2017.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,147,066 A | 11/2000 | Petit et al. |
| 7,820,380 B2 | 10/2010 | Huang |
| 7,951,382 B2 | 5/2011 | Gelber et al. |
| 7,951,776 B2 | 5/2011 | Gelber |
| 8,071,302 B2 | 12/2011 | Huang |
| 8,945,847 B2 | 2/2015 | Benvenisty et al. |
| 9,051,567 B2 | 6/2015 | Fitzgerald et al. |
| 9,072,743 B2 | 7/2015 | Dilly et al. |
| 9,328,346 B2 | 5/2016 | Lee et al. |
| 9,375,433 B2 | 6/2016 | Dilly et al. |
| 9,526,720 B2 | 12/2016 | Nagiec et al. |
| 9,574,241 B2 | 2/2017 | Ferrando et al. |
| 9,585,887 B2 | 3/2017 | Dilly et al. |
| 9,585,890 B2 | 3/2017 | Dilly et al. |
| 9,617,514 B2 | 4/2017 | Lunyak |
| 9,629,804 B2 | 4/2017 | Heartlein et al. |
| 9,632,090 B2 | 4/2017 | DePinho et al. |
| 9,677,138 B2 | 6/2017 | Steiling et al. |
| 9,796,762 B2 | 10/2017 | Kelly et al. |
| 9,808,462 B2 | 11/2017 | Dilly et al. |
| 9,816,094 B2 | 11/2017 | Lee et al. |
| 10,052,284 B2 | 8/2018 | Heartlein et al. |
| 10,577,630 B2 | 3/2020 | Zhang et al. |
| 10,767,175 B2 | 9/2020 | Dellinger et al. |
| 10,787,647 B2 | 9/2020 | Abul-Husn et al. |
| 10,961,583 B2 * | 3/2021 | Xin .................. C12Q 1/6883 |
| 2005/0158376 A1 | 7/2005 | Sardi et al. |
| 2007/0219169 A1 | 9/2007 | Becourt et al. |
| 2008/0300170 A1 | 12/2008 | Gelber et al. |
| 2009/0169585 A1 | 7/2009 | Sardi |
| 2009/0203602 A1 | 8/2009 | Gelber et al. |
| 2010/0028879 A1 | 2/2010 | Labrie et al. |
| 2010/0056384 A1 * | 3/2010 | Hobbs .................. C12Q 1/6883 506/7 |
| 2010/0209427 A1 | 8/2010 | Li et al. |
| 2010/0266618 A1 | 10/2010 | Stojdl et al. |
| 2010/0267052 A1 | 10/2010 | Gelber et al. |

(Continued)

FOREIGN PATENT DOCUMENTS

| | | |
|---|---|---|
| CN | 104698108 | 6/2015 |
| CN | 103520724 B | 5/2016 |

(Continued)

OTHER PUBLICATIONS

Zhang et al. Protein Cell. Available online Oct. 18, 2016. 8(1): 4-13 (Year: 2016).*

(Continued)

*Primary Examiner* — Carla J Myers

(74) *Attorney, Agent, or Firm* — Armstrong Teasdale LLP

(57) ABSTRACT

The disclosure provides methods of identifying a human subject as a candidate for treating or inhibiting a liver disease by inhibiting HSD17B13. The disclosure also provides methods of treating a subject who is PNPLA3 Ile148Met+ by administering an inhibitor of HSD17B13. The disclosure also provides method of detecting a PNPLA3 Ile148Met variant and functional HSD17B13 in a subject. The disclosure also provides method of identifying a subject having a protective effect against liver disease. The disclosure also provides inhibitors of HSD17B13 for use in the treatment of a liver disease.

27 Claims, 48 Drawing Sheets

Specification includes a Sequence Listing.

(56) References Cited

U.S. PATENT DOCUMENTS

| | | |
|---|---|---|
| 2011/0130442 A1 | 6/2011 | Kosaka et al. |
| 2011/0262462 A1 | 10/2011 | Platt et al. |
| 2011/0129831 A1 | 12/2011 | Cargill et al. |
| 2012/0015904 A1 | 1/2012 | Sharp et al. |
| 2012/0028816 A1 | 2/2012 | Warren et al. |
| 2012/0058088 A1 | 3/2012 | Sardi |
| 2012/0276528 A1 | 11/2012 | Cargill et al. |
| 2013/0005596 A1 | 1/2013 | Gong et al. |
| 2013/0029873 A1 | 1/2013 | de Perrot et al. |
| 2013/0079241 A1 | 3/2013 | Luo et al. |
| 2013/0237454 A1 | 9/2013 | Schutzer |
| 2013/0309769 A1 | 11/2013 | Benvenisty et al. |
| 2014/0004153 A1 | 1/2014 | Cowing et al. |
| 2014/0011889 A1 | 1/2014 | Sardi |
| 2014/0045915 A1 | 2/2014 | Skog et al. |
| 2014/0057800 A1 | 2/2014 | Brattbakk et al. |
| 2014/0072957 A1 | 3/2014 | Huang et al. |
| 2014/0088120 A1 | 3/2014 | Dilly et al. |
| 2014/0163118 A1 | 6/2014 | Giuliani et al. |
| 2014/0179536 A1 | 6/2014 | Hobbs et al. |
| 2014/0295425 A1 | 10/2014 | Nagy |
| 2014/0329704 A1 | 11/2014 | Melton et al. |
| 2014/0363502 A1 | 12/2014 | Sardi |
| 2014/0378425 A1 | 12/2014 | Wilde et al. |
| 2015/0050728 A1 | 2/2015 | Benvenisty et al. |
| 2015/0079061 A1 | 3/2015 | Casey et al. |
| 2015/0079062 A1 | 3/2015 | Casey et al. |
| 2015/0366997 A1 | 12/2015 | Guild et al. |
| 2016/0024498 A1 | 1/2016 | Fitzgerald et al. |
| 2016/0030585 A1 | 2/2016 | Barnes et al. |
| 2016/0032388 A1 | 2/2016 | Huang et al. |
| 2016/0032395 A1 | 2/2016 | Davicioni et al. |
| 2016/0184458 A1 | 6/2016 | Heartlein et al. |
| 2016/0237501 A1 | 8/2016 | Sharp et al. |
| 2016/0320395 A1 | 11/2016 | Ward et al. |
| 2016/0355806 A1 | 12/2016 | Lee et al. |
| 2016/0355813 A1 | 12/2016 | Lee et al. |
| 2016/0376598 A1 | 12/2016 | Lee et al. |
| 2017/0022504 A1 | 1/2017 | Lee et al. |
| 2017/0037396 A1 | 2/2017 | Lee et al. |
| 2017/0044550 A1 | 2/2017 | Lee et al. |
| 2017/0247758 A1 | 8/2017 | Spiller et al. |
| 2017/0247759 A1 | 8/2017 | Wilde et al. |
| 2017/0283770 A1 | 10/2017 | Lunyak |
| 2017/0335396 A1 | 11/2017 | Kennedy et al. |
| 2017/0340661 A1 | 11/2017 | Fitzgerald et al. |
| 2017/0349903 A1 | 12/2017 | Liu et al. |
| 2017/0356002 A1 | 12/2017 | Thompson et al. |
| 2018/0179553 A1 | 6/2018 | Watson et al. |
| 2018/0179593 A1 | 6/2018 | Melton et al. |
| 2018/0185516 A1 | 7/2018 | Ansell et al. |
| 2018/0201936 A1 | 7/2018 | Hinkle |
| 2018/0216084 A1 | 8/2018 | Abul-Husn et al. |
| 2018/0216104 A1 | 8/2018 | Abul-Husn et al. |
| 2018/0273955 A1 | 9/2018 | Fitzgerald et al. |
| 2019/0002869 A1 | 1/2019 | Yin et al. |
| 2019/0316121 A1 | 10/2019 | Smith et al. |
| 2019/0365924 A1 | 12/2019 | Conway et al. |
| 2019/0390195 A1 | 12/2019 | Tondera et al. |
| 2020/0354693 A1 | 11/2020 | Abul-Husn et al. |

FOREIGN PATENT DOCUMENTS

| | | |
|---|---|---|
| EP | 3011032 | 10/2019 |
| EP | 3620524 | 3/2020 |
| EP | 3011031 | 9/2020 |
| RU | 2545990 | 4/2015 |
| RU | 2562868 | 9/2015 |
| WO | 1995029255 | 11/1995 |
| WO | 9720942 | 6/1997 |
| WO | 1999046279 | 9/1999 |
| WO | 1999046281 | 9/1999 |
| WO | 2004110459 | 12/2004 |
| WO | 2005108415 | 11/2005 |
| WO | 2009039195 | 3/2009 |
| WO | 2010028110 | 3/2010 |
| WO | 2010040571 | 4/2010 |
| WO | 2010064702 | 6/2010 |
| WO | 2011006214 | 1/2011 |
| WO | 2011084747 | 7/2011 |
| WO | 2012052953 | 4/2012 |
| WO | 2012087983 | 6/2012 |
| WO | 2013126565 | 8/2013 |
| WO | 2013176772 | 11/2013 |
| WO | 2013177060 | 11/2013 |
| WO | 2013190075 | 12/2013 |
| WO | 2013166264 | 1/2014 |
| WO | 2014089313 | 6/2014 |
| WO | 2014196957 | 12/2014 |
| WO | 2015169971 | 11/2015 |
| WO | 2016004387 | 1/2016 |
| WO | 2016009246 | 1/2016 |
| WO | 2017048620 | 3/2017 |
| WO | 2017106210 | 6/2017 |
| WO | 2017106283 | 6/2017 |
| WO | 2017106292 | 6/2017 |
| WO | 2017106364 | 6/2017 |
| WO | 2017106370 | 6/2017 |
| WO | 2017106375 | 6/2017 |
| WO | 2017106382 | 6/2017 |
| WO | 2017156310 | 9/2017 |
| WO | 2017191274 | 11/2017 |
| WO | 2017211947 | 12/2017 |
| WO | 2018107026 | 6/2018 |
| WO | 2018107028 | 6/2018 |
| WO | 2018136702 | 7/2018 |
| WO | 2018136758 | 7/2018 |
| WO | 2018220211 | 12/2018 |
| WO | 2019183164 | 9/2019 |
| WO | 2019183329 | 9/2019 |
| WO | 2019237069 | 12/2019 |
| WO | 2019246203 | 12/2019 |

OTHER PUBLICATIONS

Anstee et al., "Genetic Factors That Affect Risk of Alcoholic and Nonalcoholic Fatty Liver Disease", Gastroenterology, 2016, 150(8), pp. 1728-1744.
UniProtKB-Q7Z5P4-1, "17-beta-hydroxysteroid dehydrogenase 13", 2003, p. 6.
UniProtKB-Q7Z5P4-2, "17-beta-hydroxysteroid dehydrogenase 13", 2003, pp. 6-7.
Van Der Meer, A. J., et al., "Association Between Sustained Virological Response and All-Cause Mortality Among Patients With Chronic Hepatitis C and Advanced Hepatic Fibrosis", JAMA, 2012. pp. 2584-2593, 308(24).
Victor, R. G., et al., "The Dallas Heart Study: A Population-Based Probability Sample for the Multidisciplinary Study of Ethnic Differences in Cardiovascular Health", Am J Cardiol, 2004, pp. 1473-1480, 93.
Willer, C. J., et al., "METAL: fast and efficient meta-analysis of genomewide association scans", Bioinformatics, 2010, pp. 2190-2191, 26(17).
Williams, C. D., et al., "Clinical Advances in Liver, Pancreas, and Biliary Tract", Gastroenterology, 2011, pp. 124-131, 140.
Wong, R. J., et al., "Nonalcoholic Steatohepatitis is the Second Leading Etiology of Liver Disease Among Adults Awaiting Liver Transplantation in the United States", Gastroenterology, 2015, pp. 547-555, 148.
Yang, J., et al., "GCTA: A Tool for Genome-wide Complex Trait Analysis", The American Journal of Human Genetics, 2011, pp. 76-82, 88.
Younossi, Z. M., et al., "Changes in the Prevalence of the Most Common Causes of Chronic Liver Diseases in the United States From 1988 to 2008", Clinical Gastroenterology and Hepatology, 2011, pp. 524-530, 9.
Yuan, X., et al., "Population-Based Genome-wide Association Studies Reveal Six Loci Influencing Plasma Levels of Liver Enzymes", The American Journal of Human Genetics, 2008, pp. 520-528, 83.

(56) References Cited

OTHER PUBLICATIONS

Zhang, J., et al., "PowerBLAST: A New Network BLAST Application for Interactive of Automated Sequence Analysis and Annotation", Genome Research, 1997, pp. 649-656, 7.

Kitamoto et al., "Association of polymorphisms in GCKR and TRIB1 with nonalcoholic fatty liver disease and metabolic syndrome traits", Endocrine Journal, 2014, 61(7), pp. 683-689.

Edelman et al., "Genetic analysis of nonalcoholic fatty liver disease within a Caribbean-Hispanic population", Molecular Genetics & Genomic Medicine, 2015, 3(6), pp. 558-569.

Hotta et al., "R association of the rs738409 polymorphism in PNPLA3 with liver damage and the development of nonalcoholic fatty liver disease", BMC Medical Genetics, 2010, 11(172), pp. 1-10.

Kahali et al., "Insights from Genome-Wide Association Analyses of Nonalcoholic Fatty Liver Disease", Seminars in Liver Disease, 2015, 35(4), pp. 375-391.

Oniki et al., "Influence of the PNPLA3 rs738409 Polymorphism on Non-Alcoholic Fatty Liver Disease and Renal Function among Normal Weight Subjects", PLOS ONE, 2015, 10(7), pp. e0132640.

Shen et al., "The rs738409 (I148M) variant of the PNPLA3 gene and cirrhosis: a meta-analysis", Journal of Lipid Research, 2015, 56(1), pp. 167-175.

Office Action dated Feb. 4, 2020 in related U.S. Appl. No. 15/913,366.

Leippe et al., "Bioluminescent Nicotinamide Adenine Dinucleotide Detection Assays Part 1: Technology and Features", 2014, hhtp://www.promega.com/resources/pubhub/bioluminescent-nicotinamide-adenine-dinucleotide-detection-assays/.

New England Biolabs Catalog, "Nucleic Acids, Linkers and Primers", 1998/199, pp. 121 and 284.

Schiavinato et al., "EMILIN-3, Peculiar Member of Elastin Microfibril Interface-located Protein (EMILIN) Family, Has Distinct Expression Pattern, Forms Oligomeric Assemblies, and Serves as Transforming Growth Factor B (TGF-B) Antagonist", Journal of Biological Chemistry, 2012, 187(14), pp. 11498-11515.

SNP(ss) Report in Submission Format for NCBI Assay Id (ss#): ss557289122, 2012, www.ncbi.nlm.gov/.

Non-Final Office Action dated Mar. 12, 2020 in related U.S. Appl. No. 15/875,192.

Ghanbari, et al., "Genetic Variations in MicroRNA-Binding Sites Affect MicroRNA-Mediated Regulation of Several Genes Associated With Cardio-metabolic Phenotypes," Circ. Cardiovasc. Genet., 2015, 8(3), pp. 473-486.

Gieger, et al., "New gene functions in megakaryopoiesis and platelet formation," Nature, 2012, 480(7376), pp. 201-208 plus Supplementary Information.

Haapaniemi et al., "CRISPR-Cas9 genome editing induces a p53-mediated DNA damage response," Nat. Med. doi: 10.1038/s41591-018-0049-z, (Jun. 11, 2018, epub ahead of print).

Ihry et al., "p53 inhibits CRISPR-Cas9 engineering in human pluripotent stem cells," Nat. Med. doi: 10.1038/s41591-018-0050-6 (Jun. 11, 2018, epub ahead of print).

Jiang et al., "Structural Biology. A Cas9-guide RNA complex preorganized for target DNA recognition," Science, 2015, 348(6242), pp. 1477-1481.

Jinek et al., "RNA-programmed genome editing in human cells," eLife, 2013, 2:e00471.

Komor et al., "CRISPR-Based Technologies for the Manipulation of Eukaryotic Genomes," Cell, 2017,168(1-2), pp. 20-36.

Kosicki et al., "Repair of double-strand breaks induced by CRISPR-Cas9 leads to large deletions and complex rearrangements," Nat. Biotechnol., 2018, 36(8), pp. 765-771.

Nishimasu et al., "Crystal Structure of Cas9 in Complex with Guide RNA and Target DNA," Cell, 2014, 156(5), pp. 935-949.

PubMed NCBI Search Results for ((CRISPR[Title] or Cas9[Title]) and ("Jan. 1, 2012"[PDATE] : "Jan. 22, 2017")), https://www.ncbi.nlm.nih.gov/pubmed, retrieved on Sep. 22, 2019.

Quadri, et al., "Mutations in SLC30A10 Cause Parkinsonism and Dystonia with Hypermanganesemia, Polychemia, and Chronic Liver Disease," The American Journal of Human Genetics, 2012, 90, pp. 467-477 plus Supplemental Material.

Ratziu, et al., "Current efforts and trends in the treatment of NASH," Journal of Hepatology, 2015, 62, pp. S65-S75.

Santa Cruz Biotechnology, "17β-HSD13 Antibody (K-14): sc-161285" [Retrieved from the Internet Jun. 1, 2016: www.scbt.com/datasheet-161285-17betahsd13-k-14-antibody.html].

Santa Cruz Biotechnology, "17β-HSD13 siRNA (m), shRNA and Lentiviral Particle Gene Silencers" [Retrieved from the Internet Jun. 1, 2016: www.scbt.com/datasheet-108263-17beta-hsd13-sima-m.html].

Tang, et al., "A mouse knockout library for secreted and transmembrane proteins," Nature Biotechnology, 2010, 28(7), pp. 749-755 plus Online Methods and Supplementary Information.

Non-Final Office Action dated Jul. 10, 2019 for U.S. Appl. No. 15/875,514.

Notice of Allowance dated Jan. 22, 2020 in U.S. Appl. No. 15/875,514.

International Search Report and Written Opinion of the International Searching Authority dated Jun. 6, 2018 for WIPO Application No. PCT/US2018/014454.

Notice of Allowance dated May 1, 2020 in U.S. Appl. No. 15/875,514.

Moeller et al., "Multifunctionality of human 17β-hydroxysteriod dehydrogenases", Molecular and Cellular Endocrinology, 2006, 248, pp. 47-55.

Final Office Action dated Sep. 22, 2020 for U.S. Appl. No. 15/913,366.

Final Office Action dated Dec. 3, 2020 for U.S. Appl. No. 15/875,192.

Abul-Husn et al., "A Protein-Truncating HSD17B13 Variant and Protection from Chronic Liver Disease", N Engl J Med, 2018, 378, pp. 1096-1106.

Adam, M., et al., "Hydroxysteroid (17b) dehydrogenase 13 deficiency triggers hepatic steatosis and inflammation in mice", The FASEB Journal, 2018, pp. 1-14.

Altschul, S. F., et al., "Basic Local Alignment Search Tool", J. Mol. Biol., 1990, pp. 403-410, 215.

Altschul, S. F., et al., "Gapped BLAST and PSI-BLAST: a new generation of protein database search programs", Nucleic Acids Research, 1997, pp. 3389-3402, 25 (17).

Brantly et al., "Crystal RG. Molecular basis of alpha-1-antitrypsin deficiency", Am J Med, 1988, pp. 13-31, 84.

Brasaemle, D. L., et al., "Isolation of Lipid Droplets from Cells by Density Gradient Centrifugation", Current Protocols in Cell Biology, 2005, 3.15.1-3.15.12.

Browning, J. D., et al., "Prevalence of Hepatic Steatosis in an Urban Population in the United States: Impact of Ethnicity", Hepatology, 2004, pp. 1387-1395, 40(6).

Chambers, J. C., et al., "Genome-wide association study identifies loci influencing concentrations of liver enzymes in plasma" Nat Genet, 2011, pp. 1131-1138, 43(11).

Cohen, J. C., et al., "Human Fatty Liver Disease: Old Questions and New Insights", Science, 2011, pp. 1519-1523, 332.

Denny, J. C., et al., "PheWAS: demonstrating the feasibility of a phenome-wide scan to discover gene-disease associations", Bioinformatics, 2010, pp. 1205-1210, 26(9).

Denny, J. C., et al., "Systematic comparison of phenome-wide association study of electronic medical record data and genome-wide association study data", Nat Biotechnol, 2013, pp. 1102-1110, 31(12).

Dewey, F. E., et al., "Distribution and clinical impact of functional variants in 50,726 whole-exome sequences from the DiscovEHR Study", Science, 2016, pp. aaf6814, 354(6319).

Ding, Y., et al., "Isolating lipid droplets from multiple species", Nature Protocols, 2013, pp. 43-51, 8(1).

Feitosa et al., "The ERLIN1-CHUK-CWF19L1 gene cluster influences liver fat deposition and hepatic inflammation in the NHLBI Family Heart Study", Atherosclerosis, 2013, pp. 175-180, 228.

Ford et al., "A New Assay for Picomole Levels of Androsterone and Testosterone Using Co-immobilized Luciferase, Oxidoreductase, and Steroid Dehydrogenase", Analytical Biochemistry, 1981, 110, pp. 43-48.

Huang et al., "Expression and Characterization of a PNPLA3 Protein Isoform (I148M) Associated with Nonalcoholic Fatty Liver Disease", J Biol Chem, 2011, pp. 37085-37093, 286.

(56) References Cited

OTHER PUBLICATIONS

International Search Report and Written Opinion for PCT Application PCT/US2018/014357.
Kampf, C., et al., "The human liver-specific proteome defined by transcriptomics and antibody-based profiling", The FASEB Journal, 2014, pp. 2901-2914, 28(7).
Kitamoto et al., "Genome-wide scan revealed that polymorphisms in the PNPLA3, SAMM50, and PARVB genes are associated with development and progression of nonalcoholic fatty liver disease in Japan", Hum Genet, 2013, pp. 783-792, 132.
Kleiner, D. E., et al., "Design and Validation of a Histological Scoring System for Nonalcoholic Fatty Liver Disease", Hepatology, 2005, pp. 1313-1321, 41(6).
Kochanek, K. D., et al., "Deaths: Final Data for 2014", National Viral Statistics Reports, 2016, pp. 1-122, 65(4).
Kozlitina, J., et al., "Exome-wide association study identifies a TM6SF2 variant that confers susceptibility to nonalcoholic fatty liver disease", Nat Genet, 2014, pp. 352-356, 46(4).
Krazeisen et al., "Phytoestrogens inhibit human 17β-hydroxysteroid dehydrogenase type 5", Molecular and Cellular Endocrinology, 2001, 171, pp. 151-162.
Lazo, M., et al., "Prevalence of Nonalcoholic Fatty Liver Disease in the United States: The Third National Health and Nutrition Examination Survey, 1988-1994", Am J Epidemiol, 2013, pp. 38-45, 178(1).
Li, H., et al., "Fast and accurate short read alignment with Burrows-Wheeler transform", Bioinformatics, 2009, pp. 1754-1760, 25(14).
Li, P., et al., "LTB4 causes macrophage-mediated inflammation and directly induces insulin resistance in obesity", Nat Med, 2015, pp. 239-247, 21(3).
Liu, S., et al., "Molecular cloning and expression analysis of a new gene for shortchain dehydrogenase/reductase 9", Acta Biochimica Polonica, 2007, pp. 213-218, 54(1).
Liu, Y.-L., et al., "TM6SF2 rs58542926 influences hepatic fibrosis progression in patients with non-alcoholic fatty liver disease", Nature Communications, 2014, pp. 1-6, 5(4309).
Mahdessian et al., "TM6SF2 is a regulator of liver fat metabolism influencing triglyceride secretion and hepatic lipid droplet content", PNAS, 2014, pp. 8913-8918, 111.
McKenna, A., et al., "The Genome Analysis Toolkit: A MapReduce framework for analyzing next-generation DNA sequencing data", Genome Research, 2010, pp. 1297-1303, 20.
Moeller, G., et al., "Integrated view on 17betahydroxysteroid dehydrogenases", Molecular and Cellular Endocrinology, 2009, pp. 7-19, 301.
Morgan, R. L., et al., "Eradication of Hepatitis C Virus Infection and the Development of Hepatocellular Carcinoma", Annals of Internal Medicine, 2013, pp. 329-337 and W-158-W-160, 158(5)(Part 1).
NCBI Reference Sequence: NM_178135, "*Homo spiens* hydroxysteroid 17-beta dehydrogenase 13 (HSD17B13), transcript variant A, mRNA" 2017, pp. 1-5.
NCBI Reference Sequence: NM_001136230, "*Homo sapiens* hydroxysteroid 17-beta dehydrogenase 13 (HSD17B13), transcript variant B, mRNA" 2017, pp. 1-5.
NCBI Reference Sequence: NP_835236, "17-beta-hydroxysteroid dehydrogenase 13 isoform A precursor [*Homo sapiens*]", 2017 pp. 1-4.
NCBI Reference Sequence: NP 001129702, "17-beta-hydroxysteroid dehydrogenase 13 isoform B [*Homo sapiens*]", 2017, pp. 1-4.
Pirazzi et al., "Patatin-like phospholipase domain-containing 3 (PNPLA3) I148M (rs738409) affects hepatic VLDL secretion in humans and in vitro", J Hepatol, 2012, pp. 1276-1282, 57.
Promega "Technical Manual: NAD(P)H-Glo Detection System", 2017, TM398, pp. 1-15.
Pruim, R. J., et al., "LocusZoom: regional visualization of genome-wide association scan results", Bioinformatics, 2010, pp. 2336-2337, 26(18).
Reid, J. G., et al., "Launching genomics into the cloud: deployment of Mercury, a next generation sequence analysis pipeline", BMC Bioinformatics, 2014, pp. 1-11, 15(30).
Romeo, S., et al., "Genetic variation in PNPLA3 confers susceptibility to nonalcoholic fatty liver disease", Nat Genet, 2008, pp. 1461-1465, 40(12).
Rotman, Y., et al., "The Association of Genetic Variability in PNPLA3 with Histological Severity of Non-Alcoholic Fatty Liver Disease", Hepatology, 2010, pp. 894-903, 52(3).
Shen et al., "The rs738409 (I148M) variant of the PNPLA3 gene and cirrhosis: a meta-analysis", J Lipid Res, 2015, pp. 167-175, 56.
Smagris et al., "Inactivation of Tm6sf2, a Gene Defective in Fatty Liver Disease, Impairs Lipidation but Not Secretion of Very Low Density Lipoproteins", J Biol Chem, 2016, pp. 10659-10676, 291.
Smith, T. F., et al., "Comparsion of Biosequences", Advances in Applied Mathematics, 1981, pp. 482-489, 2.
Sookoian, S., et al., "A nonsynonymous gene variant in the adiponutrin gene is associated with nonalcoholic fatty liver disease severity". Journal of Lipid Research, 2009, pp. 2111-2116, 50.
Sookoian, S., et al., "Genetic Variation in Transmembrane 6 Superfamily Member 2 and the Risk of Nonalcoholic Fatty Liver Disease and Histological Disease Severity", Hepatology, 2015, pp. 515-525, 61(2).
Speliotes, E. K., et al., "Genome-Wide Association Analysis Identifies Variants Associated with Nonalcoholic Fatty Liver Disease That Have Distinct Effects on Metabolic Traits", PLoS Genetics, 2011, e1001324, 7(3).
Su, W., et al., "Comparative proteomic study reveals 17!-HSD13 as a pathogenic protein in nonalcoholic fatty liver disease", PNAS, 2014, pp. 11437-11442, 111(31).
Trepo, E., et al., "PNPLA3 gene in liver diseases", Journal of Hepatology, 2016, pp. 399-412, 65.
Non-Final Office Action dated Feb. 4, 2022 for U.S. Appl. No. 15/875,192.
Rao et al., "Genotyping single nucleotide polymorphisms directly from genomic DNA by invasive cleavage reaction on microspheres", Nucleic Acids Research, 2003, 31(11), pp. 1-8.
Stevens et al., "Analysis of single nucleotide polymorphisms with solid phase invasive cleavage reactions", Nucleic Acid Research, 2001,29(16), pp. 1-8.
Final Office Action dated May 5, 2022 for U.S. Appl. No. 15/913,366.
Third Party Submission filed Feb. 25, 2022 in U.S. Appl. No. 16,978,947.
Elphick et al., "Conserved valproic-acid-induced lipid droplet formation in Dictyostelium and human hepatocytes dentifies structurally active compounds", Disease Models & Mechanisms, 2012, pp. 231-240.
Del Ben et al., "Non-alcoholic fatty liver disease, metabolic syndrome and patatin-like phospholipase domain-containing protein3 gene variants", European Journal of Internal Medicine, 2014, 25, pp. 566-570.
Official Action dated Jun. 12, 2019 issued in related U.S. Appl. No. 15/875,192.
RefSNP cluster report rs72613567 (printed Jun. 6, 2019 from ncbi.nlm.nih.gov).
GenBank accession DR004209 (submitted Jan. 2011, printed Jun. 10, 2019, from ncbi.nim.nih.gov).
Brooks et al., "Basics of Enzymatic Assays for HTS", Assay Guidance Manual, 2012, pp. 1-12.
Doan et al., "Breast cancer prognosis predicted by nuclear receptor-coregulator networks", Molecular Oncology, 2014, 8, pp. 998-1013.
Ducharme et al., "Minireview: Lipid Droplets in Lipogenesis and Lipolysis", Endocrinology, 2008, 149(3), pp. 942-949.
Jequier et al., "Water as an essential nutrient: the physiological basis of hydration", European Journal of Clinical Nutrition, 2010, 64, pp. 115-123.
Karlson, "Introduction to Modern Biochemistry: Chapter V Enzymes and Biocatalysis", Fourth Edition, 1975, pp. 74-100.
Kuhl et al., "Pharmacology of estrogens and progestagens: influence of different routes of administration", Climacteric, 2005, 8, pp. 3-63.
Labrie, "Multiple intracrine hormonal targets in the prostate: opportunities and challenges", BJU Int, 2007,100, pp. 48-51.
Mashek et al., "Hepatic Lipid Droplet Biology: Getting to the Root of Fatty Liver", Hepatology, 2015, 62, pp. 964-967.

(56) References Cited

OTHER PUBLICATIONS

Su et al., "Comparative proteomic study reveals 17beta-HSD13 as a pathogenic protein in nonalcoholic fatty liver disease", PNAS, 2014, 111(31), pp. 11437-11442.
Wolf et al., "To err is human: Patient misinterpretations of prescription drug label instructions", Patient Education and Counseling, 2007, 67, pp. 293-300.
Non-Final Office Action dated Sep. 8, 2021 in related U.S. Appl. No. 15/913,366.
Hassan et al., "Nonalcoholic fatty liver disease: A comprehensive review of a growing epidemic", World J Gastroenterology, 2014, 20(34), pp. 12082-12101.
Nemudryi et al., "TALEN and CRISPR/Cas Genome Editing Systems: Tools of Discovery", Acta Nature, 2014, 6 (No. 3 (22)), pp. 19-40.
Sun et al., "The CRSPR/Cas9 system for gene editing and its potential application in pain research", Transl Perioper Pain Med, 2016, 1(3), pp. 22-33.
Advisory Action dated Jan. 27, 2023 in related U.S. Appl. No. 15/875,192.

* cited by examiner

| Characteristic | GHS Discovery Cohort (N = 46,544) | GHS Bariatric Surgery Cohort (N = 2,644) | Dallas Heart Study (N = 1,357) | Penn Medicine Biobank (N = 8,526) |
|---|---|---|---|---|
| Age (years) – median (IQR) | 63 (50 - 74) | 53 (44 - 61) | 46 (38 - 54) | 68 (60 - 76) |
| Female sex – number (%) | 26,875 (58) | 2,119 (80) | 724 (53) | 3,242 (38) |
| Body mass index – median (IQR) | 30 (25 - 45) | 47 (42 - 54) | 28 (25 - 32) | 30 (25 - 32) |
| Transaminase level (U/L) – median (IQR) | | | | |
| Alanine aminotransferase (ALT) | 22.0 (17.0 - 29.0) | 23.0 (17.5 - 29.5) | 20.0 (15.0 - 27.0) | 22.0 (17.0 - 30.0) |
| Aspartate aminotransferase (AST) | 23.0 (20.0 - 27.5) | 23.0 (20.0 - 27.0) | 21.0 (18.0 - 25.0) | 24.0 (20.0 - 30.5) |
| Presence of liver disease – N (%) | | | | |
| Alcoholic liver disease | 197 (0.4) | 7 (0.3) | * | * |
| Alcoholic cirrhosis | 130 (0.3) | 3 (0.1) | * | * |
| Nonalcoholic (non-viral) liver disease | 1,938 (4.2) | 1,543 (58.4) | * | * |
| Nonalcoholic cirrhosis | 382 (0.8) | 24 (0.9) | * | * |
| Hepatocellular carcinoma | 76 (0.2) | 1 (0.04) | * | * |
| No liver disease | 30,628 (65.8) | 1 (0.04) | * | * |

Figure 1

| Trait | Chr | BP | Ref | Alt | rsID | Gene | Annotation | AA Substitution | Beta (SE) | P | AAF | N |
|---|---|---|---|---|---|---|---|---|---|---|---|---|
| ALT | 1 | 220970028 | A | G | rs2642438 | MARC1 | missense | p.Thr165Ala | 0.028 (0.001) | 4.67E-08 | 0.7067 | 40,834 |
| | 4 | 88231392 | T | TA | rs72613567 | HSD17B13 | splice donor | | -0.009 (0.001) | 4.16E-12 | 0.2634 | 40,834 |
| | 8 | 144997604 | C | T | rs371119003 | PLEC | missense | p.Ala2321Thr | -0.160 (0.026) | 1.30E-09 | 0.0005 | 40,833 |
| | 8 | 145008502 | G | A | | PLEC | missense | p.Arg522Cys | -0.268 (0.032) | 3.26E-17 | 0.0003 | 40,834 |
| | 8 | 145692918 | G | A | rs35968570 | KIFC2 | missense | p.Glu174Lys | -0.033 (0.005) | 1.40E-11 | 0.0139 | 40,834 |
| | 8 | 145738072 | G | A | rs143408057 | GPT | missense | p.Arg83His | -0.314 (0.036) | 3.28E-18 | 0.0003 | 40,834 |
| | 8 | 145730161 | C | T | rs201815297 | GPT | missense | p.Ala87Val | -0.224 (0.014) | 6.28E-59 | 0.0018 | 40,834 |
| | 8 | 145730221 | G | A | rs112574791 | GPT | missense | p.Arg107Lys | -0.033 (0.005) | 4.25E-11 | 0.0136 | 40,834 |
| | 8 | 145731636 | T | G | rs145155876 | GPT | stop gained | p.Tyr326* | -0.235 (0.031) | 1.76E-14 | 0.0004 | 40,814 |
| | 8 | 145732114 | G | C | rs141505249 | GPT | missense | p.Glu430Gln | -0.224 (0.013) | 8.84E-64 | 0.0019 | 40,795 |
| | 8 | 145732151 | G | A | rs143462595 | GPT | missense | p.Arg442His | -0.077 (0.013) | 1.18E-09 | 0.0021 | 40,826 |
| | 8 | 145732180 | G | C | rs147998249 | GPT | missense | p.Val452Leu | -0.225 (0.013) | 8.19E-65 | 0.0019 | 40,833 |
| | 8 | 145732305 | G | GC | | GPT | frameshift | p.Glu475fs | -0.271 (0.031) | 1.00E-18 | 0.0004 | 40,834 |
| | 8 | 145748532 | A | G | rs567402720 | LRRC24 | missense | p.Leu290Ser | -0.185 (0.028) | 3.42E-11 | 0.0004 | 40,813 |
| | 9 | 117122202 | C | T | rs3748177 | AKNA | synonymous | p.Glu755Glu | -0.007 (0.001) | 9.51E-09 | 0.5232 | 40,834 |
| | 9 | 117124731 | G | A | rs3748176 | AKNA | missense | p.Pro624Leu | -0.007 (0.001) | 4.31E-09 | 0.5230 | 40,832 |
| | 10 | 101595996 | T | A | rs17222773 | ABCC2 | missense | p.Val1188Glu | -0.015 (0.003) | 2.97E-08 | 0.0608 | 40,834 |
| | 10 | 101606861 | G | T | rs1137968 | ABCC2 | synonymous | p.Val1430Val | -0.015 (0.003) | 2.71E-08 | 0.0608 | 40,834 |
| | 10 | 101610533 | C | T | rs8187707 | ABCC2 | synonymous | p.His1496His | -0.015 (0.003) | 2.77E-08 | 0.0608 | 40,834 |
| | 10 | 101611294 | G | A | rs8187710 | ABCC2 | missense | p.Cys1515Tyr | -0.015 (0.003) | 2.15E-08 | 0.0611 | 40,834 |
| | 10 | 101912064 | T | C | rs2862954 | ERLIN1 | missense | p.Ile291Val | -0.012 (0.001) | 2.43E-21 | 0.4755 | 40,834 |

Gray shading indicates variants having exome-wide-significant associations with both ALT and AST.
Abbreviations: AAF, alternate allele frequency; Alt, alternate allele; ALT, alanine aminotransferase; AST, aspartate aminotransferase; Ref, reference allele; SE, standard error;

Figure 2

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
| ALT | 1 | 2.2E+08 | A | G | rs2642438 | MARC1 | missense | p.Thr165Ala | 3,515 | 17,262 | 20,637 | 23.88 | 24.52 | 24.92 |
|  | 4 | 8.8E+07 | T | TA | rs72613567 | HSD17B13 | splice donor |  | 22,441 | 16,130 | 2,843 | 25.02 | 24.26 | 24.1 |
|  | 8 | 1.4E+08 | C | T | rs371119203 | PLEC | missense | p.Ala2302Thr | 41,373 | 40 | 0 | 24.67 | 18.1 | NA |
|  | 8 | 1.5E+08 | G | A | | PLEC | missense | p.Arg522Cys | 41,387 | 27 | 0 | 24.67 | 13.8 | NA |
|  | 8 | 1.5E+08 | G | A | rs35968570 | KIFC2 | missense | p.Glu174Lys | 40,271 | 1,133 | 10 | 24.67 | 12.07 | NA |
|  | 8 | 1.5E+08 | G | A | rs143408057 | GPT | missense | p.Arg83His | 41,393 | 21 | 0 | 24.67 | 12.07 | NA |
|  | 8 | 1.5E+08 | C | T | rs201815297 | GPT | missense | p.Ala87Val | 41,270 | 144 | 0 | 24.7 | 14.68 | NA |
|  | 8 | 1.5E+08 | G | A | rs112574791 | GPT | missense | p.Arg107Lys | 40,293 | 1,111 | 10 | 24.71 | 23.09 | 18.35 |
|  | 8 | 1.5E+08 | T | G | rs145155876 | GPT | stop gained | p.Tyr326* | 41,364 | 30 | 0 | 24.67 | 14.07 | NA |
|  | 8 | 1.5E+08 | G | C | rs141505249 | GPT | missense | p.Glu430Gln | 41,223 | 150 | 2 | 24.7 | 14.48 | 13.75 |
|  | 8 | 1.5E+08 | G | A | rs143462595 | GPT | missense | p.Arg442His | 41,232 | 174 | 0 | 24.68 | 20.87 | NA |
|  | 8 | 1.5E+08 | G | C | rs147998249 | GPT | missense | p.Val452Leu | 41,254 | 159 | 0 | 24.7 | 14.74 | NA |
|  | 8 | 1.5E+08 | G | GC | | GPT | frameshift | p.Glu475fs | 41,385 | 29 | 0 | 24.67 | 14.24 | NA |
|  | 8 | 1.5E+08 | A | G | rs567402720 | LRRC24 | missense | p.Leu290Ser | 41,358 | 35 | 0 | 24.67 | 17.71 | NA |
|  | 9 | 1.2E+08 | C | T | rs3748177 | AKNA | synonymous | p.Glu755Glu | 9,414 | 20,645 | 11,355 | 25.12 | 24.72 | 24.18 |
|  | 9 | 1.2E+08 | G | A | rs3748176 | AKNA | missense | p.Pro624Leu | 9,427 | 20,634 | 11,351 | 25.12 | 24.73 | 24.17 |
|  | 10 | 1E+08 | T | A | rs17222723 | ABCC2 | missense | p.Val1188Glu | 36,543 | 4,704 | 167 | 24.77 | 23.97 | 22.12 |
|  | 10 | 1E+08 | G | T | rs1137968 | ABCC2 | synonymous | p.Val1430Val | 36,543 | 4,704 | 167 | 24.77 | 23.97 | 22.04 |
|  | 10 | 1E+08 | C | T | rs8187707 | ABCC2 | synonymous | p.His1496His | 36,542 | 4,706 | 166 | 24.77 | 23.97 | 22.03 |
|  | 10 | 1E+08 | G | A | rs8187710 | ABCC2 | missense | p.Cys1515Tyr | 36,519 | 4,726 | 169 | 24.77 | 23.97 | 21.99 |
|  | 10 | 1E+08 | T | C | rs2862984 | ERLIN1 | missense | p.Ile291Val | 11,318 | 20,819 | 9,277 | 25.32 | 24.71 | 23.77 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error;

Figure 2 (cont.)

| Trait | Chr | BP | Ref | Alt | rsID | Gene | Annotation | AA Substitution | Beta (SE) | P | AAF | N |
|---|---|---|---|---|---|---|---|---|---|---|---|---|
| | 10 | 101977883 | C | T | rs2230804 | CHUK | missense | p.Val268Ile | -0.009 (0.001) | 1.93E-13 | 0.5072 | 40,834 |
| | 10 | 113917085 | T | A | rs2254537 | GPAM | synonymous | p.Pro683Pro | -0.008 (0.001) | 4.61E-10 | 0.7073 | 40,834 |
| | 10 | 113940329 | T | C | rs2792751 | GPAM | missense | p.Ile43Val | -0.008 (0.001) | 2.54E-10 | 0.7097 | 40,832 |
| | 14 | 94844947 | C | T | rs28929474 | SERPINA1 | missense | p.Glu366Lys | 0.042 (0.005) | 9.28E-21 | 0.0171 | 40,834 |
| | 19 | 19379549 | C | T | rs58542926 | TM6SF2 | missense | p.Glu167Lys | 0.014 (0.002) | 4.76E-09 | 0.0759 | 40,833 |
| | 22 | 44324727 | C | G | rs738409 | PNPLA3 | missense | p.Ile148Met | 0.023 (0.002) | 1.34E-50 | 0.2351 | 40,834 |
| | 22 | 44324730 | C | T | rs738408 | PNPLA3 | synonymous | p.Pro149Pro | 0.023 (0.002) | 1.11E-50 | 0.2349 | 40,834 |
| | 22 | 44342116 | A | G | rs2294918 | PNPLA3 | missense | p.Lys434Glu | 0.007 (0.001) | 8.26E-08 | 0.5986 | 40,832 |
| | 22 | 44368122 | A | G | rs3761472 | SAMM50 | missense | p.Asp110Gly | 0.019 (0.002) | 8.85E-30 | 0.1682 | 40,833 |
| | 22 | 44395451 | T | C | rs1007863 | PARVB | missense | p.Trp37Arg | 0.011 (0.001) | 7.98E-16 | 0.3963 | 40,834 |
| AST | 4 | 88231392 | T | TA | rs72613567 | HSD17B13 | splice donor | | -0.005 (0.001) | 6.24E-10 | 0.2638 | 40,193 |
| | 10 | 18242311 | A | G | rs10764176 | SLC39A12 | missense | p.Ser36Gly | -0.006 (0.001) | 1.09E-10 | 0.2881 | 40,193 |
| | 10 | 101157378 | CGTT | C | | GOT1 | inframe indel | p.Asn389del | -0.221 (0.024) | 1.96E-20 | 0.0002 | 40,193 |
| | 10 | 101165533 | G | C | rs374966349 | GOT1 | missense | p.Gln208Glu | 0.271 (0.027) | 2.43E-24 | 0.0002 | 40,193 |
| | 10 | 101912064 | T | C | rs2862954 | ERLIN1 | missense | p.Ile291Val | -0.005 (0.001) | 4.82E-09 | 0.4754 | 40,193 |
| | 11 | 22271870 | A | T | rs7481951 | ANO5 | missense | p.Leu322Phe | 0.004 (0.001) | 9.61E-08 | 0.5833 | 40,162 |
| | 14 | 94844947 | C | T | rs28929474 | SERPINA1 | missense | p.Glu366Lys | 0.027 (0.003) | 2.44E-20 | 0.0172 | 40,193 |
| | 19 | 19379549 | C | T | rs58542926 | TM6SF2 | missense | p.Glu167Lys | 0.008 (0.002) | 6.54E-08 | 0.0760 | 40,192 |
| | 22 | 44324727 | C | G | rs738409 | PNPLA3 | missense | p.Ile148Met | 0.014 (0.001) | 8.31E-46 | 0.2343 | 40,193 |
| | 22 | 44324730 | C | T | rs738408 | PNPLA3 | synonymous | p.Pro149Pro | 0.014 (0.001) | 8.93E-46 | 0.2341 | 40,193 |
| | 22 | 44368122 | A | G | rs3761472 | SAMM50 | missense | p.Asp110Gly | 0.011 (0.001) | 1.22E-22 | 0.1680 | 40,192 |
| | 22 | 44395451 | T | C | rs1007863 | PARVB | missense | p.Trp37Arg | 0.006 (0.001) | 1.31E-13 | 0.3961 | 40,193 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | Ref | Alt | rsID | Gene | Annotation | AA Substitution | N Ref/Ref | N Ref/Alt | N Alt/Alt | Mean ALT or AST level (U/L) Ref/Ref | Ref/Alt | Alt/Alt |
|---|---|---|---|---|---|---|---|---|---|---|---|---|---|---|
|  | 10 | 101977883 | C | T | rs2230804 | CHUK | missense | p.Val268Ile | 10,048 | 20,733 | 10,633 | 25.18 | 24.75 | 24.01 |
|  | 10 | 113917085 | T | A | rs2254537 | GPAM | synonymous | p.Pro681Pro | 3,627 | 16,984 | 20,803 | 25 | 24.97 | 24.36 |
|  | 10 | 113940329 | T | C | rs2792751 | GPAM | missense | p.Ile43Val | 3,567 | 16,910 | 20,935 | 25 | 24.98 | 24.35 |
|  | 14 | 94844947 | C | T | rs28929474 | SERPINA1 | missense | p.Glu366Lys | 40,006 | 1,399 | 9 | 24.58 | 26.91 | 43.89 |
|  | 19 | 19379549 | C | T | rs58542926 | TM6SF2 | missense | p.Glu167Lys | 35,388 | 5,780 | 245 | 24.52 | 25.46 | 26.84 |
|  | 22 | 44324727 | C | G | rs738409 | PNPLA3 | missense | p.Ile148Met | 24,257 | 14,837 | 2,320 | 24.06 | 24.99 | 28.91 |
|  | 22 | 44324730 | C | T | rs738408 | PNPLA3 | synonymous | p.Pro149Pro | 24,273 | 14,824 | 2,317 | 24.06 | 24.98 | 28.92 |
|  | 22 | 44342116 | A | G | rs2294918 | PNPLA3 | missense | p.Lys434Glu | 6,691 | 19,833 | 14,898 | 24.15 | 24.47 | 25.15 |
|  | 22 | 44368122 | A | G | rs3761472 | SAMM50 | missense | p.Asp108Gly | 28,626 | 11,618 | 1,169 | 24.23 | 25.36 | 28.45 |
|  | 22 | 44395451 | T | C | rs1007863 | PARVB | missense | p.Trp37Arg | 15,036 | 19,920 | 6,458 | 24.15 | 24.6 | 26.09 |
| AST | 4 | 88231392 | T | TA | rs72813567 | HSD17B13 | splice donor |  | 22,068 | 15,870 | 2,815 | 24.47 | 24.1 | 23.96 |
|  | 10 | 18242311 | A | G | rs10764176 | SLC39A12 | missense | p.Ser36Gly | 20,645 | 16,738 | 3,370 | 24.47 | 24.15 | 23.85 |
|  | 10 | 101157378 | CGTT | C | rs374966349 | GOT1 | inframe indel | p.Asn384del | 40,733 | 20 | 0 | 24.29 | 14.7 | NA |
|  | 10 | 101165533 | G | C | rs2862954 | GOT1 | missense | p.Gln208Glu | 40,736 | 17 | 0 | 24.28 | 44.5 | NA |
|  | 10 | 101912064 | C | T | rs2862954 | ERLIN1 | missense | p.Ile291Val | 11,139 | 20,486 | 9,129 | 24.59 | 24.26 | 23.99 |
|  | 11 | 22271870 | A | T | rs7481951 | ANO5 | missense | p.Leu322Phe | 7,123 | 19,686 | 13,913 | 24.03 | 24.22 | 24.53 |
|  | 14 | 94844947 | C | T | rs28929474 | SERPINA1 | missense | p.Glu366Lys | 39,361 | 1,384 | 8 | 24.24 | 25.76 | 34.5 |
|  | 19 | 19379549 | C | T | rs58542926 | TM6SF2 | missense | p.Glu167Lys | 34,811 | 5,698 | 243 | 24.21 | 24.74 | 25.43 |
|  | 22 | 44324727 | C | G | rs738409 | PNPLA3 | missense | p.Ile148Met | 23,889 | 14,622 | 2,242 | 23.96 | 24.48 | 26.62 |
|  | 22 | 44324730 | C | T | rs738408 | PNPLA3 | synonymous | p.Pro149Pro | 23,905 | 14,609 | 2,239 | 23.96 | 24.47 | 26.63 |
|  | 22 | 44368122 | A | G | rs3761472 | SAMM50 | missense | p.Asp108Gly | 28,170 | 11,450 | 1,132 | 24.07 | 24.64 | 26.24 |
|  | 22 | 44395451 | T | C | rs1007863 | PARVB | missense | p.Trp37Arg | 14,761 | 19,678 | 6,314 | 24.02 | 24.23 | 25.1 |

Gray shading indicates variants having exome-wide-significant associations with both ALT and AST.

Abbreviations: AAF, alternate allele frequency; Alt, alternate allele; ALT, alanine aminotransferase; AST, aspartate aminotransferase; Ref, reference allele; SE, standard error.

Figure 2 (cont.)

| Trait | Chr | BP | RSID | Ref | Alt | Gene | Annotation | AA Substitution | GHS Discovery Cohort | | |
|---|---|---|---|---|---|---|---|---|---|---|---|
| | | | | | | | | | Beta (SE) | P discovery | N |
| ALT | 1 | 220970028 | rs2642438 | A | G | MARC1 | missense | p.Thr165Ala | 0.008 (0.001) | 4.67E-08 | 40834 |
| | 4 | 88231392 | rs72613567 | T | TA | HSD17B13 | splice donor | | -0.089 (0.001) | 4.16E-12 | 40834 |
| | 8 | 144997604 | rs371119003 | C | T | PLEC | missense | p.Ala2302Thr | -0.160 (0.026) | 1.30E-09 | 40833 |
| | 8 | 145008502 | | G | A | PLEC | missense | p.Arg522Cys | -0.268 (0.032) | 3.26E-17 | 40834 |
| | 8 | 145662918 | rs35968570 | G | A | KIFC2 | missense | p.Glu174Lys | -0.033 (0.005) | 1.40E-11 | 40834 |
| | 8 | 145730072 | rs143408057 | G | A | GPT | missense | p.Arg83His | -0.314 (0.030) | 3.28E-18 | 40834 |
| | 8 | 145730161 | rs201815297 | C | T | GPT | missense | p.Ala87Val | -0.224 (0.014) | 6.28E-59 | 40834 |
| | 8 | 145730221 | rs112574791 | G | A | GPT | missense | p.Arg107Lys | -0.033 (0.005) | 4.25E-11 | 40834 |
| | 8 | 145731636 | rs145155876 | T | G | GPT | stop gained | p.Tyr326* | -0.235 (0.031) | 1.76E-14 | 40814 |
| | 8 | 145732114 | | G | C | GPT | missense | p.Glu430Gln | -0.224 (0.013) | 8.84E-64 | 40795 |
| | 8 | 145732151 | rs141505249 | G | A | GPT | missense | p.Arg442His | -0.077 (0.013) | 1.18E-09 | 40826 |
| | 8 | 145732180 | rs143462595 | G | C | GPT | missense | p.Val452Leu | -0.225 (0.013) | 8.19E-65 | 40833 |
| | 8 | 145733305 | rs147998249 | G | GC | GPT | frameshift | p.Glu475fs | -0.271 (0.031) | 1.00E-18 | 40834 |
| | 8 | 145748532 | rs567402720 | A | G | LRRC24 | missense | p.Leu290Ser | -0.185 (0.028) | 3.42E-11 | 40813 |
| | 9 | 117122202 | rs3748177 | C | T | AKNA | synonymous | p.Glu755Glu | -0.007 (0.001) | 9.51E-09 | 40834 |
| | 9 | 117124731 | rs3748176 | G | A | AKNA | missense | p.Pro624Leu | -0.007 (0.001) | 4.31E-09 | 40832 |
| | 10 | 101595996 | rs17222723 | T | A | ABCC2 | missense | p.Val1188Glu | -0.015 (0.003) | 2.97E-08 | 40834 |

Gray shading indicates P-values meeting the Bonferroni significance threshold of $P < 1.43 \times 10^{-3}$ \* Replication meta-analysis includes the three replication cohorts: GHS Bariatric Sugery Cohort, Dallas Heart Study, and Penn Medicine Biobank \* Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3

| Trait | Chr | BP | Ref | Alt | RSID | Gene | Annotation | AA Substitution | GHS Discovery Cohort ||| 
|---|---|---|---|---|---|---|---|---|---|---|---|
| | | | | | | | | | Beta (SE) | P discovery | N |
| | 10 | 101606861 | G | T | rs113796 | ABCC2 | synonymous | p.Val1430Val | -0.015 (0.003) | 2.71E-08 | 40834 |
| | 10 | 101610533 | C | T | rs818770 | ABCC2 | synonymous | p.His1496His | -0.015 (0.003) | 2.77E-08 | 40834 |
| | 10 | 101611294 | G | A | rs818771 | ABCC2 | missense | p.Cys1515Tyr | -0.015 (0.003) | 2.15E-08 | 40834 |
| | 10 | 101912064 | T | C | rs286295 | ERLIN1 | missense | p.Ile291Val | -0.012 (0.001) | 2.43E-21 | 40834 |
| | 10 | 101977883 | C | T | rs223080 | CHUK | missense | p.Val268Ile | -0.009 (0.001) | 1.93E-13 | 40834 |
| | 10 | 113917085 | T | A | rs2254453 | GPAM | synonymous | p.Pro681Pro | -0.008 (0.001) | 4.61E-10 | 40834 |
| | 10 | 113940329 | T | C | rs2792751 | GPAM | missense | p.Ile43Val | -0.008 (0.001) | 2.54E-10 | 40832 |
| | 14 | 94844947 | C | T | rs289294 | SERPINA1 | missense | p.Glu366Lys | 0.042 (0.005) | 9.28E-21 | 40834 |
| | 19 | 19379549 | C | T | rs58542926 | TM6SF2 | missense | p.Glu167Lys | 0.014 (0.002) | 4.76E-09 | 40833 |
| | 22 | 44324727 | C | G | rs738409 | PNPLA3 | missense | p.Ile148Met | 0.023 (0.002) | 1.34E-50 | 40834 |
| | 22 | 44324730 | C | T | rs738408 | PNPLA3 | synonymous | p.Pro149Pro | 0.023 (0.002) | 1.11E-50 | 40834 |
| | 22 | 44342116 | A | G | rs2294915 | PNPLA3 | missense | p.Lys434Glu | 0.007 (0.001) | 8.26E-08 | 40832 |
| | 22 | 44368122 | A | G | rs376147 | SAMM50 | missense | p.Asp119Gly | 0.019 (0.002) | 8.85E-30 | 40833 |
| | 22 | 44395451 | T | C | rs100786 | PARVB | missense | p.Trp37Arg | 0.011 (0.001) | 7.98E-16 | 40834 |

Grey shading indicates P-values meeting the Bonferroni significance threshold of $P < 1.43 \times 10^{-3}$.
* Replication meta-analysis includes the three replication cohorts: GHS Bariatric Sugery Cohort, Dallas Heart Study, and Penn Medicine Biobank.
* Joint meta-analysis includes the discovery cohort and the three replication cohorts: GHS Discovery Cohort, GHS Bariatric Sugery Cohort, Dallas Heart Study, and Penn Medicine Biobank.
Abbreviations: AAF, alternate allele frequency; Alt, alternate allele; ALT, alanine aminotransferase; AST, aspartate aminotransferase; Ref, reference allele; SE, standard error.

Figure 3 (cont.)

| Trait | Chr | BP | Ref | Alt | RSID | Gene | Annotation | AA Substitution | GHS Discovery Cohort | | |
|---|---|---|---|---|---|---|---|---|---|---|---|
| | | | | | | | | | Beta (SE) | P discovery | N |
| AST | 4 | 98231392 | T | TA | rs72613567 | HSD17B13 | splice donor | | -0.005 (0.001) | 6.24E-10 | 40193 |
| | 10 | 18242311 | A | G | rs10764176 | SLC39A12 | missense | p.Ser36Gly | -0.006 (0.001) | 1.09E-10 | 40193 |
| | 10 | 101157378 | CGTT | C | | GOT1 | inframe indel | p.Asn389del | -0.221 (0.024) | 1.96E-20 | 40193 |
| | 10 | 101165533 | G | C | rs374966349 | GOT1 | missense | p.Gln208Glu | 0.271 (0.027) | 2.43E-24 | 40193 |
| | 10 | 101912064 | T | C | rs2862954 | ERLIN1 | missense | p.Ile291Val | -0.005 (0.001) | 4.82E-09 | 40193 |
| | 11 | 22271870 | A | T | rs7481951 | ANO5 | missense | p.Leu322Phe | 0.004 (0.001) | 9.61E-08 | 40162 |
| | 14 | 94844947 | C | T | rs28929474 | SERPINA1 | missense | p.Glu366Lys | 0.027 (0.003) | 2.44E-20 | 40193 |
| | 19 | 19379549 | C | T | rs58542926 | TM6SF2 | missense | p.Glu167Lys | 0.008 (0.002) | 6.54E-08 | 40192 |
| | 22 | 44324727 | C | G | rs738409 | PNPLA3 | missense | p.Ile148Met | 0.014 (0.001) | 8.31E-46 | 40193 |
| | 22 | 44324730 | C | T | rs738408 | PNPLA3 | synonymous | p.Pro149Pro | 0.014 (0.001) | 8.93E-46 | 40193 |
| | 22 | 44368122 | A | G | rs3761472 | SAMM50 | missense | p.Asp110Gly | 0.011 (0.001) | 1.22E-22 | 40192 |
| | 22 | 44395451 | T | C | rs1807863 | PARVB | missense | p.Trp37Arg | 0.006 (0.001) | 1.31E-13 | 40193 |

Gray shading indicates P-values meeting the Bonferroni significance threshold of P < 1.43x10-3

* Replication meta-analysis includes the three replication cohorts: GHS Bariatric Sugery Cohort, Dallas Heart Study, and Penn Medicine Biobank

* Joint meta-analysis includes the discovery cohort and the three replication cohorts: GHS Discovery Cohort, GHS Bariatric Sugery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Replication Cohorts | | | | | | |
|---|---|---|---|---|---|---|---|---|---|---|---|
| | | | | | Dallas Heart Study | | | Penn Medicine Biobank | | | |
| | | Beta (SE) | P | N | Beta (SE) | P | N | Beta (SE) | P | N | |
| ALT | 1 | 0.005 (0.005) | 3.10E-01 | 2475 | 0.009 (0.008) | 2.58E-01 | 1356 | 0.006 (0.004) | 1.81E-01 | 6158 | |
| | 4 | -0.010 (0.005) | 5.57E-02 | 2475 | -0.014 (0.008) | 9.68E-02 | 1356 | -0.012 (0.004) | 4.85E-03 | 6158 | |
| | 8 | -0.492 (0.165) | 2.84E-03 | 2475 | NA (NA) | NA | NA | -0.054 (0.071) | 4.46E-01 | 6158 | |
| | 8 | -0.161 (0.165) | 3.29E-01 | 2475 | NA (NA) | NA | NA | -0.259 (0.143) | 6.90E-02 | 6158 | |
| | 8 | -0.089 (0.02) | 6.48E-01 | 2475 | 0.027 (0.035) | 4.48E-01 | 1355 | -0.051 (0.019) | 7.52E-03 | 6158 | |
| | 8 | -0.189 (0.165) | 2.50E-01 | 2475 | NA (NA) | NA | NA | -0.305 (0.101) | 2.54E-03 | 6158 | |
| | 8 | -0.341 (0.074) | 3.64E-06 | 2475 | NA (NA) | NA | NA | -0.144 (0.054) | 7.67E-03 | 6158 | |
| | 8 | -0.089 (0.02) | 6.45E-01 | 2475 | 0.024 (0.035) | 5.01E-01 | 1356 | -0.059 (0.018) | 1.13E-03 | 6158 | |
| | 8 | -0.314 (0.165) | 5.71E-02 | 2475 | -0.334 (0.137) | 1.49E-02 | 1355 | -0.151 (0.143) | 2.90E-01 | 6157 | |
| | 8 | -0.273 (0.048) | 9.83E-09 | 2474 | -0.244 (0.073) | 8.91E-04 | 1356 | -0.188 (0.041) | 5.52E-06 | 6157 | |
| | 8 | -0.115 (0.058) | 4.82E-02 | 2475 | -0.092 (0.097) | 3.43E-01 | 1355 | -0.042 (0.043) | 3.36E-01 | 6157 | |
| | 8 | -0.273 (0.050) | 4.26E-08 | 2475 | -0.198 (0.068) | 3.90E-03 | 1356 | -0.188 (0.041) | 5.52E-06 | 6158 | |
| | 8 | -0.161 (0.165) | 3.29E-01 | 2475 | NA (NA) | NA | NA | -0.506 (0.202) | 1.22E-02 | NA | |
| | 8 | -0.161 (0.165) | 3.29E-01 | 2475 | NA (NA) | NA | NA | -0.303 (0.143) | 3.37E-02 | NA | |
| | 9 | -0.004 (0.005) | 4.09E-01 | 2475 | 0.003 (0.008) | 6.46E-01 | 1356 | -0.007 (0.004) | 6.38E-02 | 6158 | |

Gray shading indicates P-values meeting the Bonferroni significance threshold of $P < 1.43 \times 10^{-3}$

* Replication meta-analysis includes the three replication cohorts: GHS Bariatric Surgery Cohort, Dallas Heart Study, and Penn Medicine Biobank.

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| | 9 | -0.004 (0.005) | 3.90E-01 | 2475 | 0.002 (0.008) | 7.69E-01 | 1355 | -0.007 (0.004) | 5.29E-02 | 6158 |
| | 10 | -0.002 (0.010) | 8.01E-01 | 2475 | -0.003 (0.017) | 8.37E-01 | 1356 | -0.015 (0.007) | 4.49E-02 | 6158 |
| | 10 | -0.003 (0.010) | 7.74E-01 | 2475 | -0.005 (0.017) | 7.49E-01 | 1356 | -0.014 (0.007) | 4.86E-02 | 6158 |
| | 10 | -0.003 (0.010) | 7.93E-01 | 2475 | -0.005 (0.017) | 7.49E-01 | 1356 | -0.014 (0.007) | 5.02E-02 | 6158 |
| | 10 | -0.001 (0.010) | 9.11E-01 | 2475 | -0.008 (0.016) | 6.41E-01 | 1356 | -0.013 (0.007) | 7.46E-02 | 6158 |
| | 10 | -0.01 (0.005) | 2.91E-02 | 2475 | -0.006 (0.007) | 4.02E-01 | 1356 | -0.009 (0.004) | 2.06E-02 | 6158 |
| | 10 | -0.006 (0.005) | 2.05E-01 | 2475 | -0.001 (0.007) | 9.07E-01 | 1356 | -0.011 (0.004) | 5.26E-03 | 6158 |
| | 10 | -0.003 (0.005) | 5.80E-01 | 2475 | -0.014 (0.008) | 8.25E-02 | 1356 | -0.007 (0.004) | 7.45E-02 | 6158 |
| | 10 | -0.003 (0.005) | 5.61E-01 | 2475 | -0.014 (0.008) | 9.08E-02 | 1356 | -0.008 (0.004) | 6.34E-02 | 6158 |
| | 14 | 0.035 (0.020) | 7.97E-02 | 2475 | 0.044 (0.032) | 1.63E-01 | 1356 | 0.056 (0.013) | 1.38E-05 | 6158 |
| | 19 | 0.040 (0.010) | 2.40E-05 | 2475 | 0.025 (0.014) | 7.24E-02 | 1356 | 0.013 (0.008) | 1.07E-01 | 6158 |
| | 22 | 0.019 (0.006) | 5.54E-04 | 2475 | 0.005 (0.009) | 5.75E-01 | 1356 | 0.018 (0.005) | 5.51E-05 | 6158 |
| | 22 | 0.019 (0.006) | 5.51E-04 | 2475 | 0.005 (0.009) | 5.75E-01 | 1356 | 0.018 (0.005) | 5.78E-05 | 6158 |
| | 22 | 0.001 (0.005) | 7.77E-01 | 2475 | 0.004 (0.008) | 6.26E-01 | 1356 | 0.005 (0.004) | 2.00E-01 | 6158 |
| | 22 | 0.009 (0.006) | 1.66E-01 | 2475 | -0.002 (0.01) | 8.80E-01 | 1356 | 0.021 (0.005) | 5.29E-05 | 6158 |
| | 22 | 0.003 (0.005) | 5.22E-01 | 2475 | 0.007 (0.008) | 3.31E-01 | 1356 | 0.008 (0.004) | 3.82E-02 | 6158 |

Gray shading indicates P-values meeting the Bonferroni significance threshold of P < 1.43x10-3
* Replication meta-analysis includes the three replication cohorts: GHS Bariatric Surgery Cohort, Dallas Heart Study, and Penn Medicine Biobank
* Joint meta-analysis includes the discovery cohort and the three replication cohorts: GHS Discovery Cohort, GHS Bariatric Surgery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| ALT | 1 | 0.006 (0.003) | 4.77E-02 | 0.007 (0.001) | 6.91E-09 |
| | 4 | -0.012 (0.003) | 1.67E-04 | -0.010 (0.001) | 3.85E-15 |
| | 8 | -0.124 (0.066) | 5.92E-02 | -0.155 (0.024) | 2.41E-10 |
| | 8 | -0.259 (0.143) | 6.90E-02 | -0.264 (0.03) | 4.65E-18 |
| | 8 | -0.024 (0.013) | 6.89E-02 | -0.032 (0.005) | 3.36E-12 |
| | 8 | -0.305 (0.101) | 2.54E-03 | -0.308 (0.033) | 2.21E-20 |
| | 8 | -0.213 (0.044) | 1.01E-06 | -0.223 (0.013) | 4.00E-64 |
| | 8 | -0.029 (0.013) | 2.09E-02 | -0.032 (0.005) | 2.89E-12 |
| | 8 | -0.264 (0.085) | 1.84E-03 | -0.238 (0.029) | 1.35E-16 |
| | 8 | -0.227 (0.029) | 2.39E-15 | -0.224 (0.012) | 1.94E-77 |
| | 8 | -0.070 (0.033) | 3.12E-02 | -0.076 (0.012) | 1.12E-10 |
| | 8 | -0.218 (0.029) | 3.94E-14 | -0.224 (0.012) | 2.92E-77 |
| | 8 | -0.506 (0.202) | 1.22E-02 | -0.272 (0.030) | 6.42E-20 |
| | 8 | -0.303 (0.143) | 3.37E-02 | -0.189 (0.027) | 2.99E-12 |
| | 9 | -0.005 (0.003) | 9.79E-02 | -0.007 (0.001) | 3.57E-09 |

Gray shading indicates P-values meeting the Bonferroni significance threshold of $P < 1.43 \times 10^{-3}$
* Replication meta-analysis includes the three replication cohorts: GHS Bariatric Sugery Cohort, Dallas Heart Study, and Penn Medicine Biobank
* Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| | 9 | -0.005 (0.003) | 7.27E-02 | -0.007 (0.001) | 1.19E-09 |
| | 10 | -0.01 (0.006) | 8.55E-02 | -0.014 (0.002) | 9.49E-09 |
| | 10 | -0.01 (0.006) | 7.96E-02 | -0.014 (0.002) | 8.03E-09 |
| | 10 | -0.01 (0.006) | 8.38E-02 | -0.014 (0.002) | 8.70E-09 |
| | 10 | -0.009 (0.006) | 1.19E-01 | -0.014 (0.002) | 1.07E-08 |
| | 10 | -0.009 (0.003) | 1.14E-03 | -0.011 (0.001) | 1.76E-23 |
| | 10 | -0.009 (0.003) | 5.11E-03 | -0.009 (0.001) | 4.17E-15 |
| | 10 | -0.008 (0.003) | 2.44E-02 | -0.008 (0.001) | 3.82E-11 |
| | 10 | -0.007 (0.003) | 2.13E-02 | -0.008 (0.001) | 1.85E-11 |
| | 14 | 0.049 (0.010) | 1.51E-06 | 0.044 (0.004) | 9.55E-26 |
| | 19 | 0.024 (0.006) | 1.58E-05 | 0.016 (0.002) | 1.35E-12 |
| | 22 | 0.017 (0.003) | 2.60E-07 | 0.022 (0.001) | 7.75E-56 |
| | 22 | 0.017 (0.003) | 2.71E-07 | 0.022 (0.001) | 6.77E-56 |
| | 22 | 0.004 (0.003) | 2.03E-01 | 0.006 (0.001) | 6.49E-08 |
| | 22 | 0.014 (0.004) | 2.57E-04 | 0.018 (0.002) | 2.36E-32 |
| | 22 | 0.006 (0.003) | 2.63E-02 | 0.01 (0.001) | 1.83E-16 |

Gray shading indicates P-values meeting the Bonferroni significance threshold of P < $1.43 \times 10^{-3}$
* Replication meta-analysis includes the three replication cohorts: GHS Bariatric Sugery Cohort, Dallas Heart Study, and Penn Medicine Biobank
** Joint meta-analysis includes the discovery cohort and the three replication cohorts: GHS Discovery Cohort, GHS Bariatric Sugery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| Trait | Chr | GHS Bariatric Surgery Cohort | | | Dallas Heart Study | | | Penn Medicine Biobank | | |
|---|---|---|---|---|---|---|---|---|---|---|
| | | Beta (SE) | P | N | Beta (SE) | P | N | Beta (SE) | P | N |
| AST | 4 | -0.010 (0.003) | 3.12E-03 | 2469 | -0.012 (0.006) | 5.87E-02 | 1356 | -0.006 (0.004) | 1.02E-01 | 6166 |
| | 10 | -0.010 (0.003) | 2.91E-03 | 2469 | -0.003 (0.006) | 6.25E-01 | 1356 | -0.010 (0.004) | 6.75E-03 | 6166 |
| | 10 | -0.205 (0.062) | 8.57E-04 | 2469 | NA (NA) | NA | NA | -0.244 (0.089) | 5.90E-03 | 6165 |
| | 10 | NA (NA) | NA | 2469 | NA (NA) | NA | NA | 0.339 (0.079) | 1.85E-05 | 6166 |
| | 10 | -0.004 (0.003) | 1.54E-01 | 2469 | -0.007 (0.006) | 2.18E-01 | 1356 | -0.003 (0.003) | 3.13E-01 | 6166 |
| | 11 | -0.001 (0.003) | 7.85E-01 | 2466 | 0.006 (0.006) | 2.80E-01 | 1356 | -0.003 (0.003) | 3.54E-01 | 6165 |
| | 14 | 0.023 (0.013) | 7.79E-02 | 2469 | 0.046 (0.024) | 6.09E-02 | 1356 | 0.052 (0.011) | 4.75E-06 | 6166 |
| | 19 | 0.023 (0.006) | 1.99E-04 | 2469 | 0.010 (0.011) | 3.42E-01 | 1356 | 0.004 (0.007) | 5.94E-01 | 6166 |
| | 22 | 0.014 (0.004) | 1.27E-04 | 2469 | 0.004 (0.007) | 5.53E-01 | 1356 | 0.017 (0.004) | 1.16E-05 | 6166 |
| | 22 | 0.014 (0.004) | 1.32E-04 | 2469 | 0.004 (0.007) | 5.53E-01 | 1356 | 0.017 (0.004) | 1.17E-05 | 6166 |
| | 22 | 0.008 (0.004) | 6.03E-02 | 2469 | -0.001 (0.008) | 9.33E-01 | 1356 | 0.018 (0.005) | 6.47E-05 | 6166 |
| | 22 | 0.003 (0.003) | 4.12E-01 | 2469 | 0.006 (0.006) | 3.03E-01 | 1356 | 0.009 (0.003) | 1.37E-02 | 6166 |

Gray shading indicates P-values meeting the Bonferroni significance threshold of $P < 1.43 \times 10^{-3}$

* Replication meta-analysis includes the three replication cohorts: GHS Bariatric Surgery Cohort, Dallas Heart Study, and Penn Medicine Biobank

* Joint meta-analysis includes the discovery cohort and the three replication cohorts: GHS Discovery Cohort, GHS Bariatric Surgery Cohort, Dallas Heart Study, and Penn Medicine Biobank Abbreviations: AAF, alternate allele frequency; Alt, alternate allele; ALT, alanine aminotransferase; AST, aspartate aminotransferase; Ref, reference allele; SE, standard error.

Figure 3 (cont.)

| Trait | Chr | Replication Meta-analysis* (N=3) | | Joint Meta-analysis** (N=4) | |
|---|---|---|---|---|---|
| | | Beta (SE) | P replication | Beta (SE) | P joint |
| AST | 4 | -0.009 (0.002) | 1.69E-04 | -0.006 (0.001) | 1.13E-12 |
| | 10 | -0.009 (0.002) | 8.86E-05 | -0.006 (0.001) | 9.66E-14 |
| | 10 | -0.205 (0.062) | 8.57E-04 | -0.220 (0.022) | 1.66E-24 |
| | 10 | 0.339 (0.079) | 1.85E-05 | 0.271 (0.027) | 2.43E-24 |
| | 10 | -0.004 (0.002) | 3.92E-02 | -0.005 (0.001) | 5.52E-10 |
| | 11 | -0.001 (0.002) | 7.03E-01 | 0.004 (0.001) | 1.48E-06 |
| | 14 | 0.040 (0.008) | 6.56E-07 | 0.029 (0.003) | 2.78E-25 |
| | 19 | 0.014 (0.004) | 1.20E-03 | 0.009 (0.002) | 5.92E-10 |
| | 22 | 0.014 (0.002) | 2.00E-08 | 0.014 (0.001) | 1.12E-52 |
| | 22 | 0.014 (0.002) | 2.10E-08 | 0.014 (0.001) | 1.26E-52 |
| | 22 | 0.011 (0.003) | 1.77E-04 | 0.011 (0.001) | 1.01E-25 |
| | 22 | 0.005 (0.002) | 1.34E-02 | 0.006 (0.001) | 6.61E-15 |

Gray shading indicates P-values meeting the Bonferroni significance threshold of $P < 1.43 \times 10^{-3}$
* Replication meta-analysis includes the three replication cohorts: GHS Bariatric Surgery Cohort, Dallas Heart Study, and Penn Medicine Biobank
** Joint meta-analysis includes the discovery cohort and the three replication cohorts: GHS Discovery Cohort, GHS Bariatric Surgery Cohort, Dallas Heart Study, and Penn Medicine Biobank
Abbreviations: AAF, alternate allele frequency; Alt, alternate allele; ALT, alanine aminotransferase; AST, aspartate aminotransferase; Ref, reference allele; SE, standard error;

Figure 3 (cont.)

| CHR:BP:Ref:Alt | Gene | rsID | Alcoholic liver disease | | Alcoholic cirrhosis | |
|---|---|---|---|---|---|---|
| | | | OR (95% CI) | P | OR (95% CI) | P |
| 4:88231392:T:TA | HSD17B13 | rs72613567 | 0.62 (0.48-0.81) | 1.82E-04 | 0.56 (0.41-0.78) | 3.35E-04 |
| 8:145730161:C:T | GPT | rs201815297 | 3.83 (1.05-13.94) | 8.88E-02 | 6.33 (1.71-23.43) | 2.88E-02 |
| 8:145732114:G:C | GPT | rs141505249 | 0.77 (0.06-10.73) | 8.43E-01 | 1.13 (0.08-15.39) | 9.30E-01 |
| 8:145732180:G:C | GPT | rs147998249 | 0.73 (0.05-11.76) | 8.17E-01 | 1.07 (0.07-17.16) | 9.60E-01 |
| 10:18242311:A:G | SLC39A12 | rs10764176 | 0.85 (0.68-1.07) | 1.64E-01 | 0.92 (0.70-1.22) | 5.80E-01 |
| 10:101157378:CGTT:C | GOT1 | | 4.60 (0.25-86.41) | 3.93E-01 | 7.11 (0.38-133.19) | 3.00E-01 |
| 10:101165533:G:C | GOT1 | rs3749663649 | 2.20 (0.13-37.68) | 6.24E-01 | 3.47 (0.20 - 59.04) | 4.70E-01 |
| 10:101912064:T:C | ERLIN1 | rs2862954 | 0.92 (0.75-1.12) | 4.05E-01 | 1.05 (0.82-1.34) | 7.13E-01 |
| 14:94844947:C:T | SERPINA1 | rs28929474 | 2.49 (1.49-4.17) | 2.30E-03 | 3.35 (1.93-5.83) | 3.01E-04 |
| 19:19379549:C:T | TM6SF2 | rs58542926 | 1.47 (1.06-2.04) | 2.76E-02 | 1.35 (0.89-2.04) | 1.80E-01 |
| 22:44324727:C:G | PNPLA3 | rs738409 | 1.76 (1.43-2.18) | 4.98E-07 | 2.07 (1.60-2.67) | 1.08E-07 |
| 22:44324730:C:T | PNPLA3 | rs738408 | 1.77 (1.43-2.18) | 4.70E-07 | 2.07 (1.61-2.67) | 1.03E-07 |
| 22:44368122:A:G | SAMM50 | rs3761472 | 1.90 (1.52-2.38) | 1.36E-07 | 2.28 (1.75-2.98) | 1.83E-08 |

Gray shading indicates P-values meeting the Bonferroni significance threshold of $P < 1.92 \times 10^{-3}$

Figure 4

| CHR:BP:Ref:Alt | Gene | rsID | Nonalcoholic liver disease | | Nonalcoholic cirrhosis | | Hepatocellular carcinoma | |
|---|---|---|---|---|---|---|---|---|
| | | | OR (95% CI) | P | OR (95% CI) | P | OR (95% CI) | P |
| 4:8823192:T:A | HSD17B13 | rs72613567 | 0.84 (0.78-0.91) | 1.31E-05 | 0.74 (0.62-0.88) | 4.48E-04 | 0.67 (0.45-1.00) | 4.66E-02 |
| 8:145730161:C:T | GPT | rs201815297 | 0.23 (0.04-1.14) | 1.86E-02 | 1.25 (0.24-6.38) | 7.98E-01 | 3.66 (0.70-19.01) | 2.01E-01 |
| 8:145732114:G:C | GPT | rs141505249 | 1.02 (0.49-2.11) | 9.70E-01 | 0.36 (0.02-5.37) | 3.82E-01 | 1.84 (0.15-23.25) | 6.88E-01 |
| 8:145732180:G:C | GPT | rs147998249 | 1.03 (0.49-2.17) | 9.30E-01 | 0.34 (0.02-5.59) | 3.67E-01 | 1.74 (0.11-27.05) | 7.21E-01 |
| 10:18242311:A:G | SLC39A12 | rs10764176 | 0.92 (0.86-0.99) | 3.43E-02 | 1.03 (0.88-1.21) | 7.15E-01 | 1.29 (0.93-1.79) | 1.37E-01 |
| 10:101157378:CGTT:C | GOT1 | | 2.37 (0.61-9.27) | 2.50E-01 | 8.27 (1.44-47.49) | 5.92E-02 | 9.81 (0.52-183.54) | 2.43E-01 |
| 10:101165533:G:C | GOT1 | rs374946349 | 1.63 (0.53-4.96) | 4.20E-01 | 1.17 (0.07-20.09) | 9.13E-01 | 5.37 (0.32-91.12) | 3.55E-01 |
| 10:101912064:T:C | ERLIN1 | rs2862954 | 0.98 (0.91-1.04) | 4.61E-01 | 1.13 (0.98-1.31) | 9.90E-02 | 0.94 (0.69-1.28) | 6.94E-01 |
| 14:94844947:C:T | SERPINA1 | rs28929474 | 1.50 (1.21-1.87) | 5.29E-04 | 2.99 (2.11-4.24) | 9.08E-08 | 1.86 (0.74-4.67) | 2.40E-01 |
| 19:19379549:C:T | TM6SF2 | rs58542926 | 1.36 (1.21-1.52) | 2.42E-07 | 1.64 (1.31-2.05) | 6.04E-05 | 1.93 (1.22-3.04) | 1.08E-02 |
| 22:44324727:C:G | PNPLA3 | rs738409 | 1.65 (1.54-1.78) | 1.31E-41 | 2.05 (1.76-2.38) | 1.70E-19 | 2.20 (1.60-3.02) | 5.59E-06 |
| 22:44324730:C:T | PNPLA3 | rs738408 | 1.65 (1.54-1.78) | 1.42E-41 | 2.05 (1.77-2.38) | 1.45E-19 | 2.20 (1.60-3.03) | 5.41E-06 |
| 22:44368122:A:G | SAMM50 | rs3761472 | 1.52 (1.41-1.65) | 7.33E-24 | 1.86 (1.58-2.19) | 1.81E-12 | 1.66 (1.16-2.39) | 1.05E-02 |

Gray shading indicates P-values meeting the Bonferroni significance threshold of P < 1.92×10-3

Figure 4 (cont.)

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) – median (IQR) | 55 (48 - 60) | 44 (36 - 53) | 12 (10 - 15) | 12 (11 - 14) |
| Female sex – number (%) | 277 (54) | 2,494 (58) | 65 (32) | 126 (52) |
| Body mass index – median (IQR) | 30 (27 - 35) | 30 (26 - 35) | 30 (27 - 34) | 31 (28 - 35) |
| Self-reported ethnicity | | | | |
| African American | 33 (6) | 2,291 (54) | - | - |
| European American | 158 (31) | 1,266 (30) | - | - |
| Hispanic American | 326 (63) | 722 (17) | 203 (100) | 244 (100) |
| Presence of liver disease – N (%) | | | | |
| Alcoholic liver disease | 223 (43) | - | - | - |
| Alcoholic cirrhosis | 215 (42) | - | - | - |
| Nonalcoholic (non-viral) liver disease | 212 (20) | - | - | - |
| Nonalcoholic cirrhosis | 100 (19) | - | - | - |
| Hepatocellular carcinoma | 44 (9) | - | - | - |
| No liver disease | - | 4,279 (100) | - | 244 (100) |

Figure 5

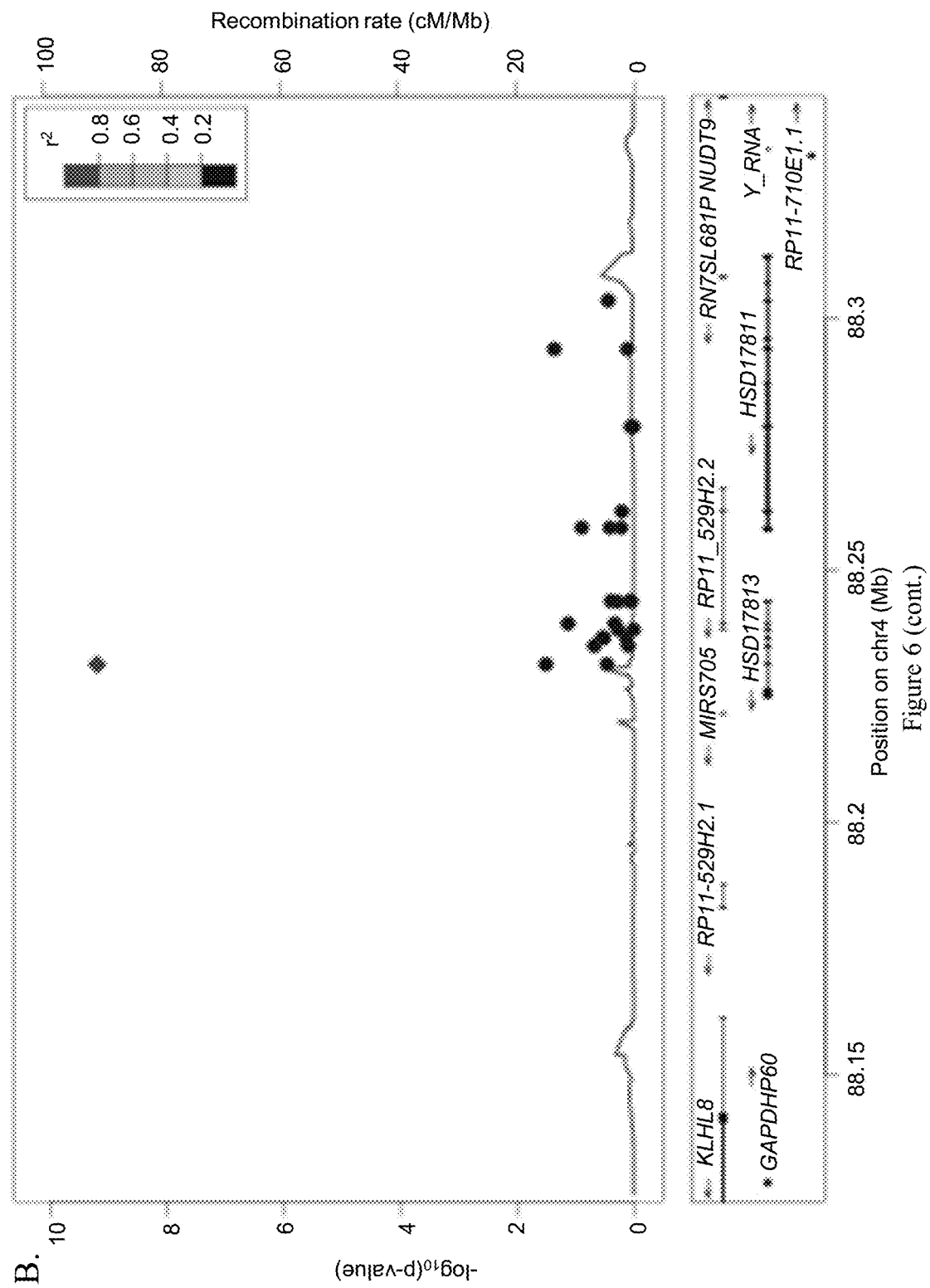

| Phenotype/Subset | N | | HSD17B13 rs72613567 [Interaction effect] | | | HSD17B13 rs72613567 [Main effect] | | | | PNPLA3 rs738409 [Main effect] | | |
|---|---|---|---|---|---|---|---|---|---|---|---|---|
| log₁₀(ALT) | | | | | | | | | | | | |
| Subset | N | | Effect (95% CI) | p | AAF | Effect (95% CI) | p | AAF | | Effect (95% CI) | p | |
| All | 43,309 | | -0.007 (-0.011,-0.002) | 1.80E-03 | 26.36% | -0.006 (-0.009,-0.003) | 1.88E-04 | 23.54% | | 0.026 (0.022,0.029) | 1.97E-50 | |
| Obese | 23,051 | | -0.01 (-0.015,-0.004) | 1.01E-03 | 26.48% | -0.009 (-0.013,-0.005) | 6.53E-05 | 23.57% | | 0.037 (0.032,0.042) | 3.13E-55 | |
| Non-obese | 20,258 | | -0.004 (-0.01,0.002) | 1.49E-01 | 26.22% | -0.002 (-0.007,0.002) | 3.53E-01 | 23.51% | | 0.013 (0.008,0.018) | 1.56E-07 | |
| log₁₀(AST) | | | | | | | | | | | | |
| Subset | N | | Effect (95% CI) | p | AAF | Effect (95% CI) | p | AAF | | Effect (95% CI) | p | |
| All | 42,662 | | -0.004 (-0.007,-0.001) | 4.53E-03 | 26.40% | -0.004 (-0.006,-0.002) | 4.78E-04 | 23.47% | | 0.016 (0.014,0.018) | 9.69E-46 | |
| Obese | 22,719 | | -0.006 (-0.01,-0.003) | 1.04E-03 | 26.51% | -0.006 (-0.009,-0.003) | 1.42E-04 | 23.53% | | 0.023 (0.02,0.027) | 7.65E-49 | |
| Non-obese | 19,943 | | -0.001 (-0.005,0.003) | 4.97E-01 | 26.26% | -0.001 (-0.004,0.002) | 3.42E-01 | 23.41% | | 0.008 (0.005,0.011) | 1.56E-06 | |
| Nonalcoholic liver disease | | | | | | | | | | | | |
| Subset | N Controls | N Cases | OR (95% CI) | p | AAF | OR (95% CI) | p | AAF | | OR (95% CI) | p | |
| All | 29,928 | 1,857 | 0.919 (0.812,1.039) | 1.78E-01 | 26.43% | 0.88 (0.787,0.983) | 2.40E-02 | 23.51% | | 1.764 (1.606,1.938) | 1.76E-32 | |
| Obese | 14,243 | 1,445 | 0.906 (0.786,1.044) | 1.74E-01 | 26.36% | 0.894 (0.788,1.012) | 7.81E-02 | 23.65% | | 1.714 (1.537,1.91) | 2.06E-22 | |
| Non-obese | 15,685 | 412 | 0.964 (0.75,1.239) | 7.71E-01 | 26.50% | 0.845 (0.662,1.069) | 1.67E-01 | 23.38% | | 1.887 (1.566,2.269) | 1.96E-11 | |
| Alcoholic liver disease | | | | | | | | | | | | |
| Subset | N Controls | N Cases | OR (95% CI) | p | AAF | OR (95% CI) | p | AAF | | OR (95% CI) | p | |
| All | 29,928 | 190 | 1.112 (0.749,1.637) | 5.94E-01 | 26.57% | 0.578 (0.391,0.834) | 4.56E-03 | 22.99% | | 1.689 (1.298,2.185) | 7.80E-05 | |
| Obese | 14,243 | 97 | 1.295 (0.741,2.224) | 3.56E-01 | 26.53% | 0.501 (0.283,0.839) | 1.22E-02 | 22.83% | | 1.533 (1.052,2.201) | 2.30E-02 | |
| Non-obese | 15,685 | 93 | 0.956 (0.544,1.65) | 8.72E-01 | 26.55% | 0.666 (0.382,1.105) | 1.33E-01 | 23.13% | | 1.853 (1.275,2.664) | 1.00E-03 | |

Figure 9

E.
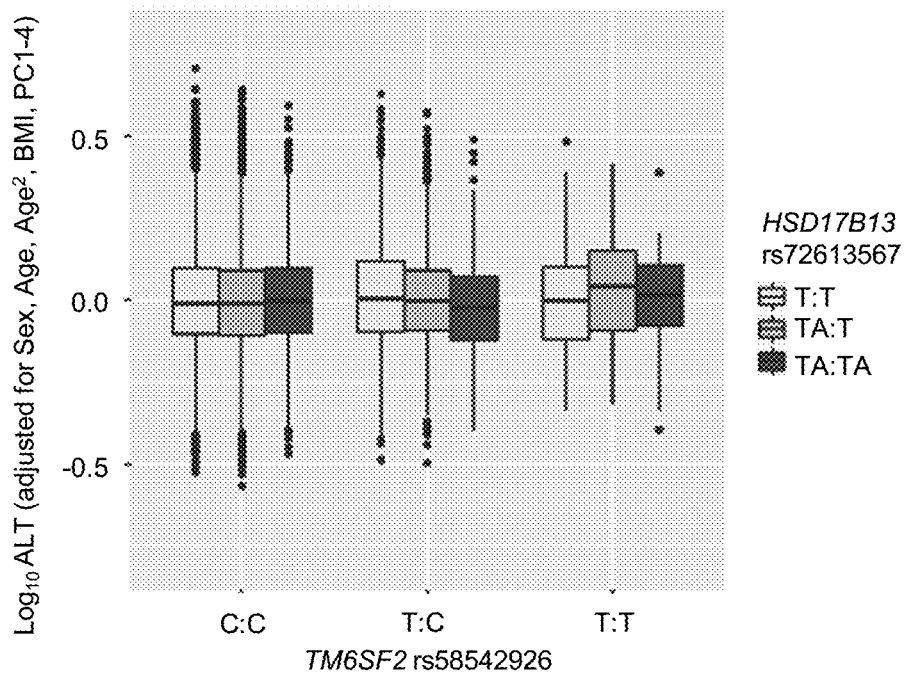
F.
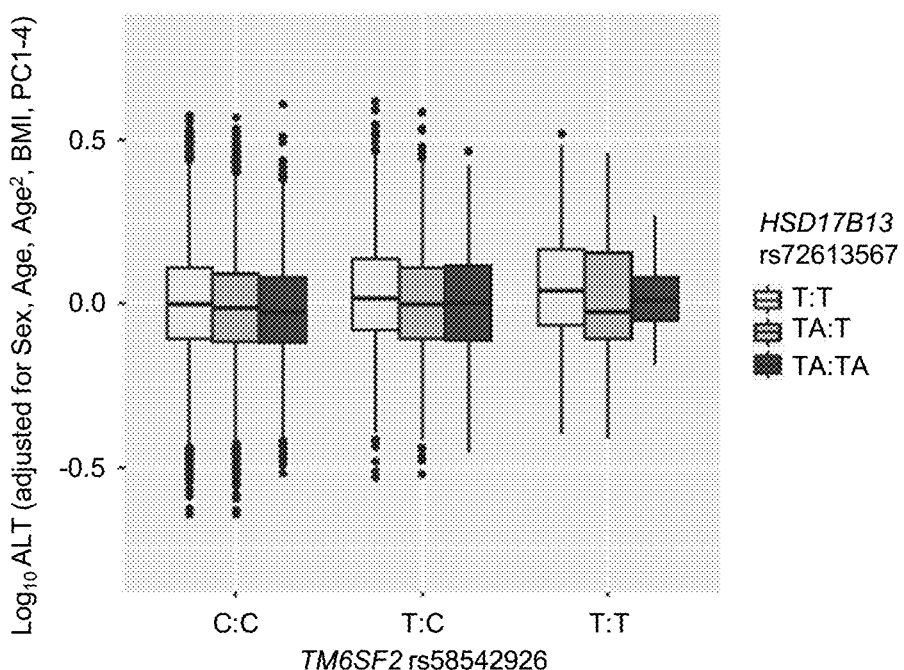
Figure 11 (cont.)

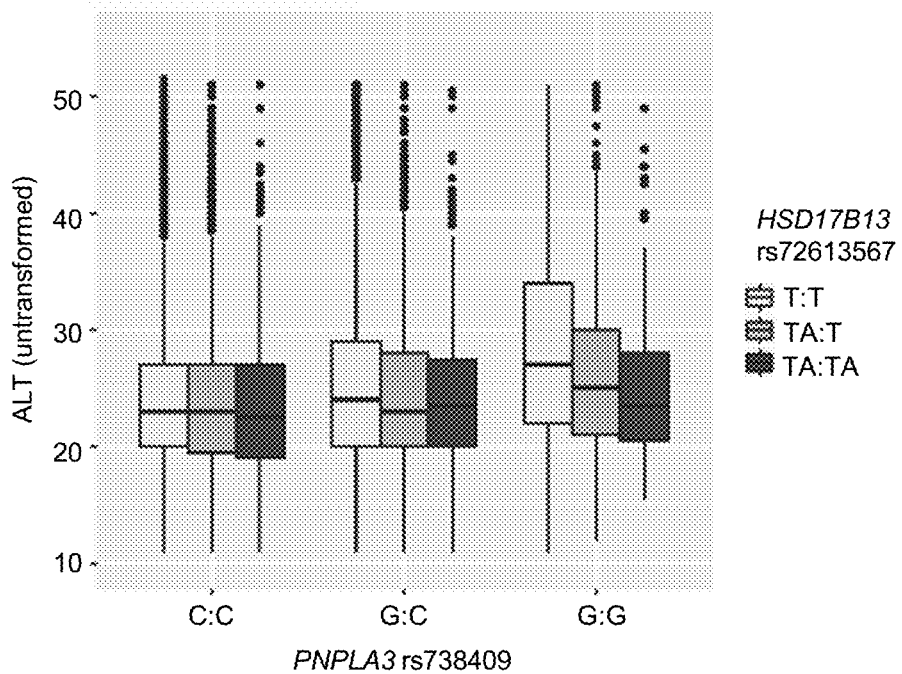
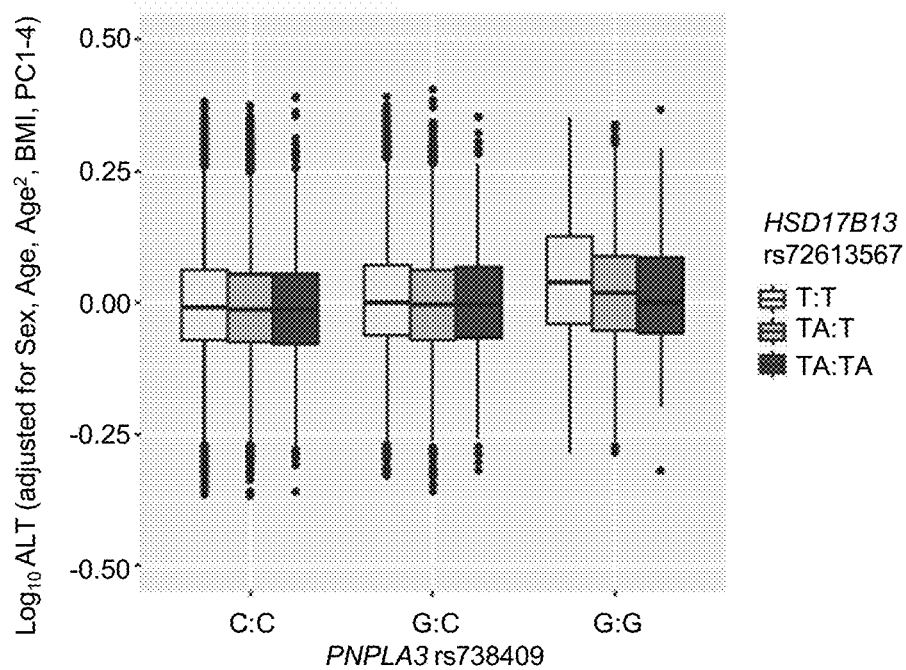
Figure 12 (cont.)

E.
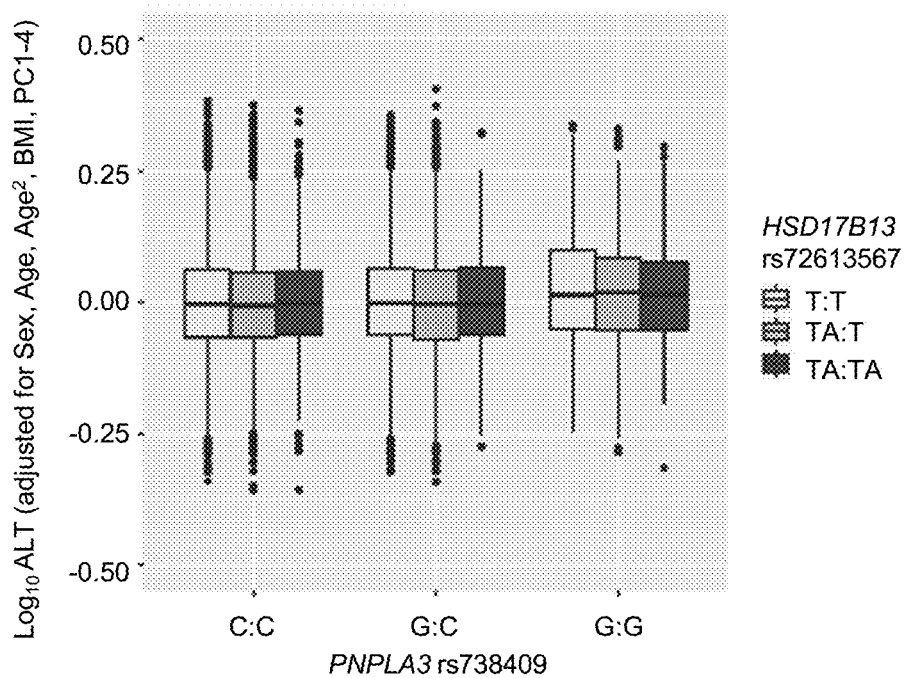
F.
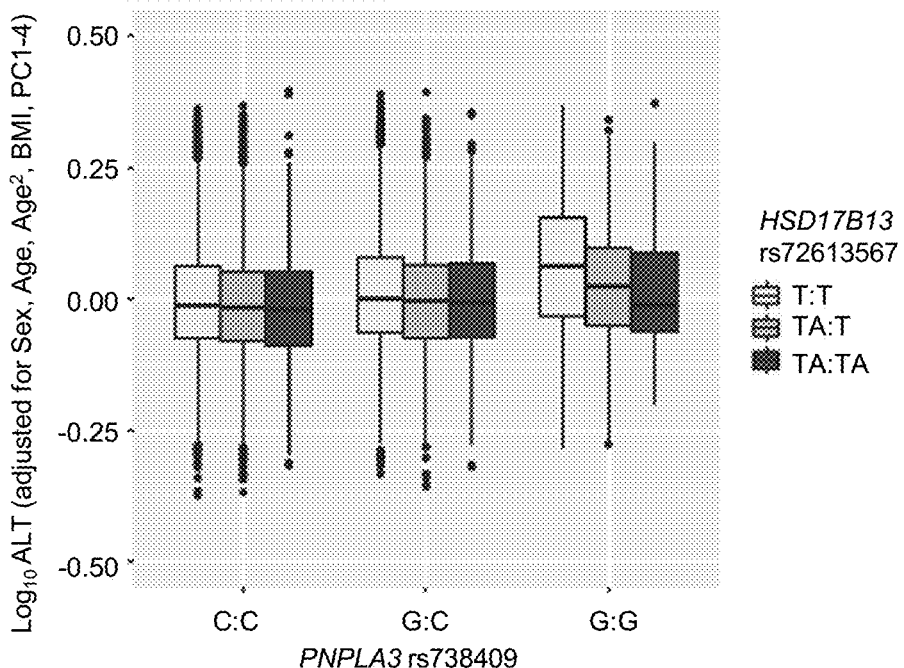
Figure 12 (cont.)

C.
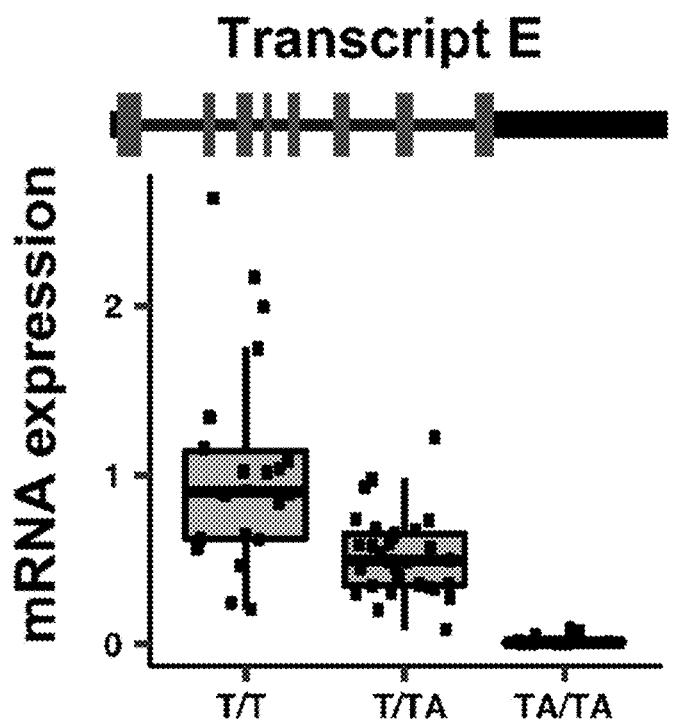
D.
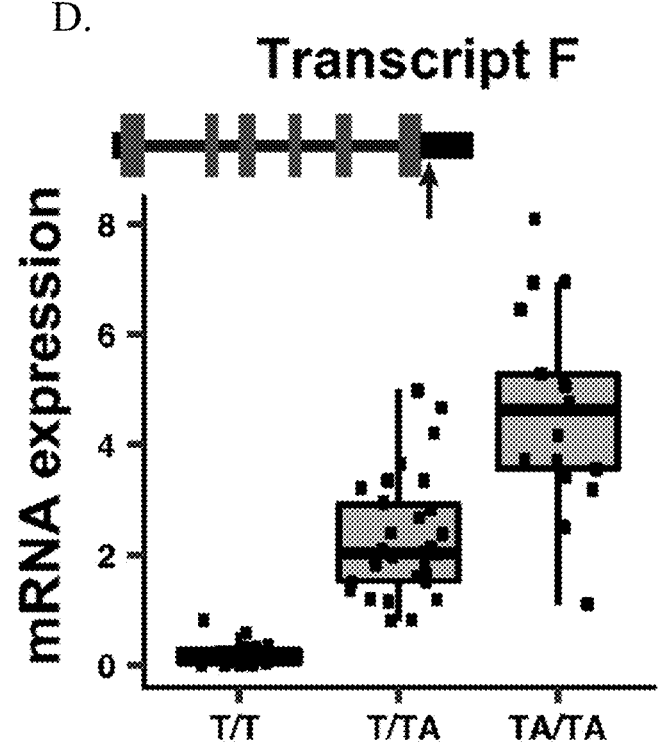
Figure 13 (cont.)

E.
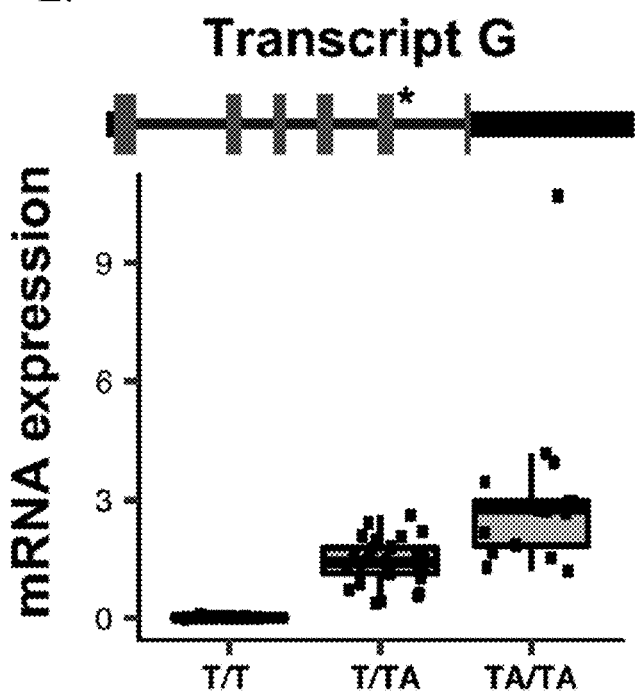
F.
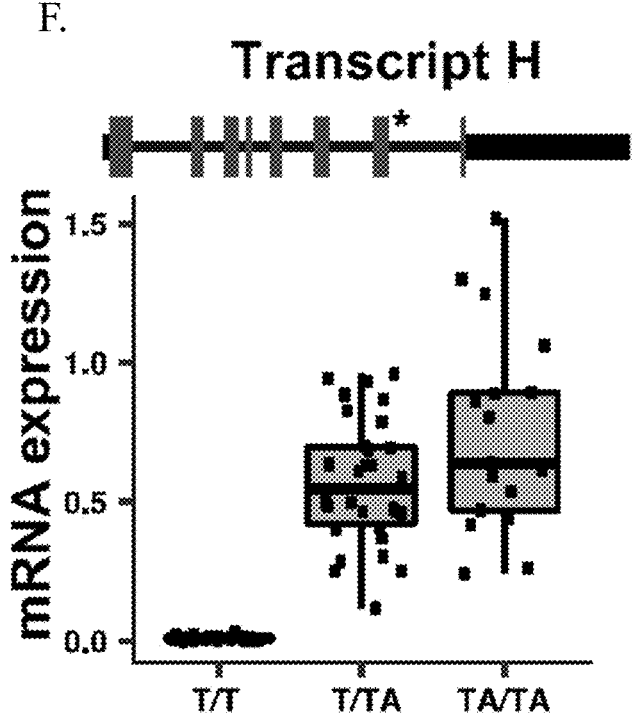
Figure 13 (cont.)

B.

| Description | Genotype | Case | Control | Genotypic OR (95% CI) | Allelic OR (95% CI) | P-value |
|---|---|---|---|---|---|---|
| Any liver disease (n=517) vs. Normal (n=4279) | T/T | 399 | 3238 | 1(--) | 0.70 (0.57-0.88) | 1.77e-03 |
| | T/TA | 108 | 910 | 0.74 (0.57-0.97) | | |
| | TA/TA | 10 | 131 | 0.41 (0.21-0.83) | | |
| Alcoholic liver disease (n=223) vs. Normal (n=4279) | T/T | 167 | 3238 | 1(--) | 0.77 (0.57-1.04) | 7.65e-02 |
| | T/TA | 52 | 910 | 0.85 (0.59-1.23) | | |
| | TA/TA | 4 | 131 | 0.37 (0.13-1.08) | | |
| Alcoholic cirrhosis (n=215) vs. Normal (n=4279) | T/T | 163 | 3238 | 1(--) | 0.72 (0.53-0.99) | 4.37e-02 |
| | T/TA | 49 | 910 | 0.83 (0.57-1.20) | | |
| | TA/TA | 3 | 131 | 0.29 (0.09-0.97) | | |

A.
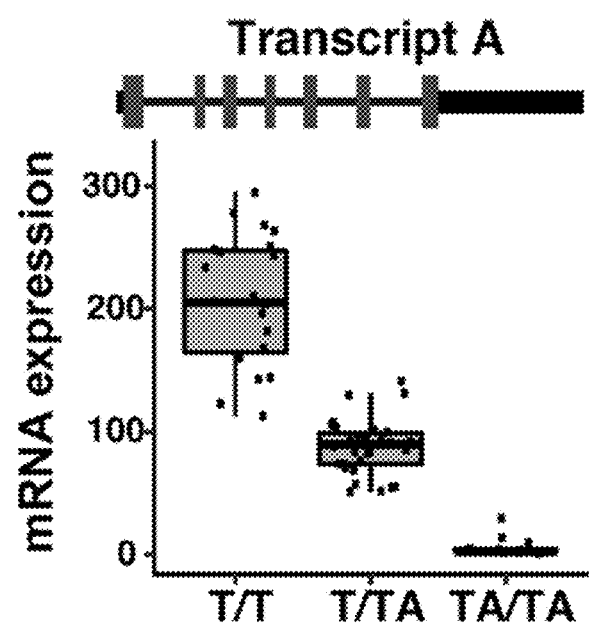
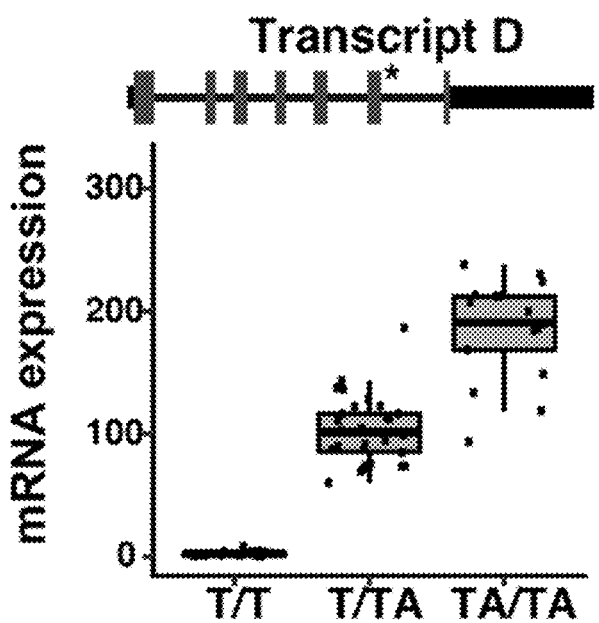
Figure 18

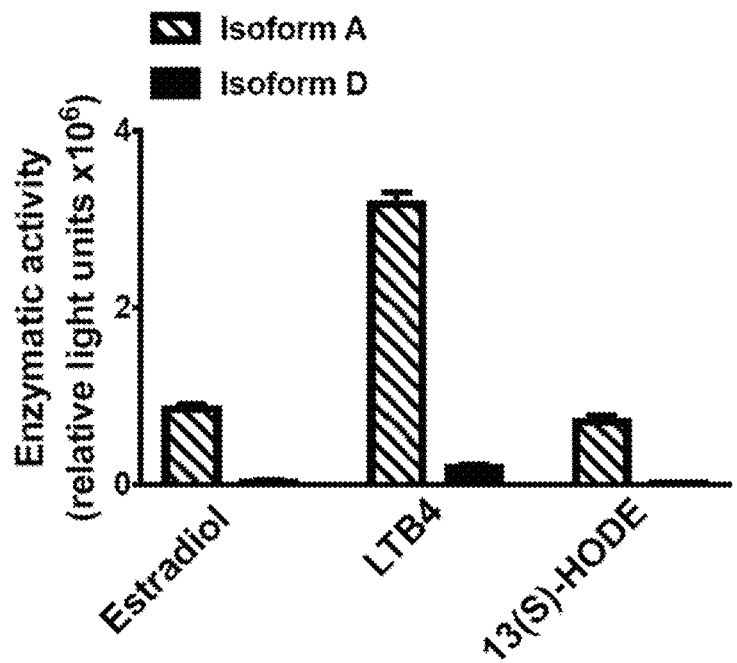
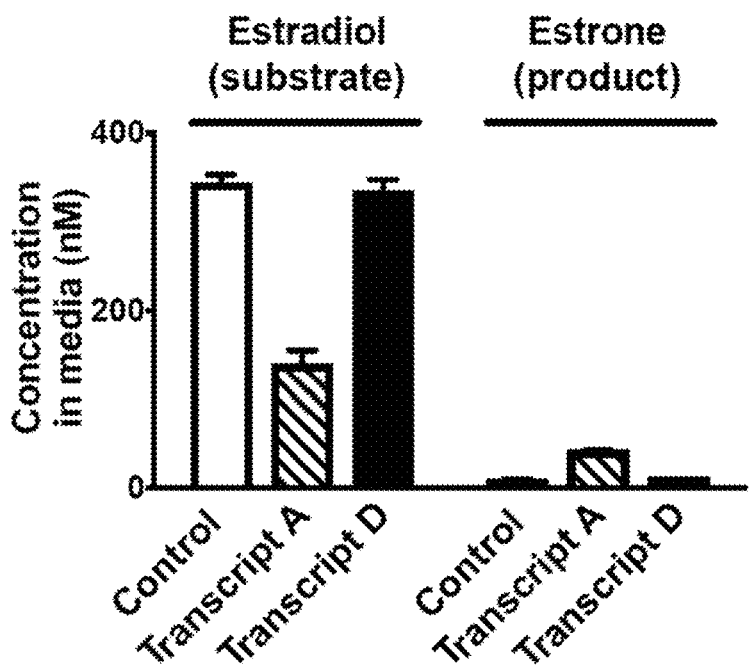
Figure 18 (cont.)

SEQUENCE LISTING

<160> NUMBER OF SEQ ID NOS: 66

<210> SEQ ID NO 1
<211> LENGTH: 19118
<212> TYPE: DNA
<213> ORGANISM: Homo sapien

```
<400> SEQUENCE: 1
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataaggtaat gtatacatct tccaactttt   300
taaagtcaca gagtaagata tgtattttaa gaattatttg acttaccatc tacttatctt   360 tgtattttg tttttcaaag tttgataaat tccctggtcc cttagtctgt atatgtgtca   420
ggttagttag atgaagggaa tgtaattaag aactaagcag cgatttttat gacatggtgt   480
gcaggttgat agaaagactc aggagccagt ctccttccaa gctgctaaat gaggcaagtc   540
acatattatc tctcagcctg ttttcttggc tctgaagtgg ggataataac ttaggggatg   600
ggcaagaacg ggatctgaaa attacagcta caaacaaaag tcaaacgaag aacttgcaac   660
agaaaccttt agtgcctccc ctcatgcaca agcaacacag ttctaaaata tttactgtct   720 gacccttta c agaaaatgtt tgccagtccg tagtcaaaag gattaaataa gtaatatttt   780
cagcacttag catatgataa acgatacgtg gcacatgata aacaataact gtgttaaata   840
aaatatgtgc gcagtgagtc aggcttttcc ttggacatta gtattttcc tgtgttctta   900 cttgtaaaca ctacattaac aaccccaaat aaaactgaag gaactgaaat cttgtatcat   960
tttctctaaa cttgtaaatt ctggtaaggc catgaaaata tatgcagaga agtgtttaca  1020
ggattttagg attggaaaaa ttgtgaagta ctccttgaga atcacatttt ctgcaaatta  1080
cagtggtttt aattaccatt atattattac tttctcatgt tctttgctgt catgtttagt  1140
tgaaacctaa aatgtctctt acacttagag aactaattct tttctgtttt ttttctgaat  1200
agtgaagaat actatacaaa aaagctacta cattttatt taacagatat gagcatttat  1260
ataatagagg agttgatgta tataaaaatg atttgccatc ttttggtct ttgaagaaat  1320 tcgaatgaac tttctggaag atagcaagaa tttacaaata gagaaaattg ttgcctgctg  1380
ttctcaggca tttgtccaaa aatataaata agtataaatc tatgaaaagg gcttgatgaa  1440
atctaacctt caaatctctt tccagatgtg tattttggg gaagggcta tatttattaa  1500 gtttttta aattttaaaa tttccagaga caagagaaaa gtaaattaga aggaagtcgt  1560
attaaaaatg acttaagggc gggtgcagtg gctcacacct gtaatcccag cactttggga  1620
gacggaggtg ggcagattgc tggagcccag gagttcaaga ccagcctggg cagcacagca  1680
aaacccccaa ctctacaaaa aatacaaaaa ttagctgggt gcggggtgc acaccctgtag  1740 tcccagctac tcgggaggct gaggtgggag gatcgtttca gttcaggaag ccaaggctgc  1800
aatgagctat gatggcatca ttgcactcca agctgggcaa tagagccagg ctctgtctca  1860
aaaaaaataa aaaagacttt aagaaaaata ggtaacccaa cctcaaaaat tctctttgaa  1920
tcattaaatt tcatggttaa acatttaagc tactgaatga ttcactctaa ggctgtaatg  1980
taactcagat ctcctttagg cgaggaagat gctggctgag ttttcatcat aactggctcc  2040
ttttgccctg tgagatgaga gacacagtag cagtttggct cttatgcaat ctaaactgtt  2100
gcgttgggaa tacggttcaa aaaacacatt ggagtttaag ctaaagcaag tgttttgcta  2160
acaaaaagac aaggcatcac attttgcaat tgtctagctc agttataaaa cagaagaata  2220
ggccggacgc ggtggctcac gcctgtaatc ccagcacttt gggaggccga gacgggcgga  2280
tcacgaggtc aggagatcga gaccatcctg gataacacag tgaaaccccg tctctactaa  2340
```

```
aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaaa    2520
aaaactgaag aataattaat tcttcaatca aacatctga tgaatgctct ggtaacttat     2580
gctctctact gacctagaaa caaatgagag agtatggtgt ggtttgtgca atctggcagt    2640
gagcaagcta ccaactaaat cagtgaaaga ctctcctatt cttttttac tcttctgcaa     2700 tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaaatat gatgggcaga ggcatacagt ttaccattac cactagttta    3360
gaattactac ttagcacttt actgcctatt acatagttgg tgctcaacaa atgtatgata    3420
aattaatggt tgagttttc tttcttctcc atattcatct tccatgacac cacgaagagc     3480
aatgtttttc aagaatgttc ttcaaggttt gaaagtagcc tgcttagag aaactgccta     3540 ctgtacagcc tccaaccaag aggaaaagct gaaaaaagca tgaagggatt ttgttttgtt    3600
ttgtttgttt tggttttaat atgagcattc cctggcagaa aagccagggg taatctcatt    3660
gcaactaggc aatcactctc aagaaatttt ctaacaaata aggaggccaa ttttatttt     3720 attttgagac gaagtcccac tctgtcaccc aggttggagt gcaatggaat gatttcagct    3780
cactgcaacc tccgcctccc gggttcaagt gattctcctg tctaaacttc ccagtagct     3840 gggattacag gctcccacca ccacgcccag ctaatttttt gtattttag tagagatggg     3900 gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat ttttttttt tttttttttg agacagagtc tcactctgtt gcccaggctg     4140
gagtccagtg gcactatctc cactcactgc aacttcctcc tcccaggttc aagcaattat    4200
cctgcctcag cctcccaagt agctgggatt acaggcccac accatcaggc ctggctaatt    4260
tttgtatttt tagtagagac ggggtttcac catgttggcc aggctggtct tgaactcctg    4320
acctcgtgat ccgccctcct cggccaacca aagtgctggg attacaggcg tgagccaccg    4380
cgcctagccg aatgttaatt gtctaaaaat ttttcttctc caatgtcttc tcctccactt    4440
ttttcggaat ttgtttcttc ctaattacag cgcggtgtgg aggaaactgc agctgagtgc    4500
cgaaaactag gcgtcactgc gcatgcgtat gtggtagact gcagcaacag agaagagatc    4560
tatcgctctc taaatcaggt gagactgcag gttcacaaat tcttcagat tattttgttt     4620 cctaggacgc tgacgtggaa aatgagaaag gtctttatga ctgcctgatt taaattggat    4680
```

```
tttagctgct aactgaagta gttatgtcac caaggaagga tatatacttt ttttcttgta    4740
tgtaatccac tcagctctgc ccattattat tgttcatatt attaatcaat ttcattctga    4800
tcagaagtgt gagcagtggc acagagtgac tgacaaaaga tttatcatca gggaatatgg    4860
atcacttcct agttttgttt tagtcctatt aactttgcag taattccagc ttctctttaa    4920
ttatttccct tgtgagattt tattttggtg ttaatgtagt cttctgtaga aaatgtaata    4980
ttaataatta ttatcacaat tattttaaaa gagtaaatac caaataatca caatgaacta    5040
agcactctaa caaactttac attttttaat tcaatcccta caataactct gtaaacttca    5100
ttttacagat aagcaaatta tgactcgagg aggttaagcc agacccaggt catgtagtta    5160
ttaggttatg aaaccaggat ttctcaacca gcactttaga ccaggtgcgg tggttcacac    5220
atgtaatccc agcactttgt gaggccaagg tggaaggatc acatgagacc aagagttcaa    5280
gaccagccca ggcaacatag tgagacccta tctctaaaaa aaaaaaaaaa aaaaaaaaa    5340 aaagtttaaa gaaaaacaca ttttaaaaa atgaacactt taaaaatatt tggtcagaat    5400
ttatatagga atttatcaac ataaatgtta atttcacttt actgataaac ttgcaaaaca    5460
tgatgtgctg ggtactgaaa tttagatgtt aaaagaacag tttatcccac ctttatgaca    5520
gtgttccctt ggcctccacg atttgagctc aacagtctgt cttgcctgaa ctctgagaga    5580
cctcatacaa tagaagaaag actctcatct ttggattata ttggtcccaa aactttgagt    5640
ttgaataata cacccagtga agtgttctt tcaatttcaa aaggtgaaga aagaagtggg    5700
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgacacaaa    6060
gcttggcatg taccaggagc tcaacaaatg tttgtggagg tttgttaagg gttgtcagtg    6120
tacatctttt caatgctgtc acttgtgact tcattttttt ccctccacac catgattttg    6180
taatgtgtcc tcattttgtg gaattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tcccccttac ctttaccagc tcttcacata tgtgaattgg ctcccatgcc    6540
caccaaacta cacggagacc tcatacatta gctacctata gctgcataac aaattataca    6600
aaacttagtg gtttaaagca acaatgtatg ttcactatcc tctcacagtt tctatgggtt    6660
gggaatttgg aggtagcttg ggttgggagt tctagttcta tgaatttgca taggatttat    6720
taaattctta taaaatttta ttgatgtttc tcacaaaaga ggttttgga aaaaagaaa    6780 gacttgtttt ctgtaacatc aacatataat atacaatatt acaaataggg agatagtgaa    6840
ttcaatcatg attcattagt gtggtgtaga actctcagct tacactactc aactgtctta    6900
atacagttac acaagatttc actcttttaa ttagaatgat aaagcccaa accaaaaaat    6960 tatatgacac caaattatca taaggaataa ttttagttct gaaaactctg aattttccc    7020 ttaatattgt ttagatgaca tatccaaaaa aggatctatt tgattccttc tgaagggaag    7080
```

-continued

```
gaggggagt actgagatta gtgttggcat ggggcttacc ataccaataa atttgtatct    7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg ccacatcgt cacagtggct tcagtgtgcg    7380
gccacgaagg gattccttac ctcatcccat attggtaagt atcacatgcc agccatgtta    7440
tatattttta tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag atatttcct gtcatagctg    7800
gagtgtttcc atttgattta gttctaggaa gtcagcatga atcggcctta tgttccctgc    7860
ctccagaccc tgttctcctg cctcaagatt acaatgctga gagcagagtg atttggattt    7920
acagaattta aatttatagt agtttagaat gattttttaa atgactttt ctaaaacaat    7980
gaaaccaggt tgtaattata tttaagatat ttttagattt ctgcaaactc ctctgtagaa    8040
caatgagaga aaacagtaat gccaagcatg tttccattgt ttcctggaat aagaaacaga    8100
aaccccacag actgagaagc aaaacctaca gaagctaaaa tgaacacatg tctatgtcat    8160
ggccttggtg cccaagataa gacaatcaga gtggtccctg atcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataagggga aggaggtgag aggcgttaag gatgtactgc tgtatttgcc aaatatcctt    8400
tcctgtaaac tcttctccag atcctcataa taaaattaag aggccaaagt ggcaaccatt    8460
gtcaagagaa aaactatcaa ccattgtcaa gagataact cagttattga gagagagagg    8520
agaaatgagc agagtcctac agaagtctgt caacacagat accagttttg tagaatttct    8580
aaatgtattt ttcctgattc atattttca aaataaaagc agcaataaaa actgattaga    8640
aaacagttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaaatgaa ttgccattta tactctcaga    8820
aaaatcacaa gtggctgatt tttggcttcc acttgttctt aagccaaatg ataccgcctt    8880
ctcacagaaa gctgaggatt ggtttcactc tcccttagct aacaatgctt aataattctc    8940
ttacagttcc agcaaatttg ccgctgttgg ctttcacaga ggtctgacat cagaacttca    9000
ggccttggga aaaactggta tcaaaaccctc atgtctctgc ccagttttg tgaatactgg    9060
gttcaccaaa atccaagca caaggtaagg tcaaaatcaa gttagaatgg gtatgtggta    9120
tgataaattg atatgaaaac taatgagaaa tgtttaggca ggccaactaa tagaagaaaa    9180
tgaagaagga aaaataattt ttcttattat tattattatc ttgaaattaa aggaataaag    9240
ggggaaaaca cattagggac tagcaggaat gatcagccac cgatgaactg ggatatttat    9300
ttgtgtccgg gagaaagcac atacatttga tcaccgttac caccctgtct ttaaaatgca    9360
aatgttccaa ggaccagcaa ataaattgag tatctagctc cttagtcaag gtgaatttct    9420
```

```
gcaagaactc ttgtctctgg tgagacagga tttgagacca caagagaaga aaaattagtc    9480
ctgaaaggag aagaaaaaag caggaaggtg tggataagaa cccgaaaatt aagccatctg    9540
cttaacaaat tttctaatc ctagtatata ttctgctgca ggttaacaaa atatactaag    9600
cttaatgatt cgaaaccaat tttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttgttt ttattttgt     9840 ttttttgag acagagtctc actctgtcac ccaggctgga gtacagtggc gcgatctcag    9900
ctcaccgcaa cctccgcctt tctgggttca agcaattctc cttcctcagc ctcctgagta    9960
tttggattac aggcgcccac caccacgcct ggctaatttt tgtatttta gtagagacgg    10020 ggtttcacca tgttggccag gctggtctca aactcctgac ctcaggtgtc ctacctgcct    10080
tggcctccta aaatgctggg attacaggag tgagccacca tgcccggcca aaaaataag    10140 ttttaaaga attaaaggtc atcctggcta acacagtgaa accccgtctc tactaaaaaa    10200
cacaaaaaaa ttagccgggc gtggtggcgg gcgcctgtag tcccagctgc gcgggaggct    10260
gaggcaggag aatggcgtga acccgggagg cggagcttgc agtgagccga gatcgcgcca    10320
ctgcactcca gcctgggcga cagagcgaga ctccgtctca aaaaaaaaa aaaaaaaaa    10380 aaaaaaaga attaaaggtg ttaattttat ttagaagcct tactgaagac tacagtcgga    10440
ggcctatagc ctgagagcag cccttagag aggttcagtt gaactgttct gatagtgggg    10500
gccatgtgct ctatcctgta ttgtcttcaa agcatctttc cagagagctg cacattgtca    10560
cagagtcagg gactttgtga aattatgctg acaaccagaa gtgagtaaac gtggcttctt    10620
acatttgcta cgttgtctca cagtacttaa taagtatgca atatgtaagt aaatactata    10680
gtactattgc aactcctgat tgttttctta gacaaggaat tgggcccaat aaaaaccctc    10740
ttggtaggca ttcaggcttc gtgtaccatg agctttccta agggtatcct gccactcttg    10800
gggaaggcat gatagatgag gggagtaagg ataatggaac tctgggtaca gggttcctgg    10860
gggctaactt agaggtagac acaggcaatg ctaaatattt gggattgatt ttatagaggt    10920
tgctagattg tgaatttcct tagtaagggc taaggcattg atatgtaatg tcacacttgg    10980
ctccgaggct gggttgttgg atccatgtag atgaaatcag ggagagaag gcagaacgg     11040 agtaatttag aaatgtattg atttgtatta ctctctgttg gcttgctatt caaggcagtg    11100
gagaactcaa tcacataata atctgcagca aaccacagat catcccaggg aatgaagttt    11160
taacattcgc tggctcccta actcctcacc cagcctttac attcactggc tgttcagtcc    11220
atgcctggac atcttaattt gaatacaaca ttttaaatcc attttctgt catcatcttg     11280 cactaacaga caattctaca ctaagcctat gtttatgaat atttctcaag agtacatgta    11340
cacagccttc agtataagga aaactggaag tatgacatac ctccagttgt catactcctt    11400
gggcccctct taaattctca ttaaactgca ggataggcaa gtcagaggtg aatctcaaat    11460
acgaaattct taccggaaag gggttccaat ccagacccca agagagggtt cttagatttc    11520
tcgcaagaaa taattcgggg caaggccaca gtgcaaagca aaagcaagtt tattaggaaa    11580
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc ccctttttag gccatatagg    11760
gtaacttcct gccattgcca tggtatttgt aaactgtcat agtgctggtg aagtgtctc     11820
```

```
ttagcttgct aatgtattat agttagctta taatgagcag tgaggacaac cagaggtcac  11880
tttcatcacc atcttggttt tggtgggttt tggccggctt ctttactgca ccctatttta  11940
tcaacaaggt ctttatgacc tgaatcttgt gccaacctcc tatctcatcc tgtgacaaag  12000
aatgccttaa cttcctggga atgcagccca gtaggtgtca gccttatttt acccagaccc  12060
tattcaagat ggagttgctc tgatttaaac gcctctgaca aaatgacgac ctcaaaacaa  12120
tccagcttta tggaatacct ccacaagaaa gaaagtatac ttagctatag aattttctcc  12180
ttgcatccaa caggctttga gatgtcagat gtttccttcc tgtcccatga ttaatcctag  12240
ccattcctct ttcttgtctg gctccactac tccttaccat ctaatgcctc gccaccattt  12300
tgatattttg actaagtgag ctatgaaaca cacctactgg atatgaaagt ataagtttct  12360
gataacaaaa catcaacatg ggatgtggag gaagtgggta gggtggcatt aatgcagcaa  12420
atcctggaat attttaaatc ttcattctaa atttagtaaa aatataggat aattttcctg  12480
ccatcattta cttataaaat taaaatttta gaaaataaaa ataatatttt cctctttta  12540
atcacagatt atggcctgta ttggagacag atgaagtcgt aagaagtctg atagatggaa  12600
tacttaccaa taagaaaatg attttttgttc catcgtatat caatatcttt ctgagactac  12660
agaagtaagt acagcacaga acacccaaat actaaaacac caatagagct ttttttttg   12720
cttttttttt tttagacag agtctcactc tgtcaccctg gctggattgc ggtggttgca   12780
gtggcatgat cttggctcac tgcaacctcc gcctcctggg ttcaagcaat tctcatgcct  12840
cagaccccca gtaactggg attataggtg tgtgctgcca cactcaccc agctaatttt    12900
tgtatttttt gatagagaca ggtttcccca tgttggccag gctggactcg aactcctgac  12960
ctcaagttat cctcctgtct cggcctccca aagtgctggg attacagtca tgagccacca  13020
tgcctggccc aatagagcta ttattatgga gcatctttca gttgtgaaaa ttggcatgga  13080
aactctccat ccctggggag aacagttatt tcctctgtta ttttcctacc cagtctataa  13140
aaagagagtg attcattttc tctaccaaat ctactgtctc tgcccaaact tgctgaaga   13200
ctattctaac taaaggaaac acagtttaaa aagaatgcaa tatagtgaag tagttaataa  13260
taaagactcc attttaaaa gtctgctgga agtttggttg ggattgcact gaatctatag   13320
agcaattggg gagtattgac atatcaacaa tattgagttt tctaatccaa gaacataata  13380
tctattttta aaatcttctt caaaatcttt aaatctttaa attgtatttt gtagttttg   13440
gtgtttaagt cttgcacata ttttgtcaga tttattccaa agtatttcac gggttctttt  13500
tttttttttt tttttttttt ttgagacaga gtttcaccct tgttgcccag gctggagtgc  13560
agtggcgtga tcttggctca ctgcagcttc tgcctcctgg cttcaagtga ttctcctgcc  13620
tcagcctccc aagtagctgg gattacaggc acctgccccc tcgcccaact aacttttgt   13680
gtttgtagta gagacagggt ttcaccatgt tggccaggct ggtctcgaac tcctgacctc  13740
atgtgatcca cctgcctcag cctcccaaag tgctgggatt acaggcatga gccatcatgc  13800
ccagccctat ttgacggttt ttgacgctaa tgcaagtggc attttaaaaa attttatatt  13860
tcccattgtt tgttgtcagt atatattgga ttttgtaat ttgatctcat attttgcagt   13920
cttgctaaat tgctaaacct cttttgcta aactcgataa gcttttttt ttttggtaga    13980
ttcctgggcc tctaattttc tttatgggaa agtttttaat tacaaattta atttctttaa  14040
tagctacatg gctattcaat ttacttatta attcttggta atgtgtgtct ttcaaggaat  14100
ttgtccattt catctaagtt gtagaatttc tttggcataa atttgtacat aacattccct  14160
```

-continued

```
tattatcctt ttaatgtctt tagaatgtct tatttattta tttatttatt tttattatat    14220 tttttttgaga cagagtctcg ctctgttgcc caggctggag tgcagtggca caatcttggc   14280
tcactgcaag ctccgccttc tgggttcatg ccattctcct gcctcagcct ccctagttgc   14340
tgggactaca ggcgcctgca accatgccca gcttattttt tttttttttt tttttttttt   14400
tttttttttt tttttttttt tagtagagac ggggtttcac cctgttagcc aggatggtct   14460
cgatctcctg acctggtgat ccgcccgcct cagcctccca aagtgctggg attacaggcg   14520
tgagccacca agcccagcct atttatttat ttagtagaga cagtctcact ttgctgccca   14580
ggcaacaaag gttttgaatg cctggcctca agcagtcctc ctgccttggc ctcccaaagt   14640
gctgggatta caggcatgag ccactgcacc tggccaaatg aatatgctga taatatcttc   14700
tttataagga tgacataaga ataaaataat gtaatacaaa caaagcccct gtcactgaaa   14760
atgtatagac ttcaaatgtt aaagtcttag agaacagaat ttatatgaaa tagcaacagc   14820
aacaatttcc cagaggaaat actctctcag ctttcttctg aggagcagtt tctaaattga   14880
aattgtatca gtgagaagat aactatacta acttcataag ccttgggcct ttttgaaaca   14940
aatccatata aactatgaac aaacttgaaa tagaacaatt tgagaacagg gtacaaactg   15000
cattggtgta tcaatttcag tatttggttt tagcttaaat agactgactt gagataacat   15060
aaggagaacc ttgaccccca agcaacatca tctcgcgagt tgactaggcc gggtgtggtg   15120
tctcacgcct gtaattccag cactttggga ggccacagca ggcagatcac ttgaggtcag   15180
gcattcgaga ccagcctggc caacatggtg aaaccctcagc tctactaaag atacgaaaat   15240
tagcaggcat agtggcctgc acctgtaata ccaggcactc gcaggagaat cccttgaacc   15300
cggaaggcgg agattgcagt aaaccatgat tgtgccactg cactccagcc tgggcaacag   15360
gagactctgt ctcggaaaaa taaattttt aaaaaaatga aaaaaaataa aagttgacta    15420
aattagtgtc ttggtactaa gcactgtagg aagtgagttt catggaaccc caactctctt   15480
ggggcccaaa gcaagtcata ttaatattga aaattacatg catatacatg catatgacca   15540
aggtgataaa acaattatt ctgcctgagt tggagaatag tatcccagta aaataaacaa    15600
gagtctcaaa gtcttttgta tcctttgaag ctgtcatggt ggtttgtaac taggcaacag   15660
gtatatattg ttaatcttct ttgcatttaa ttcctttat agagagacac aattttacga    15720
gcagatgcaa ttactagcat gaaggtttct ttgtgagggt agttaaaagg cccacatgag   15780
ctctcttctt atccttgtcc ttctttcagc cagatcttcc ctgccccttt gctcattcca   15840
tctttcaccc acctaccccc aaaacaagga agtaaatctt gcattagtca acaataccaa   15900
agtgattttc aatatgactt tctctgcaga atgttattat ttctgcctct ttacattcac   15960
atactgtctt ccttttttt tttttttt tttttttttt tagattgggt ctcactctgt     16020
tgcccaggct ggagtgcagt ggcttgatct cagctcactg taacctccac ctcctgagtt   16080
caagcaattc tcctgcctca gcctcctgag tagctgggat tacaggcatg tgccaccaca   16140
cctggctagt tttttgtat ttttagtaga cagggtttt caccatgttg gtcaagctgg     16200
tctcgaactc ctgacctcat gatctgacca cctgtgcctc tcaaagtgct gggattacag   16260
gcgtgagcca ccgggccagc cactctcttc ctttcagttg cctactcatc tcttatgcat   16320
tcctggacat cagttgtcct tttgaagctt tcctccacta tcccagccca tgtgaatcct   16380
ccttccagtt atagcccta attctagatg gctgatattt ttcaataatt gtttaagat     16440 gaccatttta gcctatcagc taaacaatat caaagacaat agctattttt caagtacttt   16500
agtttacctt attatagagt gcataataga tattcagtaa atagtaaagg agaggtgaag   16560
```

```
gcttgcatag aatggattct ggtggtgtct cttggtgagc ttttagcatc aagattaatc   16620
agcagtttca gcaatgagct cagaccttca gttttagatc tttactcata tcagataaga   16680
gagtgagaag agtggtatgt atcagtgctt tatttatatt tgcatccaat ttgaactatg   16740
aatattacaa aggtgcacac ataggttcag acagattgat ttaaaatgac caaagatgac   16800
ctgtcgtaag caacctgggt atcttaagat gcactccttg gagagggaat gttcctaaaa   16860
acattttcag agggacgaac tgtatgaaat tcagtaaaac ataaatcatg ggaaaactg    16920 attactctct ttttgacatg aaatgagagt tttaatgcat ggttacgatt attaacgtac   16980
tccgctgcaa gacgttaata aagttactgt tttgcaggct agaatgtctt gatgctgtaa   17040
tcagaacaca cttttttcccc tttcttccag cttcaaatgc agattcataa ttgggctgac  17100
ttctaataac tgcaatgttt tctgccttgg gcttgcagca gaagcctgac aaaatagtgt   17160
ttgtttaggc aataatttat ttatttattt attgagatgg agtttcattc ttgtcgccca   17220
ggctggagtg caatggcgtg atctcggctc actgcaacct ctgtgttcag gcaataattt   17280
agactttacc ttacttgtga ttactatagc aattactata gccacaaggc ataattttac   17340
tgtctcattt caattttatg aatttgaatg ttttacact tttcctaatg aagtccacta    17400
tgaagttatg tcaaaaaaaa aaaagaaaaa gaaagatgca cacgtaaaag agaggtggtt   17460
gcaagagaag aaaagaacgg aggaaagtta acgcaaacc agataactct cagcgtattc    17520
taaatgacca aaaacagaac tctgttgtca agatttttaa atggaaaatt tttcaatttt   17580
tttttctttt ttgtacaggt ttcttcctga acgcgcctca gcgattttaa atcgtatgca   17640
gaatattcaa tttgaagcag tggttggcca caaaatcaaa atgaaatgaa taaataagct   17700
ccagccagag atgtatgcat gataatgata tgaatagttt cgaatcaatg ctgcaaagct   17760
ttatttcaca tttttttcagt cctgataata ttaaaaacat tggtttggca ctagcagcag   17820
tcaaacgaac aagattaatt acctgtcttc ctgtttctca agaatattta cgtagttttt   17880
cataggtctg ttttttccttt catgcctctt aaaaacttct gtgcttacat aaacatactt   17940
aaaaggtttt ctttaagata tttttatttt ccatttaaag gtggacaaaa gctacctccc   18000
taaaagtaaa tacaaagaga acttatttac acagggaagg tttaagactg ttcaagtagc   18060
attccaatct gtagccatgc cacagaatat caacaagaac acagaatgag tgcacagcta   18120
agagatcaag tttcagcagg cagctttatc tcaacctgga catattttaa gattcagcat   18180
ttgaaagatt tccctagcct cttccttttt cattagccca aaacggtgca actctattct   18240
ggactttatt acttgattct gtcttctgta taactctgaa gtccaccaaa agtggaccct   18300
ctatatttcc tccctttttta tagtcttata agatacatta tgaaaggtga ccgactctat   18360
tttaaatctc agaattttaa gttctagccc catgataacc tttttctttg taatttatgc   18420
tttcatatat ccttggtccc agagatgttt agacaatttt aggctcaaaa attaaagcta   18480
acacaggaaa aggaactgta ctggctatta cataagaaac aatggaccca agagaagaaa   18540
aggaagaaag aaaggttttt tggttttttgt tttgtttgt tttgtttttt gttttttga    18600 gatggagtct cactctttcg cccaggctgg agtgcagtgg tatgatctca gctcactgca   18660
agctccacct cccgggttca cgccattctc ctgcctcagc ctcctgagta gctgggacta   18720
caggcgcccg ccaccacacc cggctaattt tttgtatttt tgtagagac ggggtttcac    18780 catgttagcc aagatggtct cgatctcctg acctcgtgat ccacctgcct cggcctccca   18840
aagtgctggg attacgggtg tgagccaccg tgcccagcct tttttttttt aatagaaaaa   18900
```

```
ataatccgac tcccactaca tcaagactaa tcttgttttg tgtgtttttc acatgtatta    18960
tagaatgctt ttgcatggac tatcctcttg tttttattaa aaacaaatga ttttttaaa     19020 agtcacaaaa acaattcact aaaaataaat atgtcattgt gctttaaaaa aataacctct    19080
tgtagttata aaataaaacg tttgacttct aaactctg                            19118
```

<210> SEQ ID NO 2
<211> LENGTH: 19119
<212> TYPE: DNA
<213> ORGANISM: Homo sapien

<400> SEQUENCE: 2

```
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataaggtaat gtatacatct tccaactttt     300
taaagtcaca gagtaagata tgtattttaa gaattatttg acttaccatc tacttatctt     360 tgtattttg tttttcaaag tttgataaat tccctggtcc cttagtctgt atatgtgtca     420
ggttagttag atgaagggaa tgtaattaag aactaagcag cgattttat gacatggtgt     480 gcaggttgat agaaagactc aggagccagt ctccttccaa gctgctaaat gaggcaagtc     540
acatattatc tctcagcctg ttttcttggc tctgaagtgg ggataataac ttaggggatg     600
ggcaagaacg ggatctgaaa attacagcta caaacaaaag tcaaacgaag aacttgcaac     660
agaaaccttt agtgcctccc ctcatgcaca agcaacacag ttctaaaata tttactgtct     720
gaccctttac agaaaatgtt tgccagtccg tagtcaaaag gattaaataa gtaatatttt     780
cagcacttag catatgataa acgatacgtg gcacatgata aacaataact gtgttaaata     840
aaatatgtgc gcagtgagtc aggctttcc ttggacatta gtattttcc tgtgttctta     900 cttgtaaaca ctacattaac aaccccaaat aaaactgaag gaactgaaat cttgtatcat     960
tttctctaaa cttgtaaatt ctggtaaggc catgaaaata tatgcagaga agtgtttaca    1020
ggattttagg attggaaaaa ttgtgaagta ctccttgaga atcacatttt ctgcaaatta    1080
cagtggtttt aattaccatt atattattac tttctcatgt tctttgctgt catgtttagt    1140
tgaaacctaa aatgtctctt acacttagag aactaattct tttctgttt ttttctgaat    1200 agtgaagaat actatacaaa aaagctacta cattttatt taacagatat gagcatttat    1260
ataatagagg agttgatgta tataaaaatg atttgccatc tttttggtct ttgaagaaat    1320
tcgaatgaac tttctggaag atagcaagaa tttacaaata gagaaaattg ttgcctgctg    1380
ttctcaggca tttgtccaaa aatataaata agtataaatc tatgaaaagg gcttgatgaa    1440
atctaaccct caaatctctt tccagatgtg tattttggg gaaagggcta tatttattaa    1500
gtttttttta aattttaaaa tttccagaga caagagaaaa gtaaattaga aggaagtcgt    1560
attaaaaatg acttaagggc gggtgcagtg gctcacacct gtaatcccag cactttggga    1620
gacggaggtg ggcagattgc tggagcccag gagttcaaga ccagcctggg cagcacagca    1680 aaaccccaa ctctacaaaa aatacaaaaa ttagctgggt gcggggtgc acccgtag       1740 tcccagctac tcgggaggct gaggtgggag gatcgtttca gttcaggaag ccaaggctgc    1800
aatgagctat gatggcatca ttgcactcca agctgggcaa tagagccagg ctctgtctca    1860
aaaaaaataa aaaagactt aagaaaaata ggtaacccaa cctcaaaaat tctctttgaa    1920
```

```
tcattaaatt tcatggttaa acatttaagc tactgaatga ttcactctaa ggctgtaatg    1980
taactcagat ctcctttagg cgaggaagat gctggctgag ttttcatcat aactggctcc    2040
ttttgccctg tgagatgaga gacacagtag cagtttggct cttatgcaat ctaaactgtt    2100
gcgttgggaa tacggttcaa aaaacacatt ggagtttaag ctaaagcaag tgttttgcta    2160
acaaaaagac aaggcatcac attttgcaat tgtctagctc agttataaaa cagaagaata    2220
ggccggacgc ggtggctcac gcctgtaatc ccagcacttt gggaggccga gacgggcgga    2280
tcacgaggtc aggagatcga accatcctg gataacacag tgaaacccg tctctactaa    2340 aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaa    2520 aaaactgaag aataattaat tcttcaatca aaacatctga tgaatgctct ggtaacttat    2580
gctctctact gacctagaaa caaatgagag agtatggtgt ggtttgtgca atctggcagt    2640
gagcaagcta ccaactaaat cagtgaaaga ctctcctatt cttttttac tcttctgcaa    2700 tcccacaaaa ggctatttga ggggatactg actttgagac tgggtcctaa catccatgtt    2760
tggggagttc aggctgctgc tccagggttt agcctacagt agcgaaatac aaaggaccca    2820 gagccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta aattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaaatat gatgggcaga ggcatacagt ttaccattac cactagttta    3360
gaattactac ttagcacttt actgcctatt acatagttgg tgctcaacaa atgtatgata    3420
aattaatggt tgagtttttc tttcttctcc atattcatct tccatgacac cacgaagagc    3480 aatgttttc aagaatgttc ttcaaggttt gaaagtagcc tgctttagag aaactgccta    3540
ctgtacagcc tccaaccaag aggaaaagct gaaaaaagca tgaagggatt tgtttttgtt    3600
ttgtttgttt tggtttttaat atgagcattc cctggcagaa aagccagggg taatctcatt    3660
gcaactaggc aatcactctc aagaaatttt ctaacaaata aggaggccaa ttttattt    3720 attttgagac gaagtcccac tctgtcaccc aggttggagt gcaatggaat gatttcagct    3780
cactgcaacc tccgcctccc gggttcaagt gattctcctg tctaaacttc ccgagtagct    3840
gggattacag gctcccacca ccacgcccag ctaatttttt gtattttag tagagatggg    3900 gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat ttttttttt ttttttttg agacagagtc tcactctgtt gcccaggctg    4140
gagtccagtg gcactatctc cactcactgc aacttcctcc tcccaggttc aagcaattat    4200
cctgcctcag cctcccaagt agctgggatt acaggcccac accatcaggc ctggctaatt    4260
```

```
tttgtattttt tagtagagac ggggtttcac catgttggcc aggctggtct tgaactcctg    4320
acctcgtgat ccgccctcct cggccaacca aagtgctggg attacaggcg tgagccaccg    4380
cgcctagccg aatgttaatt gtctaaaaat ttttcttctc caatgtcttc tcctccactt    4440
ttttcggaat ttgtttcttc ctaattacag cgcggtgtgg aggaaactgc agctgagtgc    4500
cgaaaactag gcgtcactgc gcatgcgtat gtggtagact gcagcaacag agaagagatc    4560
tatcgctctc taaatcaggt gagactgcag gttcacaaat ttcttcagat tattttgttt    4620
cctaggacgc tgacgtggaa aatgagaaag gtctttatga ctgcctgatt taaattggat    4680
tttagctgct aactgaagta gttatgtcac caaggaagga tatatacttt ttttcttgta    4740
tgtaatccac tcagctctgc ccattattat tgttcatatt attaatcaat ttcattctga    4800
tcagaagtgt gagcagtggc acagagtgac tgacaaaaga tttatcatca gggaatatgg    4860
atcacttcct agttttgttt tagtcctatt aactttgcag taattccagc ttctctttaa    4920
ttatttccct tgtgagattt tattttggtg ttaatgtagt cttctgtaga aaatgtaata    4980
ttaataatta ttatcacaat tatttaaaa gagtaaatac caaataatca caatgaacta    5040
agcactctaa caaactttac attttttaat tcaatcccta caataactct gtaaacttca    5100
ttttacagat aagcaaatta tgactcagag aggttaagcc agaccaggt catgtagtta    5160 ttaggttatg aaaccaggat ttctcaacca gcactttaga ccaggtgcgg tggttcacac    5220
atgtaatccc agcactttgt gaggccaagg tggaaggatc acatgagacc aagagttcaa    5280
gaccagccca ggcaacatag tgagacccta tctctaaaaa aaaaaaaaaa aaaaaaaaa    5340 aaagtttaaa gaaaaacaca ttttaaaaa atgaacactt taaaaatatt tggtcagaat    5400
ttatatagga atttatcaac ataaatgtta atttcacttt actgataaac ttgcaaaaca    5460
tgatgtgctg ggtactgaaa tttagatgtt aaaagaacag tttatcccac ctttatgaca    5520
gtgttccctt ggcctccacg atttgagctc aacagtctgt cttgcctgaa ctctgagaga    5580
cctcatacaa tagaagaaag actctcatct ttggattata ttggtcccaa aactttgagt    5640
ttgaataata cacccagtga aagtgttctt tcaatttcaa aaggtgaaga aagaagtggg    5700
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgacacaaa    6060
gcttggcatg taccaggagc tcaacaaatg tttgtggagg tttgttaagg gttgtcagtg    6120
tacatctttt caatgctgtc acttgtgact tcattttttt ccctccacac catgattttg    6180
taatgtgtcc tcattttgtg gaattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tccccttac ctttaccagc tcttcacata tgtgaattgg ctcccatgcc    6540
caccaaacta cacggagacc tcatacatta gctacctata gctgcataac aaattataca    6600
aaacttagtg gtttaaagca acaatgtatg ttcactatcc tctcacagtt tctatgggtt    6660
```

```
gggaatttgg aggtagcttg ggttgggagt tctagttcta tgaatttgca taggatttat    6720
taaattctta taaaatttta ttgatgtttc tcacaaaaga ggttttttgga aaaaaagaaa    6780
gacttgtttt ctgtaacatc aacatataat atacaatatt acaaatagggg agatagtgaa    6840
ttcaatcatg attcattagt gtggtgtaga actctcagct tacactactc aactgtctta    6900
atacagttac acaagatttc actcttttaa ttagaatgat aaagccccaa accaaaaaat    6960
tatatgacac caaattatca taaggaataa ttttagttct gaaaactctg aattttccc     7020
ttaatattgt ttagatgaca tatccaaaaa aggatctatt tgattccttc tgaagggaag    7080
gaggggggagt actgagatta tgttggcat ggggcttacc ataccaataa atttgtatct    7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg gccacatcgt cacagtggct tcagtgtgcg    7380
gccacgaagg gattccttac ctcatcccat attggtaagt atcacatgcc agccatgtta    7440
tatattttta tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag gatatttcct gtcatagctg    7800
gagtgtttcc atttgattta gttctaggaa gtcagcatga atcggcctta tgttccctgc    7860
ctccagaccc tgttctcctg cctcaagatt acaatgctga gagcagagtg atttggattt    7920
acagaatta aatttatagt agtttagaat gatttttaaa atgactttt ctaaacaat     7980
gaaaccaggt tgtaattata tttaagatat tttagattt ctgcaaactc ctctgtagaa    8040
caatgagaga aaacagtaat gccaagcatg tttccattgt ttcctggaat aagaaacaga    8100
aaccccacag actgagaagc aaaacctaca gaagctaaaa tgaacacatg tctatgtcat    8160
ggccttggtg cccaagataa acaatcaga gtggtccctg gatcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataaaggga aggaggtgag aggcgttaag gatgtactgc tgtatttgcc aaatatcctt    8400
tcctgtaaac tcttctccag atcctcataa taaaattaag aggccaaagt ggcaaccatt    8460
gtcaagagaa aaactatcaa ccattgtcaa gagataact cagttattga gagagagagg    8520
agaaatgagc agagtcctac agaagtctgt caacacagat accagttttg tagaatttct    8580
aaatgtattt ttcctgattc atattttca aaataaaagc agcaataaaa actgattaga    8640
aaacagtttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaaatgaa ttgccattta tactctcaga    8820
aaaatcacaa gtggctgatt tttggcttcc acttgttctt aagccaaatg ataccgcctt    8880
ctcacagaaa gctgaggatt ggtttcactc tcccttagct aacaatgctt aataattctc    8940
ttacagttcc agcaaatttg ccgctgttgg ctttcacaga ggtctgacat cagaacttca    9000
```

```
ggccttggga aaaactggta tcaaaacctc atgtctctgc ccagttttg tgaatactgg      9060
gttcaccaaa aatccaagca caaggtaagg tcaaaatcaa gttagaatgg gtatgtggta      9120
tgataaattg atatgaaaac taatgagaaa tgtttaggca ggccaactaa tagaagaaaa      9180
tgaagaagga aaaataattt ttcttattat tattattatc ttgaaattaa aggaataaag      9240
ggggaaaaca cattagggac tagcaggaat gatcagccac cgatgaactg ggatatttat      9300
ttgtgtccgg gagaaagcac atacatttga tcaccgttac caccctgtct ttaaaatgca      9360
aatgttccaa ggaccagcaa ataaattgag tatctagctc cttagtcaag gtgaatttct      9420
gcaagaactc ttgtctctgg tgagacagga tttgagacca caagagaaga aaaattagtc      9480
ctgaaaggag aagaaaaaag caggaaggtg tggataagaa cccgaaaatt aagccatctg      9540
cttaacaaat ttttctaatc ctagtatata ttctgctgca ggttaacaaa atatactaag      9600
cttaatgatt cgaaaccaat ttttactgg aagggaatta atcctaaata tattcattca      9660
aaagaactaa acaattctct gttgagtgcc gcctcatttg aggatactga ctcttacagc      9720
ctgagttagc tatgtggtct ctgcagctgg aatcactccc tgccactgga gtccttcatg      9780
gtgttagacc ataggtactg ttgactaaag aaaaaaaaaa gttttgttt ttattttgt      9840
ttttttgag acagagtctc actctgtcac ccaggctgga gtacagtggc gcgatctcag      9900
ctcaccgcaa cctccgcctt tctgggttca agcaattctc cttcctcagc ctcctgagta      9960
tttggattac aggcgcccac caccacgcct ggctaatttt tgtattttta gtagagacgg     10020
ggtttcacca tgttggccag gctggtctca aactcctgac ctcaggtgtc ctacctgcct     10080
tggcctccta aaatgctggg attacaggag tgagccacca tgcccggcca aaaaaataag     10140
ttttttaaaga attaaaggtc atcctggcta acacagtgaa accccgtctc tactaaaaaa     10200
cacaaaaaaa ttagccgggc gtggtggcgg gcgcctgtag tcccagctgc gcggaggct     10260
gaggcaggag aatggcgtga acccgggagg cggagcttgc agtgagccga tcgcgcca     10320
ctgcactcca gcctgggcga cagagcgaga ctccgtctca aaaaaaaaaa aaaaaaaaa     10380
aaaaaaaga attaaaggtg ttaattttat ttagaagcct tactgaagac tacagtcgga     10440
ggcctatagc ctgagagcag ccctttagag aggttcagtt gaactgttct gatagtgggg     10500
gccatgtgct ctatcctgta ttgtcttcaa agcatctttc cagagagctg cacattgtca     10560
cagagtcagg gactttgtga aattatgctg acaaccagaa gtgagtaaac gtggcttctt     10620
acatttgcta cgttgtctca cagtacttaa taagtatgca atatgtaagt aaatactata     10680
gtactattgc aactcctgat tgttttctta gacaaggaat tgggcccaat aaaaacctc     10740
ttggtaggca ttcaggcttc gtgtaccatg agcttcccta agggtatcct gccactcttg     10800
gggaaggcat gatagatgag gggagtaagg ataatgaaac tctgggtaca gggttcctgg     10860
gggctaactt agaggtagac acaggcaatg ctaaatattt gggattgatt ttatagaggt     10920
tgctagattg tgaatttcct tagtaagggc taaggcattg atatgtaatg tcacacttgg     10980
ctccgaggct gggttgttgg atccatgtag atgaaatcag ggagagaaag ggcagaacgg     11040
agtaatttag aaatgtattg atttgtatta ctctctgttg gcttgctatt caaggcagtg     11100
gagaactcaa tcacataata atctgcagca aaccacagat catcccaggg aatgaagttt     11160
taacattcgc tggctcccta actcctcacc cagcctttac attcactggc tgttcagtcc     11220
atgcctggac atcttaattt gaatacaaca ttttaaatcc attttctgt catcatcttg     11280
cactaacaga caattctaca ctaagcctat gtttatgaat atttctcaag agtacatgta     11340
cacagccttc agtataagga aaactggaag tatgacatac ctccagttgt catactcctt     11400
```

```
gggcccctct taaattctca ttaaactgca ggataggcaa gtcagaggtg aatctcaaat    11460
acgaaattct taccggaaag gggttccaat ccagaccccca agagagggtt cttagatttc    11520
tcgcaagaaa taattcgggg caaggccaca gtgcaaagca aaagcaagtt tattaggaaa    11580
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc ccctttttag gccatatagg    11760
gtaacttcct gccattgcca tggtatttgt aaactgtcat agtgctggtg gaagtgtctc    11820
ttagcttgct aatgtattat agttagctta taatgagcag tgaggacaac cagaggtcac    11880
tttcatcacc atcttggttt tggtgggttt tggccggctt ctttactgca ccctattta    11940 tcaacaaggt cttatgacc tgaatcttgt gccaacctcc tatctcatcc tgtgacaaag    12000
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gttttccttcc tgtcccatga ttaatcctag    12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat attttaaatc ttcattctaa atttagtaaa aatataggat aattttcctg    12480
ccatcattta cttataaaat taaaatttta gaaaataaaa ataatatttt cctcttttta    12540
atcacagatt atggcctgta ttggagacag atgaagtcgt aagaagtctg atagatggaa    12600
tacttaccaa taagaaaatg attttttgttc catcgtatat caatatcttt ctgagactac    12660
agaagttaag tacagcacag aacacccaaa tactaaaaca ccaatagagc ttttttttt    12720 gcttttttt tttttagaca gagtctcact ctgtcaccct ggctggattg cggtggttgc    12780
agtggcatga tcttggctca ctgcaacctc cgcctcctgg gttcaagcaa ttctcatgcc    12840
tcagaccccc aagtaactgg gattataggt gtgtgctgcc acactacacc cagctaattt    12900
ttgtattttt tgatagagac aggtttcccc atgttggcca ggctggactc gaactcctga    12960
cctcaagtta tcctcctgtc tcggcctccc aaagtgctgg gattacagtc atgagccacc    13020
atgcctggcc caatagagct attattatgg agcatctttc agttgtgaaa attggcatgg    13080
aaactctcca tccctgggga gaacagttat ttcctctgtt attttcctac ccagtctata    13140
aaaagagagt gattcatttt ctctaccaaa tctactgtct ctgcccaaac tttgctgaag    13200
actattctaa ctaaaggaaa cacagtttaa aaagaatgca atatagtgaa gtagttaata    13260
ataaagactc cattttttaaa agtctgctgg aagtttggtt gggattgcac tgaatctata    13320
gagcaattgg ggagtattga catatcaaca atattgagtt ttctaatcca agaacataat    13380
atctattttt aaaatcttct tcaaaatctt taaatcttta aattgtattt tgtagttttt    13440
ggtgtttaag tcttgcacat attttgtcag atttattcca aagtatttca cgggttcttt    13500 ttttttttt tttttttttt tttgagacag agtttcaccc ttgttgccca ggctggagtg    13560
cagtggcgtg atcttggctc actgcagctt ctgcctcctg gcttcaagtg attctcctgc    13620
ctcagcctcc caagtagctg ggattacagg cacctgcccc ctcgcccaac taactttttg    13680
tgtttgtagt agagacaggg tttcaccatg ttggccaggc tggtctcgaa ctcctgacct    13740
```

```
catgtgatcc acctgcctca gcctcccaaa gtgctgggat tacaggcatg agccatcatg   13800
cccagcccta tttgacggtt tttgacgcta atgcaagtgg cattttaaaa aattttatat   13860
ttcccattgt ttgttgtcag tatatattgg attttttgtaa tttgatctca tattttgcag   13920
tcttgctaaa ttgctaaacc tcttttttgct aaactcgata agcttttttt ttttttggtag  13980
attcctgggc ctctaatttt ctttatggga aagtttttaa ttacaaattt aatttcttta   14040
atagctacat ggctattcaa tttacttatt aattcttggt aatgtgtgtc tttcaaggaa   14100
tttgtccatt tcatctaagt tgtagaattt ctttggcata aatttgtaca taacattccc   14160
ttattatcct tttaatgtct ttagaatgtc ttatttattt atttatttat ttttattata   14220
tttttttgag acagagtctc gctctgttgc ccaggctgga gtgcagtggc acaatcttgg   14280
ctcactgcaa gctccgcctt ctgggttcat gccattctcc tgcctcagcc tccctagttg   14340
ctgggactac aggcgcctgc aaccatgccc agcttatttt ttttttttttt tttttttttt  14400
tttttttttt tttttttttt ttagtagaga cggggtttca ccctgttagc caggatggtc   14460
tcgatctcct gacctggtga tccgcccgcc tcagcctccc aaagtgctgg gattacaggc   14520
gtgagccacc aagcccagcc tatttattta tttagtagag acagtctcac tttgctgccc   14580
aggcaacaaa ggttttgaat gcctggcctc aagcagtcct cctgccttgg cctcccaaag   14640
tgctgggatt acaggcatga gccactgcac ctggccaaat gaatatgctg ataatatctt   14700
ctttataagg atgacataag aataaaataa tgtaatacaa acaaagcccc tgtcactgaa   14760
aatgtataga cttcaaatgt taaagtctta gagaacagaa tttatatgaa atagcaacag   14820
caacaatttc ccagaggaaa tactctctca gctttcttct gaggagcagt ttctaaattg   14880
aaattgtatc agtgagaaga taactatact aacttcataa gccttgggcc tttttgaaac   14940
aaatccatat aaactatgaa caaacttgaa atagaacaat ttgagaacag ggtacaaact   15000
gcattggtgt atcaatttca gtatttggtt ttagcttaaa tagactgact tgagataaca   15060
taaggagaac cttgaccccc aagcaacatc atctcgcgag ttgactaggc cgggtgtggt   15120
gtctcacgcc tgtaattcca gcactttggg aggccacagc aggcagatca cttgaggtca   15180
ggcattcgag accagcctgg ccaacatggt gaaaccctcag ctctactaaa gatacgaaaa  15240
ttagcaggca tagtggcctg cacctgtaat accaggcact cgcaggagaa tcccttgaac   15300
ccggaaggcg gagattgcag taaaccatga ttgtgccact gcactccagc ctgggcaaca   15360
ggagactctg tctcggaaaa ataaattttt taaaaaaatg aaaaaaaata aagttgact   15420
aaattagtgt cttggtacta agcactgtag gaagtgagtt tcatggaacc ccaactctct   15480
tggggcccaa agcaagtcat attaatattg aaaattacat gcatatacat gcatatgacc   15540
aaggtgataa aaacaattat tctgcctgag ttggagaata gtatcccagt aaaataaaca   15600
agagtctcaa agtcttttgt atcctttgaa gctgtcatgg tggtttgtaa ctaggcaaca   15660
ggtatatatt gttaatcttc tttgcattta attccttta tagagagaca caattttacg    15720
agcagatgca attactagca tgaaggtttc tttgtgaggg tagttaaaag gcccacatga   15780
gctctcttct tatccttgtc cttctttcag ccagatcttc cctgcccctt tgctcattcc   15840
atctttcacc cacctacccc caaaacaagg aagtaaatct tgcattagtc aacaatacca   15900
aagtgatttt caatatgact ttctctgcag aatgttatta tttctgcctc tttacattca   15960
catactgtct tccttttttt ttttttttttt ttttttttt ttagattggg tctcactctg   16020
ttgcccaggc tggagtgcag tggcttgatc tcagctcact gtaacctcca cctcctgagt   16080
tcaagcaatt ctcctgcctc agcctcctga gtagctggga ttacaggcat gtgccaccac   16140
```

```
acctggctag ttttttttgta tttttagtag agacagggtt tcaccatgtt ggtcaagctg    16200
gtctcgaact cctgacctca tgatctgacc acctgtgcct ctcaaagtgc tgggattaca    16260
ggcgtgagcc accgggccag ccactctctt cctttcagtt gcctactcat ctcttatgca    16320
ttcctggaca tcagttgtcc ttttgaagct ttcctccact atcccagccc atgtgaatcc    16380
tccttccagt tatagccctt aattctagat ggctgatatt tttcaataat tgttttaaga    16440
tgaccatttt agcctatcag ctaaacaata tcaaagacaa tagctatttt tcaagtactt    16500
tagtttacct tattatagag tgcataatag atattcagta aatagtaaag gagaggtgaa    16560
ggcttgcata gaatggattc tggtggtgtc tcttggtgag cttttagcat caagattaat    16620
cagcagtttc agcaatgagc tcagaccttc agttttagat ctttactcat atcagataag    16680
agagtgagaa gagtggtatg tatcagtgct ttatttatat ttgcatccaa tttgaactat    16740
gaatattaca aaggtgcaca cataggttca gacagattga tttaaaatga ccaaagatga    16800
cctgtcgtaa gcaacctggg tatcttaaga tgcactcctt ggagagggaa tgttcctaaa    16860
aacattttca gagggacgaa ctgtatgaaa ttcagtaaaa cataaatcat gaggaaaact    16920
gattactctc tttttgacat gaaatgagag ttttaatgca tggttacgat tattaacgta    16980
ctccgctgca agacgttaat aaagttactg ttttgcaggc tagaatgtct tgatgctgta    17040
atcagaacac acttttttccc ctttcttcca gcttcaaatg cagattcata attgggctga    17100
cttctaataa ctgcaatgtt ttctgccttg ggcttgcagc agaagcctga caaaatagtg    17160
tttgtttagg caataatttta tttatttatt tattgagatg gagtttcatt cttgtcgccc    17220
aggctggagt gcaatggcgt gatctcggct cactgcaacc tctgtgttca ggcaataatt    17280
tagactttac cttacttgtg attactatag caattactat agccacaagg cataatttta    17340
ctgtctcatt tcaattttat gaatttgaat gttttttacac ttttcctaat gaagtccact    17400
atgaagttat gtcaaaaaaa aaaagaaaa agaaagatgc acacgtaaaa gagaggtggt    17460
tgcaagagaa gaaaagaacg gaggaaagtt aaacgcaaac cagataactc tcagcgtatt    17520
ctaaatgacc aaaaacagaa ctctgttgtc aaagatttta aatggaaaat ttttcaattt    17580 tttttttcttt tttgtacagg tttcttcctg aacgcgcctc agcgatttta aatcgtatgc    17640
agaatattca atttgaagca gtggttggcc acaaaatcaa aatgaaatga ataaataagc    17700
tccagccaga gatgtatgca tgataatgat atgaatagtt tcgaatcaat gctgcaaagc    17760
tttatttcac atttttttcag tcctgataat attaaaaaca ttggtttggc actagcagca    17820
gtcaaacgaa caagattaat tacctgtctt cctgtttctc aagaatattt acgtagtttt    17880
tcataggtct gttttttcctt tcatgcctct taaaaacttc tgtgcttaca taaacatact    17940
taaaaggttt tctttaagat atttttatttt tccatttaaa ggtggacaaa agctacctcc    18000
ctaaaagtaa atacaaagag aacttattta cacagggaag gtttaagact gttcaagtag    18060
cattccaatc tgtagccatg ccacagaata tcaacaagaa cacagaatga gtgcacagct    18120
aagagatcaa gtttcagcag gcagctttat ctcaacctgg acatatttta agattcagca    18180
tttgaaagat ttccctagcc tcttcctttt tcattagccc aaaacggtgc aactctattc    18240 tggacttat tacttgattc tgtcttctgt ataactctga agtccaccaa aagtggaccc    18300
tctatatttc ctccctttttt atagtcttat aagatacatt atgaaaggtg accgactcta    18360
ttttaaatct cagaattttta agttctagcc ccatgataac cttttctttt gtaatttatg    18420
ctttcatata tccttggtcc cagagatgtt tagacaattt taggctcaaa aattaaagct    18480
```

| | |
|---|---|
| aacacaggaa aaggaactgt actggctatt acataagaaa caatggaccc aagagaagaa | 18540 |
| aaggaagaaa gaaaggtttt ttggttttg ttttgttttg ttttgttttt tgttttttg | 18600 |
| agatggagtc tcactctttc gcccaggctg gagtgcagtg gtatgatctc agctcactgc | 18660 |
| aagctccacc tcccgggttc acgccattct cctgcctcag cctcctgagt agctgggact | 18720 |
| acaggcgccc gccaccacac ccggctaatt ttttgtattt tttgtagaga cggggtttca | 18780 |
| ccatgttagc caagatggtc tcgatctcct gacctcgtga tccacctgcc tcggcctccc | 18840 |
| aaagtgctgg gattacgggt gtgagccacc gtgcccagcc tttttttttt taatagaaaa | 18900 |
| aataatccga ctcccactac atcaagacta atcttgtttt gtgtgttttt cacatgtatt | 18960 |
| atagaatgct tttgcatgga ctatcctctt gtttttatta aaaacaaatg attttttaa | 19020 |
| aagtcacaaa aacaattcac taaaaataaa tatgtcattg tgctttaaaa aataacctc | 19080 |
| ttgtagttat aaaataaaac gtttgacttc taaactctg | 19119 |

<210> SEQ ID NO 3
<211> LENGTH: 900
<212> TYPE: DNA
<213> ORGANISM: Homo sapien

<400> SEQUENCE: 3

| | |
|---|---|
| augaacauca uccuagaaau ccuucugcuu cugaucacca ucaucuacuc cuacuuggag | 60 |
| ucguuggugu aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau gugguagacu gcagcaacag agaagagauc | 300 |
| uaucgcucuc uaaaucaggu gaagaaagaa guggugaug uaacaaucgu ggugaauaau | 360 |
| gcugggacag uauuccagc cgaucuucuc agcaccaagg augaagagau uaccaagaca | 420 |
| uuugagguca caauccuagg acauuuuugg aucacaaaag cacuucuucc aucgaugaug | 480 |
| gagagaaauc auggccacau cgucacagug gcuucagugu gcggccacga agggauuccu | 540 |
| uaccucaucc cauauuguuc cagcaaauuu gccgcguug gcuuucacag aggcucugaca | 600 |
| ucagaacuuc aggccuuggg aaaaacuggu aucaaaaccu caugucucug cccaguuuuu | 660 |
| gugaauacug gguucaccaa aaauccaagc acaagauuau ggccuguauu ggagacagau | 720 |
| gaagucguaa gaagucugau agauggaaua cuuaccaaua agaaaugau uuuuguucca | 780 |
| ucguauauca auaucuuucu gagacuacag aaguuucuuc cugaacgcgc ucagcgauu | 840 |
| uuaaaucgua ugcagaauau ucaauuugaa gcagugguug gccacaaaau caaaaugaaa | 900 |

<210> SEQ ID NO 4
<211> LENGTH: 792
<212> TYPE: DNA
<213> ORGANISM: Homo sapien

<400> SEQUENCE: 4

| | |
|---|---|
| augaacauca uccuagaaau ccuucugcuu cugaucacca ucaucuacuc cuacuuggag | 60 |
| ucguuggugu aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag guaagaaag aguggguga uguaacaauc | 240 |
| guggugaaua augcugggac aguauaucca gccgaucuuc ucagcaccaa ggaugaagag | 300 |
| auuaccaaga cauuugaggu caacauccua ggacauuuuu ggaucacaaa agcacuucuu | 360 |

```
ccaucgauga uggagagaaa ucauggccac aucgucacag uggcuucagu gugcggccac    420
gaagggauuc cuuaccucau cccauauugu uccagcaaau uugccgcugu uggcuuucac    480
agaggucuga caucgaaacu ucaggccuug ggaaaaacug guaucaaaac cucaugucuc    540
ugcccaguuu uugugaauac uggguucacc aaaaauccaa gcacaagauu auggccugua    600
uuggagacag augaagucgu aagaagucug auagauggaa acuuaccaa uaagaaaaug     660 auuuuuguuc caucguauau caauaucuuu cugagacuac agaaguuucu uccgaacgc     720 gccucagcga uuuuaaaucg uaugcagaau auucaauuug aagcaguggu uggccacaaa    780
aucaaaauga aa                                                        792

<210> SEQ ID NO 5
<211> LENGTH: 783
<212> TYPE: DNA
<213> ORGANISM: Homo sapien

<400> SEQUENCE: 5
augaacauca uccuagaaau ccuucugcuu cugaucacca ucaucuacuc cuacuuggag     60
ucguuggnga aguuuuucau uccucagagg agaaaaucug uggcugggga gauuguucuc    120
auuacuggag cugggcaugg aauaggcagg cagacuacuu augaauuugc aaaacgacag    180
agcauauugg uucuguggga uauuaauaag cgcggugugg aggaaacugc agcugagugc    240
cgaaaacuag gcgucacugc gcaugcguau guggauacu gcagcaacag agaagagauc     300
uaucgcucuc uaaaucaggu gaagaaagaa guggggugau guaacaaucgu ggugaauaau   360 gcugggacag uauauccagc cgaucuucuc agcaccaagg augaagagau uaccaagaca    420
uuugagguca acauccuagg acauuuuugg aucacaaaag cacuucuucc aucgaugaug    480
gagagaaauc auggccacau cgucacagug gcuucagugu gcggccacga agggauuccu    540
uaccucaucc cauauuguuc cagcaaauuu gccgcuguug gcuuucacag gggucugaca    600
ucagaacuuc aggccuuggg aaaaacuggu aucaaaaccu caugucucug cccaguuuuu    660
gugaauacug guucaccaaa aauccaagc acaagguuuc uuccgaacg cgccucagcg      720 auuuuaaauc guaugcagaa uauucaauuu gaagcagugg uuggccacaa aaucaaaaug    780
aaa                                                                  783

<210> SEQ ID NO 6
<211> LENGTH: 822
<212> TYPE: DNA
<213> ORGANISM: Homo sapien

<400> SEQUENCE: 6
augaacauca uccuagaaau ccuucugcuu cugaucacca ucaucuacuc cuacuuggag     60
ucguuggnga aguuuucau uccucagagg agaaaaucug uggcugggga gauuguucuc     120
auuacuggag cugggcaugg aauaggcagg cagacuacuu augaauuugc aaaacgacag    180
agcauauugg uucuguggga uauuaauaag cgcggugugg aggaaacugc agcugagugc    240
cgaaaacuag gcgucacugc gcaugcguau guggauacu gcagcaacag agaagagauc     300
uaucgcucuc uaaaucaggu gaagaaagaa guggggugau guaacaaucgu ggugaauaau   360 gcugggacag uauauccagc cgaucuucuc agcaccaagg augaagagau uaccaagaca    420
uuugagguca acauccuagg acauuuuugg aucacaaaag cacuucuucc aucgaugaug    480
gagagaaauc auggccacau cgucacagug gcuucagugu gcggccacga agggauuccu    540
```

| | |
|---|---|
| uaccucaucc cauauuguuc cagcaaauuu gccgcuguug gcuuucacag aggucugaca | 600 |
| ucagaacuuc aggccuuggg aaaaacuggu aucaaaaccu caugucucug cccaguuuuu | 660 |
| gugaauacug gguucaccaa aaauccaagc acaagauuau ggccuguauu ggagacagau | 720 |
| gaagucguaa aagucugaua agauggaaua cuuaccaaua agaaaaugau uuuguucca | 780 |
| ucguauauca auaucuuucu gagacuacag aagguuucuu cc | 822 |

<210> SEQ ID NO 7
<211> LENGTH: 972
<212> TYPE: DNA
<213> ORGANISM: Homo sapien

<400> SEQUENCE: 7

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucgugggga uauuaauaag cgcggugugg aggaaacgc agcugagugc | 240 |
| cgaaaacuag gcgucacugc gcaugcguau gugguagacu gcagcaacag agaagagauc | 300 |
| uaucgcucuc uaaaucaggu gaagaaagaa guggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aauggaaagg acaucagaag uaauuacuug | 480 |
| gauguauaua ggaucgagga cacuuuugga cgagacucug agaucacaaa agcacuucuu | 540 |
| ccaucgauga uggagagaaa ucauggccac aucgucacag uggcuucagu gugcggccac | 600 |
| gaagggauuc cuuaccucau cccauauugu ccagcaaaau ugccgcugu ggcuuucac | 660 |
| agaggucuga caucgaacu ucaggccuug ggaaaaacug guaucaaaac cucaugucuc | 720 |
| ugcccaguuu uugugaauac ugggguucacc aaaaauccaa gcacaagauu auggccugua | 780 |
| uuggagacag augaagucgu aagaagcug auagauggaa uacuuaccaa uaagaaaaug | 840 |
| auuuuuguuc caucguauau caauaucuuu cugagacuac agaaguuucu uccugaacgc | 900 |
| gcccucagcga uuuuaaaucg uaugcagaau auucaauuug aagcaguggu uggccacaaa | 960 |
| aucaaaauga aa | 972 |

<210> SEQ ID NO 8
<211> LENGTH: 852
<212> TYPE: DNA
<213> ORGANISM: Homo sapien

<400> SEQUENCE: 8

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucgugggga uauuaauaag cgcggugugg aggaaacgc agcugagugc | 240 |
| cgaaaacuag gcgucacugc gcaugcguau gugguagacu gcagcaacag agaagagauc | 300 |
| uaucgcucuc uaaaucaggu gaagaaagaa guggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aucacaaaag cacucuccc aucgaugaug | 480 |
| gagagaaauc auggccacau cgucacagug gcuucagugu gcggcacga agggauuccu | 540 |
| uaccucaucc cauauuguuc cagcaaauuu gccgcuguug gcuuucacag aggucugaca | 600 |

```
ucagaacuuc aggccuuggg aaaaacuggu aucaaaaccu caugucucug cccaguuuuu    660
gugaauacug gguucaccaa aaauccaagc acaagauuau ggccuguauu ggagacagau    720
gaagucguaa aagucugau agauggaaua cuuaccauaa agaaaaugau uuuuguucca    780
ucguauauca auaucuuucu gagacuacag aaguuaagua cagcacagaa cacccaaaua    840
cuaaaacacc aa                                                       852
```

```
<210> SEQ ID NO 9
<211> LENGTH: 714
<212> TYPE: DNA
<213> ORGANISM: Homo sapien

<400> SEQUENCE: 9
augaacauca uccuagaaau ccuucugcuu cugaucacca ucaucuacuc cuacuuggag     60
ucguugguga aguuuuucau uccucagagg agaaaaucug uggcugggga gauuguucuc    120
auuacuggag cugggcaugg aauaggcagg cagacuacuu augaauuugc aaaacgacag    180
agcauauugg uucguggga uauuaauaag gugaagaaag aaguggguga uguaacaauc    240
guggugaaua augcugggac aguauaucca gccgaucuuc ucagcaccaa ggaugaagag    300
auuaccaaga cauuugaggu caacauccua ggacauuuuu ggaucacaaa agcacuucuu    360
ccaucgauga uggagagaaa ucauggccac aucgucacag uggcuucagu gugcggccac    420
gaagggauuc cuuaccucau cccauauugu uccagcaaau uugccgcugu uggcuuucac    480
agaggucuga caucgaacu ucaggccuug gaaaaacug guaucaaaac cucaugucuc    540
ugcccaguuu uugugaauac uggguucacc aaaaauccaa gcacaagauu auggccugua    600
uuggagacag augaagucgu aagaagcug auagauggaa uacuuaccaa uaagaaaaug    660
auuuuuguuc caucguauau caauaucuuu cugagacuac agaagguuuc uucc          714
```

```
<210> SEQ ID NO 10
<211> LENGTH: 894
<212> TYPE: DNA
<213> ORGANISM: Homo sapien

<400> SEQUENCE: 10
augaacauca uccuagaaau ccuucugcuu cugaucacca ucaucuacuc cuacuuggag     60
ucguugguga aguuuuucau uccucagagg agaaaaucug uggcugggga gauuguucuc    120
auuacuggag cugggcaugg aauaggcagg cagacuacuu augaauuugc aaaacgacag    180
agcauauugg uucguggga uauuaauaag cgcggugugg aggaaacugc agcugagugc    240
cgaaaacuag cgucacugc gcaugcguau gugguagacu gcagcaacag agaagagauc    300
uaucgcucuc uaaacaggu gaagaaagaa ggggugaug uaacaaucgu ggugaauaau    360
gcugggacag uauuccagc cgaucuucuc agcaccaagg augaagagau uaccaagaca    420
uuugagguca caucccuagg acauuuuugg aauggaaagg acaucagaag uaauuacuug    480
gauguauaua ggaucgagga cacuuuugga cgagacucug agaucacaaa agcacuucuu    540
ccaucgauga uggagagaaa ucauggccac aucgucacag uggcuucagu gugcggccac    600
gaagggauuc cuuaccucau cccauauugu uccagcaaau uugccgcugu uggcuuucac    660
agaggucuga caucgaacu ucaggccuug gaaaaacug guaucaaaac cucaugucuc    720
ugcccaguuu uugugaauac uggguucacc aaaaauccaa gcacaagauu auggccugua    780
uuggagacag augaagucgu aagaagcug auagauggaa uacuuaccaa uaagaaaaug    840
```
auuuuuguuc caucguauau caauaucuuu cugagacuac agaagguuuc uucc    894

<210> SEQ ID NO 11
<211> LENGTH: 813
<212> TYPE: DNA
<213> ORGANISM: Homo sapien

<400> SEQUENCE: 11
augaacauca uccuagaaau ccuucugcuu cugaucacca ucaucuacuc cuacuuggag    60
ucguuggUga aguuuucau uccucagagg agaaaaucug uggcugggga gauuguucuc    120
auuacuggag cugggcaugg aauaggcagg cagacuacuu augaauuugc aaaacgacag    180
agcauauugg uucuguggga uauuaauaag cgcggugugg aggaaacugc agcugagugc    240
cgaaaacuag gcgucacugc gcaugcguau gugguagacu gcagcaacag agaagagauc    300
uaucgcucuc uaaaucaggu gaagaaagaa guggugaug uaacaaucgu ggugaauaau    360
gcugggacag uauauccagc cgaucuucuc agcaccaagg augaagagau uaccaagaca    420
uuugagguca acauccuagg acauuuuugg aucacaaaag cacuucuucc aucgaugaug    480
gagagaaauc auggccacau cgucacagug gcuucagugu gcggccacga agggauuccu    540
uaccucaucc cauauuguuc cagcaaauuu gccgcguuug gcuuucacag aggucugaca    600
ucagaacuuc aggccuuggg aaaaacuggu aucaaaaccu caugucucug cccaguuuuu    660
gugaauacug gguucaccaa aaauccaagc acaagauuau ggccuguauu ggagacagau    720
gaagucguaa aagucugau agauggaaua cuuaccaaua agaaaaugau uuuuguucca    780
ucguauauca auaucuuucu gagacuacag aag    813

<210> SEQ ID NO 12
<211> LENGTH: 900
<212> TYPE: DNA
<213> ORGANISM: Homo sapien

<400> SEQUENCE: 12
atgaacatca tcctagaaat ccttctgctt ctgatcacca tcatctactc ctacttggag    60
tcgttggtga agtttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttggg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg gctttcacag aggtctgaca    600
tcagaacttc aggccttggg aaaaactggt atcaaaacct catgtctctg cccagttttt    660
gtgaatactg ggttcaccaa aaatccaagc acaagattat ggcctgtatt ggagacagat    720
gaagtcgtaa aagtctgat agatggaata cttaccaata agaaaatgat ttttgttcca    780
tcgtatatca atatctttct gagactacag aagtttcttc ctgaacgcgc tcagcgatt    840 ttaaatcgta tgcagaatat tcaatttgaa gcagtggttg ccacaaaat caaaatgaaa    900

<210> SEQ ID NO 13
<211> LENGTH: 792

<212> TYPE: DNA
<213> ORGANISM: Homo sapien

<400> SEQUENCE: 13

```
atgaacatca tcctagaaat ccttctgctt ctgatcacca tcatctactc ctacttggag      60
tcgttggtga agttttcat tcctcagagg agaaaatctg tggctgggga gattgttctc     120
attactggag ctgggcatgg aataggcagg cagactactt atgaatttgc aaaacgacag     180
agcatattgg ttctgtggga tattaataag gtgaagaaag aagtgggtga tgtaacaatc     240
gtggtgaata atgctgggac agtatatcca gccgatcttc tcagcaccaa ggatgaagag     300
attaccaaga catttgaggt caacatccta ggacatttt ggatcacaaa agcacttctt     360
ccatcgatga tggagagaaa tcatggccac atcgtcacag tggcttcagt gtgcggccac     420
gaagggattc cttacctcat cccatattgt tccagcaaat ttgccgctgt tggctttcac     480
agaggtctga catcagaact tcaggccttg ggaaaaactg gtatcaaaac ctcatgtctc     540
tgcccagttt ttgtgaatac tgggttcacc aaaaatccaa gcacaagatt atggcctgta     600
ttggagacag atgaagtcgt aagaagtctg atagatggaa tacttaccaa taagaaaatg     660
attttgttc catcgtatat caatatcttt ctgagactac agaagtttct tcctgaacgc     720
gcctcagcga ttttaaatcg tatgcagaat attcaatttg aagcagtggt tggccacaaa     780
atcaaaatga aa                                                        792
```

<210> SEQ ID NO 14
<211> LENGTH: 783
<212> TYPE: DNA
<213> ORGANISM: Homo sapien

<400> SEQUENCE: 14

```
atgaacatca tcctagaaat ccttctgctt ctgatcacca tcatctactc ctacttggag      60
tcgttggtga agttttcat tcctcagagg agaaaatctg tggctgggga gattgttctc     120
attactggag ctgggcatgg aataggcagg cagactactt atgaatttgc aaaacgacag     180
agcatattgg ttctgtggga tattaataag cgcggtgtgg aggaaactgc agctgagtgc     240
cgaaaactag gcgtcactgc gcatgcgtat gtggtagact gcagcaacag agaagagatc     300
tatcgctctc taaatcaggt gaagaaagaa gtgggtgatg taacaatcgt ggtgaataat     360
gctgggacag tatatccagc cgatcttctc agcaccaagg atgaagagat taccaagaca     420
tttgaggtca acatcctagg acattttgg atcacaaaag cacttcttcc atcgatgatg     480
gagagaaatc atggccacat cgtcacagtg gcttcagtgt gcggccacga agggattcct     540
tacctcatcc catattgttc cagcaaattt gccgctgttg gctttcacag aggtctgaca     600
tcagaacttc aggccttggg aaaaactggt atcaaaacct catgtctctg cccagttttt     660
gtgaatactg ggttcaccaa aaatccaagc acaaggtttc ttcctgaacg cgcctcagcg     720
attttaaatc gtatgcagaa tattcaattt gaagcagtgg ttggccacaa aatcaaaatg     780
aaa                                                                  783
```

<210> SEQ ID NO 15
<211> LENGTH: 822
<212> TYPE: DNA
<213> ORGANISM: Homo sapien

<400> SEQUENCE: 15

```
atgaacatca tcctagaaat ccttctgctt ctgatcacca tcatctactc ctacttggag      60
```

| | |
|---|---|
| tcgttggtga agttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat taccaagaca | 420 |
| tttgaggtca acatcctagg acatttttgg atcacaaaag cacttcttcc atcgatgatg | 480 |
| gagagaaatc atggccacat cgtcacagtg gcttcagtgt gcggccacga agggattcct | 540 |
| tacctcatcc catattgttc cagcaaattt gccgctgttg gctttcacag aggtctgaca | 600 |
| tcagaacttc aggccttggg aaaaactggt atcaaaacct catgtctctg cccagttttt | 660 |
| gtgaatactg ggttcaccaa aaatccaagc acaagattat ggcctgtatt ggagacagat | 720 |
| gaagtcgtaa aagtctgat agatggaata cttaccaata agaaaatgat ttttgttcca | 780 |
| tcgtatatca atatctttct gagactacag aaggtttctt cc | 822 |

<210> SEQ ID NO 16
<211> LENGTH: 972
<212> TYPE: DNA
<213> ORGANISM: Homo sapien

<400> SEQUENCE: 16

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat taccaagaca | 420 |
| tttgaggtca acatcctagg acatttttgg aatggaaagg acatcagaag taattacttg | 480 |
| gatgtatata ggatcgagga cacttttgga cgagactctg agatcacaaa agcacttctt | 540 |
| ccatcgatga tggagagaaa tcatggccac atcgtcacag tggcttcagt gtgcggccac | 600 |
| gaagggattc cttacctcat cccatattgt tccagcaaat ttgccgctgt tggctttcac | 660 |
| agaggtctga catcagaact tcaggccttg ggaaaaactg gtatcaaaac ctcatgtctc | 720 |
| tgcccagttt ttgtgaatac tgggttcacc aaaaatccaa gcacaagatt atggcctgta | 780 |
| ttggagacag atgaagtcgt aagaagtctg atagatggaa tacttaccaa taagaaaatg | 840 |
| atttttgttc catcgtatat caatatcttt ctgagactac agaagtttct tcctgaacgc | 900 |
| gcctcagcga ttttaaatcg tatgcagaat attcaatttg aagcagtggt tggccacaaa | 960 |
| atcaaaatga aa | 972 |

<210> SEQ ID NO 17
<211> LENGTH: 852
<212> TYPE: DNA
<213> ORGANISM: Homo sapien

<400> SEQUENCE: 17

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |

| | |
|---|---|
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat taccaagaca | 420 |
| tttgaggtca acatcctagg acattttgg atcacaaaag cacttcttcc atcgatgatg | 480 |
| gagagaaatc atggccacat cgtcacagtg gcttcagtgt gcggccacga agggattcct | 540 |
| tacctcatcc catattgttc cagcaaattt gccgctgttg gctttcacag aggtctgaca | 600 |
| tcagaacttc aggccttggg aaaaactggt atcaaaacct catgtctctg cccagttttt | 660 |
| gtgaatactg ggttcaccaa aaatccaagc acaagattat ggcctgtatt ggagacagat | 720 |
| gaagtcgtaa aagtctgat agatggaata cttaccaata agaaaatgat ttttgttcca | 780 |
| tcgtatatca atatctttct gagactacag aagttaagta cagcacagaa cacccaaata | 840 |
| ctaaaacacc aa | 852 |

<210> SEQ ID NO 18
<211> LENGTH: 714
<212> TYPE: DNA
<213> ORGANISM: Homo sapien

<400> SEQUENCE: 18

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag gtgaagaaag aagtgggtga tgtaacaatc | 240 |
| gtggtgaata atgctgggac agtatatcca gccgatcttc tcagcaccaa ggatgaagag | 300 |
| attaccaaga catttgaggt caacatccta ggacattttt ggatcacaaa agcacttctt | 360 |
| ccatcgatga tggagagaaa tcatggccac atcgtcacag tggcttcagt gtgcggccac | 420 |
| gaagggattc cttacctcat cccatattgt tccagcaaat ttgccgctgt tggctttcac | 480 |
| agaggtctga catcagaact tcaggccttg ggaaaaactg gtatcaaaac ctcatgtctc | 540 |
| tgcccagttt ttgtgaatac tggggttcacc aaaaatccaa gcacaagatt atggcctgta | 600 |
| ttggagacag atgaagtcgt aagaagtctg atagatggaa tacttaccaa taagaaaatg | 660 |
| attttgttc atcgtatat caatatcttt ctgagactac agaaggtttc ttcc | 714 |

<210> SEQ ID NO 19
<211> LENGTH: 894
<212> TYPE: DNA
<213> ORGANISM: Homo sapien

<400> SEQUENCE: 19

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |

-continued

```
gctgggacag tatatccagc cgatcttctc agcaccaagg atgaagagat taccaagaca    420
tttgaggtca acatcctagg acattttggg aatggaaagg acatcagaag taattacttg    480
gatgtatata ggatcgagga cacttttgga cgagactctg agatcacaaa agcacttctt    540
ccatcgatga tggagagaaa tcatggccac atcgtcacag tggcttcagt gtgcggccac    600
gaagggattc cttacctcat cccatattgt tccagcaaat ttgccgctgt tggctttcac    660
agaggtctga catcagaact tcaggccttg ggaaaaactg gtatcaaaac ctcatgtctc    720
tgcccagttt ttgtgaatac tgggttcacc aaaaatccaa gcacaagatt atggcctgta    780
ttggagacag atgaagtcgt aagaagtctg atagatggaa tacttaccaa taagaaaatg    840 attttttgttc catcgtatat caatatcttt ctgagactac agaaggtttc ttcc          894
```

<210> SEQ ID NO 20
<211> LENGTH: 813
<212> TYPE: DNA
<213> ORGANISM: Homo sapien

<400> SEQUENCE: 20

```
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttggg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg gctttcacag aggtctgaca    600
tcagaacttc aggccttggg aaaaactggt atcaaaacct catgtctctg cccagttttt    660
gtgaatactg ggttcaccaa aaatccaagc acaagattat ggcctgtatt ggagacagat    720
gaagtcgtaa gaagtctgat agatggaata cttaccaata gaaaatgat ttttgttcca    780 tcgtatatca atatctttct gagactacag aag                                   813
```

<210> SEQ ID NO 21
<211> LENGTH: 300
<212> TYPE: PRT
<213> ORGANISM: Homo sapien

<400> SEQUENCE: 21

```
Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95
```

```
Arg Glu Glu Ile Tyr Arg Ser Leu Asn Gln Val Lys Lys Glu Val Gly
                100                 105                 110

Asp Val Thr Ile Val Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
        130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285

Phe Glu Ala Val Val Gly His Lys Ile Lys Met Lys
    290                 295                 300

<210> SEQ ID NO 22
<211> LENGTH: 264
<212> TYPE: PRT
<213> ORGANISM: Homo sapien

<400> SEQUENCE: 22

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
    130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
```

-continued

```
                    165                 170                 175
Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
        195                 200                 205

Ser Leu Ile Asp Gly Ile Leu Thr Asn Lys Lys Met Ile Phe Val Pro
    210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
            245                 250                 255

Val Gly His Lys Ile Lys Met Lys
            260

<210> SEQ ID NO 23
<211> LENGTH: 261
<212> TYPE: PRT
<213> ORGANISM: Homo sapien

<400> SEQUENCE: 23

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
            85                  90                  95

Arg Glu Glu Ile Tyr Arg Ser Leu Asn Gln Val Lys Lys Glu Val Gly
        100                 105                 110

Asp Val Thr Ile Val Val Asn Asn Ala Gly Thr Val Tyr Pro Ala Asp
    115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
            165                 170                 175

Glu Gly Ile Pro Tyr Leu Ile Pro Tyr Cys Ser Ser Lys Phe Ala Ala
        180                 185                 190

Val Gly Phe His Arg Gly Leu Thr Ser Glu Leu Gln Ala Leu Gly Lys
    195                 200                 205

Thr Gly Ile Lys Thr Ser Cys Leu Cys Pro Val Phe Val Asn Thr Gly
    210                 215                 220

Phe Thr Lys Asn Pro Ser Thr Arg Phe Leu Pro Glu Arg Ala Ser Ala
225                 230                 235                 240

Ile Leu Asn Arg Met Gln Asn Ile Gln Phe Glu Ala Val Val Gly His
            245                 250                 255

Lys Ile Lys Met Lys
            260
```

```
<210> SEQ ID NO 24
<211> LENGTH: 274
<212> TYPE: PRT
<213> ORGANISM: Homo sapien

<400> SEQUENCE: 24

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Val
            260                 265                 270

Ser Ser

<210> SEQ ID NO 25
<211> LENGTH: 324
<212> TYPE: PRT
<213> ORGANISM: Homo sapien

<400> SEQUENCE: 25

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
```

```
            50                  55                  60

Leu Trp Asp Ile Asn Lys Arg Gly Val Glu Glu Thr Ala Ala Glu Cys
 65                  70                  75                  80

Arg Lys Leu Gly Val Thr Ala His Ala Tyr Val Val Asp Cys Ser Asn
                 85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
             115                 120                 125

Leu Leu Ser Thr Lys Asp Glu Glu Ile Thr Lys Thr Phe Glu Val Asn
        130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn
        275                 280                 285

Ile Phe Leu Arg Leu Gln Lys Phe Leu Pro Glu Arg Ala Ser Ala Ile
    290                 295                 300

Leu Asn Arg Met Gln Asn Ile Gln Phe Glu Ala Val Val Gly His Lys
305                 310                 315                 320

Ile Lys Met Lys

<210> SEQ ID NO 26
<211> LENGTH: 284
<212> TYPE: PRT
<213> ORGANISM: Homo sapien

<400> SEQUENCE: 26

Met Asn Ile Ile Leu Glu Ile Leu Leu Leu Ile Thr Ile Ile Tyr
 1               5                  10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
         50                  55                  60

Leu Trp Asp Ile Asn Lys Arg Gly Val Glu Glu Thr Ala Ala Glu Cys
 65                  70                  75                  80

Arg Lys Leu Gly Val Thr Ala His Ala Tyr Val Val Asp Cys Ser Asn
                 85                  90                  95

Arg Glu Glu Ile Tyr Arg Ser Leu Asn Gln Val Lys Lys Glu Val Gly
```

```
            100                 105                 110
Asp Val Thr Ile Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                    165                 170                 175

Glu Gly Ile Pro Tyr Leu Ile Pro Tyr Cys Ser Ser Lys Phe Ala Ala
                180                 185                 190

Val Gly Phe His Arg Gly Leu Thr Ser Glu Leu Gln Ala Leu Gly Lys
            195                 200                 205

Thr Gly Ile Lys Thr Ser Cys Leu Cys Pro Val Phe Val Asn Thr Gly
        210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Leu
                260                 265                 270

Ser Thr Ala Gln Asn Thr Gln Ile Leu Lys His Gln
            275                 280

<210> SEQ ID NO 27
<211> LENGTH: 238
<212> TYPE: PRT
<213> ORGANISM: Homo sapien

<400> SEQUENCE: 27

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
    130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190
```

```
Pro Ser Thr Arg Leu Trp Pro Val Leu Glu Thr Asp Glu Val Val Arg
        195                 200                 205

Ser Leu Ile Asp Gly Ile Leu Thr Asn Lys Lys Met Ile Phe Val Pro
    210                 215                 220

Ser Tyr Ile Asn Ile Phe Leu Arg Leu Gln Lys Val Ser Ser
225                 230                 235

<210> SEQ ID NO 28
<211> LENGTH: 298
<212> TYPE: PRT
<213> ORGANISM: Homo sapien

<400> SEQUENCE: 28

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
    210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn
        275                 280                 285

Ile Phe Leu Arg Leu Gln Lys Val Ser Ser
    290                 295

<210> SEQ ID NO 29
<211> LENGTH: 271
<212> TYPE: PRT
<213> ORGANISM: Homo sapien
```

<400> SEQUENCE: 29

```
Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys
            260                 265                 270
```

<210> SEQ ID NO 30
<211> LENGTH: 23830
<212> TYPE: DNA
<213> ORGANISM: Homo sapien

<400> SEQUENCE: 30

| | |
|---|---:|
| atggtccgag ggggcgggg ctgacgtcgc gctgggaatg ccctggccga gacactgagg | 60 |
| cagggtagag agcgcttgcg ggcgccgggc ggagctgctg cggatcagga cccgagccga | 120 |
| ttcccgatcc cgacccagat cctaacccgc gccccgccc cgccgccgcc gccatgtacg | 180 |
| acgcagagcg cggctggagc ttgtccttcg cgggctgcgg cttcctgggc ttctaccacg | 240 |
| tcggggcgac ccgctgcctg agcgagcacg ccccgcacct cctccgcgac gcgcgcatgt | 300 |
| tgttcggcgc ttcggccggg gcgttgcact gcgtcggcgt cctctccggt atcccgctgg | 360 |
| gtgcgtctgg ggacgctgcc cgggctccac gtgcggagtg ggtgccccct aggccgggga | 420 |
| gcggggatc cccaggggtc gcggggccct ggaggagcgg gcatcggacg cggacacggc | 480 |
| ggggtgcatc ccgagggccc cctccgaggc agatgcttcc tgcggggcg ctgttcctgg | 540 |

```
gcccgggaag ggggcgttgg aaccccgagc ggtccgggcc gaagcctggg actctcgtgc    600
gtccccaccc ctaccccat caggcgcccg tgcatgaagg gagaccctca cctccggact    660
gagagtcgga gcgtctcgga gcgacgggga gtagggagcg ggacccgggg cggagggtag    720
tgctggcccc tgcggactcc gggtcccctg tgtcctctcg ggaggggctg gacgggctga    780
gctgccgagg ggccgatttg ccctgggccg gacaaagagt ggggctttgg ccggtccccc    840
acggtgggct ccttccctct ggggattgag ggactcaaga caccccgcgc ctgcgctttt    900
cttttctttt tttcttttttt tttttttgag acggagtttc gctcagtcgc ccaggctgga    960
gtgcagtggc gtgatctcaa ctcactgcaa gctccacctc ccaggttcac gccattctcc   1020
tgcctcagcc tcccgagtag ctgggactac aggcgccagc caccaagccc ggctaatttt   1080
ttgtattttt tagtagagac ggggtttcac cgtgttagcc aggatggtct cgatctcctg   1140
acctcgtgat ctgcccacct cggcctccca gaatgctggg gttacaggcg tgagccactg   1200
ctccctgctg cctacgctct ctgggtcgca gcccagcctt ctgggggctg ggtagcctcc   1260
cagaagggca accctgggca tcctccaggg caggctaact ggagtctagt ggggaggggt   1320
accttgaaag aggaaagttg tttcctcctc ctcctcctcc tccagtgttt gggacccttc   1380
ctgggggctg gagtgcatcc ctggacaccc cccaatccca tcctcttctc tagtttccac   1440
tgacctaggc ccaccctccc ctctccggct cagtactcct ggaaatgaga ttccgtacat   1500
ttgaatcttg tcctaatgaa atatttgtcc atgtgggtac ctgtgtgtgt gtggtggggg   1560
tgcagacgga gggtttgttt ctcactagct ggaactactg gggtgtggta tgcttcctgg   1620
gaatttgtgt gccacagtcc tggaggcgag gaggggttg tgagccagta ggcagggct    1680 ggggcaagta gcattgtgaa gctattgaca cccagacgtc cccaggcagg agattatgcc   1740
cccattagcc ccctttttatc tgggcttcct taacaatgga ctctttgccc tgcctgccag   1800
agccagcagg gagtgactgt tcagtggtga ggaagcgggc agaggaagcc ctgccattgg   1860
gtaggagcag tgggcagccc ctgggctgac tgggaggtgg ggattaggga ttagacagtc   1920
ctggctgtct gccttcccct aagccagggg gagaggagca aagggcacga aatgtggcct   1980
ccaggaggat tagaccgcca catgatcatt tgcacaccct ggggtttagc aacaataaaa   2040
gtcagctttt ttgtatccca aggtggcctg tggacaccca catggacaaa tgtttacact   2100
gggacagaat tcaaatgcag aggtcccagg agcctaaagt acactcactc tggtatagaa   2160
aggattcctt actgggcaga ggacaggtgc agcctggggc tttcccaggc aggacacagg   2220
gaggctcagg aaccaccaag tccctggaag gtggatctgg aggcgttggc aggagccact   2280
ccctgggttc cagggctcca ggttcctgct ttaacccct gtctcacaga gggctgtgca   2340
cttgggggct gctgagcatg tcccagaggc tgcatcctgg acacagcacc tcagtgcatc   2400
tgagctgagg ctaacttggc aggagggaca ggcagaacct gccagccacg tgcaattcca   2460
cccctctggc cactcaggga aggagagctg tgagtcaaga tcagatttgg gtcaggacag   2520
gctggggcct gcctgtccct gtgcatccca agatttatgg ctggccaggg gttgggctgg   2580
gaggggtggt cttgcatgcc aggagagtgc agatcagcct gagaggccag gccagtaagt   2640
gaggtcagat ctcctgcacc tgatagcatt aaggccatct acaccaaagc tctaatgctg   2700
atatgttcct ggcctctatg tgggcatgg aggtggggca tggaggtgag gcctgctcgc   2760
ctgggcttct ggaagtggga gactcattcc tgtggctgag gcctacagca gtgctgtgtg   2820
gtaggaatac actggaagcc atgatgtcat tgtgcatttt ctagaagcca cattgaataa   2880
```

| | |
|---|---|
| agtaaaagac acaggtagaa ttaatttcat tgagcccaat atatccaaaa taatatcatt | 2940 |
| ttcacatcta ttcaatataa aaatttacta atgagatatt tcatactaag ccactgaaat | 3000 |
| ccagtttgta tcttacacat ctcagttttg acgagccaca tttcaagggc gtgatagcca | 3060 |
| catgtggctc ccatagtaga cagtactggt ctagagaaat gttggtggca tccttgctgt | 3120 |
| ctggtttctg gccttgccaa aagtattacc atcccagtgt ggtacattct ttcatgtatt | 3180 |
| tgtctcctgt ccccagagca gactctgcag gtcctctcag atcttgtgcg gaaggccagg | 3240 |
| agtcggaaca ttggcatctt ccatccatcc ttcaacttaa gcaagttcct ccgacagggt | 3300 |
| ctctgcaaat gcctcccggc caatgtccac cagctcatct ccggcaaaat aggcatctct | 3360 |
| cttaccagag tgtctgatgg ggaaaacgtt ctggtgtctg actttcggtc caaagacgaa | 3420 |
| gtcgtggatg taagcagttt gcttatctgg acgttgtcaa gttagaaaag ctgttttggg | 3480 |
| atgggtgtgg tggctcatgc ctgtcatccc ggcactttgg gaggccgaag cgggtgggtt | 3540 |
| gcttgagccc aggagctcga gaccaacatg atgaaaccca gtctctacaa aaattacaga | 3600 |
| aaaattagct aggcatggtg ttgtgggccc atagtcccag ctactaggga ggctgaggca | 3660 |
| ggagaattgc ttgagcctgg gaggtggagg ttgcagtaag tcatgatcat gccactgtac | 3720 |
| tccagcccgg gtgacagtga gatgctgtct ggaaaaaaaa aaaaagaaa gactgttttg | 3780 |
| ttttggaagc aacacaggca gttgtaggcc ccctgtgcca gagtgacata aactctgtac | 3840 |
| acctccagtg atttggtcca tgtttgtaaa ccctgaatgt tccagggcag tttcttttct | 3900 |
| tcactttta tctcttttt ttgggtgggg gggcggggta cagagtcttg ctctgtctcc | 3960 |
| caggctggag tgcagtggcg caatctcaac ctcccgagga gctgggacta caggcacagg | 4020 |
| ccatcacacc ttgctaatgt ttgtactttt tgtagagacg gggttttgcc ctgttgccca | 4080 |
| ggctggtccc aaactcctgc acccaagtaa tctgcccacc tctgcctggc agttacaatt | 4140 |
| tcaaataatt cctccctttc cttcaacact tggctcatga ccgtccagtc caaggaacct | 4200 |
| gtcctgcagg tgtgcctctc ccgagcttcc tctatgcatc ttccataatg aagatgcctt | 4260 |
| ctcactggaa accctacaag ggtgggaacg tgccttattt gcctgtatcc tcagggtcta | 4320 |
| gcagagagaa gataatttgt aataccaaaa caccattaaa ttcagctgat gctttcataa | 4380 |
| gcgctccttg gaggaaggac tccatttact tgacagatct gtgcaagaca gcagcctggc | 4440 |
| gcgtctaacc tgcagccagt tgcatcctct gtttaacctt gtttgcggaa gctttctcta | 4500 |
| aacagccagc acttgtctgt tcccacatgg gtccgttctc ccagtgaatc accgtggtgc | 4560 |
| ctgctgactg ctctgtagca cagtgcttcg caaagtgtga tcctgggacc agcagagcag | 4620 |
| cagctccttt gagcttattg gaatggcaga ccctcaggtc ccacctctga cctgctgcat | 4680 |
| gggaattctg ggagggacg cagaatctct ggttccacag gctctccggt gatgctaatg | 4740 |
| aataccggca tttgaacagc accgatctag cccctttcag tccatgagcc aacaacccctt | 4800 |
| ggtcctgtct gtggtgaccc agtgtgactc tcatggggag caaggagagg aagttgaagt | 4860 |
| tcactgacag ggttgttaag gggattatgc aatagatgag acccatgggc ctgaagtccg | 4920 |
| agggtgtatg ttagttcccc gttcttttga cccatggatt aacctactct gtgcaaaggg | 4980 |
| cattttcaag tttgttgccc tgctcacttg gagaaagctt atgaaggatc aggaaaatta | 5040 |
| aaagggtgct ctcgcctata acttctctct cctttgcttt cacaggcctt ggtatgttcc | 5100 |
| tgcttcatcc ccttctacag tggccttatc cctccttcct tcagaggcgt ggtaagtcgg | 5160 |
| cttttctctgc tagcgctgag tcctgggggc tctgaagtg tgctcacaca tctcctgcct | 5220 |
| gcagggcact ggtgtcgggc acctcagggt ctgtcccatg gtggagcccc atgcctcact | 5280 |

```
gcctttcaga cagagtagcc acagctggcc ctatttccag gctacccggg cagcaaaact      5340
tactgcatgt gtaattaatt atttggctat ctgtaaggta aactggctgg ttcacttaat      5400 ctgcaccttaa gcatcagat agcttctcag tgatctagtt aaactatatg atgttggcca      5460
ggcgcggtgg ctcatgtctg taatcccagc actttgggag cctgaagcag gcagatcact      5520
tgaggtcagg agttcgagac cagcctggcc aacagtgtga aactctgtct ctcctaaaaa      5580
tacaaaaatt agctgggcat ggtggtgtgc acctgtaatc ccagctgctc gggaggctga      5640
ggcaggagaa ttgcttgaac ttgggaggcg gaagttgcag tgagccaaga tcgcaccact      5700
gcactccatc ctgggtgaca gagcgagact ctatctcaaa agaaaaaaa aaaaaaaggt      5760 aaataaagta tatgacactg aagaatctgt taccctggaa aggtggagct ttactcttag      5820
ggggaactat aacagtcata tatatatatt tttttctttt cttttttttt tttttttgaga      5880 tggagtctgg ctctgtcgcc caggctggag tgcagtggtg caatctcggc tcactgcaac      5940
ctccacctca caggttcagg caattctcct gcctcaacct cccgagtagc tgggattaca      6000
ggtgcctgcc gtcacgccaa gctaatttttt gtattttttag tagagacagg gtttcatcat      6060
attggccagg ctggtctcca actcctgacc tcaggtgatc cgcccgcctt ggcctcccaa      6120
agtgctgaga ttacaggcgt gagccatggt gcccggccaa caatcacatg tgttgtaaac      6180
aacaacaaaa atctgtcagc ctggtctaac ctagatttgt gctttgtttt gttttgccac      6240
tttgtgatgc acaggaggaa gtttaggctg taaaatacta gccttttagg gtaattttttg      6300 aactcacaag agcagcagcg gaacctttga tgcaatcctg tatgtagcac cagcagagcc      6360
acgtggcaga gggactcgca ttaggagcct cccattacag actacgtgct cctgtgcgtt      6420
atcttatagg gtccccacaa ccaaggggag atgtgattat tcatcctgtg tggctgtggg      6480
gaacttgaga gtcatacttg cccaaagagc acggccagcg agcttgcacc caggtcactc      6540
tctgctcctc tgtcagaaca gggcatgtct tggttcactg cagggcggct cttctcattc      6600
tctgtagttt ggggtccagg atagtggtcc acggagccac tggagtgccc agctactgag      6660
tgaccaaagc atattttgga tttccgacat tgccacagca tggttgggca tcagcaggac      6720
cccaacccct tgttatgctg gtggctttat gtggttattt gatcttcccc agaactcagc      6780
aggagtgcac ccagcagcac cgtagtgatg ctctctggct ccccagtgca cggttctggc      6840
tttccttcct ggtcgagagt ttcaagcccc ctgggtccta ctctgtcctt ttcagcccat      6900
agctttgttc aaaagctgct ggcagtgttc agatttggct gagttcagtg aatatgtgca      6960
ttggctgatt tctgagccat gccaggggga tggagaagcc gaagcaggag tgtttgttct      7020
gcaggctctg gagtaggcat tgggtctgtg ccggctcact tgctagtctt gcatccttcc      7080
ccaaccccct ctggggatgt ctggccacat cagaagacag tttgggttgt cagaactggg      7140
ggagtaccag gccgaggtgg gtggatcatg aggtcaggag atcgagacca tcctggctaa      7200
cacagtgaaa cctcatctct actaaacata cgaaaaaaat tagctgggcg tggtggcggg      7260
cgcctgtagt cccagctact cgggaggctg aggcaggaga atggtgtgaa cccgggggggc      7320 ggagcttgca gtgagctgag atcctgccac tgcactccag cctgggcaac aaagcgagac      7380
tccgtctcac aaacaaaaca aaacaaaaca aaacaaaatc tggggagtg ccactggcat      7440 ctgatgtata gaggcccgag atgctgtgtc atcacccgtt gagtgcgctc ataggcatct      7500
tcctgacaat tagaacccat tattcttcaa attcaatgca agcaaattca aagcattact      7560
gtgtacatac cgcatgctaa tcaattgcac cactggagct cctaaattca aaacattact      7620
```

```
ataaaaaagt tcaaaatgca tggaaaagtt gtacatggca ggagaatatt tgggcttctg    7680
actacccctt gaatgaagat gatccaccag ccgccttcct ccttggtctt cactccagat    7740
tcctagcatt tcattctgtg tctctttatg cagtgaggtt tttgtttgtt ttttgagaca    7800
gagtctcact gtatcaccta ggcctggagt gcagtggcgc gatctcagct cactgcaacc    7860
ctcggctcct gggtttaagc gattctcctg cctcagcctc ccgagcagct gagattacaa    7920
gcacacatcc ccatgcccag ctaattttg tatttttagc agagacaggg tttcaccatg    7980
ttgcccaggc tggtctcgaa ctcctggcct caagtgatcc atgtgcctca gccttccaaa    8040
gtgctgggat tacaggcgtg agccaccatg cccagctcct agtgaggttt ttgatgcctt    8100
gctacatctg ccctagaaat tgtgtgacta cgattttgga aatgttgctg tgtaaacttg    8160
tgatcatttc tggactccag gcaagaatct tgatggctaa ggtgtggctg aacatgtctg    8220
attctctcct ggacctgttt taggccaaac tctgctctga aattcctccg tgtggaaggg    8280
cgggctgggg agagcctccc agctggaatc ttttggatgc cttctctgt gggtatctga    8340
tggctggctc tgatggctgg ctgtgatggc tgtggctgga atcattgtt gacatgagtt    8400
tcacagatgc aggctctgtc caaattgtag caaaagctgc ctgccccagc cgagctatgg    8460
gcaataaggt ggtttaagga tatagatgaa ggaaaactca cccttagaat aatttatcca    8520
aaatgctgct gtgttgtggg ttagaggaca ttttctgagg tcccaggttc attgtttcat    8580
ttaagtctca aaagtccctc caggtgttgg ttctaattgt caaagcatgg ggggagatgg    8640
gctcatgggt taaaggtctt atcccagatt tctgtatcct ccttgcaagc agcaaagggg    8700
tctggattg aatccatgac catgtttctc ctttgggttt ccatcacact ctgtccccgt    8760
gcactgagca ccctttagtt catatgaccc cttaggcat gttacatggg cactcctata    8820
ggtgcccatc tggccctagg acttggccaa cacaacatgg actccagttt ccatctgcct    8880
ctttgccagg cacttttgtg cagtgcacac actgtacaac agtagacggc aaccctgaga    8940
gccagagtag agcctgtcct agcaccggaa tgctcggtaa ggatttgtcg caggagtgat    9000
tccaaagcca atgtcctccc tccatatcag cctgtttgtg gctctgagaa gctctgccca    9060
catgtgaaag cttgttaagc acttaagcac taacccagag cttcagacag tgccagtcct    9120
ttttcccctt ctttaaaagc gatatgtgga tggaggagtg agtgacaacg tacccttcat    9180
tgatgccaaa acaaccatca ccgtgtcccc cttctatggg gagtacgaca tctgccctaa    9240
agtcaagtcc acgaactttc ttcatgtgga catcaccaag ctcagtctac gcctctgcac    9300
agggaacctc taccttctct cgagagcttt tgtcccccg gatctcaagg tgagttggtg    9360
gtgagggggc aggtgttctg gggtgcagct cttctttgcc tccctgattg ccaggagcta    9420
ccagttactg tctgcacaat caaacagaaa tagacctgtc cttgatggtt aacggaaata    9480
aaaggcgctt gtcccagaag ctcaggtgag gcaccaccct gattatggga atcacctggg    9540
aacatatacc cagacctaaa actcagatcc acttccagg ctgtggttat atagtcaggg    9600
gggtgcagta tgggtattag gattttttat ttttagtta taaagatttt ttttggttt    9660
gttttttgaga cagggtcttg ctctgccgct taggctggag tgcagtggtg caatcatagc    9720
tcactgaagc ctcagactcc tgggttcaag cagtcctccc acctcagcct cctaaggagc    9780
tgggacccac aggcatgcag caccacacct ggctaatttt taaaaatttt gtggagtgtt    9840
gcccaggctg gtctcacact cctgccctca gcgatcctc ccaccccagc ctcccaatgt    9900
gttgggatta caggcatgag ccattgtacc cagccactaa gatgattctt atttggaaac    9960
acggtcaaga acaactgcgt tcggtagttt aaccttttt gattgtggtg gttttagtat   10020
```

```
gccttaccac tctaccatag taagaaattt gcagaccatg tacaccaacc tttggtgctc    10080
ctggggagaa agaaagaagg ctatgcaatg caatgcatgc tcacagtcca agggagaggg    10140
aaagctgtct aacaggattg gttttcccgt gtgctttata agcagatgag tagaggagac    10200
agctcttatt gtcctagtgg caattgggat aggctgcaaa gtttgttagg gtggaggctt    10260
attccgggac caagggagcc caaagaaaca agctcctgcc aggcgcggtg gctcacgcct    10320
gtaatcccag cactttggga ggctgaggca ggtggatcac ctgaggtcag gagtttgaga    10380
ccagcctggc caacatggtg aaaccccgtc tccatgaaaa atacaaaaat tacccgggca    10440
tggtggcggg cacctgtaat cccagctact agggaggctg aggcaggaaa atggcttgaa    10500
cctcggaagt ggaggtggcc gttagccgag atcacgccac tgcactccag cctgggcaac    10560
agagcaagac tctgccttaa aaaaaaaaaa aaaaaaaga aaagtaaaag gaaaaaaaag    10620
aggctctggc ctgctggggt gcctgcaaag tctccgtgga agggtgacat tcaagccgag    10680
acctccaggg aactgtctcc tgggagcaca gagcccttg ctcagccccc aggtggctca    10740
gtgcccccag ccagcagact cagagcttgc atgattcttt ggtgctctct gcggtcttcc    10800
aatgatgctg aaataaatgg tgcttggtgt ctccctgctg tagtccccctt gcttgctttg    10860 ctcacaggtg ctgggagaga tatgccttcg aggatatttg gatgcattca ggttcttgga    10920
agagaagggt atgtatgggc tgggaggatc agccatgccc ttttgacaag catttactag    10980
cggtcttggt aaagacttga gatttgcctt agttctaaca cttagtgccc aacgccttcc    11040
ttgtgttgct caacctactc atgagcccag gagataggaa atctccgtcc cattgtacag    11100
atggggaaac agaattttgg aaaggagagc caagcagcac acacccctcc ctgagggca    11160 gagccgagat ttgaactggg atgtcatgac tccagggccc tctccctccc cagggtcccc    11220
ttatctgaag gcggttttttc tttccagctc gacctcttgt gaccccttagt ttaacaaggg    11280 ccgaagttaa agagtttctg cgcctggacc ccaaatgaag caatcagatt tctcatctcc    11340
agtcaggtgt gggtccaagc ccactagaca agtttgctct tcccagagca catttctgcc    11400
ttcaagtcat cctggcttgt cagggctggg ggagttctgc tgtagaaaata ttagagtgga    11460 aggaaaaaga tgtgttggga gctatttttc tttaatacta aaagttggtt gatgaatttg    11520
tcgttggcca agaccaagga gactgcattt ttaaggacat atgtgtattt atctgctcag    11580
aaaatgttca ttgctgtgtg ctagggatac tgcagtgaac acagaggtgt gacccttgcc    11640
agccttgtga gagaagtgag cagataagta agcagaaggg tgatgctgtg tcgatgggaa    11700
agtacaggtg ccaatgagaa ggcacaggtg tcaaggagaa gacacaggat gctggaggct    11760
catgcaggat ggatctccaa ggcccagggg aagaagggcc tctcggagga cgtgaatcca    11820
cattaagact tgggataa gtaggagcgc cttaggcatg ggacccatg gatgcgaggc    11880 ctgtaggaca cagacaggat ggcatgaagg cctgtgcaac tggaggggtg gggatgggga    11940
cactaagaga tggctggaag tgtgggggtg gggacactaa gagatgactg gagaagaggg    12000
ggtcaggagt ggtgaaaaat gggagaggag ggcaggctgg gccttttgga tacagggga    12060 ttgcatcctg cagtggtagg gagccactga gggctgctgc agtaggagtg aggggatcag    12120
aggagagctt tggaagcccc ctggatgcgg gacaggaagc gagataccag tgtctaggag    12180
gccagtgagg cagccacagg ctccaccagg atcagggctg cgagggtcat gaggaggaaa    12240
ccaatttgaa gggagtccagg ggaataggac ttggaaatga ccgatgggac atttgggaag    12300
aggaagacag aagagcgcag tcccggcttc tggctttagc agttgggcaa ggggagatgg    12360
```

-continued

```
ggagatgtgc ccatgggttg agggttgagg acattaggag ggagccggta tggcaggaag    12420
agctggtgtg ccagagatgc tggaagcagc atctgcctga gaacagatac ctggcaatat    12480
tcctaaggga aagtgacatc tcggagggtg aggagggcat ctgatagggc ctggaaagag    12540
ccggggcaag catgaatgtg aggttatctt gggggcaag gctcaggcgt tgaggagcag    12600
cccctggtct cttcagcctg aagttggaag ccagagttgg gccaggtgca gctgtggttg    12660
tctgaagtcc ccctccccca gcccagtgtg ccaatgctgt aagagcaagg gccgctcact    12720
ggtgctggtg gctgagtccc agcacccagg acagggcctg gcacatactg gtgcccaatc    12780
ctcccttctg ggtgcttctt ccaaggcctt gtgatggaag tgagtaccct cttcgacatc    12840
agacccagct tcaaatcctg gctctgctat gtattggctg cgtggcttta gacaagtctt    12900
ttaaccttgc tgtgcttctg atttctcagc tgaaaaatgg agatgatgat agtggtttct    12960
gtaaggcctt atggtgaagc acctagctca gggcctggaa ggcaggtgta accagtggtt    13020
cagttgttat aaaccaacac taaccctcgc ctttgcacct catgaaacca gatatgtaga    13080
tggagcccac aaagctagca ggagccaagc tcacgtgtgt cctgctttaa gccccatac    13140 cccttctcc gggtgacaaa cacctgtgct cgttctcttc ccttccctc ttcccttgc    13200 atttggctaa taacaggcca gctgcctgcc tccctgcagt ttggtagatg ggtgggtaac    13260
gaccaccact cccacgttcg cctgatgggc ttgttttccg tgcccttcac aggcatctgc    13320
aacaggcccc agccaggcct gaagtcatcc tcagaaggga tggatcctga ggtcgccatg    13380
cccagctggg caaacatgag tctggattct tccccggagt cggctgcctt ggctgtgagg    13440 ctggaggag atgagctgct agaccacctg cgtctcagca tcctgccctg ggatgagagc    13500
atcctggaca ccctctcgcc caggctcgct acaggtaccc actcctcggg gtgagcacgg    13560
gcagcacctt gttttctttc ttgtgcatta tggaggaaga tggtactgcc acatgggagc    13620
gatagggtga ggcaaccatg acaggtggtt gggaacatct ccttccatgt gtacagcctg    13680
ggctgctgcc atcactccca gcacagcccc caacccccc aatcctggaa ccttgccaag    13740
tctcccttcc catggggtca tgaccaggag gaaaacaaac tccagctgag ccccttgggg    13800
ttccccatat aggctcctgc ctgtggcagc tgggccctct gtaccccttt ccaactctgt    13860
ctccctaaca tggcacctga gctcctgcca tcctggattt catggacccc aaggatgggg    13920
gtcctgcatc tgggacttgg cctattactc ggagctcctt ttcagccgcc tcctccacc    13980 tgtccaccca cctcaaggct cctttcttga gacctctcct aatttctccc ttccctaaa    14040 cccacaattt tgaacctcca tcgaatggtg ctgtatttta taatgtcatc aaatatcaaa    14100
tggagacagt gctatggtcc aaatgattgt gtaccccca gaatttgtct tttgaaatcc    14160
taacccccaa catgatggtc ttaggaggtg gggcctttgg gaggagatta ggtcatgagg    14220
aaagggctgt catgaatggg attggtgccc ttattaaaca gacccaagag aggtcccttg    14280
tcccttctac tgtgtgagga ctcagaaggt ggtgtctatg aagaagcagg ccctcaccag    14340
acaccaacat gtctgctgcc ccttgatctg ggaccttgca gcctctagaa ctctgaaaaa    14400
tcgatgtttg ttgttttata agccactcag ttggtggcat tttgttagag tagcctgaac    14460
acggactaag tcaaacagaa gaacccacaa accagctaca gagttgggca tttgagaaa    14520 ttcaaaaatg agtcagacat aactccttat tcttgaggtg ccctaagaga tgggacacag    14580
cagctgccca ggtgcattag tttgttctca cattgctata aagaaatacc tgagactggg    14640
taactcataa agaagaggt tgaattggct cacagttgca caggctggac aggaagcatg    14700
gtgctggcat ctgctcagct tctggggagg cctcaggaaa cttacaatca tggcagaagg    14760
```

```
tgaacgggaa gcatgcacat cccatgactg gagcaggagt gagagagaga gggaaataga   14820
gggaaggtgc catacacttt taaacaacca gatctcatga gaacacattc actatcaaga   14880
gaacagcacc agtggggaaa tccgccccca tgatccaatc acctcccatc aggctccgcc   14940
tccaacactg ggaattacaa tttgacatga gatgtgggca gggacacaga tccaaaccat   15000
atgaccagat taatacgatt tgaggcatca cgaggtcatt aaagagaggg aataaaagac   15060
tggggctcca ggaagaaggc tctggaatcc agcagagggt caaggaccag cttgtaaagc   15120
tggtggtgcc tgagaagtac ctaggagaac atagatgctg tgacgtttga tgtagctgtt   15180
ttttgttttg tgttttggtt tttgagacag agtctcactc tgttgcccag gctggagtgt   15240
gcagtggcgt gatcttggct cactggagcc tccatctccc aggttcaaat gatcctcatg   15300
cctcagcctc ctgagttgct gggattacag gtgcacacca ccacgcctgg ctaattttg   15360 tgttttcagt agagacaggg tttcaccatg ttggccaggc tggtcttgaa ctcctgacct   15420
caagtgatcc aacaacttca gcctcccaaa gtgctgggat tacaggcatg agccaccatg   15480
cccagcctga tgtagctgtt tctgtgcaca ttatttgctg tggggtatat tcagatttct   15540
taatacaaga tgattctttg cctcatgact tacacaccat tttctattta atttcagcta   15600
tgatattgga aatggacatg tcttttcaag gaaaataaaa gcaggctttc tggaatggcg   15660
acttccaaac atatttgtca atttaaagga gctgggagtg gggaccctat gctccgtaag   15720
cactctctta gctgttcttg gctgtgctcc ccgcttcagc ttcacactgc ccttgctgtg   15780
aagggagcag cctgggccgg gcgcggtggc ttacacctgt aatcctagca ctttgggagg   15840
ccgaggtggg tggatcacct gaggtcagga gttcaagacc agcctggcca acatggtgaa   15900
actccatctc tactaaaaat acaaaaaatt agctgggcat ggtggcaggt gcctgtaatc   15960
ccagctactt gggaggctga ggcagaagaa tcgcttgaac ccaggaggcg gaggttgcag   16020
tgagccgaga ttgcgccatt gcactccagc ctggggcaa caagagcaaa actctgtctg   16080
gaaaaaaaag aaaggagcag cttggcaaac cccaccttgt cgcttttgtg agtgcctctg   16140 acccctttggc tgccaggacg ggcgtatttt atggaaatgc taagcaccaa cagagtaaag   16200
tggtttggtt tttcacagtg gtgggagata atagctccaa attgtctttt tcagcactga   16260
gtgaagaaat gaaagacaaa ggtggataca tgagcaagat ttgcaacttg ctacccatta   16320
ggataatgtc ttatgtaatg ctgccctgta ccctgcctgt ggaatctgcc attgcgattg   16380
tccagaggtg agcattttag gtggctccgt gtcttcctca cagggttgat atgaggatga   16440
aacaagatga tagatcatgg tggcatgtag tctgggacct ggattgtcgt gccacagatc   16500
acagctcaca gtctatgtgc aatgcccctg aatgttgccc acctgtcctc aagccacaca   16560
tgcacctgta actcagtgca agcccagaaa ctccccgtgg ggactcctag agctgtcagt   16620
ggcctcacat agcagctggt ccagtctctt gtgattgccc aaggaaactg aggcctggag   16680
agcttggggt cactgctctg aggccataga gatgcctagt agaagggcca ggcctagaag   16740
caggatcctt gctgcccctc tgagctgttt ccatttaaaa tcacatgaag gccggcgccg   16800
tggctcacgg ctgtaatccc agcatttttgg gaggccaagg tgggtggatc atgtgaggtc   16860
aggagtttga accagcttg gccaacatgg tgaaatgcca tctgtactaa aaatacaaaa   16920
attagtggag catggtggca cgtgcctgta ctcccagcta cttggaaggc tgggcagaa   16980 gaatcgcttg agcctgggag gcagaggttg tagtgagcca agattgtacc actgcactcc   17040
agcctgggtg acaggagaga aaccctatct caaaataaaa tgaaaggtaa tgaaatgaat   17100
```

```
aaaataataa atcaagtcac ggccgggcac ggtggctcac acctgtaatc ccagcgcttt    17160
gggaggccga ggtgggtgga taatgaggtc aggagttcaa gaccagcctg gccaacatgg    17220
tgaaaccatg tctctactaa aaatacaaaa attagctggg catggtggtg catgcctgta    17280
atcccagcta ctccggaggc taaggcagga gaattgcttg aagcaggacc taggaggcgg    17340
aggttggttg cagtgagccg agatcatgcc actgcactct agcctgggct acagagcgaa    17400
actccgactc aaaaaaaaaa aaaaaaaaa atcaaatcac atgaaagtag aacataggga    17460
attccatctt tcgttctagg catagtttgt taatatgatt cagagccagc agttaggaga    17520
acacagtgtg actctcctag aacttcttga ttgggcttcc tctgattggg tttcctctga    17580
ttgggcttcc tctgaaagtg gggggatgg ggggtgggga gcagaatggt cagagcttgg    17640
ctcagcagtc agactgctct tcttcaaatc ctggctgcat tgcttactac agctgtgtga    17700
ctccagatga ctgaatccac ctctctgtgc tgcagcttcc cgtctagaga gatcacctgg    17760
agcagagggt ggtcaggaga ctcaatctgg ttactgactc acagtgcagg agtactcatc    17820
ccatagtaag catccagcta gagatgttga tttctatttt caggtaataa tgatgatcgt    17880
aaaattagag acagataaaa ggtatgggca ttaggccagg gcactgcaat ttctaagctg    17940
tgtgacctca ggcaagttac tcgacttctc tgagcctcag cggtttcatc cgcaatatat    18000
ggataggaaa accgacctca gtgggttgtc tgacagtgga gggcacttga ttaaaaaaaa    18060
aaaaattacc ctggtctgaa tattaccctg gactgaaaga aaatattga gctaatacag    18120
gcatcaggaa tggggctgca gggagtccag ggaagggaga acgaagagcc tgaaggtgtg    18180
aggaggtgcg agtgctgatc tgtctgctac aaagaggctg ctgagcctcc tgtggatgtg    18240
gccctggact tggcagttta atacctgagc tgttaaaata acctcagatg ctgtgttctt    18300
taaggggtag gattcagatt cctgctgaaa tgcttctgaa agggagggaa tgagccagcc    18360
catccccagt tgcttttaa gatcattggg aagttctggt cttgccattt gtccctggac    18420
cactcttagg tcctcctgcc ccacttccat ctgggtgtgt gccctgggct gtccaccaca    18480
cagctacatc ctgccatctt ccctcctgga gccactgtgc catgcatgga tctgtagctt    18540
cattttctt ggcttttccc tggttttct ggagcagagt ctctagtaaa ctcccaagga    18600
agaaaacgtt tgactttatg tgtgttggga acgtgctttt ttttctatta catctcagtg    18660
ataggttggc catgtctaga attgcaggtt gaaaatcatt tcctctcagt atattggtta    18720
gtgagaagcc tgggactgag acagtcacat tctcacttct ttgcaggtga gtgctcttag    18780
gactgtcttt ttatccctta tactctgaaa tgtcatatgt cttggtgtaa gtccttattt    18840
cagttattga gctggacaag tactggagac cccttcagtc aaagccttct gtcattctcc    18900
agctctagga aattatcttc tattgttatt tctgttattc cttcccttcc attttctttt    18960
ttctttttt ttttttttt ttgagacagg gtcttactct ggtgcccagg ctggaatgca    19020
gtgacctgat catggtacac tgcagcctga acctcccaga ctcaagtgat cctcccacct    19080
caacctccta agtagctggg actgcaagca cacatcacca cacccaacaa atatttttta    19140
aaaatttgt aagatgggat cttactatgt tgcccagact ttttcttcct cttcctgggg    19200
ctcttattag gaagatgttt gacttcctgg gttggattcc tgtctccgtg tctgactttc    19260
tctctttgtc atattttca tcactcgttg tcttttgcg tctgctctga cagatttcct    19320
caaatttgt cttctagtcc tatcctacag ttttactttt cagcaaatat aatttaatct    19380
ccaagagtac tctcttgttc tttttctta gcattctgtt cttgtttat ggatgtaaca    19440
ttctcttgga atatttgctg tcctctagat catcccttct ccatttcttc ttgggctagt    19500
```

```
tttctgttt cttcatcttt ctcttttatg ctacttattc tgggcgtgtt cttggtgggt    19560
tttttcccat atagcaacag aggacttgga gctcagggag aaaagggtag gtgcatcacc    19620
tggcagagct cccagacagt gacaggcagg ctgcgggaag gatgtctact tggcggtgct    19680
accgctttcc tagaaaccct ttccctggag ctggttgaac tgttgggttt tgccctggtg    19740
gtgaacgctg gctccccgtg ctctgcctgt ttcatcacca gcccctccc cttctgcctg     19800
gggtccagta atctgttgaa atatatatct tgctcattgg tgagctcctg ctccttcctc    19860
gttgctcttg cagatttatc acttctcgta aggctgcgct tgtacttcgg gattttctct    19920
gtgccacact gggaaacata gggtggttgc atgctgcagt cctgagcact tatttcactc    19980
acatctttac acgaagattt ggtgggtgtt tactttgttt ttagtaagtt agtctgtcat    20040
gtcctttgat cctttttttt tgttttttga gatggagtct ctctgtgtcc tccaggctgg    20100
agtgcaatgt cgcgatctca gctcactgca acctccacct cctgggctca agagattctc    20160
ctgcttcagt ctcctgagta gctgggatta caggcatgtg ccaccacacc tggctaattt    20220
ttgtattttt agtagaggtg gggtttggca tgttggccag cctggtctca aactcctgac    20280
ctcctgacct gcctgccttg gcctcccaaa gtgctgggat tacaggtgtg agccaccaca    20340
cctggccctg attaatcttt taatgcccag tctctccttc aaaagccggc tcctttctct    20400
ccctcgcctt cctagattcc ttctccactc cccaggatca gcctcctcct ccccacccca    20460
ccactgccgg ggggatgtct gtggtcaggc atttatcaga gaccctgagg tggggtcct    20520
ttatgtgtct gggggatgga gagtctagag gaggtagcgt tcagacctct ccatggtgcc    20580
tctgctgggc tcacatgtga ccaagcacag caaaccatga ggcagggat ggtcttgacc     20640
atgagagccc ttgcagcagc tgccatgggc ctcagctcct ctccaagctg gaagagccc     20700
tgaaaagcca aggtgttttt ttttcccctct ttatttcagt gtaagtccct tgagctttct    20760
tgaaccagaa gtgggctcat tttgcttag agatttcagg tgggcttgtc cttgtcctag     20820
catcccagat ccaccttctg ggaagtcatc agattggagg tgatgttggc agcttttgta    20880
aacaaagggt agtgttgtaa gctgttgtgt ctgcctatgt gtgtgtttgt gtacttggtc    20940
tcatctctgc agactggtga catggcttcc agatatgccc gacgatgtcc tgtggttgca    21000
gtgggtgacc tcacaggtgt tcactcgagt gctgatgtgt ctgctccccg cctccaggta    21060
aatactttgg ctgtgggtgt gtgggccgga cgggcacctc tctcatctga tgaggcctca    21120
cacgacattc tagaaacagc tggctgaaca ccaagcaagg agcttgccct tgggtgtggg    21180
gaccctgtct catgggaggc agctgagtca gtcagaggtc ctggcacacc tgctgagagc    21240
tgccacccag gccaacctga accggagcct gggaagactt cccgtcggat gagtctcttt    21300
gagtgcagca ttgatggtgg aagagcagag aggcccagga taagcaggga aaggtgcttc    21360
agacagagtg gctgggatga ggactgggga gtgtcagata gcgctggcgt gtctgagcga    21420
aggagctctg gcacccatgg cacaggaagg aggtgggacc ctggaggggc agggctagca    21480
gagctcctcg gagcgtgtgg ctaggtgcct ggtaatgcaa gccccctgtc ctccaccctc    21540
tgttgtactg agtcacagtc tccggggtga agcctagcag tctgcgttga caggccccag    21600
gggatgccgc tacttcctga attctgaatt ctggaaactg agccggagtt cagggcctgg    21660
ctcccattac cagggttggg cgttatcctg aaaatcatag gccttggttt cctcacttgg    21720
ctaacagggg tgatccccat cccctcaatg ggtttccgtg agctcctgag agcccgtagc    21780
atggtacttg gcacatgctg ggcatcagga ggtatggcct ctcttgctat tgttgttatt    21840
```

```
ggtagacaca gaaggattta aaagtagggg aatgcaaaga tccgatttgc tagggaagag    21900
ggcagtagtg gccaagtaga gggtggatcc tgggccctgg ctggcagcag gcagcaaggg    21960
gggctgccag ggcccaggca gggacgatct gtagaccgag aggcttccta aggctcttgg    22020
acaggaggag gtgtcggttc caagcctaag gagtggggca gccctggtga ctggtggtca    22080
gtggtgccag gcggtgggtg gtaggacacc ctggcaggca agtaggtttg tgtgggggaa    22140
actgataggc ccctccaggg attcgttggt ggacaacacc tgtgatgtcc agtgggaggt    22200
gtccaggtag ctgggagggc cacaggcttg gaagacctag gtggtgacat cagcccagca    22260
ctgagggcta aagaagctg tgtctctggc tgtgacggca ccctagagtg tgtgtggtgc    22320
cctctactgg ccggcaatgt gggtccaccg tagctcagac tgcacactgc agcagcggga    22380
acggcctcta agccaacttc ctccatgtgt ttcaggtccc aaatgccagt gagcagccaa    22440
caggcctccc catgcacacc tgagcaggac tggccctgct ggactccctg ctcccccaag    22500
ggctgtccag cagagaccaa agcagaggcc accccgcggt ccatcctcag gtccagcctg    22560
aacttcttct tgggcaataa agtacctgct ggtgctgagg ggctctccac ctttcccagt    22620
ttttcactag agaagagtct gtgagtcact tgaggaggcg agtctagcag attctttcag    22680
aggtgctaaa gtttcccatc tttgtgcagc tacctccgca ttgctgtgta gtgacccctg    22740
cctgtgacgt ggaggatccc agcctctgag ctgagttggt tttatgaaaa gctaggaagc    22800
aacctttcgc ctgtgcagcg gtccagcact taactctaat acatcagcat gcgttaattc    22860
agctggttgg gaaatgacac caggaagccc agtgcagagg gtcccttact gactgtttcg    22920
tggccctatt aatggtcaga ctgttccagc atgaggttct tagaatgaca ggtgtttgga    22980
tgggtggggg ccttgtgatg gggggtaggc tggcccatgt gtgatcttgt ggggtggagg    23040
gaagagaata gcatgatccc acttccccat gctgtgggaa ggggtgcagt tcgtccccaa    23100
gaacgacact gcctgtcagg tggtctgcaa agatgataac cttgactact aaaaacgtct    23160
ccatggcggg ggtaacaaga tgataatcta cttaatttta gaacacctt ttcacctaac    23220 taaaataatg tttaaagagt tttgtataaa aatgtaagga agcgttgtta cctgttgaat    23280
tttgtattat gtgaatcagt gagatgttag tagaataagc cttaaaaaaa aaaaaatcgg    23340
ttgggtgcag tggcacacgg ctgtaatccc agcactttgg gaggccaagg ttggcagatc    23400
acctgaggtc aggagttcaa gaccagtctg gccaacatag caaaaccctg tctctactaa    23460
aaatacaaaa attatctggg catggtggtg catgcctgta atcccagcta ttcggaaggc    23520
tgaggcagga gaatcacttg aacccaggag gcggaggttg cggtgagctg agattgcacc    23580
atttcattcc agcctgggca acatgagtga aagtctgact caaaaaaaaa aaatttaaaa    23640
aacaaaataa tctagtgtgc agggcattca cctcagcccc ccaggcagga gccaagcaca    23700
gcaggagctt ccgcctcctc tccactggag cacacaactt gaacctggct tattttctgc    23760
agggaccagc cccacatggt cagtgagttt ctccccatgt gtggcgatga gagagtgtag    23820
aaataaagac                                                          23830

<210> SEQ ID NO 31
<211> LENGTH: 23830
<212> TYPE: DNA
<213> ORGANISM: Homo sapien

<400> SEQUENCE: 31
atggtccgag gggggcgggg ctgacgtcgc gctgggaatg ccctggccga gacactgagg       60
cagggtagag agcgcttgcg ggcgccgggc ggagctgctg cggatcagga cccgagccga      120
```

```
ttcccgatcc cgacccagat cctaacccgc gcccccgccc cgccgccgcc gccatgtacg      180
acgcagagcg cggctggagc ttgtccttcg cgggctgcgg cttcctgggc ttctaccacg      240
tcggggcgac ccgctgcctg agcgagcacg ccccgcacct cctccgcgac gcgcgcatgt      300
tgttcggcgc ttcggccggg gcgttgcact gcgtcggcgt cctctccggt atcccgctgg      360
gtgcgtctgg ggacgctgcc cgggctccac gtgcggagtg ggtgcccccct aggccgggga      420 gcggggatc cccaggggtc gcggggccct ggaggagcgg gcatcggacg cggacacggc       480
ggggtgcatc ccgagggccc cctccgaggc agatgcttcc tgcggggcg ctgttcctgg       540 gcccgggaag gggcgttgg aaccccgagc ggtccgggcc gaagcctggg actctcgtgc       600
gtccccaccc ctaccccat caggcgcccg tgcatgaagg gagaccctca cctccggact       660
gagagtcgga gcgtctcgga gcgacgggga gtagggagcg ggacccgggg cggagggtag      720
tgctggcccc tgcggactcc gggtcccctg tgtcctctcg ggaggggctg gacgggctga      780
gctgccgagg ggccgatttg ccctgggccg gacaaagagt gggggctttgg ccggtccccc     840 acggtgggct ccttcccttct ggggattgag ggactcaaga caccccgcgc ctgcgctttt    900
cttttctttt tttcttttt tttttttgag acggagtttc gctcagtcgc ccaggctgga      960
gtgcagtggc gtgatctcaa ctcactgcaa gctccacctc ccaggttcac gccattctcc     1020
tgcctcagcc tcccgagtag ctgggactac aggcgccagc caccaagccc ggctaatttt    1080
ttgtattttt tagtagagac ggggtttcac cgtgttagcc aggatggtct cgatctcctg    1140
acctcgtgat ctgcccacct cggcctccca gaatgctggg gttacaggcg tgagccactg    1200
ctccctgctg cctacgctct ctgggtcgca gcccagcctt ctggggggctg ggtagcctcc  1260 cagaagggca accctgggca tcctccaggg caggctaact ggagtctagt ggggagggggt   1320 accttgaaag aggaaagttg tttcctcctc ctcctcctcc tccagtgttt gggacccttc   1380 ctggggggctg gagtgcatcc ctggacaccc cccaatccca tcctcttctc tagtttccac   1440
tgacctaggc ccaccctccc ctctccggct cagtactcct ggaaatgaga ttccgtacat    1500
ttgaatcttg tcctaatgaa atatttgtcc atgtgggtac ctgtgtgtgt gtggtggggg    1560
tgcagacgga gggtttgttt ctcactagct ggaactactg gggtgtggta tgcttcctgg    1620
gaatttgtgt gccacagtcc tggaggcgag gaggggggttg tgagccagta ggcaggggct   1680
ggggcaagta gcattgtgaa gctattgaca cccagacgtc cccaggcagg agattatgcc   1740
cccattagcc cccttttatc tgggcttcct taacaatgga ctctttgccc tgcctgccag   1800
agccagcagg gagtgactgt tcagtggtga ggaagcgggc agaggaagcc ctgccattgg   1860
gtaggagcag tgggcagccc ctgggctgac tgggaggtgg ggattaggga ttagacagtc   1920
ctggctgtct gccttcccct aagccagggg gagaggagca aagggcacga aatgtggcct   1980
ccaggaggat tagaccgcca catgatcatt tgcacaccct ggggtttagc aacaataaaa    2040
gtcagctttt ttgtatccca aggtggcctg tggacaccca catggacaaa tgtttacact    2100
gggacagaat tcaaatgcag aggtcccagg agcctaaagt acactcactc tggtatagaa    2160
aggattcctt actgggcaga ggacaggtgc agcctgggc tttccaggc aggacacagg      2220 gaggctcagg aaccaccaag tccctggaag gtggatctgg aggcgttggc aggagccact    2280
ccctgggttc cagggctcca ggttcctgct ttaaccccct gtctcacaga gggctgtgca   2340
cttgggggct gctgagcatg tcccagaggc tgcatcctgg acacagcacc tcagtgcatc   2400
tgagctgagg ctaacttggc aggagggaca ggcagaacct gccagccacg tgcaattcca   2460
```

```
cccctctggc cactcaggga aggagagctg tgagtcaaga tcagatttgg gtcaggacag    2520 gctgggcct gcctgtccct gtgcatccca agatttatgg ctggccaggg gttgggctgg    2580
gaggggtggt cttgcatgcc aggagagtgc agatcagcct gagaggccag gccagtaagt    2640
gaggtcagat ctcctgcacc tgatagcatt aaggccatct acaccaaagc tctaatgctg    2700
atatgttcct ggcctctatg tggggcatgg aggtggggca tggaggtgag gcctgctcgc    2760
ctgggcttct ggaagtggga gactcattcc tgtggctgag gcctacagca gtgctgtgtg    2820
gtaggaatac actggaagcc atgatgtcat tgtgcatttt ctagaagcca cattgaataa    2880
agtaaaagac acaggtagaa ttaatttcat tgagcccaat atatccaaaa taatatcatt    2940
ttcacatcta ttcaatataa aaatttacta atgagatatt tcatactaag ccactgaaat    3000
ccagtttgta tcttacacat ctcagttttg acgagccaca tttcaagggc gtatagccca    3060
catgtggctc ccatagtaga cagtactggt ctagagaaat gttggtggca tccttgctgt    3120
ctggtttctg gccttgccaa aagtattacc atcccagtgt ggtacattct ttcatgtatt    3180
tgtctcctgt ccccagagca gactctgcag gtcctctcag atcttgtgcg gaaggccagg    3240
agtcggaaca ttggcatctt ccatccatcc ttcaacttaa gcaagttcct ccgacagggt    3300
ctctgcaaat gcctcccggc caatgtccac cagctcatct ccggcaaaat aggcatctct    3360
cttaccagag tgtctgatgg ggaaaacgtt ctggtgtctg actttcggtc caaagacgaa    3420
gtcgtggatg taagcagttt gcttatctgg acgttgtcaa gttagaaaag ctgttttggg    3480
atgggtgtgg tggctcatgc ctgtcatccc ggcactttgg gaggccgaag cgggtgggtt    3540
gcttgagccc aggagctcga gaccaacatg atgaaaccca gtctctacaa aaattacaga    3600
aaaattagct aggcatggtg ttgtgggccc atagtcccag ctactaggga ggctgaggca    3660
ggagaattgc ttgagcctgg gaggtggagg ttgcagtaag tcatgatcat gccactgtac    3720
tccagcccgg gtgacagtga gatgctgtct ggaaaaaaaa aaaaagaaa gactgttttg    3780 ttttggaagc aacacaggca gttgtaggcc ccctgtgcca gagtgacata aactctgtac    3840
acctccagtg atttggtcca tgtttgtaaa ccctgaatgt tccagggcag tttcttttct    3900
tcacttttta tctcttttttt ttgggtgggg ggcggggta cagagtcttg ctctgtctcc    3960
caggctggag tgcagtggcg caatctcaac ctcccgagga gctgggacta caggcacagg    4020
ccatcacacc ttgctaatgt ttgtactttt tgtagagacg gggttttgcc ctgttgccca    4080
ggctggtccc aaactcctgc acccaagtaa tctgcccacc tctgcctggc agttacaatt    4140
tcaaataatt cctcccttttc cttcaacact tggctcatga ccgtccagtc caaggaacct    4200
gtcctgcagg tgtgcctctc ccgagcttcc tctatgcatc ttccataatg aagatgcctt    4260
ctcactggaa accctacaag ggtgggaacg tgccttattt gcctgtatcc tcagggtcta    4320
gcagagagaa gataatttgt aataccaaaa caccattaaa ttcagctgat gctttcataa    4380
gcgctccttg gaggaaggac tccatttact tgacagatct gtgcaagaca gcagcctggc    4440
gcgtctaacc tgcagccagt tgcatcctct gtttaacctt gtttgcggaa gctttctcta    4500
aacagccagc acttgtctgt tcccacatgg gtccgttctc ccagtgaatc accgtggtgc    4560
ctgctgactg ctctgtagca cagtgcttcg caaagtgtga tcctgggacc agcagagcag    4620
cagctccttt gagcttattg gaatggcaga ccctcaggtc ccacctctga cctgctgcat    4680
gggaattctg gggagggacg cagaatctct ggttccacag gctctccggt gatgctaatg    4740
aataccggca tttgaacagc accgatctag ccccctttcag tccatgagcc aacaacccctt    4800 ggtcctgtct gtggtgaccc agtgtgactc tcatggggag caaggagagg aagttgaagt    4860
```

```
tcactgacag ggttgttaag gggattatgc aatagatgag acccatgggc ctgaagtccg   4920
agggtgtatg ttagttcccc gttcttttga cccatggatt aacctactct gtgcaaaggg   4980
cattttcaag tttgttgccc tgctcacttg gagaaagctt atgaaggatc aggaaaatta   5040
aaagggtgct ctcgcctata acttctctct cctttgcttt cacaggcctt ggtatgttcc   5100
tgcttcatgc ccttctacag tggccttatc cctccttcct tcagaggcgt ggtaagtcgg   5160
ctttctctgc tagcgctgag tcctgggggc tctgaagtg tgctcacaca tctcctgcct    5220
gcagggcact ggtgtcgggc acctcagggt ctgtcccatg gtggagcccc atgcctcact   5280
gcctttcaga cagagtagcc acagctggcc ctatttccag ctacccggg cagcaaaact    5340 tactgcatgt gtaattaatt atttggctat ctgtaaggta aactggctgg ttcacttaat   5400
ctgcaccttc agcatcagat agcttctcag tgatctagtt aaactatatg atgttggcca   5460
ggcgcggtgg ctcatgtctg taatcccagc actttgggag cctgaagcag gcagatcact   5520
tgaggtcagg agttcgagac cagcctggcc aacagtgtga aactctgtct ctcctaaaaa   5580
tacaaaaatt agctgggcat ggtggtgtgc acctgtaatc ccagctgctc gggaggctga   5640
ggcaggagaa ttgcttgaac ttgggaggcg gaagttgcag tgagccaaga tcgcaccact   5700
gcactccatc ctgggtgaca gagcgagact ctatctcaaa agaaaaaaa aaaaaaggt    5760 aaataaagta tatgacactg aagaatctgt taccccctgga aggtggagct ttactcttag   5820
ggggaactat aacagtcata tatatatatt tttttctttt cttttttttt tttttttgaga  5880 tggagtctgg ctctgtcgcc caggctggag tgcagtggtg caatctcggc tcactgcaac   5940
ctccacctca caggttcagg caattctcct gcctcaacct cccgagtagc tgggattaca   6000
ggtgcctgcc gtcacgccaa gctaattttt gtattttttag tagagacagg gtttcatcat   6060
attggccagg ctggtctcca actcctgacc tcaggtgatc cgcccgcctt ggcctcccaa   6120
agtgctgaga ttacaggcgt gagccatggt gcccggccaa caatcacatg tgttgtaaac   6180
aacaacaaaa atctgtcagc ctggtctaac ctagatttgt gctttgtttt gttttgccac   6240
tttgtgatgc acaggaggaa gtttaggctg taaaatacta gccttttagg gtaattttg    6300 aactcacaag agcagcagcg gaacctttga tgcaatcctg tatgtagcac cagcagagcc   6360
acgtggcaga gggactcgca ttaggagcct cccattacag actacgtgct cctgtgcgtt   6420
atcttatagg gtccccacaa ccaaggggag atgtgattat tcatcctgtg tggctgtggg   6480
gaacttgaga gtcatacttg cccaaagagc acggccagcg agcttgcacc caggtcactc   6540
tctgctcctc tgtcagaaca gggcatgtct tggttcactg cagggcggct cttctcattc   6600
tctgtagttt ggggtccagg atagtggtcc acggagccac tggagtgccc agctactgag   6660
tgaccaaagc atattttgga tttccgacat tgccacagca tggttgggca tcagcaggac   6720 cccaaccccct tgttatgctg gtggctttat gtggttattt gatcttcccc agaactcagc   6780
aggagtgcac ccagcagcac cgtagtgatg ctctctggct ccccagtgca cggttctggc   6840
tttccttcct ggtcgagagt ttcaagccct ctgggtccta ctctgtcctt ttcagcccat   6900
agctttgttc aaaagctgct ggcagtgttc agatttggct gagttcagtg aatatgtgca   6960
ttggctgatt tctgagccat gccaggggga tggagaagcc gaagcaggag tgtttgttct   7020
gcaggctctg gagtaggcat tgggtctgtg ccggctcact tgctagtctt gcatccttcc   7080 ccaacccccct ctggggatgt ctggccacat cagaagacag tttgggttgt cagaactggg   7140
ggagtaccag gccgaggtgg gtggatcatg aggtcaggag atcgagacca tcctggctaa   7200
```

```
cacagtgaaa cctcatctct actaaacata cgaaaaaaat tagctgggcg tggtggcggg      7260
cgcctgtagt cccagctact cgggaggctg aggcaggaga atggtgtgaa cccgggggc       7320 ggagcttgca gtgagctgag atcctgccac tgcactccag cctgggcaac aaagcgagac      7380
tccgtctcac aaacaaaaca aaacaaaaca aacaaaatc tggggagtg ccactggcat        7440 ctgatgtata gaggcccgag atgctgtgtc atcacccgtt gagtgcgctc ataggcatct      7500
tcctgacaat tagaacccat tattcttcaa attcaatgca agcaaattca aagcattact      7560
gtgtacatac cgcatgctaa tcaattgcac cactggagct cctaaattca aaacattact     7620
ataaaaaagt tcaaaatgca tggaaaagtt gtacatggca ggagaatatt tgggcttctg     7680
actacccctt gaatgaagat gatccaccag ccgccttcct ccttggtctt cactccagat     7740
tcctagcatt tcattctgtg tctctttatg cagtgaggtt tttgtttgtt ttttgagaca     7800
gagtctcact gtatcaccta ggcctggagt gcagtggcgc gatctcagct cactgcaacc     7860
ctcggctcct gggtttaagc gattctcctg cctcagcctc ccgagcagct gagattacaa     7920
gcacacatcc ccatgcccag ctaattttg tattttagc agagacaggg tttcaccatg       7980
ttgcccaggc tggtctcgaa ctcctggcct caagtgatcc atgtgcctca gccttccaaa     8040
gtgctgggat tacaggcgtg agccaccatg cccagctcct agtgaggttt ttgatgcctt     8100
gctacatctg ccctagaaat tgtgtgacta cgattttgga aatgttgctg tgtaaacttg     8160
tgatcatttc tggactccag gcaagaatct tgatggctaa ggtgtggctg aacatgtctg     8220
attctctcct ggacctgttt taggccaaac tctgctctga aattcctccg tgtggaaggg     8280
cgggctgggg agagcctccc agctggaatc ttttggatgc cttctctgt gggtatctga      8340 tggctggctc tgatggctgg ctgtgatggc tgtggctgga aatcattgtt gacatgagtt     8400
tcacagatgc aggctctgtc caaattgtag caaaagctgc ctgccccagc cgagctatgg     8460
gcaataaggt ggtttaagga tatagatgaa ggaaaactca cccttagaat aatttatcca     8520
aaatgctgct gtgttgtggg ttagaggaca ttttctgagg tcccaggttc attgtttcat     8580
ttaagtctca aaagtccctc caggtgttgg ttctaattgt caaagcatgg ggggagatgg     8640
gctcatgggt taaaggtctt atcccagatt tctgtatcct ccttgcaagc agcaaagggg    8700
tctggatttg aatccatgac catgtttctc ctttgggttt ccatcacact ctgtccccgt     8760
gcactgagca ccctttagtt catatgaccc cctaggcat gttacatggg cactcctata      8820
ggtgcccatc tggccctagg acttggccaa cacaacatgg actccagttt ccatctgcct     8880 cttttgccagg cactttttgtg cagtgcacac actgtacaac agtagacggc aaccctgaga   8940
gccagagtag agcctgtcct agcaccggaa tgctcggtaa ggattttgtcg caggagtgat    9000 tccaaagcca atgtcctccc tccatatcag cctgtttgtg gctctgagaa gctctgccca    9060
catgtgaaag cttgttaagc acttaagcac taacccagag cttcagacag tgccagtcct    9120
ttttcccctt ctttaaaagc gatatgtgga tggaggagtg agtgacaacg tacccttcat    9180
tgatgccaaa acaaccatca ccgtgtcccc cttctatggg gagtacgaca tctgccctaa    9240
agtcaagtcc acgaactttc ttcatgtgga catcaccaag ctcagtctac gcctctgcac    9300
agggaacctc taccttctct cgagagcttt tgtcccccg gatctcaagg tgagttggtg     9360
gtgagggggc aggtgttctg gggtgcagct cttctttgcc tccctgattg ccaggagcta    9420
ccagttactg tctgcacaat caaacagaaa tagacctgtc cttgatggtt aacggaaata    9480
aaaggcgctt gtcccagaag ctcaggtgag gcaccaccct gattatggga atcacctggg    9540
aacatatacc cagacctaaa actcagatcc acttcccagg ctgtggttat atagtcaggg    9600
```

```
gggtgcagta tgggtattag gatttttat ttttagtta taaagatttt ttttggttt      9660 gttttgaga cagggtcttg ctctgccgct taggctggag tgcagtggtg caatcatagc    9720
tcactgaagc ctcagactcc tgggttcaag cagtcctccc acctcagcct cctaaggagc   9780
tgggacccac aggcatgcag caccacacct ggctaatttt taaaaattt gtggagtgtt    9840 gcccaggctg gtctcacact cctggcctca gcgatcctc ccaccccagc ctcccaatgt    9900
gttgggatta caggcatgag ccattgtacc cagccactaa gatgattctt atttggaaac   9960
acggtcaaga caactgcgt tcggtagttt aaccttttt gattgtggtg gttttagtat    10020
gccttaccac tctaccatag taagaaattt gcagaccatg tacaccaacc tttggtgctc   10080
ctggggagaa agaaagaagg ctatgcaatg caatgcatgc tcacagtcca agggagaggg   10140
aaagctgtct aacaggattg gttttcccgt gtgctttata agcagatgag tagaggagac   10200
agctcttatt gtcctagtgg caattgggat aggctgcaaa gtttgttagg gtggaggctt   10260
attccgggac caagggagcc caaagaaaca agctcctgcc aggcgcggtg gctcacgcct   10320
gtaatcccag cactttggga ggctgaggca ggtggatcac ctgaggtcag gagtttgaga   10380
ccagcctggc caacatggtg aaaccccgtc tccatgaaaa atacaaaaat tacccgggca   10440
tggtggcggg cacctgtaat cccagctact agggaggctg aggcaggaaa atggcttgaa   10500
cctcggaagt ggaggtggcc gttagccgag atcacgccac tgcactccag cctgggcaac   10560
agagcaagac tctgccttaa aaaaaaaaa aaaaaaaga aaagtaaaag gaaaaaaaag     10620
aggctctggc ctgctggggt gcctgcaaag tctccgtgga agggtgacat tcaagccgag   10680
acctccaggg aactgtctcc tgggagcaca gagccctttg ctcagccccc aggtggctca   10740
gtgcccccag ccagcagact cagagcttgc atgattcttt ggtgctctct gcggtcttcc   10800
aatgatgctg aaataaatgg tgcttggtgt ctccctgctg tagtcccctt gcttgctttg   10860
ctcacaggtg ctgggagaga tatgccttcg aggatatttg gatgcattca ggttcttgga   10920
agagaagggt atgtatgggc tgggaggatc agccatgccc ttttgacaag catttactag   10980
cggtcttggt aaagacttga gatttgcctt agttctaaca cttagtgccc aacgccttcc   11040
ttgtgttgct caacctactc atgagcccag gagataggaa atctccgtcc cattgtacag   11100
atggggaaac agaattttgg aaaggagagc caagcagcac acacccctcc ctgaggggca   11160
gagccgagat ttgaactggg atgtcatgac tccagggccc tctccctccc cagggtcccc   11220
ttatctgaag gcggttttc tttccagctc gacctcttgt gacccttagt ttaacaaggg    11280
ccgaagttaa agagtttctg cgcctggacc ccaaatgaag caatcagatt tctcatctcc   11340
agtcaggtgt gggtccaagc ccactagaca agtttgctct tcccagagca catttctgcc   11400
ttcaagtcat cctggcttgt cagggctggg ggagttctgc tgtagaaata ttagagtgga   11460
aggaaaaaga tgtgttggga gctattttc tttaatacta aaagttggtt gatgaatttg    11520
tcgttggcca agaccaagga gactgcattt taaggacat atgtgtattt atctgctcag    11580
aaaatgttca ttgctgtgtg ctagggatac tgcagtgaac acagaggtgt gacccttgcc   11640
agccttgtga gagaagtgag cagataagta agcagaaggg tgatgctgtg tcgatgggaa   11700
agtacaggtg ccaatgagaa ggcacaggtg tcaaggagaa gacacaggat gctggaggct   11760
catgcaggat ggatctccaa ggcccagggg aagaagggcc tctcggagga cgtgaatcca   11820
cattaagact ttggggataa gtaggagcgc cttaggcatg ggacccatg gatgcgaggc    11880 ctgtaggaca cagacaggat ggcatgaagg cctgtgcaac tggaggggtg gggatgggga   11940
```

```
cactaagaga tggctggaag tgtgggggtg gggacactaa gagatgactg gagaagaggg    12000
ggtcaggagt ggtgaaaaat gggagaggag ggcaggctgg gccttttgga tacaggggga    12060
ttgcatcctg cagtggtagg gagccactga gggctgctgc agtaggagtg aggggatcag    12120
aggagagctt tggaagcccc ctggatgcgg gacaggaagc gagataccag tgtctaggag    12180
gccagtgagg cagccacagg ctccaccagg atcagggctg cgagggtcat gaggaggaaa    12240
ccaatttgaa ggagtccagg ggaataggac ttggaaatga ccgatgggac atttgggaag    12300
aggaagacag aagagcgcag tcccggcttc tggctttagc agttgggcaa ggggagatgg    12360
ggagatgtgc ccatgggttg agggttgagg acattaggag ggagccggta tggcaggaag    12420
agctggtgtg ccagagatgc tggaagcagc atctgcctga aacagatac ctggcaatat     12480 tcctaaggga aagtgacatc tcggagggtg aggagggcat ctgatagggc ctggaaagag    12540
ccggggcaag catgaatgtg aggttatctt gggggcaag gctcaggcgt tgaggagcag     12600
cccctggtct cttcagcctg aagttggaag ccagagttgg gccaggtgca gctgtggttg    12660
tctgaagtcc ccctccccca gcccagtgtg ccaatgctgt aagagcaagg gccgctcact    12720
ggtgctggtg gctgagtccc agcacccagg acagggcctg gcacatactg gtgcccaatc    12780
ctcccttctg ggtgcttctt ccaaggcctt gtgatgaag tgagtaccct cttcgacatc     12840
agacccagct tcaaatcctg gctctgctat gtattggctg cgtggcttta gacaagtctt    12900
ttaaccttgc tgtgcttctg atttctcagc tgaaaaatgg agatgatgat agtggttct      12960 gtaaggcctt atggtgaagc acctagctca gggcctggaa ggcaggtgta accagtggtt    13020
cagttgttat aaaccaacac taaccctcgc ctttgcacct catgaaacca gatatgtaga    13080
tggagcccac aaagctagca ggagccaagc tcacgtgtgt cctgctttaa agccccatac    13140 cccttttctcc gggtgacaaa cacctgtgct cgttctcttc ccttccctc ttcccctttgc    13200 atttggctaa taacaggcca gctgcctgcc tccctgcagt ttggtagatg ggtgggtaac    13260
gaccaccact cccacgttcg cctgatgggc ttgttttccg tgcccttcac aggcatctgc    13320
aacaggcccc agccaggcct gaagtcatcc tcagaaggga tggatcctga ggtcgccatg    13380
cccagctggg caaacatgag tctggattct tccccggagt cggctgcctt ggctgtgagg    13440
ctggagggag atgagctgct agaccacctg cgtctcagca tcctgccctg ggatgagagc    13500
atcctggaca ccctctcgcc caggctcgct acaggtaccc actcctcggg gtgagcacgg    13560
gcagcacctt gttttctttc ttgtgcatta tggaggaaga tggtactgcc acatgggagc    13620
gatagggtga ggcaaccatg acaggtggtt gggaacatct ccttccatgt gtacagcctg    13680
ggctgctgcc atcactccca gcacagcccc caacccccc aatcctggaa ccttgccaag     13740
tctcccttcc catggggtca tgaccaggag gaaaacaaac tccagctgag cccccttgggg   13800 ttccccatat aggctcctgc ctgtggcagc tgggccctct gtaccccttt ccaactctgt    13860
ctccctaaca tggcacctga gctcctgcca tcctggattt catggacccc aaggatgggg    13920
gtcctgcatc tgggacttgg cctattactc ggagctcctt ttcagccgcc tcctccacc    13980 tgtccaccca cctcaaggct ccttttcttga gacctctcct aatttctccc ttcccctaaa   14040
cccacaattt tgaacctcca tcgaatggtg ctgtattta taatgtcatc aaatatcaaa    14100
tggagacagt gctatggtcc aaatgattgt gtaccccca gaatttgtct tttgaaatcc     14160 taaccccccaa catgatggtc ttaggaggtg gggcctttgg gaggagatta ggtcatgagg    14220
aaagggctgt catgaatggg attggtgccc ttattaaaca gacccaagag aggtcccttg    14280
tcccttctac tgtgtgagga ctcagaaggt ggtgtctatg aagaagcagg ccctcaccag    14340
```

```
acaccaacat gtctgctgcc ccttgatctg ggaccttgca gcctctagaa ctctgaaaaa    14400
tcgatgtttg ttgttttata agccactcag ttggtggcat tttgttagag tagcctgaac    14460
acggactaag tcaaacagaa gaacccacaa accagctaca gagttgggca tttggagaaa    14520
ttcaaaaatg agtcagacat aactccttat tcttgaggtg ccctaagaga tgggacacag    14580
cagctgccca ggtgcattag tttgttctca cattgctata aagaaatacc tgagactggg    14640
taactcataa agaagaggt tgaattggct cacagttgca caggctggac aggaagcatg    14700
gtgctggcat ctgctcagct tctggggagg cctcaggaaa cttacaatca tggcagaagg    14760
tgaacgggaa gcatgcacat cccatgactg gagcaggagt gagagagaga gggaaataga    14820
gggaaggtgc catacacttt taaacaacca gatctcatga gaacacattc actatcaaga    14880
gaacagcacc agtggggaaa tccgccccca tgatccaatc acctcccatc aggctccgcc    14940
tccaacactg ggaattacaa tttgacatga gatgtgggca gggacacaga tccaaaccat    15000
atgaccagat taatacgatt tgaggcatca cgaggtcatt aaagagaggg aataaaagac    15060
tggggctcca ggaagaaggc tctggaatcc agcagagggt caaggaccag cttgtaaagc    15120
tggtggtgcc tgagaagtac ctaggagaac atagatgctg tgacgtttga tgtagctgtt    15180
ttttgttttg tgttttggtt tttgagacag agtctcactc tgttgcccag gctggagtgt    15240
gcagtggcgt gatcttggct cactggagcc tccatctccc aggttcaaat gatcctcatg    15300
cctcagcctc ctgagttgct gggattacag gtgcacacca ccacgcctgg ctaatttttg    15360
tgttttcagt agagacaggg tttcaccatg ttggccaggc tggtcttgaa ctcctgacct    15420
caagtgatcc aacaacttca gcctcccaaa gtgctgggat gacaggcatg agccaccatg    15480
cccagcctga tgtagctgtt tctgtgcaca ttatttgctg tggggtatat tcagatttct    15540
taatacaaga tgattctttg cctcatgact tacacaccat tttctattta atttcagcta    15600
tgatattgga aatggacatg tcttttcaag gaaaataaaa gcaggctttc tggaatggcg    15660
acttccaaac atatttgtca atttaaagga gctgggagtg gggaccctat gctccgtaag    15720
cactctctta gctgttcttg gctgtgctcc ccgcttcagc ttcacactgc ccttgctgtg    15780
aagggagcag cctgggccgg gcgcggtggc ttacacctgt aatcctagca ctttgggagg    15840
ccgaggtggg tggatcacct gaggtcagga gttcaagacc agcctggcca acatggtgaa    15900
actccatctc tactaaaaat acaaaaaatt agctgggcat ggtggcaggt gcctgtaatc    15960
ccagctactt gggaggctga ggcagaagaa tcgcttgaac ccaggaggcg gaggttgcag    16020
tgagccgaga ttgcgccatt gcactccagc ctggggcaa caagagcaaa actctgtctg    16080
gaaaaaaaag aaaggagcag cttggcaaac cccaccttgt cgcttttgtg agtgcctctg    16140 acccctttggc tgccaggacg ggcgtatttt atggaaatgc taagcaccaa cagagtaaag    16200
tggtttggtt tttcacagtg gtgggagata atagctccaa attgtctttt tcagcactga    16260
gtgaagaaat gaaagacaaa ggtggataca tgagcaagat ttgcaacttg ctacccatta    16320
ggataatgtc ttatgtaatg ctgccctgta ccctgcctgt ggaatctgcc attgcgattg    16380
tccagaggtg agcattttag gtggctccgt gtcttcctca cagggttgat atgaggatga    16440
aacaagatga tagatcatgg tggcatgtag tctgggacct ggattgtcgt gccacagatc    16500
acagctcaca gtctatgtgc aatgcccctg aatgttgccc acctgtcctc aagccacaca    16560
tgcacctgta actcagtgca agcccagaaa ctccccgtgg ggactcctag agctgtcagt    16620
ggcctcacat agcagctggt ccagtctctt gtgattgccc aaggaaactg aggcctggag    16680
```

```
agcttggggt cactgctctg aggccataga gatgcctagt agaagggcca ggcctagaag    16740
caggatcctt gctgcccctc tgagctgttt ccatttaaaa tcacatgaag gccggcgccg    16800
tggctcacgg ctgtaatccc agcattttgg gaggccaagg tgggtggatc atgtgaggtc    16860
aggagtttga ccagccttg gccaacatgg tgaaatgcca tctgtactaa aaatacaaaa     16920
attagtggag catggtggca cgtgcctgta ctcccagcta cttggaaggc tggggcagaa    16980
gaatcgcttg agcctgggag gcagaggttg tagtgagcca agattgtacc actgcactcc    17040
agcctgggtg acaggagaga aaccctatct caaaataaaa tgaaaggtaa tgaaatgaat    17100
aaaataataa atcaagtcac ggccgggcac ggtggctcac acctgtaatc ccagcgcttt    17160
gggaggccga ggtgggtgga taatgaggtc aggagttcaa gaccagcctg gccaacatgg    17220
tgaaaccatg tctctactaa aaatacaaaa attagctggg catggtggtg catgcctgta    17280
atcccagcta ctccggaggc taaggcagga gaattgcttg aagcaggacc taggaggcgg    17340
aggttggttg cagtgagccg agatcatgcc actgcactct agcctgggct acagagcgaa    17400
actccgactc aaaaaaaaaa aaaaaaaaaa atcaaatcac atgaaagtag aacataggga    17460
attccatctt tcgttctagg catagtttgt taatatgatt cagagccagc agttaggaga    17520
acacagtgtg actctcctag aacttcttga ttgggcttcc tctgattggg tttcctctga    17580
ttgggcttcc tctgaaagtg ggggggatgg ggggtgggga gcagaatggt cagagcttgg    17640
ctcagcagtc agactgctct tcttcaaatc ctggctgcat tgcttactac agctgtgtga    17700
ctccagatga ctgaatccac ctctctgtgc tgcagcttcc cgtctagaga gatcacctgg    17760
agcagagggt ggtcaggaga ctcaatctgg ttactgactc acagtgcagg agtactcatc    17820
ccatagtaag catccagcta gagatgttga tttctatttt caggtaataa tgatgatcgt    17880
aaaattagag acagataaaa ggtatgggca ttaggccagg gcactgcaat ttctaagctg    17940
tgtgacctca ggcaagttac tcgacttctc tgagcctcag cggtttcatc cgcaatatat    18000
ggataggaaa accgacctca gtgggttgtc tgacagtgga gggcacttga ttaaaaaaaa    18060
aaaaattacc ctggtctgaa tattaccctg gactgaaaga aaaatattga gctaatacag    18120
gcatcaggaa tggggctgca gggagtccag ggaagggaga acgaagagcc tgaaggtgtg    18180
aggaggtgcg agtgctgatc tgtctgctac aaagaggctg ctgagcctcc tgtggatgtg    18240
gccctggact tggcagttta atacctgagc tgttaaaata acctcagatg ctgtgttctt    18300 taagggtag gattcagatt cctgctgaaa tgcttctgaa agggagggaa tgagccagcc    18360
catccccagt tgcttttaa gatcattggg aagttctggt cttgccattt gtccctggac     18420
cactcttagg tcctcctgcc ccacttccat ctgggtgtgt gccctgggct gtccaccaca    18480
cagctacatc ctgccatctt ccctcctgga gccactgtgc catgcatgga tctgtagctt    18540
catttttctt ggcttttccc tggttttttct ggagcagagt ctctagtaaa ctcccaagga   18600
agaaaacgtt tgacttttatg tgtgttggga aacgtgctttt ttttctatta catctcagtg  18660
ataggttggc catgtctaga attgcaggtt gaaaatcatt tcctctcagt atattggtta    18720
gtgagaagcc tgggactgag acagtcacat tctcacttct tgcaggtga gtgctcttag    18780 gactgtcttt ttatccctta tactctgaaa tgtcatatgt cttggtgtaa gtccttattt    18840
cagttattga gctggacaag tactggagac cccttcagtc aaagccttct gtcattctcc    18900
agctctagga aattatcttc tattgttatt tctgttattc cttcccttcc attttctttt    18960 ttctttttttt ttttttttttt ttgagacagg tcttactct ggtgcccagg ctggaatgca    19020
gtgacctgat catggtacac tgcagcctga acctcccaga ctcaagtgat cctcccacct    19080
```

```
caacctccta agtagctggg actgcaagca cacatcacca cacccaacaa atatttttta   19140
aaaattttgt aagatgggat cttactatgt tgcccagact ttttcttcct cttcctgggg   19200
ctcttattag gaagatgttt gacttcctgg gttggattcc tgtctccgtg tctgactttc   19260
tctctttgtc atatttttca tcactcgttg tcttttttgcg tctgctctga cagatttcct   19320
caaattttgt cttctagtcc tatcctacag tttttacttt cagcaaatat aatttaatct   19380
ccaagagtac tctcttgttc tttttttctta gcattctgtt cttgttttat ggatgtaaca   19440
ttctcttgga atatttgctg tcctctagat catcccttct ccatttcttc ttgggctagt   19500
ttttctgttt cttcatcttt ctcttttatg ctacttattc tgggcgtgtt cttggtgggt   19560
tttttcccat atagcaacag aggacttgga gctcagggag aaaagggtag gtgcatcacc   19620
tggcagagct cccagacagt gacaggcagg ctgcgggaag gatgtctact tggcggtgct   19680
accgctttcc tagaaaccct ttccctggag ctggttgaac tgttgggttt tgccctggtg   19740
gtgaacgctg gctccccgtg ctctgcctgt ttcatcacca gcccctccc cttctgcctg   19800 gggtccagta atctgttgaa atatatatct tgctcattgg tgagctcctg ctccttcctc   19860
gttgctcttg cagatttatc acttctcgta aggctgcgct tgtacttcgg gattttctct   19920
gtgccacact gggaaacata gggtggttgc atgctgcagt cctgagcact tatttcactc   19980
acatctttac acgaagattt ggtgggtgtt tactttgttt ttagtaagtt agtctgtcat   20040
gtcctttgat cctttttttt tgtttttttga gatggagtct ctctgtgtcc tccaggctgg   20100
agtgcaatgt cgcgatctca gctcactgca acctccacct cctgggctca agagattctc   20160
ctgcttcagt ctcctgagta gctgggatta caggcatgtg ccaccacacc tggctaattt   20220 ttgtatttttt agtagaggtg gggtttggca tgttggccag cctggtctca aactcctgac   20280
ctcctgacct gcctgccttg gcctcccaaa gtgctgggat tacaggtgtg agccaccaca   20340
cctggccctg attaatcttt taatgcccag tctctccttc aaaagccggc tcctttctct   20400
ccctcgcctt cctagattcc ttctccactc cccaggatca gcctcctcct ccccacccca   20460
ccactgccgg ggggatgtct gtggtcaggc atttatcaga gaccctgagg tgggggtcct   20520
ttatgtgtct gggggatgga gagtctagag gaggtagcgt tcagacctct ccatggtgcc   20580
tctgctgggc tcacatgtga ccaagcacag caaaccatga ggcaggggat ggtcttgacc   20640
atgagagccc ttgcagcagc tgccatgggc ctcagctcct ctccaagctg ggaagagccc   20700
tgaaaagcca aggtgttttt ttttcccctct ttatttcagt gtaagtccct tgagcttttct   20760 tgaaccagaa gtgggctcat tttgctttag agatttcagg tgggcttgtc cttgtcctag   20820
catcccagat ccaccttctg ggaagtcatc agattggagg tgatgttggc agcttttgta   20880
aacaaagggt agtgttgtaa gctgttgtgt ctgcctatgt gtgtgtttgt gtacttggtc   20940
tcatctctgc agactggtga catggcttcc agatatgccc gacgatgtcc tgtggttgca   21000
gtgggtgacc tcacaggtgt tcactcgagt gctgatgtgt ctgctccccg cctccaggta   21060
aatactttgg ctgtgggtgt gtgggccgga cgggcacctc tctcatctga tgaggcctca   21120
cacgacattc tagaaacagc tggctgaaca ccaagcaagg agcttgccct tgggtgtggg   21180
gaccctgtct catgggaggc agctgagtca gtcagaggtc ctggcacacc tgctgagagc   21240
tgccacccag gccaacctga accggagcct gggaagactt cccgtcggat gagtctcttt   21300
gagtgcagca ttgatggtgg aagagcagag aggcccagga taagcaggga aaggtgcttc   21360
agacagagtg gctgggatga ggactgggga gtgtcagata gcgctggcgt gtctgagcga   21420
```

```
aggagctctg gcacccatgg cacaggaagg aggtgggacc ctggaggggc agggctagca    21480
gagctcctcg gagcgtgtgg ctaggtgcct ggtaatgcaa gccccctgtc ctccaccctc    21540
tgttgtactg agtcacagtc tccggggtga agcctagcag tctgcgttga caggcccag     21600 gggatgccgc tacttcctga attctgaatt ctggaaactg agccgagtt cagggcctgg     21660 ctcccattac cagggttggg cgttatcctg aaaatcatag gccttggttt cctcacttgg    21720
ctaacagggg tgatccccat cccctcaatg ggtttccgtg agctcctgag agcccgtagc    21780
atggtacttg gcacatgctg ggcatcagga ggtatggcct ctcttgctat tgttgttatt    21840
ggtagacaca gaaggattta aaagtagggg aatgcaaaga tccgatttgc tagggaagag    21900
ggcagtagtg gccaagtaga gggtggatcc tgggccctgg ctggcagcag gcagcaaggg    21960
gggctgccag ggcccaggca gggacgatct gtagaccgag aggcttccta aggctcttgg    22020
acaggaggag gtgtcggttc caagcctaag gagtggggca gccctggtga ctggtggtca    22080
gtggtgccag gcggtgggtg gtaggacacc ctggcaggca agtaggtttg tgtggggaa     22140 actgataggc ccctccaggg attcgttggt ggacaacacc tgtgatgtcc agtgggaggt    22200
gtccaggtag ctgggagggc cacaggcttg gaagacctag gtggtgacat cagcccagca    22260
ctgagggcta gaagaagctg tgtctctggc tgtgacggca ccctagagtg tgtgtggtgc    22320
cctctactgg ccggcaatgt gggtccaccg tagctcagac tgcacactgc agcagcggga    22380
acggcctcta agccaacttc ctccatgtgt ttcaggtccc aaatgccagt gagcagccaa    22440
caggcctccc catgcacacc tgagcaggac tggccctgct ggactccctg ctcccccaag    22500
ggctgtccag cagagaccaa agcagaggcc accccgcggt ccatcctcag gtccagcctg    22560
aacttcttct tgggcaataa agtacctgct ggtgctgagg ggctctccac ctttcccagt    22620
ttttcactag agaagagtct gtgagtcact tgaggaggcg agtctagcag attctttcag    22680
aggtgctaaa gtttcccatc tttgtgcagc tacctccgca ttgctgtgta gtgacccctg    22740
cctgtgacgt ggaggatccc agcctctgag ctgagttggt tttatgaaaa gctaggaagc    22800
aacctttcgc ctgtgcagcg gtccagcact taactctaat acatcagcat gcgttaattc    22860
agctggttgg gaaatgacac caggaagccc agtgcagagg gtcccttact gactgtttcg    22920
tggccctatt aatggtcaga ctgttccagc atgaggttct tagaatgaca ggtgtttgga    22980
tgggtggggg ccttgtgatg gggggtaggc tggcccatgt gtgatcttgt ggggtggagg    23040
gaagagaata gcatgatccc acttccccat gctgtgggaa ggggtgcagt tcgtccccaa    23100
gaacgacact gcctgtcagg tggtctgcaa agatgataac cttgactact aaaaacgtct    23160
ccatggcggg ggtaacaaga tgataatcta cttaatttta gaacaccttt ttcacctaac    23220
taaaataatg tttaaagagt tttgtataaa aatgtaagga agcgttgtta cctgttgaat    23280
tttgtattat gtgaatcagt gagatgttag tagaataagc cttaaaaaaa aaaaaatcgg    23340
ttgggtgcag tggcacacgg ctgtaatccc agcactttgg gaggccaagg ttggcagatc    23400
acctgaggtc aggagttcaa gaccagtctg gccaacatag caaaaccctg tctctactaa    23460
aaatacaaaa attatctggg catggtggtg catgcctgta atcccagcta ttcggaaggc    23520
tgaggcagga gaatcacttg aacccaggag gcggaggttg cggtgagctg agattgcacc    23580
atttcattcc agcctgggca acatgagtga aagtctgact caaaaaaaaa aaatttaaaa    23640
aacaaaataa tctagtgtgc agggcattca cctcagcccc ccaggcagga gccaagcaca    23700
gcaggagctt ccgcctcctc tccactggag cacacaactt gaacctggct tattttctgc    23760
agggaccagc cccacatggt cagtgagttt ctccccatgt gtggcgatga gagagtgtag    23820
```

| | |
|---|---|
| aaauaaagac | 23830 |

<210> SEQ ID NO 32
<211> LENGTH: 1443
<212> TYPE: DNA
<213> ORGANISM: Homo sapien

<400> SEQUENCE: 32

| | |
|---|---|
| auguacgacg cagagcgcgg cuggagcuug uccuucgcgg gcugcggcuu ccugggcuuc | 60 |
| uaccacgucg gggcgacccg cugccugagc gagcacgccc cgcaccuccu ccgcgacgcg | 120 |
| cgcauguugu ucggcgcuuc ggccggggcg uugcacugcg ucggcguccu cuccgguauc | 180 |
| ccgcuggagc agacucugca gguccucuca gaucuugugc ggaaggccag gagucggaac | 240 |
| auuggcaucu ccauccauc cuucaacuua agcaaguucc uccgacaggg ucucugcaaa | 300 |
| ugccucccgg ccaaugucca ccagcucauc uccggcaaaa uaggcaucuc ucuuaccaga | 360 |
| gugucugaug gggaaaacgu ucggugucu gacuuucggu ccaaagacga agucguggau | 420 |
| gccuugguau guuccugcuu caucccccuu uacaguggcc uuaucccucc uccuucaga | 480 |
| ggcgugcgau augguggaugg aggagugagu gacaacguac ccuucauuga ugccaaaaca | 540 |
| accaucaccg ugucccccuu cuaugggggag uacgacaucu gcccuaaagu caaguccacg | 600 |
| aacuuucuuc augguggacau caccaagcuc agucuacgcc ucugcacagg gaaccucuac | 660 |
| cuucucucga gagcuuuugu cccccggau cucaaggugc ugggagagau augccuucga | 720 |
| ggauauuugg augcauucag guucuuggaa gagaagggca ucugcaacag gccccagcca | 780 |
| ggccugaagu cauccucaga agggauggau ccugaggucg ccaugcccag cugggcaaac | 840 |
| augagcuugg auucuccccc ggagucggcu gccuuggcug ugaggcugga gggagaugag | 900 |
| cugcuagacc accugcgucu cagcauccug cccugggaug agagcauccu ggacacccuc | 960 |
| ucgcccaggc ucgcuacagc acugagugaa gaaaugaaag acaaaggugg auacaugagc | 1020 |
| aagauuugca acugcuacc cauuaggaua augucuuaug uaaugcugcc cuguacccug | 1080 |
| ccuguggaau cugccauugc gauuguccag agacugguga cauggcuucc agauaugccc | 1140 |
| gacgaugucc ugugguugca gugggugacc ucacaggugu cacucgagu gcugauguug | 1200 |
| cugcuccccg ccuccagguc ccaaaugcca gugagcagcc aacaggccuc cccaugcaca | 1260 |
| ccugagcagg acuggcccug cuggacuccc ugcuccccca agggcuguc agcagagacc | 1320 |
| aaagcagagg ccaccccgcg guccauccuc aggucagcc ugaacuucuu cuugggcaau | 1380 |
| aaaguaccug cuggugcuga ggggcucucc accuuuccca guuuucacu agagaagagu | 1440 |
| cug | 1443 |

<210> SEQ ID NO 33
<211> LENGTH: 1431
<212> TYPE: DNA
<213> ORGANISM: Homo sapien

<400> SEQUENCE: 33

| | |
|---|---|
| auguacgacg cagagcgcgg cuggagcuug uccuucgcgg gcugcggcuu ccugggcuuc | 60 |
| uaccacgucg gggcgacccg cugccugagc gagcacgccc cgcaccuccu ccgcgacgcg | 120 |
| cgcauguugu ucggcgcuuc ggccggggcg uugcacugcg ucggcguccu cuccgagcag | 180 |
| acucugcagg uccucucaga ucuugugcgg aaggccagga gucggaacau uggcaucuuc | 240 |
| cauccauccu ucaacuuaag caaguccuc cgacagggcu cugcaaaug ccucccggcc | 300 |

| | |
|---|---|
| aauguccacc agcucaucuc cggcaaaaua ggcaucucuc uuaccagagu gucugauggg | 360 |
| gaaaacguuc ggugucuga cuuucgqucc aaagacgaag ucguggaugc cuugguaugu | 420 |
| uccugcuuca uccccuucua cagugqccuu aucccuccuu ccuucagagg cgucgauau | 480 |
| guggauggag gagugaguga caacguaccc uucauugaug ccaaaacaac caucaccgug | 540 |
| uccccuucu auggggagua cgacaucugc ccuaaaguca aguccacgaa cuuucuucau | 600 |
| guggacauca ccaagcucag ucuacgccuc ugcacaggga accucuaccu ucucucgaga | 660 |
| gcuuugucc ccccggaucu caaggugcug ggagagauau gccuucgagg auauuuggau | 720 |
| gcauucaggu ucuuggaaga aagggcauc ugcaacaggc cccagccagg ccugaaguca | 780 |
| uccucagaag ggauggauc ugaggucgcc augcccagcu gggcaaacau gagucuggau | 840 |
| ucuuccccgg agucggcugc cuuggcugug aggcuggagg gagaugagcu gcuagaccac | 900 |
| cugcgucuca gcauccugcc cugggaugag agcauccugg acacccucuc gcccaggcuc | 960 |
| gcuacagcac ugagugaaga aaugaaagac aaaggggau acaugagcaa gauuugcaac | 1020 |
| uugcuaccca uuaggauaau gucuuaugua augcugcccu guaccugcc uguggaaucu | 1080 |
| gccaugcga uuguccagag acuggugaca uggcuuccag auaugcccga cgauguccug | 1140 |
| ugguugcagu gggugaccuc acaggguuc acucgagugc ugaugugucu gcuccccgcc | 1200 |
| uccaggucc aaaugccagu gagcagccaa caggccuccc caugcacacc ugagcaggac | 1260 |
| uggcccugcu ggacucccug cuccccaag ggcugugccag cagagaccaa agcagaggcc | 1320 |
| accccgcggu ccauccucag guccagccug aacuucuucu ugggcaauaa aguaccugcu | 1380 |
| ggugcugagg ggcucuccac cuuucccagu uuuucacuag agaagagucu g | 1431 |

<210> SEQ ID NO 34
<211> LENGTH: 1443
<212> TYPE: DNA
<213> ORGANISM: Homo sapien

<400> SEQUENCE: 34

| | |
|---|---|
| auguacgacg cagagcgcgg cuggagcuug ccuucgcgg gcugcggcuu ccugggcuuc | 60 |
| uaccacgucg gggcgacccg cugccugagc gagcacgccc cgcaccuccu ccgcgacgcg | 120 |
| cgcauguugu ucggcgcuuc ggccggggcg uugcacugcg ucggcguccu cuccgguauc | 180 |
| ccgcuggagc agacucugca ggucucucua gaucuugugc ggaaggccag gagucggaac | 240 |
| auuggcaucu uccauccauc cuucaacuua agcaaguucc uccgacaggg ucucugcaaa | 300 |
| ugccucccgg ccaaugucca ccagcucauc uccggcaaaa uaggcaucuc ucuuaccaga | 360 |
| gugucugaug gggaaaacgu ucugguqucu gacuuucggu ccaaagacga agucguggau | 420 |
| gccuugguau guccugcuu caugcccuuc uacagugqcc uuaucccucc uuccuucaga | 480 |
| ggcgugcgau augqggaugg aggagugagu gacaacguac ccuucauuga ugccaaaaca | 540 |
| accaucaccg uguccccuu cuauggggag uacgacaucu gcccuaaagu caaguccacg | 600 |
| aacuuucuuc auguggacau caccaagcuc agucuacgcc ucugcacagg gaaccucuac | 660 |
| cuucucucga gagcuuuugu cccccggau cucaaggugc ugggagagau augccuucga | 720 |
| ggauauuugg augcauucag guucuuggaa gagaaagggca ucugcaacag gccccagcca | 780 |
| ggccugaagu cauccucaga agggauggau ccugaggucg ccaugcccag cugggcaaac | 840 |
| augagucugg auucuccccc ggagucggcu gccuuggcug ugaggcugga gggagaugag | 900 |
| cugcuagacc accugcgucu cagcauccug cccugggaug agagcauccu ggacacccuc | 960 |
| ucgcccaggc ucgcuacagc acugagugaa gaaaugaaag acaaaggugg auacaugagc | 1020 |

| | | |
|---|---|---|
| aagauuugca acuugcuacc cauuaggaua augucuuaug uaaugcugcc cguacccug | | 1080 |
| ccuguggaau cugccauugc gauuguccag agacuggugu cauggcuucc agauaugccc | | 1140 |
| gacgaugucc uggguugca gugggugacc ucacaggugu cacucgagu gcugaugugu | | 1200 |
| cugcuccccg ccuccagguc ccaaaugcca gugagcagcc aacaggccuc cccaugcaca | | 1260 |
| ccugagcagg acuggcccug cuggacuccc ugcuccccca agggcuguc agcagagacc | | 1320 |
| aaagcagagg ccaccccgcg guccauccuc aggccagcc ugaacuucuu cuugggcaau | | 1380 |
| aaaguaccug cuggugcuga ggggcucucc accuucccca guuuucacu agagaagagu | | 1440 |
| cug | | 1443 |

<210> SEQ ID NO 35
<211> LENGTH: 1431
<212> TYPE: DNA
<213> ORGANISM: Homo sapien

<400> SEQUENCE: 35

| | | |
|---|---|---|
| auguacgacg cagagcgcgg cuggagcuug ccuucgcgg gcugcggcuu ccugggcuuc | | 60 |
| uaccacgucg gggcgacccg cugccugagc gagcacgccc cgcaccuccu ccgcgacgcg | | 120 |
| cgcauguugu ucggcgcuuc ggccggggcg uugcacugcg ucggcguccu cuccgagcag | | 180 |
| acucugcagg uccucucaga ucuugugcgg aaggccagga gucggaacau uggcaucuuc | | 240 |
| cauccauccu ucaacuuaag caaguccuc cgacagdggguc ucugcaaaug ccucccggcc | | 300 |
| aaugccacc agcucaucuc cggcaaaaua ggcaucucuc uuaccagagu gucugauggg | | 360 |
| gaaaacguuc uggugucuga cuuucggucc aaagacgaag ucguggaugc cuugguaugu | | 420 |
| uccugcuuca ugcccuucua caggggccuu aucccuccuu ccuucagagg cgucgcgauau | | 480 |
| guggauggag gagugaguga caacguaccc uucauggaug ccaaaacaac caucaccgug | | 540 |
| ucccccuucu auggggagua cgacaucugc ccuaaaguca aguccacgaa cuuucuucau | | 600 |
| guggacauca ccaagcucag ucuacgcccu ugcacaggga ccucuaccu ucucucgaga | | 660 |
| gcuuuuguc cccccggaucu caagguccug ggaagagauau gccuucgagg auauuuggau | | 720 |
| gcauucaggu ucuggaaga aagggcauc ugcaacaggc cccagccagg ccugaaguca | | 780 |
| uccucagaag ggauggaucc ugaggucgcc augcccagcu gggcaaacau gagucuggau | | 840 |
| ucuucccgg agucgcugc cuggcugug aggcuggagg gagaugagcu gcuagaccac | | 900 |
| cugcgucuca gcauccugcc cugggaugag agcauccugg acacccucuc gcccaggcuc | | 960 |
| gcuacagcac ugagugaaga aaugaaagac aaagguggau acaugagcaa gauuugcaac | | 1020 |
| uugcuaccca uuaggauaau gucuuaugua augcugcccu guacccugcc cguggaaucu | | 1080 |
| gccauugcga uuguccagag acuggugaca uggcuuccag auaugccga cgaugucccug | | 1140 |
| ugguugcagu gggugaccuc acagguguuc acucgagugc ugauugucu gcuccccgcc | | 1200 |
| uccaggucc aaaugccagu gagcagccaa caggccuccc caugcacacc ugagcaggac | | 1260 |
| uggcccugcu ggacucccug cuccccaag gcuguccag cagagaccaa agcagaggcc | | 1320 |
| accccgcggu ccauccucag guccagccug aacuucucu ugggcaauaa aguaccugcu | | 1380 |
| ggugcugagg ggcucuccac cuuucccagu uuuucacuag agaagagucu g | | 1431 |

<210> SEQ ID NO 36
<211> LENGTH: 1443
<212> TYPE: DNA
<213> ORGANISM: Homo sapien

<400> SEQUENCE: 36

```
atgtacgacg cagagcgcgg ctggagcttg tccttcgcgg gctgcggctt cctgggcttc      60
taccacgtcg gggcgacccg ctgcctgagc gagcacgccc cgcacctcct ccgcgacgcg     120
cgcatgttgt tcggcgcttc ggccggggcg ttgcactgcg tcggcgtcct ctccggtatc     180
ccgctggagc agactctgca ggtcctctca gatcttgtgc ggaaggccag gagtcggaac     240
attggcatct tccatccatc cttcaactta agcaagttcc tccgacaggg tctctgcaaa     300
tgcctcccgg ccaatgtcca ccagctcatc tccggcaaaa taggcatctc tcttaccaga     360
gtgtctgatg gggaaaacgt tctggtgtct gactttcggt ccaaagacga agtcgtggat     420
gccttggtat gttcctgctt catccccttc tacagtggcc ttatccctcc ttccttcaga     480
ggcgtgcgat atgtggatgg aggagtgagt gacaacgtac ccttcattga tgccaaaaca     540
accatcaccg tgtcccccct ctatggggag tacgacatct gccctaaagt caagtccacg     600
aactttcttc atgtggacat caccaagctc agtctacgcc tctgcacagg gaacctctac     660
cttctctcga gagcttttgt ccccccggat ctcaaggtgc tggagagat atgccttcga     720
ggatatttgg atgcattcag gttcttggaa gagaagggca tctgcaacag gccccagcca     780
ggcctgaagt catcctcaga agggatggat cctgaggtcg ccatgcccag ctgggcaaac     840
atgagtctgg attcttcccc ggagtcggct gccttggctg tgaggctgga gggagatgag     900
ctgctagacc acctgcgtct cagcatcctg ccctgggatg agagcatcct ggacaccctc     960
tcgcccaggc tcgctacagc actgagtgaa gaaatgaaag acaaaggtgg atacatgagc    1020
aagatttgca acttgctacc cattaggata atgtcttatg taatgctgcc ctgtaccctg    1080
cctgtggaat ctgccattgc gattgtccag agactggtga catggcttcc agatatgccc    1140
gacgatgtcc tgtggttgca gtgggtgacc tcacaggtgt tcactcgagt gctgatgtgt    1200
ctgctccccg cctccaggtc ccaaatgcca gtgagcagcc aacaggcctc cccatgcaca    1260
cctgagcagg actggccctg ctggactccc tgctccccca agggctgtcc agcagagacc    1320
aaagcagagg ccaccccgcg gtccatcctc aggtccagcc tgaacttctt cttgggcaat    1380
aaagtacctg ctggtgctga ggggctctcc acctttccca gttttcact agagaagagt    1440
ctg                                                                 1443
```

<210> SEQ ID NO 37
<211> LENGTH: 1431
<212> TYPE: DNA
<213> ORGANISM: Homo sapien

<400> SEQUENCE: 37

```
atgtacgacg cagagcgcgg ctggagcttg tccttcgcgg gctgcggctt cctgggcttc      60
taccacgtcg gggcgacccg ctgcctgagc gagcacgccc cgcacctcct ccgcgacgcg     120
cgcatgttgt tcggcgcttc ggccggggcg ttgcactgcg tcggcgtcct ctccgagcag     180
actctgcagg tcctctcaga tcttgtgcgg aaggccagga gtcggaacat ggcatcttc     240
catccatcct tcaacttaag caagttcctc cgacagggtc tctgcaaatg cctcccggcc     300
aatgtccacc agctcatctc cggcaaaata ggcatctctc ttaccagagt gtctgatggg     360
gaaaacgttc tggtgtctga ctttcggtcc aaagacgaag tcgtggatgc cttggtatgt     420
tcctgcttca tccccttcta cagtggcctt atccctcctt ccttcagagg cgtgcgatat     480
gtggatggag gagtgagtga caacgtaccc ttcattgatg ccaaaacaac catcaccgtg    540
tcccccttct atggggagta cgacatctgc cctaaagtca agtccacgaa ctttcttcat    600
```

```
gtggacatca ccaagctcag tctacgcctc tgcacaggga acctctacct tctctcgaga      660
gcttttgtcc ccccggatct caaggtgctg ggagagatat gccttcgagg atatttggat      720
gcattcaggt tcttggaaga aagggcatc tgcaacaggc cccagccagg cctgaagtca       780
tcctcagaag ggatggatcc tgaggtcgcc atgcccagct gggcaaacat gagtctggat      840
tcttccccgg agtcggctgc cttggctgtg aggctggagg gagatgagct gctagaccac      900
ctgcgtctca gcatcctgcc ctgggatgag agcatcctgg acaccctctc gcccaggctc      960
gctacagcac tgagtgaaga aatgaaagac aaaggtggat acatgagcaa gatttgcaac     1020
ttgctaccca ttaggataat gtcttatgta atgctgccct gtaccctgcc tgtggaatct     1080
gccattgcga ttgtccagag actggtgaca tggcttccag atatgcccga cgatgtcctg     1140
tggttgcagt gggtgacctc acaggtgttc actcgagtgc tgatgtgtct gctccccgcc     1200
tccaggtccc aaatgccagt gagcagccaa caggcctccc catgcacacc tgagcaggac     1260
tggccctgct ggactccctg ctcccccaag ggctgtccag cagagaccaa agcagaggcc     1320
accccgcggt ccatcctcag gtccagcctg aacttcttct tgggcaataa agtacctgct     1380
ggtgctgagg ggctctccac ctttcccagt ttttcactag agaagagtct g              1431
```

<210> SEQ ID NO 38
<211> LENGTH: 1443
<212> TYPE: DNA
<213> ORGANISM: Homo sapien

<400> SEQUENCE: 38

```
atgtacgacg cagagcgcgg ctggagcttg tccttcgcgg gctgcggctt cctgggcttc       60
taccacgtcg gggcgacccg ctgcctgagc gagcacgccc cgcacctcct ccgcgacgcg      120
cgcatgttgt tcggcgcttc ggccggggcg ttgcactgcg tcggcgtcct ctccggtatc      180
ccgctggagc agactctgca ggtcctctca gatcttgtgc ggaaggccag gagtcggaac      240
attggcatct tccatccatc cttcaactta agcaagttcc tccgacaggg tctctgcaaa      300
tgcctcccgg ccaatgtcca ccagctcatc tccggcaaaa taggcatctc tcttaccaga      360
gtgtctgatg gggaaaacgt tctggtgtct gactttcggt ccaaagacga agtcgtggat      420
gccttggtat gttcctgctt catgcccttc tacagtggcc ttatccctcc ttccttcaga      480
ggcgtgcgat atgtggatgg aggagtgagt gacaacgtac ccttcattga tgccaaaaca      540
accatcaccg tgtccccctt ctatgggag tacgacatct gccctaaagt caagtccacg      600
aactttcttc atgtggacat caccaagctc agtctacgcc tctgcacagg aacctctac       660 cttctctcga gagcttttgt cccccggat ctcaaggtgc tgggagagat atgccttcga       720
ggatatttgg atgcattcag gttcttggaa gagaagggca tctgcaacag gccccagcca      780
ggcctgaagt catcctcaga agggatggat cctgaggtcg ccatgcccag ctgggcaaac      840
atgagtctgg attcttcccc ggagtcggct gccttggctg tgaggctgga gggagatgag      900
ctgctagacc acctgcgtct cagcatcctg ccctgggatg agagcatcct ggacaccctc      960
tcgcccaggc tcgctacagc actgagtgaa gaaatgaaag acaaaggtgg atacatgagc     1020
aagatttgca acttgctacc cattaggata atgtcttatg taatgctgcc ctgtaccctg     1080
cctgtggaat ctgccattgc gattgtccag actggtgaca tggcttccag atatgccc       1140 gacgatgtcc tgtggttgca gtgggtgacc tcacaggtgt tcactcgagt gctgatgtgt     1200
ctgctccccg cctccaggtc ccaaatgcca gtgagcagcc aacaggcctc ccatgcaca      1260
```

```
cctgagcagg actggccctg ctggactccc tgctccccca agggctgtcc agcagagacc      1320
aaagcagagg ccaccccgcg gtccatcctc aggtccagcc tgaacttctt cttgggcaat      1380
aaagtacctg ctggtgctga ggggctctcc acctttccca gttttttcact agagaagagt     1440 ctg                                                                    1443
```

<210> SEQ ID NO 39
<211> LENGTH: 1431
<212> TYPE: DNA
<213> ORGANISM: Homo sapien

<400> SEQUENCE: 39

```
atgtacgacg cagagcgcgg ctggagcttg tccttcgcgg gctgcggctt cctgggcttc       60
taccacgtcg gggcgacccg ctgcctgagc gagcacgccc cgcacctcct ccgcgacgcg      120
cgcatgttgt tcggcgcttc ggccggggcg ttgcactgcg tcggcgtcct ctccgagcag      180
actctgcagg tcctctcaga tcttgtgcgg aaggccagga gtcggaacat tggcatcttc      240
catccatcct tcaacttaag caagttcctc cgacagggtc tctgcaaatg cctcccggcc      300
aatgtccacc agctcatctc cggcaaaata ggcatctctc ttaccagagt gtctgatggg      360
gaaaacgttc tggtgtctga cttcggtcc aaagacgaag tcgtggatgc cttggtatgt       420
tcctgcttca tgcccttcta cagtggcctt atccctcctt ccttcagagg cgtgcgatat      480
gtggatggag gagtgagtga caacgtaccc ttcattgatg ccaaaacaac catcaccgtg      540 tccccttct atggggagta cgacatctgc cctaaagtca agtccacgaa ctttcttcat       600
gtggacatca ccaagctcag tctacgcctc tgcacaggga acctctacct tctctcgaga      660
gcttttgtcc ccccggatct caaggtgctg ggagagatat gccttcgagg atatttggat      720
gcattcaggt tcttggaaga aagggcatc tgcaacaggc cccagccagg cctgaagtca       780
tcctcagaag ggatggatcc tgaggtcgcc atgcccagct gggcaaacat gagtctggat      840
tcttccccgg agtcggctgc cttggctgtg aggctggagg gagatgagct gctagaccac      900
ctgcgtctca gcatcctgcc ctgggatgag agcatcctgg acaccctctc gcccaggctc      960
gctacagcac tgagtgaaga aatgaaagac aaaggtggat acatgagcaa gatttgcaac     1020
ttgctaccca ttaggataat gtcttatgta atgctgccct gtaccctgcc tgtggaatct     1080
gccattgcga ttgtccagag actggtgaca tggcttccag atatgcccga cgatgtcctg     1140
tggttgcagt gggtgacctc acaggtgttc actcgagtgc tgatgtgtct gctccccgcc     1200
tccaggtccc aaatgccagt gagcagccaa caggcctccc catgcacacc tgagcaggac     1260
tggccctgct ggactccctg ctcccccaag ggctgtccag cagagaccaa gcagaggcc      1320 accccgcggt ccatcctcag gtccagcctg aacttcttct tgggcaataa agtacctgct     1380
ggtgctgagg ggctctccac ctttcccagt ttttcactag agaagagtct g              1431
```

<210> SEQ ID NO 40
<211> LENGTH: 481
<212> TYPE: PRT
<213> ORGANISM: Homo sapien

<400> SEQUENCE: 40

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
```

-continued

```
                35                  40                  45
Gly Ala Leu His Cys Val Gly Val Leu Ser Gly Ile Pro Leu Glu Gln
 50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Pro Cys Ser
            420                 425                 430

Pro Lys Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460
```

```
Gly Ala Glu Gly Leu Ser Thr Phe Pro Ser Phe Ser Leu Glu Lys Ser
465                 470                 475                 480

Leu

<210> SEQ ID NO 41
<211> LENGTH: 477
<212> TYPE: PRT
<213> ORGANISM: Homo sapien

<400> SEQUENCE: 41

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
                20                  25                  30

Ala Pro His Leu Leu Arg Asp Ala Arg Met Leu Phe Gly Ala Ser Ala
            35                  40                  45

Gly Ala Leu His Cys Val Gly Val Leu Ser Glu Gln Thr Leu Gln Val
50                  55                  60

Leu Ser Asp Leu Val Arg Lys Ala Arg Ser Arg Asn Ile Gly Ile Phe
65                  70                  75                  80

His Pro Ser Phe Asn Leu Ser Lys Phe Leu Arg Gln Gly Leu Cys Lys
                85                  90                  95

Cys Leu Pro Ala Asn Val His Gln Leu Ile Ser Gly Lys Ile Gly Ile
            100                 105                 110

Ser Leu Thr Arg Val Ser Asp Gly Glu Asn Val Leu Val Ser Asp Phe
        115                 120                 125

Arg Ser Lys Asp Glu Val Val Asp Ala Leu Val Cys Ser Cys Phe Ile
130                 135                 140

Pro Phe Tyr Ser Gly Leu Ile Pro Pro Ser Phe Arg Gly Val Arg Tyr
145                 150                 155                 160

Val Asp Gly Gly Val Ser Asp Asn Val Pro Phe Ile Asp Ala Lys Thr
                165                 170                 175

Thr Ile Thr Val Ser Pro Phe Tyr Gly Glu Tyr Asp Ile Cys Pro Lys
            180                 185                 190

Val Lys Ser Thr Asn Phe Leu His Val Asp Ile Thr Lys Leu Ser Leu
        195                 200                 205

Arg Leu Cys Thr Gly Asn Leu Tyr Leu Leu Ser Arg Ala Phe Val Pro
210                 215                 220

Pro Asp Leu Lys Val Leu Gly Glu Ile Cys Leu Arg Gly Tyr Leu Asp
225                 230                 235                 240

Ala Phe Arg Phe Leu Glu Glu Lys Gly Ile Cys Asn Arg Pro Gln Pro
                245                 250                 255

Gly Leu Lys Ser Ser Glu Gly Met Asp Pro Glu Val Ala Met Pro
            260                 265                 270

Ser Trp Ala Asn Met Ser Leu Asp Ser Ser Pro Glu Ser Ala Ala Leu
        275                 280                 285

Ala Val Arg Leu Glu Gly Asp Glu Leu Leu Asp His Leu Arg Leu Ser
290                 295                 300

Ile Leu Pro Trp Asp Glu Ser Ile Leu Asp Thr Leu Ser Pro Arg Leu
305                 310                 315                 320

Ala Thr Ala Leu Ser Glu Glu Met Lys Asp Lys Gly Gly Tyr Met Ser
                325                 330                 335

Lys Ile Cys Asn Leu Leu Pro Ile Arg Ile Met Ser Tyr Val Met Leu
            340                 345                 350
```

-continued

```
Pro Cys Thr Leu Pro Val Glu Ser Ala Ile Ala Ile Val Gln Arg Leu
        355                 360                 365

Val Thr Trp Leu Pro Asp Met Pro Asp Val Leu Trp Leu Gln Trp
    370                 375                 380

Val Thr Ser Gln Val Phe Thr Arg Val Leu Met Cys Leu Leu Pro Ala
385                 390                 395                 400

Ser Arg Ser Gln Met Pro Val Ser Ser Gln Gln Ala Ser Pro Cys Thr
                405                 410                 415

Pro Glu Gln Asp Trp Pro Cys Trp Thr Pro Cys Ser Pro Lys Gly Cys
                420                 425                 430

Pro Ala Glu Thr Lys Ala Glu Ala Thr Pro Arg Ser Ile Leu Arg Ser
                435                 440                 445

Ser Leu Asn Phe Phe Leu Gly Asn Lys Val Pro Ala Gly Ala Glu Gly
                450                 455                 460

Leu Ser Thr Phe Pro Ser Phe Ser Leu Glu Lys Ser Leu
465                 470                 475

<210> SEQ ID NO 42
<211> LENGTH: 481
<212> TYPE: PRT
<213> ORGANISM: Homo sapien

<400> SEQUENCE: 42

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
                20                  25                  30

Ala Pro His Leu Leu Arg Asp Ala Arg Met Leu Phe Gly Ala Ser Ala
                35                  40                  45

Gly Ala Leu His Cys Val Gly Val Leu Ser Gly Ile Pro Leu Glu Gln
            50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
                100                 105                 110

Lys Ile Gly Ile Ser Leu Thr Arg Val Ser Asp Gly Glu Asn Val Leu
            115                 120                 125

Val Ser Asp Phe Arg Ser Lys Asp Glu Val Val Asp Ala Leu Val Cys
    130                 135                 140

Ser Cys Phe Met Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
                180                 185                 190

Ile Cys Pro Lys Val Lys Ser Thr Asn Phe Leu His Val Asp Ile Thr
            195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
```

```
                    245                 250                 255
Arg Pro Gln Pro Gly Leu Lys Ser Ser Glu Gly Met Asp Pro Glu
            260                 265                 270

Val Ala Met Pro Ser Trp Ala Asn Met Ser Leu Asp Ser Pro Glu
            275                 280                 285

Ser Ala Leu Ala Val Arg Leu Glu Gly Asp Glu Leu Leu Asp His
        290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
                340                 345                 350

Tyr Val Met Leu Pro Cys Thr Leu Pro Val Glu Ser Ala Ile Ala Ile
                355                 360                 365

Val Gln Arg Leu Val Thr Trp Leu Pro Asp Met Pro Asp Asp Val Leu
        370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Lys Gly Cys Pro Ala Glu Thr Lys Ala Glu Ala Thr Pro Arg Ser
            435                 440                 445

Ile Leu Arg Ser Ser Leu Asn Phe Phe Leu Gly Asn Lys Val Pro Ala
        450                 455                 460

Gly Ala Glu Gly Leu Ser Thr Phe Pro Ser Phe Ser Leu Glu Lys Ser
465                 470                 475                 480

Leu

<210> SEQ ID NO 43
<211> LENGTH: 477
<212> TYPE: PRT
<213> ORGANISM: Homo sapien

<400> SEQUENCE: 43

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Glu Gln Thr Leu Gln Val
    50                  55                  60

Leu Ser Asp Leu Val Arg Lys Ala Arg Ser Arg Asn Ile Gly Ile Phe
65                  70                  75                  80

His Pro Ser Phe Asn Leu Ser Lys Phe Leu Arg Gln Gly Leu Cys Lys
                85                  90                  95

Cys Leu Pro Ala Asn Val His Gln Leu Ile Ser Gly Lys Ile Gly Ile
            100                 105                 110

Ser Leu Thr Arg Val Ser Asp Gly Glu Asn Val Leu Val Ser Asp Phe
        115                 120                 125

Arg Ser Lys Asp Glu Val Val Asp Ala Leu Val Cys Ser Cys Phe Met
```

```
                130             135             140
Pro Phe Tyr Ser Gly Leu Ile Pro Pro Ser Phe Arg Gly Val Arg Tyr
145                 150                 155                 160

Val Asp Gly Gly Val Ser Asp Asn Val Pro Phe Ile Asp Ala Lys Thr
                165                 170                 175

Thr Ile Thr Val Ser Pro Phe Tyr Gly Glu Tyr Asp Ile Cys Pro Lys
                180                 185                 190

Val Lys Ser Thr Asn Phe Leu His Val Asp Ile Thr Lys Leu Ser Leu
                195                 200                 205

Arg Leu Cys Thr Gly Asn Leu Tyr Leu Leu Ser Arg Ala Phe Val Pro
                210                 215                 220

Pro Asp Leu Lys Val Leu Gly Glu Ile Cys Leu Arg Gly Tyr Leu Asp
225                 230                 235                 240

Ala Phe Arg Phe Leu Glu Glu Lys Gly Ile Cys Asn Arg Pro Gln Pro
                245                 250                 255

Gly Leu Lys Ser Ser Ser Glu Gly Met Asp Pro Glu Val Ala Met Pro
                260                 265                 270

Ser Trp Ala Asn Met Ser Leu Asp Ser Ser Pro Glu Ser Ala Ala Leu
                275                 280                 285

Ala Val Arg Leu Glu Gly Asp Glu Leu Leu Asp His Leu Arg Leu Ser
                290                 295                 300

Ile Leu Pro Trp Asp Glu Ser Ile Leu Asp Thr Leu Ser Pro Arg Leu
305                 310                 315                 320

Ala Thr Ala Leu Ser Glu Glu Met Lys Asp Lys Gly Gly Tyr Met Ser
                325                 330                 335

Lys Ile Cys Asn Leu Leu Pro Ile Arg Ile Met Ser Tyr Val Met Leu
                340                 345                 350

Pro Cys Thr Leu Pro Val Glu Ser Ala Ile Ala Ile Val Gln Arg Leu
                355                 360                 365

Val Thr Trp Leu Pro Asp Met Pro Asp Asp Val Leu Trp Leu Gln Trp
                370                 375                 380

Val Thr Ser Gln Val Phe Thr Arg Val Leu Met Cys Leu Leu Pro Ala
385                 390                 395                 400

Ser Arg Ser Gln Met Pro Val Ser Ser Gln Gln Ala Ser Pro Cys Thr
                405                 410                 415

Pro Glu Gln Asp Trp Pro Cys Trp Thr Pro Cys Ser Pro Lys Gly Cys
                420                 425                 430

Pro Ala Glu Thr Lys Ala Glu Ala Thr Pro Arg Ser Ile Leu Arg Ser
                435                 440                 445

Ser Leu Asn Phe Phe Leu Gly Asn Lys Val Pro Ala Gly Ala Glu Gly
                450                 455                 460

Leu Ser Thr Phe Pro Ser Phe Ser Leu Glu Lys Ser Leu
465                 470                 475

<210> SEQ ID NO 44
<211> LENGTH: 2397
<212> TYPE: DNA
<213> ORGANISM: Homo sapien

<400> SEQUENCE: 44
agacaguacc uccucccuag gacuacacaa ggacugaacc agaaggaaga ggacagagca      60
aagccaugaa caucauccua gaaauccuuc ugcuucugau caccaucauc uacuccuacu     120
uggagucguu ggugaaguuu uucauuccuc agaggagaaa aucuguggcu ggggagauug     180
```

| | |
|---|---|
| uucucauuac uggagcuggg cauggaauag gcaggcagac uacuuaugaa uuugcaaaac | 240 |
| gacagagcau auugguucug ugggauauua auaagcgcgg ugguggaggaa acugcagcug | 300 |
| agugccgaaa acuaggcguc acugcgcaug cguaugggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaucaa aaaagcacuu cuuccaucga | 540 |
| ugauggagag aaaucauggc cacaucguca cagugcuuc agugugcggc cacgaaggga | 600 |
| uuccuuaccu caucccauau guuccagca aauuugccgc uguuggcuuu cacagagguc | 660 |
| ugacaucaga acuucaggcc uugggaaaaa cugguaucaa aaccucaugu cucugcccag | 720 |
| uuuuugugaa uacuggguuc accaaaaauc caagcacaag auuauggccu guauuggaga | 780 |
| cagaugaagu cguaagaagu cugauagaug gaauacuuac caauaagaaa augauuuuug | 840 |
| uuccaucgua uaucaauauc uuucugagac uacagaaguu ucuuccgaaa cgcgccucag | 900 |
| cgauuuuaaa ucguaugcag auauuucaau ugaagcagu gguuggccac aaaaucaaaa | 960 |
| ugaaaugaau aaauaagcuc cagccagaga uguaugcaug auaaugauau gaauaguuuc | 1020 |
| gaaucaaugc ugcaaagcuu uauuucacau uuuuucaguc cugauaauau uaaaaacauu | 1080 |
| gguuuggcac uagcagcagu caaacgaaca agauuaauua ccugucuucc uguuucucaa | 1140 |
| gaauauuuac guaguuuuuc auaggucugu uuuuccuuuc augccucuua aaaacuucug | 1200 |
| ugcuuacaua aacauacuua aaagguuuuc uuuaagauau uuuauuuuuc cauuuaaagg | 1260 |
| uggacaaaag cuacccccu aaaaguaaau acaaagagaa cuuauuuaca cagggaaggu | 1320 |
| uuaagacugu ucaaguagca uuccaaucug uagccaugcc acagaauauc aacaagaaca | 1380 |
| cagaaugagu gcacagcuaa gagaucaagu ucagcaggc agcuuaucu caaccuggac | 1440 |
| auauuuuaag auucagcauu ugaaagauuu cccuagccuc uuccuuuuuc auuagcccaa | 1500 |
| aacggugcaa cucuauucug gacuuuauua cuugauucug ucuucuguau aaccucugaag | 1560 |
| uccaccaaaa guggacccuc uauauuuccu cccuuuuuau agucuuauaa gauacauuau | 1620 |
| gaaaggugac cgacucuauu uuaaaucuca gaauuuaag uucuagcccc augauaaccu | 1680 |
| uuuucuuugu aauuuaugcu ucauauauc cuuggucca gagauguuua gacaauuuua | 1740 |
| ggcucaaaaa uuaaagcuaa cacaggaaaa ggaacuguac uggcuauuac auaagaaaca | 1800 |
| auggacccaa gagaagaaaa ggaagaaaga aagguuuuuu gguuuugu uuguuuuguu | 1860 |
| uuguuuuug uuuuuugag auggagucuc acucuuucgc ccaggcugga gugcagugu | 1920 |
| augaucucag cucacugcaa gcuccaccuc ccggguucac gccauucucc ugccucagcc | 1980 |
| uccugaguag cugggacuac aggcgcccgc caccacaccc ggcuaauuu uuguauuuuu | 2040 |
| uguagagacg ggguuucacc auguuagcca agauggucuc gaucuccuga ccucgugauc | 2100 |
| caccugccuc ggccucccaa agugcuggga uuacgggugu gagccaccgu gcccagccuu | 2160 |
| uuuuuuuua auagaaaaaa uaauccgacu cccacuacau caagacuaau cuuguuugu | 2220 |
| guguuuuuca cauguauuau agaaugcuuu ugcauggacu auccucuugu uuuuauuaaa | 2280 |
| aacaaaugau uuuuuaaaa gucacaaaaa caauucacua aaaauaaaua ugucauugug | 2340 |
| cuuuaaaaaa auaaccucuu guaguuauaa aauaaaacgu uugacuucua aacucug | 2397 |

<210> SEQ ID NO 45
<211> LENGTH: 2289
<212> TYPE: RNA
<213> ORGANISM: Homo sapien

<400> SEQUENCE: 45

```
agacaguacc uccucccuag gacuacacaa ggacugaacc agaaggaaga ggacagagca      60
aagccaugaa caucauccua gaaauccuuc ugcuucugau caccaucauc uacuccuacu     120
uggagucguu ggugaaguuu ucauuccuc agaggagaaa aucuguggcu ggggagauug      180
uucucauuac uggagcuggg cauggaauag gcaggcagac uacuuaugaa uuugcaaaac     240
gacagagcau auugguucug ugggauauua auaaggugaa gaaagaagug ggugauguaa     300
caaucguggu gaauaaugcu gggacaguau auccagccga ucuucucagc accaaggaug     360
aagagauuac caagacauuu gaggucaaca uccuaggaca uuuuuggauc acaaaagcac     420
uucuuccauc gaugauggag agaaaucaug ccacaucgu cacaguggcu ucagugugcg      480
gccacgaagg gauuccuuac cucaucccau auuguccag caaauuugcc gcuguuggcu      540
uucacagagg ucugacauca gaacuucagg ccuugggaaa aacugguauc aaaaccucau     600
gucucugccc aguuuuugug aauacugggu ucaccaaaaa uccaagcaca agauuauggc     660
cuguauugga gacagaugaa gucguaagaa gucugauaga uggaauacuu accaauaaga     720
aaaugauuuu ugucaucg uauaucaaua ucuuucugag acuacagaag uuucuuccug       780
aacgcgccuc agcgauuuua aaucguaugc agaauauuca auugaagca guguuggcc       840
acaaaucaa aaugaauga auaaauaagc uccagccaga gauguaugca ugauaaugau     900
augaauaguu ucgaaucaau gcugcaaagc uuuauuucac auuuuucag uccugauaau     960
auuaaaaaca uugguuuggc acuagcagca gucaaacgaa caagauuaau uaccugucuu   1020
ccuguuucuc aagaauauuu acguaguuuu ucauaggucu guuuuuccuu ucaugccucu   1080
uaaaaacuuc ugugcuuaca uaaacauacu uaaaaggu uu ucuuuaagau auuuuauuuu   1140
uccauuuaaa ggugacaaa agcuaccucc cuaaaaguaa auacaaagag aacuuauuua   1200
cacagggaag guuuaagacu guucaaguag cauuccaauc uguagccaug ccacagaaua   1260
ucaacaagaa cacagaauga gugcacagcu aagagaucaa guuucagcag gcagcuuuau   1320
cucaaccugg acauauuuua agauucagca uuugaaagau ucccuagcc ucuuccuuuu     1380
ucauuagccc aaaacggugc aacucuauuc uggacuuuau uacuugauuc ugucuucugu   1440
auaacucuga aguccaccaa aaguggaccc ucuauauuuc ucccuuuuuu auagucuuau   1500
aagauacauu augaaaggug accgacucua uuuuaaaucu cagaauuuua aguucuagcc   1560
ccaugauaac cuuuuucuuu guaauuuaug cuuucauaua uccuuggucc cagagauguu   1620
uagacaauuu uaggcucaaa aauuaaagcu aacacaggaa aaggaacugu acuggcuauu   1680
acauaagaaa caauggacc aagagaagaa aaggaagaaa gaaagguuuu uugguuuuug     1740
uuuuguuuug uuuuguuuuu uguuuuuuug agauggaguc ucacucuuuc gcccaggcug   1800
gagugcagug guaugaucuc agcucacugc aagcuccacc uccgggguuc acgccauucu   1860
ccugccucag ccuccugagu agcugggacu acaggcgccc gccaccacac ccggcuaauu   1920
uuuuguauuu uuuguagaga cggggguuuuca ccauguuagc caagaugguc ucgaucccu   1980
gaccucguga uccaccugcc ucggccuccc aaagugcugg gauuacgggu gugagccacc   2040
gugcccagcc uuuuuuuuuu uaauagaaaa aauaauccga cucccacuac aucaagacua   2100
aucuuguuuu gugaguuuuu cacaugauuu auagaaugcu uuugcaugga cuauccucuu   2160
guuuuuauua aaacaaaug auuuuuuuaa aagcacaaaa aacaauucac uaaaauaaaa   2220
uaugucauug ugcuuuaaaa aaauaaccuc uuguaguuau aaaauaaaac guugacuuc   2280
```

| | |
|---|---|
| uaaacucug | 2289 |

<210> SEQ ID NO 46
<211> LENGTH: 2280
<212> TYPE: RNA
<213> ORGANISM: Homo sapien

<400> SEQUENCE: 46

| | | | | |
|---|---|---|---|---|
| agacaguacc uccucccuag gacuacacaa ggacugaacc agaaggaaga ggacagagca | | | | 60 |
| aagccaugaa caucauccua gaaauccuuc ugcuucugau caccaucauc uacuccuacu | | | | 120 |
| uggagucguu ggugaaguuu ucauuccuc agaggagaaa aucguggcu ggggagauug | | | | 180 |
| uucucauuac uggagcuggg cauggaauag gcaggcagac uacuuaugaa uuugcaaaac | | | | 240 |
| gacagagcau auugguucug ugggauauua auaagcgcgg uggaggaa acugcagcug | | | | 300 |
| agugccgaaa acuaggcguc acugcgcaug cguaugugu agacugcagc aacagagaag | | | | 360 |
| agaucuaucg cucucuaaau caggugaaga aagaaguggg ugauguaaca aucgugguga | | | | 420 |
| auaaugcugg gacaguauau ccagccgauc uucucagcac caaggaugaa gagauuacca | | | | 480 |
| agacauuuga ggucaacauc cuaggacauu uuggaucac aaaagcacuu cuuccaucga | | | | 540 |
| ugauggagag aaaucauggc cacaucguca cagugguuc agugugcggc cacgaaggga | | | | 600 |
| uuccuuaccu caucccauau uguuccagca aauugccgc uguuggcuuu cacagaggc | | | | 660 |
| ugacaucaga acuucaggcc uugggaaaaa cuggauaaa aaccucaugu cucugcccag | | | | 720 |
| uuuuugugaa uacuggguuc accaaaaauc caagcacaag guuucuuccu gaacgcgccu | | | | 780 |
| cagcgauuuu aaaucguaug cagaauauuc aauuugaagc aguguuggc cacaaaauca | | | | 840 |
| aaaugaaaug aauaaauaag cuccagccag agaugauaugc augauaauga uaugaauagu | | | | 900 |
| uucgaaucaa ugcugcaaag cuuuauuuca cauuuuuca guccgauaa auuuaaaaac | | | | 960 |
| auugguuugg cacuagcagc agucaaacga acaagauuaa uuaccugucu uccuguuucu | | | | 1020 |
| caagaauauu uacguaguuu ucauagguc uguuuuccu uucaugccuc uuaaaaacuu | | | | 1080 |
| cugugcuuac auaaacauac uuaaaagguu ucuuuaaga uauuuauuu uuccauuuaa | | | | 1140 |
| aggggacaa aagcuaccuc ccuaaaagua aauacaaaga gaacuuauuu acacagggaa | | | | 1200 |
| gguuuaagac uguucaagua gcauuccaau cuguagccau gccacagaau aucaacaaga | | | | 1260 |
| acacagaaug agugcacagc uaagagauca aguucagca ggcagcuuua ucucaaccug | | | | 1320 |
| gacauauuuu aagauucagc auuugaagaa uucccuagc cucuuccuuu uucauuagcc | | | | 1380 |
| caaaacggug caacucuauu cuggacuuua uuacuugauu cugucuucug uauaacucug | | | | 1440 |
| aaguccacca aaagaggacc cucuauauu ccucccuuuu uauagcuua uaagauacau | | | | 1500 |
| uaugaaaggu gaccgacucu auuuuaaauc ucagaauuuu aaguucuagc cccaugauaa | | | | 1560 |
| ccuuuuucuu uguaauuuau gcuuacauau accuuggguc ccagagaugu uuagacaauu | | | | 1620 |
| uuaggcucaa aaauuaaagc uaacacagga aaaggaacug uacuggcuau uacauaagaa | | | | 1680 |
| acaauggacc caagagaaga aaaggaagaa agaaagguu uuggguuuuu guuuguuuu | | | | 1740 |
| guuuuguuuu uuguuuuuuu gagauggagu cucacucuuu cgcccaggcu ggagugcagu | | | | 1800 |
| gguaugaucu cagcucacug caagcuccac cucccggguu cacgccauuc uccugccuca | | | | 1860 |
| gccuccugag uagcugggac uacaggcgcc cgccaccaca cccggcuaau uuuuguauu | | | | 1920 |
| uuuuguagag acggggguuuc accauguuag ccaagauggu cucgaucucc ugacccgug | | | | 1980 |
| auccaccugc cucggccucc caaagugcug ggauuacggg ugugagccac cgugcccagc | | | | 2040 |
| cuuuuuuuuu uuaauagaaa aaauaauccg acucccacua caucaagacu aaucuuguuu | | | | 2100 |

-continued

| | |
|---|---|
| ugugugutuuu ucacauguau uauagaaugc uuuugcaugg acuauccucu uguuuuauu | 2160 |
| aaaaacaaau gauuuuuuua aaagucacaa aaacaauuca cuaaaaauaa auaugucauu | 2220 |
| gugcuuuaaa aaaauaaccu cuuguaguua uaaaauaaaa cguuugacuu cuaaacucug | 2280 |

<210> SEQ ID NO 47
<211> LENGTH: 2398
<212> TYPE: RNA
<213> ORGANISM: Homo sapien

<400> SEQUENCE: 47

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucguggcu ggggagauug | 180 |
| uucucauuac uggagcuggg cauggaauag gcaggcagac uacuuaugaa uuugcaaaac | 240 |
| gacagagcau auugguucug ugggauauua uaagcgcgg uggaggaa acugcagcug | 300 |
| agugccgaaa acuaggcguc acugcgcaug cguauggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuggaucac aaaagcacuu cuuccaucga | 540 |
| ugauggagag aaaucauggc cacaucguca caguggcuuc agugugcggc cacgaaggga | 600 |
| uuccuuaccu caucccauau uguuccagca aauuugccgc uguuggcuuu cacagagguc | 660 |
| ugacaucaga acuucaggcc uugggaaaaa cugguaucaa aaccucaugu cucugcccag | 720 |
| uuuuugugaa uacuggguuc accaaaaauc caagcacaag auuauggccu guauggaga | 780 |
| cagaugaagu cguaagaagu cugauagaug gaauacuuac caauaagaaa augauuuuug | 840 |
| uuccaucgua uaucaauauc uuucugagac uacagaaggu uucuuccuga acgcgccuca | 900 |
| gcgauuuuaa aucguaugca gaauauucaa uuugaagcag ugguuggcca caaaaucaaa | 960 |
| augaaaugaa uaauaagcu ccagccagag auguaugcau gauaaugaua ugaauaguuu | 1020 |
| cgaaucaaug cugcaaagcu uuauuucaca uuuuuucagu ccugauaaua uuaaaaacau | 1080 |
| ugguuuggca cuagcagcag ucaaacgaac aagauuaauu accugucuuc cuguuucuca | 1140 |
| agaauauuua cguaguuuuu cauggcucug uuuuuccuuu caugccucuu aaaaacuucu | 1200 |
| gugcuuacau aaaacauacuu aaaagguuuu cuuuaagaua uuuuauuuuu ccauuuaaag | 1260 |
| guggacaaaa gcuaccuccc uaaaaguaaa uacaaagaga acuauuuac acagggaagg | 1320 |
| uuuaagacug uucaaguagc auccaaucu guagccaugc cacagaauau caacaagaac | 1380 |
| acagaaugag ugcacagcua agagaucaag uuucagcagg cagcuuuauc ucaaccugga | 1440 |
| cauauuuuaa gauucagcau uugaaagauu ucccuagccu cuuccuuuuu cauuagccca | 1500 |
| aaacggugca acucuauucu ggacuuuauu acuugauucu gucuucgua uaacucugaa | 1560 |
| guccaccaaa aguggacccu cuauauuucc ucccuuuuua uagucuuaua agauacauua | 1620 |
| ugaaaggugaa ccgacucuau uuuaaaucuc agaauuuuaa guucuagccc caugauaacc | 1680 |
| uuuuucuuug uaauuuaugc uuucauauau ccuuggcccc agagauguuu agacaauuuu | 1740 |
| aggcucaaaa auuaaagcua acacaggaaa aggaacugua cuggcuauua cauaagaaac | 1800 |
| aauggaccca agaagagaaa aggaagagaag aaagguuuuu ugguuuugu uuguuuugu | 1860 |
| uuuguuuuuu guuuuuuuga gauggagucu cacucuuucg cccaggcugg agugcagugg | 1920 |

| | |
|---|---|
| uaugaucuca gcucacugca agcuccaccu cccgggeuuca cgccauucuc cugccucagc | 1980 |
| cuccugagua gcugggacua caggcgcccg ccaccacacc cggcuaauuu uuuguauuuu | 2040 |
| uuguagagac gggguuucac cauguuagcc aagauggucu cgaucuccug accucgugau | 2100 |
| ccaccugccu cggccuccca aagugcuggg auuacgggug ugagccaccg ugcccagccu | 2160 |
| uuuuuuuuuu aauagaaaaa auaauccgac ucccacuaca ucaagacuaa ucuuguuuug | 2220 |
| uguguuuuuc acauguauua uagaaugcuu ugcauggac uauccucuug uuuuuauuaa | 2280 |
| aaacaaauga uuuuuuaaa agucacaaaa acaauucacu aaaaauaaau augucauugu | 2340 |
| gcuuuaaaaa aauaaccucu guaguuaua aaauaaaacg uuugacuucu aaacucug | 2398 |

<210> SEQ ID NO 48
<211> LENGTH: 2469
<212> TYPE: RNA
<213> ORGANISM: Homo sapien

<400> SEQUENCE: 48

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug ugggauauua uaagcgcgg uguggaggaa acugcagcug | 300 |
| agugccgaaa acuaggcguc acugcgcaug cguauguggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaugg aaaggacauc agaaguaauu | 540 |
| acuuggaugu auauaggauc gaggacacuu uggacgaga cucugagauc acaaaagcac | 600 |
| uucuuccauc gaugauggag agaaaucaug gccaucgu cacagugguu ucagugugcg | 660 |
| gccacgaagg gauuccuuac cucaucccau auuguccag caaauuugcc gcuguuggcu | 720 |
| uucacagagu cugacauca gaacuucagg ccuugggaaa aacugguauc aaaaccucau | 780 |
| gucucugccc aguuuugug aauacugggu ucaccaaaaa uccaagcaca agauuauggc | 840 |
| cuguauugga gacagaugaa gucguaagaa gucugauaga uggaauacuu accaauaaga | 900 |
| aaaugauuuu uguuccaucg uauaucaaua ucuuucugag acuacagaag uuucuuccug | 960 |
| aacgcgccuc agcgauuuua aaucguaugc agaauauuca auuugaagca gugguuggcc | 1020 |
| acaaaaucaa aaugaaauga auaaauaagc uccagccaga gauguaugca ugauaaugau | 1080 |
| augaauaguu ucgaaucaau gcugcaaagc uuuauucac auuuuucag uccgauaaau | 1140 |
| auuaaaaaca uugguugggc acuagcagca gucaaacgaa caagauuaau uaccugucuu | 1200 |
| ccuguuucuc aagaauauuu acguaguuuu caauagcucu guuuuccuu ucaugccucu | 1260 |
| uaaaaacuuc ugugcuuaca uaaacauacu uaaaagguuu ucuuuaagau auuuuauuuu | 1320 |
| uccauuuaaa gguggacaaa agcuaccucc cuaaaaguaa auacaaagag aacuauuuua | 1380 |
| cacagggaag guuuaagacu guucaaguag cauuccaauc uguagccaug ccacagaaua | 1440 |
| ucaacaagaa cacagaauga gugcacagcu aagagaucaa guucagcag gcagcuuuau | 1500 |
| cucaaccugg acauuuuua agauucagca uuugaaagau ucccuagcc cuuccuuuu | 1560 |
| ucauuagccc aaaacggugc aacucuauuc uggacuuuau acuugauuc ugucuucugu | 1620 |
| auaacucuga aguccaccaa aaguggaccc ucuauauuuc cucccuuuuu auagucuuau | 1680 |

```
aagauacauu augaaaggug accgacucua uuuuaaaucu cagaauuuua aguucuagcc      1740
ccaugauaac cuuuuucuuu guaauuuaug cuuucauaua uccuuggucc cagagauguu      1800
uagacaauuu uaggcucaaa aauuaaagcu aacacaggaa aaggaacugu acuggcuauu      1860
acauaagaaa caauggaccc aagagaagaa aaggaagaaa gaaagguuuu uggguuuug       1920 uuuguuuug uuuuguuuuu uguuuuuug agauggaguc ucacucuuuc gcccaggcug        1980
gagugcagug guaugaucuc agcucacugc aagcuccacc uccggguuc acgccauucu       2040 ccugccucag ccuccugagu agcugggacu acaggcgccc gccaccacac ccggcuaauu      2100
uuuuguauuu uuuguagaga cggggauuuca ccauguuagc caagauggauc ucgaucuccu    2160 gaccucguga uccaccugcc ucggccucc aaagugcugg gauuacgggu gugagccacc       2220
gugcccagcc uuuuuuuuu aauagaaaa aauaauccga cucccacuac aucaagacua        2280
aucuuguuuu guguguuuuu cacauguauu auagaaugcu uuugcaugga cuauccucuu      2340
guuuuuauua aaacaaaug auuuuuuaa aagucacaaa aacaauucac uaaaauaaa         2400 uaugucauug ugcuuuaaaa aaauaaccuc uuguaguuau aaaauaaaac guuugacuuc      2460
uaaacucug                                                             2469
```

<210> SEQ ID NO 49
<211> LENGTH: 1715
<212> TYPE: RNA
<213> ORGANISM: Homo sapien

<400> SEQUENCE: 49

```
agacaguacc uccucccuag gacuacacaa ggacugaacc agaaggaaga ggacagagca      60
aagccaugaa caucauccua gaauccuuc ugcuucugau caccaucauc uacuccuacu       120
uggagucguu gguggaaguuu ucauuccuc agaggagaaa aucuggggcu ggggagauug      180
uucucauuac uggagcuggg cauggaauag gcaggcagac uacuuaugaa uuugcaaaac      240
gacagagcau auugguucug ugggauauua auaagcgcgg uggaggaa acugcagcug        300 agugccgaaa acuaggcguc acugcgcaug cguaugggu agacugcagc aacagagaag      360
agaucuaucg cucucuaaau caggugaaga aagaagugg ugauguaaca aucggguga       420 auaaugcugg gacaguauau ccagccgauc uucagcac caaggaugaa gagauuacca       480
agacauuuga ggucaacauc cuaggacauu uuggaucac aaaagcacuu cuuccaucga     540
ugauggagag aaaucauggc cacaucguca cagguggcuuc agugugcggc acgaagggaa    600
uuccuuaccu cauccauu uguuccagca aauuugccgc uguggcuuu cacagaggu         660 ugacaucaga acuucaggcc uugggaaaaa cugguaucaa aaccucaugu cucugcccag     720
uuuuugugaa uacgggguuc accaaaaaaauc caagcacaag auuauggccu guauggaga    780 cagaugaagu cguaagaagu cugauagaug gaauacuuac caauaagaaa augauuuug      840 uuccaucgua uaucaauauc uuucugagac uacagaaguu aaguacagca cagaacaccc    900
aaauacuaaa acaccaauag agcuuuuuu uuugcuuuuu uuuuuuag acagagucuc        960 acucugucac ccuggcugga uugcgguggu ugcagugca ugaucuuggc ucacugcaac     1020 cuccgccuu ggguucaag caauucuau gccucagacc ccaaguaac ugggauuaua        1080 ggugugugcu gccacacuac acccagcuaa uuuuguauu uuugauaga cagguuc         1140 cccauguugg ccaggcugga cucgaaccuc ugaccaag uuauccuccu gucucggccu     1200
cccaaagugc ugggauuaca gucaugagcc accaugccug gccaauaga gcuauuaua      1260
```

| | |
|---|---|
| uggagcaucu uucaguugug aaaauuggca uggaaacucu ccaucccugg ggagaacagu | 1320 |
| uauuuccucu guuauuuucc uacccagucu auaaaaagag agugauucau uuucucuacc | 1380 |
| aaaucuacug ucucugccca aacuuugcug aagacuauuc aacuaaagg aaacacaguu | 1440 |
| uaaaaagaau gcauauagu gaaguaguua auaauaaga cuccauuuuu aaaagucugc | 1500 |
| uggaaguuug guugggauug cacugaaucu auagagcaau uggggaguau ugacauauca | 1560 |
| acaauauuga guuucuaau ccaagaacau aauaucuauu uuuaaaaucu cuucaaaau | 1620 |
| cuuuaaaucu uuaaauugua uuuguaguu uuuggguguuu aagucuugca cauauuugu | 1680 |
| cagauuuauu ccaaaguauu ucacggguuc uuuuu | 1715 |

<210> SEQ ID NO 50
<211> LENGTH: 2290
<212> TYPE: RNA
<213> ORGANISM: Homo sapien

<400> SEQUENCE: 50

| | |
|---|---|
| agacaguacc uccucccuag gacuacacaa ggacugaacc agaaggaaga ggacagagca | 60 |
| aagccaugaa caucauccua gaaauccuug ugcuucugau caccaucauc uaccccuacu | 120 |
| uggagucguu ggugaaguuu uucauuccuc agaggagaaa aucuguggcu ggggagauug | 180 |
| uucucauuac uggagcuggg cauggaauag gcaggcagac uacuuaugaa uuugcaaaac | 240 |
| gacagagcau auuggucug ugggauauua auaaggugaa gaaagaagug ggugauguaa | 300 |
| caaucguggu gaauaaugcu gggacaguau auccagccga ucuucucagc accaaggaug | 360 |
| aagagauuac caagacauuu gaggucaaca uccuaggaca uuuuuggauc acaaaagcac | 420 |
| uucuuccauc gaugauggag agaaaucaug ccacaucgu cacaguggcu ucagugugcg | 480 |
| gccacgaagg gauccuuac cucaucccau auuguuccag caaauuugcc gcuguugcu | 540 |
| uucacagagg ucugacauca gaacuucagg ccuugggaaa aacugguauc aaaaccucau | 600 |
| gucucugccc aguuuuugug aauacugggu ucaccaaaaa uccaagcaca agauuauggc | 660 |
| cuguauugga gacagaugaa gucguaagaa gucugauaga uggaauacuu accaauaaga | 720 |
| aaaugauuuu uguccaucg uauaucaaua ucuuucugag acuacagaag guuucuccu | 780 |
| gaacgcgccu cagcgauuuu aaaucguaug cagaauauuc aauugaagc aguggcuggc | 840 |
| cacaaaauca aaaugaaaug aauaaauaag cuccagccag agauguaugc augauaauga | 900 |
| uaugaauagu uucgaaucaa ugcugcaaag cuuuauuuca cauuuuuuca guccugauaa | 960 |
| uauuaaaaac auugguuugg cacuagcagc agucaaacga acaagauuaa uuaccugucu | 1020 |
| uccuguuucu caagaauauu uacguaguuu ucauagguc uguuuuccu uucaugccuc | 1080 |
| uuaaaaacuu cugugcuuac auaaacauac uuaaaagguu ucuuaaga uauuuauuu | 1140 |
| uuccauuuaa aggggacaa agcuaccuc ccuaaaagua aauacaaaga gaacuuauuu | 1200 |
| acacagggaa gguuuaagac uguucaagua gcauuccaau cuguagccau gccacagaau | 1260 |
| aucaacaaga acacagaaug agugcacagc uaagagauca aguucagca ggcagcuuua | 1320 |
| ucucaaccug gacauauuu aagauucagc auuugaaaga uuucccuagc cucuuccuuu | 1380 |
| uucauuagcc caaaacgguy caacucuauu cuggacuuua uuacuugauu cugucuucg | 1440 |
| uauaacucug aaguccacca aaguggacc cucuauauuu ccucccuuuu uauagucuua | 1500 |
| uaagauacau uaugaagguu gaccgacucu auuuuaaauc ucagaauuuu aaguucuagc | 1560 |
| cccaugauaa ccuuuuucuu uguaauuuau gcuuucauau auccuggguc ccagagaugu | 1620 |
| uuagacaauu uuaggcucaa aaauuaaagc uaacacagga aaaggaacug uacuggcuau | 1680 |

-continued

| | |
|---|---:|
| uacauaagaa acaauggacc caagagaaga aaaggaagaa agaaagguuu uuugguuuuu | 1740 |
| guuuuguuuu guuuuguuuu uuguuuuuuu gagauggagu cucacucuuu cgcccaggcu | 1800 |
| ggagugcagu gguaugaucu cagcucacug caagcuccac cucccgdggu cacgccauuc | 1860 |
| uccugccuca gccuccugag uagcgggac uacaggcgcc cgccaccaca cccggcuaau | 1920 |
| uuuuuguauu uuuuguagag acggguuuc accauguuag ccaagauggu cucgaucucc | 1980 |
| ugaccucgug auccaccugc cucggccucc caaagugcgg gauuacggg gugagccac | 2040 |
| cgugcccagc cuuuuuuuu uuaauagaaa aaauaauccg acucccacua caucaagacu | 2100 |
| aaucuuguuu ugugguuuu ucacauguau uauagaaugc uuuugcaugg acuauccucu | 2160 |
| uguuuuauu aaaacaaau gauuuuuua aaagucacaa aaacaauuca cuaaaaauaa | 2220 |
| auaugucauu gugcuuuaaa aaauaaccu cuuguaguua uaaauaaaa cguuugacuu | 2280 |
| cuaaacucug | 2290 |

<210> SEQ ID NO 51
<211> LENGTH: 2470
<212> TYPE: RNA
<213> ORGANISM: Homo sapien

<400> SEQUENCE: 51

| | |
|---|---:|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucguggcu ggggagauug | 180 |
| uucucauuac uggagcuggg cauggaauag gcaggcagac uacuuaugaa uuugcaaaac | 240 |
| gacagagcau auugguucug uggauauua uaagcgcgg uggaggaa acugcagcug | 300 |
| agugccgaaa acuaggcguc acugcgcaug cguauguggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaaugg aaaggacauc agaaguaauu | 540 |
| acuuggaugu auauaggauc gaggacacuu uggacgaga cucugagauc acaaaagcac | 600 |
| uucuuccauc gaugauggag agaaaucaug ccacaucgu cacaguggcu ucagugugcg | 660 |
| gccacgaagg gauuccuuac cucauccau auuguuccag caaauuugcc gcuguuggcu | 720 |
| uucacagagg ucugacauca gaacuucagg ccuugggaaa aacugguauc aaaaccucau | 780 |
| gucucugccc aguuuugug aauacuggu ucaccaaaaa uccaagcaca agauuauggc | 840 |
| cuguauugga gacagaugaa gucguaagaa gucugauaga uggaauacuu accaauaaga | 900 |
| aaaugauuu uguccaucg uauaucaaua ucuuucugag acuacagaag guucuuccu | 960 |
| gaacgcgccu cagcgauuuu aaaucguaug cagaauauuc aauugaagc aguggguggc | 1020 |
| cacaaaauca aaaugaaaug aauaaauaag uccagccag agauguaugc augauaauga | 1080 |
| uaugaauagu uucgaaucaa ugcugcaaag cuuuauuuca cauuuuuca guccugauaa | 1140 |
| uauuaaaaac auugguuugg cacuagcagc agucaaacga acaagauuaa uuaccugucu | 1200 |
| uccuguuucu caagaauauu uacguaguuu ucauaggguc uguuuuccu uucaugccuc | 1260 |
| uuaaaaacuu cugugcuuac auaaacauac uuaaaagguu ucuuaagaa uauuuuauuu | 1320 |
| uuccauuuaa aggguggacaa aagcuacccuc ccuaaaaguua aauacaaaga gaacuuauuu | 1380 |
| acacagggaa gguuuaagac uguucaagua gcauccaauu cuguagccau gccacagaau | 1440 |

| | |
|---|---|
| aucaacaaga acacagaaug agugcacagc uaagagauca aguuucagca ggcagcuuua | 1500 |
| ucucaaccug gacauauuuu aagauucagc auuugaaaga uucccuagc cucuuccuuu | 1560 |
| uucauuagcc caaaacggug caacucuauu cuggacuuua uuacuugauu cugucuucug | 1620 |
| uauaacucug aaguccacca aaaguggacc cucuauauuu ccucccuuuu uauagucuua | 1680 |
| uaagauacau uaugaaaggu gaccgacucu auuuaaauc ucagaauuuu aaguucuagc | 1740 |
| cccaugauaa ccuuuucuu uguaauuuau gcuuucauau uccuugguc ccagagaugu | 1800 |
| uuagacaauu uuaggcucaa aaauuaaagc uaacacagga aaaggaacug uacuggcuau | 1860 |
| uacauaagaa acaauggacc caagagaaga aaaggaagaa agaaagguuu uugguuuuu | 1920 |
| guuuuguuuu guuuuguuuu uuguuuuuuu gagauggagu cucacucuuu cgcccaggcu | 1980 |
| ggagugcagu gguaugaucu cagcucacug caagcuccac cucccggguu cacgccauuc | 2040 |
| uccugccuca gccuccugag uagcugggac uacaggcgcc cgccaccaca cccggcuaau | 2100 |
| uuuuuguauu uuuuguagag acggguuuuc accauguuag ccaagauggu ucgaucucc | 2160 |
| ugaccucgug auccaccugc cucggccucc caaagugcug ggauuacggg ugugagccac | 2220 |
| cgugcccagc cuuuuuuuuu uuaauagaaa aaauaauccg acucccacua caucaagacu | 2280 |
| aaucuuguuu ugugguguuu ucacauguau uauagaaugc uuuugcaugg acuauccucu | 2340 |
| uguuuuuauu aaaacaaau gauuuuuua aagucacaa aaacaauuca cuaaaauaa | 2400 |
| auaugucauu gugcuuuaaa aaauaaccu cuuguaguua uaaauaaaa cguuugacuu | 2460 |
| cuaaacucug | 2470 |

<210> SEQ ID NO 52
<211> LENGTH: 1714
<212> TYPE: RNA
<213> ORGANISM: Homo sapien

<400> SEQUENCE: 52

| | |
|---|---|
| agacaguacc uccucccuag gacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucguggcu ggggagauug | 180 |
| uucucauuac uggagcuggg cauggaauag gcaggcagac uacuuaugaa uuugcaaaac | 240 |
| gacagagcau auugguucug ugggauauua auaagcgcgg uguggaggaa acugcagcug | 300 |
| agugccgaaa acuaggcguc acugcgcaug cguauguggu agacugcagc aacagagaag | 360 |
| agaucuaucg cucucuaaau caggugaaga agaaguggg ugauguaaca aucguggugca | 420 |
| auaaugcugg gacaguauau ccagccgauc uucucagcac caaggaugaa gagauuacca | 480 |
| agacauuuga ggucaacauc cuaggacauu uuuggaucac aaaagcacuu cuuccaucga | 540 |
| ugauggagag aaaucauggc cacaucguca cagugcuuc agugugcggc cacgaaggga | 600 |
| uccuuaccu cauccccauau uguuccagca aauuugccgc uguuggcuuu cacagagguc | 660 |
| ugacaucaga acuucaggcc uugggaaaaa cugguaucaa aaccucaugu ucugcccag | 720 |
| uuuuugugaa uacuggguuc accaaaaauc caagcacaag auuauggccu guauuggaga | 780 |
| cagaugaagu cguaagaagu cugauagaug gaauacuuac caauaagaaa augauuuug | 840 |
| uccaucgua uaucaauauc uuucugagac uacagaagua aguacagcac agaacacca | 900 |
| aauacuaaaa caccaauaga gcuuuuuuu uugcuuuuu uuuuuuaga cagagucuca | 960 |
| cucugucacc cuggcuggau ugcggugguu gcaguggcau gaucuggcu cacugcaacc | 1020 |
| uccgccuccu ggguucaagc aauucucaug ccucagaccc ccaaguaacu gggauuauag | 1080 |

```
gugugugcug ccacacuaca cccagcuaau uuuuguauuu uuugauagag acagguuucc    1140
ccauguuggc caggcuggac ucgaacuccu gaccucaagu uauccuccug ucucggccuc    1200
ccaaagugcu gggauuacag ucaugagcca ccaugccugg cccaauagag cuauuauuau    1260
ggagcaucuu ucaguguga aaauuggcau ggaaacucuc cauccuggg gagaacaguu      1320 auuuccucug uuauuuuccu acccagucua uaaaagaga gugauucauu uucucuacca    1380
aaucuacugu cucugcccaa acuuugcuga agacuauucu aacuaaagga aacacaguuu    1440
aaaaagaaug caauauagug aaguaguuaa uaauaaagac uccauuuuua aagucugcu     1500 ggaaguuugg uugggauugc acugaaucua uagagcaauu ggggaguauu gacauaucaa    1560
caauauugag uuucuaaauc caagaacaua auacuauuu uuaaaaucuu cuucaaaauc     1620
uuuaaaucuu uaaauuguau uuuguaguuu uggguguuua agucuugcac auauuuuguc    1680
agauuuauuc caaaguauuu cacggguucu uuuu                                1714
```

<210> SEQ ID NO 53
<211> LENGTH: 2397
<212> TYPE: DNA
<213> ORGANISM: Homo sapien

<400> SEQUENCE: 53

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta taagcgcgg tgtggaggaa actgcagctg    300
agtgccgaaa actaggcgtc actgcgcatg cgtatgtggt agactgcagc aacagagaag   360
agatctatcg ctctctaaat caggtgaaga agaagtggg tgatgtaaca atcgtggtga    420
ataatgctgg gacagtatat ccagccgatc ttctcagcac caaggatgaa gagattacca    480
agacatttga ggtcaacatc ctaggacatt ttggatcac aaaagcactt cttccatcga    540
tgatggagag aaatcatggc cacatcgtca cagtggcttc agtgtgcggc cacgaaggga   600
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg aatacttac caataagaaa atgatttttg    840
ttccatcgta tatcaatatc tttctgagac tacagaagtt tcttcctgaa cgcgcctcag    900
cgattttaaa tcgtatgcag aatattcaat ttgaagcagt ggttggccac aaaatcaaaa    960
tgaaatgaat aaataagctc cagccagaga tgtatgcatg ataatgatat gaatagtttc   1020
gaatcaatgc tgcaaagctt tatttcacat tttttcagtc ctgataatat taaaaacatt    1080
ggtttggcac tagcagcagt caaacgaaca agattaatta cctgtcttcc tgtttctcaa    1140
gaatatttac gtagtttttc ataggtctgt ttttcctttc atgcctctta aaaacttctg    1200
tgcttacata aacatactta aaaggttttc tttaagatat tttattttc catttaaagg    1260 tggacaaaag ctacctccct aaaagtaaat acaaagagaa cttatttaca cagggaaggt    1320
ttaagactgt tcaagtagca ttccaatctg tagccatgcc acagaatatc aacaagaaca    1380
cagaatgagt gcacagctaa gagatcaagt ttcagcaggc agctttatct caacctggac    1440
```

| | |
|---|---|
| atatttaag attcagcatt tgaaagattt ccctagcctc ttccttttc attagcccaa | 1500 |
| aacggtgcaa ctctattctg gactttatta cttgattctg tcttctgtat aactctgaag | 1560 |
| tccaccaaaa gtggaccctc tatatttcct ccctttttat agtcttataa gatacattat | 1620 |
| gaaaggtgac cgactctatt ttaaatctca gaatttaag ttctagcccc atgataacct | 1680 |
| ttttctttgt aatttatgct ttcatatatc cttggtccca gagatgttta gacaattta | 1740 |
| ggctcaaaaa ttaaagctaa cacaggaaaa ggaactgtac tggctattac ataagaaaca | 1800 |
| atggacccaa gagaagaaaa ggaagaaaga aaggttttt ggttttgtt ttgttttgtt | 1860 |
| ttgtttttg ttttttgag atggagtctc actctttcgc ccaggctgga gtgcagtggt | 1920 |
| atgatctcag ctcactgcaa gctccacctc ccgggttcac gccattctcc tgcctcagcc | 1980 |
| tcctgagtag ctgggactac aggcgcccgc caccacaccc ggctaatttt ttgtatttt | 2040 |
| tgtagagacg gggtttcacc atgttagcca agatggtctc gatctcctga cctcgtgatc | 2100 |
| cacctgcctc ggcctcccaa agtgctggga ttacgggtgt gagccaccgt gcccagcctt | 2160 |
| ttttttta atagaaaaaa taatccgact cccactacat caagactaat cttgttttgt | 2220 |
| gtgttttca catgtattat agaatgcttt tgcatggact atcctcttgt ttttattaaa | 2280 |
| aacaaatgat tttttaaaa gtcacaaaaa caattcacta aaaataaata tgtcattgtg | 2340 |
| ctttaaaaaa ataacctctt gtagttataa aataaaacgt ttgacttcta aactctg | 2397 |

<210> SEQ ID NO 54
<211> LENGTH: 2289
<212> TYPE: DNA
<213> ORGANISM: Homo sapien

<400> SEQUENCE: 54

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta taaggtgaa gaaagaagtg ggtgatgtaa | 300 |
| caatcgtggt gaataatgct gggacagtat atccagccga tcttctcagc accaaggatg | 360 |
| aagagattac caagcatttt gaggtcaaca tcctaggaca tttttggatc acaaaagcac | 420 |
| ttcttccatc gatgatggag agaaatcatg gccacatcgt cacagtggct tcagtgtgcg | 480 |
| gccacgaagg gattccttac ctcatcccat attgttccag caaatttgcc gctgttggct | 540 |
| tcacagagg tctgacatca gaacttcagg ccttgggaaa aactggtatc aaaacctcat | 600 |
| gtctctgccc agtttttgtg aatactgggt tcaccaaaaa tccaagcaca agattatggc | 660 |
| ctgtattgga gacagatgaa gtcgtaagaa gtctgataga tggaatactt accaataaga | 720 |
| aaatgatttt tgttccatcg tatatcaata tctttctgag actacagaag tttcttcctg | 780 |
| aacgcgcctc agcgattta atcgtatgc agaatattca atttgaagca gtggttggcc | 840 |
| acaaaatcaa aatgaaatga ataaataagc tccagccaga gatgtatgca tgataatgat | 900 |
| atgaatagtt tcgaatcaat gctgcaaagc tttatttcac attttttcag tcctgataat | 960 |
| attaaaaaca ttggtttggc actagcagca gtcaaacgaa caagattaat tacctgtctt | 1020 |
| cctgtttctc aagaatattt acgtagtttt tcataggtct gttttccctt tcatgcctct | 1080 |
| taaaaacttc tgtgcttaca taaacatact taaaaggttt tctttaagat attttatttt | 1140 |
| tccatttaaa ggtggacaaa agctacctcc ctaaaagtaa atacaaagag aacttattta | 1200 |

-continued

```
cacagggaag gtttaagact gttcaagtag cattccaatc tgtagccatg ccacagaata      1260
tcaacaagaa cacagaatga gtgcacagct aagagatcaa gtttcagcag gcagctttat      1320
ctcaacctgg acatatttta agattcagca tttgaaagat ttccctagcc tcttcctttt      1380
tcattagccc aaaacggtgc aactctattc tggactttat tacttgattc tgtcttctgt      1440
ataactctga agtccaccaa aagtggaccc tctatatttc ctccctttt atagtcttat       1500 aagatacatt atgaaaggtg accgactcta ttttaaatct cagaattta agttctagcc       1560 ccatgataac cttttctt gtaatttatg ctttcatata tccttggtcc cagagatgtt       1620
tagacaattt taggctcaaa aattaaagct aacacaggaa aaggaactgt actggctatt      1680
acataagaaa caatggaccc aagagaagaa aaggaagaaa gaaaggtttt ttggttttg     1740 tttgttttg tttgtttttt tgttttttg agatggagtc tcactctttc gcccaggctg       1800
gagtgcagtg gtatgatctc agctcactgc aagctccacc tcccgggttc acgccattct      1860
cctgcctcag cctcctgagt agctgggact acaggcgccc gccacacac ccggctaatt       1920 ttttgtattt tttgtagaga cggggtttca ccatgttagc caagatggtc tcgatctcct      1980
gacctcgtga tccacctgcc tcggcctccc aaagtgctgg gattacgggt gtgagccacc      2040
gtgcccagcc ttttttttt aatagaaaa aataatccga ctcccactac atcaagacta       2100
atcttgtttt gtgtgttttt cacatgtatt atagaatgct tttgcatgga ctatcctctt      2160
gtttttatta aaacaaatg attttttaa aagtcacaaa acaattcac taaaaataaa        2220 tatgtcattg tgctttaaaa aaataaccctc ttgtagttat aaaataaaac gtttgacttc    2280
taaactctg                                                              2289
```

<210> SEQ ID NO 55
<211> LENGTH: 2280
<212> TYPE: DNA
<213> ORGANISM: Homo sapien

<400> SEQUENCE: 55

```
agacagtacc tcctccctag gactacacaa ggactgaacc agaaggaaga ggacagagca      60
aagccatgaa catcatccta gaaatccttc tgcttctgat caccatcatc tactcctact      120
tggagtcgtt ggtgaagttt ttcattcctc agaggagaaa atctgtggct ggggagattg      180
ttctcattac tggagctggg catggaatag gcaggcagac tacttatgaa tttgcaaaac      240
gacagagcat attggttctg tgggatatta ataagcgcgg tgtggaggaa actgcagctg      300
agtgccgaaa actaggcgtc actgcgcatg cgtatgtggt agactgcagc aacagagaag      360
agatctatcg ctctctaaat caggtgaaga aagaagtggg tgatgtaaca atcgtggtga      420
ataatgctgg gacagtatat ccagccgatc ttctcagcac caaggatgaa gagattacca      480
agacatttga ggtcaacatc ctaggacatt tttggatcac aaaagcactt cttccatcga      540
tgatggagag aaatcatggc cacatcgtca gtggcttc agtgtgcggc cacgaaggga      600
ttccttacct catcccatat tgttccagca aatttgccgc tgttggcttt cacagaggtc      660
tgacatcaga acttcaggcc ttgggaaaaa ctggtatcaa aacctcatgt ctctgcccag      720 ttttttgtgaa tactgggttc accaaaaatc caagcacaag gttcttcct gaacgcgcct      780 cagcgatttt aaatcgtatg cagaatattc aatttgaagc agtggttggc cacaaaatca      840
aaatgaaatg aataaataag ctccagccag agatgtatgc atgataatga tatgaatagt      900
ttcgaatcaa tgctgcaaag ctttatttca cattttttca gtcctgataa tattaaaaac      960
```

```
attggtttgg cactagcagc agtcaaacga acaagattaa ttacctgtct tcctgtttct   1020
caagaatatt tacgtagttt ttcataggtc tgttttcct ttcatgcctc ttaaaaactt   1080
ctgtgcttac ataaacatac ttaaaaggtt ttctttaaga tattttattt ttccatttaa   1140
aggtggacaa aagctacctc cctaaaagta aatacaaaga gaacttattt acacagggaa   1200
ggtttaagac tgttcaagta gcattccaat ctgtagccat gccacagaat atcaacaaga   1260
acacagaatg agtgcacagc taagagatca agtttcagca ggcagcttta tctcaacctg   1320
gacatatttt aagattcagc atttgaaaga tttccctagc ctcttccttt ttcattagcc   1380
caaaacggtg caactctatt ctggactta ttacttgatt ctgtcttctg tataactctg   1440
aagtccacca aaagtggacc ctctatattt cctccctttt tatagtctta taagatacat   1500
tatgaaaggt gaccgactct attttaaatc tcagaatttt aagttctagc cccatgataa   1560 ccttttctt tgtaatttat gctttcatat atccttggtc ccagagatgt ttagacaatt   1620
ttaggctcaa aaattaaagc taacacagga aaggaactg tactggctat tacataagaa   1680
acaatggacc caagagaaga aaaggaagaa agaaaggttt tttggttttt gttttgtttt   1740
gttttgtttt ttgtttttttt gagatggagt ctcactcttt cgcccaggct ggagtgcagt   1800
ggtatgatct cagctcactg caagctccac ctcccgggtt cacgccattc tcctgcctca   1860
gcctcctgag tagctgggac tacaggcgcc cgccaccaca cccggctaat ttttttgtatt   1920 ttttgtagag acggggtttc accatgttag ccaagatggt ctcgatctcc tgacctcgtg   1980
atccacctgc ctcggcctcc caaagtgctg ggattacggg tgtgagccac cgtgcccagc   2040
cttttttttt ttaatagaaa aaataatccg actcccacta catcaagact aatcttgttt   2100
tgtgtgtttt tcacatgtat tatagaatgc ttttgcatgg actatcctct tgttttatt   2160 aaaaacaaat gattttttta aaagtcacaa aaacaattca ctaaaaataa atatgtcatt   2220
gtgctttaaa aaaataacct cttgtagtta taaaataaaa cgtttgactt ctaaactctg   2280
```

<210> SEQ ID NO 56
<211> LENGTH: 2398
<212> TYPE: DNA
<213> ORGANISM: Homo sapien

<400> SEQUENCE: 56

```
agacagtacc tcctccctag gactacacaa ggactgaacc agaaggaaga ggacagagca     60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta taagcgcgg tgtggaggaa actgcagctg   300
agtgccgaaa actaggcgtc actgcgcatg cgtatgtggt agactgcagc aacagagaag   360
agatctatcg ctctctaaat caggtgaaga agaagtggg tgatgtaaca atcgtggtga   420
ataatgctgg gacagtatat ccagccgatc ttctcagcac caaggatgaa gagattacca   480
agacatttga ggtcaacatc ctaggacatt tttggatcac aaaagcactt cttccatcga   540
tgatggagag aaatcatggc cacatcgtca agtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgcccag   720
tttttgtgaa tactgggttc accaaaaatc caagcacaag attatggcct gtattggaga   780
cagatgaagt cgtaagaagt ctgatagatg gaatacttac caataagaaa atgattttg   840
```

| | | | | |
|---|---|---|---|---|
| ttccatcgta | tatcaatatc | tttctgagac | tacagaaggt | ttcttcctga acgcgcctca | 900 |
| gcgattttaa | atcgtatgca | gaatattcaa | tttgaagcag | tggttggcca caaaatcaaa | 960 |
| atgaaatgaa | taaataagct | ccagccagag | atgtatgcat | gataatgata tgaatagttt | 1020 |
| cgaatcaatg | ctgcaaagct | ttatttcaca | ttttttcagt | cctgataata ttaaaaacat | 1080 |
| tggtttggca | ctagcagcag | tcaaacgaac | aagattaatt | acctgtcttc ctgtttctca | 1140 |
| agaatattta | cgtagttttt | cataggtctg | tttttccttt | catgcctctt aaaaacttct | 1200 |
| gtgcttacat | aaacatactt | aaaaggtttt | ctttaagata | ttttattttt ccatttaaag | 1260 |
| gtggacaaaa | gctacctccc | taaaagtaaa | tacaaagaga | acttatttac acagggaagg | 1320 |
| tttaagactg | ttcaagtagc | attccaatct | gtagccatgc | cacagaatat aacaagaac | 1380 |
| acagaatgag | tgcacagcta | agagatcaag | tttcagcagg | cagctttatc tcaacctgga | 1440 |
| catattttaa | gattcagcat | ttgaaagatt | tccctagcct | cttcctttt cattagccca | 1500 |
| aaacggtgca | actctattct | ggactttatt | acttgattct | gtcttctgta taactctgaa | 1560 |
| gtccaccaaa | agtggaccct | ctatatttcc | tcccttttta | tagtcttata agatacatta | 1620 |
| tgaaaggtga | ccgactctat | tttaaatctc | agaattttaa | gttctagccc catgataacc | 1680 |
| ttttttcttg | taatttatgc | tttcatatat | ccttggtccc | agagatgttt agacaatttt | 1740 |
| aggctcaaaa | attaaagcta | acacaggaaa | aggaactgta | ctggctatta cataagaaac | 1800 |
| aatggaccca | agagaagaaa | aggaagaaag | aaaggttttt | tggttttgt tttgttttgt | 1860 |
| tttgttttt | gtttttttga | gatggagtct | cactctttcg | cccaggctgg agtgcagtgg | 1920 |
| tatgatctca | gctcactgca | agctccacct | cccgggttca | cgccattctc ctgcctcagc | 1980 |
| ctcctgagta | gctgggacta | caggcgcccg | ccaccacacc | cggctaattt tttgtatttt | 2040 |
| ttgtagagac | ggggtttcac | catgttagcc | aagatggtct | cgatctcctg acctcgtgat | 2100 |
| ccacctgcct | cggcctccca | aagtgctggg | attacgggtg | tgagccaccg tgcccagcct | 2160 |
| ttttttttt | aatagaaaaa | ataatccgac | tcccactaca | tcaagactaa tcttgttttg | 2220 |
| tgtgttttc | acatgtatta | tagaatgctt | ttgcatggac | tatcctcttg tttttattaa | 2280 |
| aaacaaatga | ttttttaaa | agtcacaaaa | acaattcact | aaaaataaat atgtcattgt | 2340 |
| gctttaaaaa | aataaccctct | tgtagttata | aaataaaacg | tttgacttct aaactctg | 2398 |

<210> SEQ ID NO 57
<211> LENGTH: 2469
<212> TYPE: DNA
<213> ORGANISM: Homo sapien

<400> SEQUENCE: 57

| | | | | |
|---|---|---|---|---|
| agacagtacc | tcctccctag | gactacacaa | ggactgaacc | agaaggaaga ggacagagca | 60 |
| aagccatgaa | catcatccta | gaaatccttc | tgcttctgat | caccatcatc tactcctact | 120 |
| tggagtcgtt | ggtgaagttt | ttcattcctc | agaggagaaa | atctgtggct ggggagattg | 180 |
| ttctcattac | tggagctggg | catggaatag | gcaggcagac | tacttatgaa tttgcaaaac | 240 |
| gacagagcat | attggttctg | tgggatatta | taagcgcgg | tgtggaggaa actgcagctg | 300 |
| agtgccgaaa | actaggcgtc | actgcgcatg | cgtatgtggt | agactgcagc aacagagaag | 360 |
| agatctatcg | ctctctaaat | caggtgaaga | agaagtggg | tgatgtaaca atcgtggtga | 420 |
| ataatgctgg | gacagtatat | ccagccgatc | ttctcagcac | caaggatgaa gagattacca | 480 |
| agacatttga | ggtcaacatc | ctaggacatt | tttggaatgg | aaaggacatc agaagtaatt | 540 |

```
acttggatgt atataggatc gaggacactt ttggacgaga ctctgagatc acaaaagcac    600
ttcttccatc gatgatggag agaaatcatg gccacatcgt cacagtggct tcagtgtgcg    660
gccacgaagg gattccttac ctcatcccat attgttccag caaatttgcc gctgttggct    720
ttcacagagg tctgacatca gaacttcagg ccttgggaaa aactggtatc aaaacctcat    780
gtctctgccc agttttttgtg aatactgggt tcaccaaaaa tccaagcaca agattatggc    840
ctgtattgga gacagatgaa gtcgtaagaa gtctgataga tggaatactt accaataaga    900
aaatgatttt tgttccatcg tatatcaata tctttctgag actacagaag tttcttcctg    960
aacgcgcctc agcgatttta aatcgtatgc agaatattca atttgaagca gtggttggcc   1020
acaaaatcaa aatgaaatga ataaataagc tccagccaga gatgtatgca tgataatgat   1080
atgaatagtt tcgaatcaat gctgcaaagc tttatttcac attttttcag tcctgataat   1140
attaaaaaca ttggtttggc actagcagca gtcaaacgaa caagattaat tacctgtctt   1200
cctgtttctc aagaatattt acgtagtttt tcataggtct gttttttcctt tcatgcctct   1260
taaaaacttc tgtgcttaca taaacatact taaaaggttt tctttaagat attttatttt   1320
tccatttaaa ggtggacaaa agctacctcc ctaaaagtaa atacaaagag aacttattta   1380
cacagggaag gtttaagact gttcaagtag cattccaatc tgtagccatg ccacagaata   1440
tcaacaagaa cacagaatga gtgcacagct aagagatcaa gtttcagcag gcagctttat   1500
ctcaacctgg acatatttta agattcagca tttgaaagat ttccctagcc tcttcctttt   1560
tcattagccc aaaacggtgc aactctattc tggactttat tacttgattc tgtcttctgt   1620
ataactctga gtccaccaa aagtggaccc tctatatttc ctcccttttt atagtcttat    1680
aagatacatt atgaaaggtg accgactcta ttttaaatct cagaatttta agttctagcc   1740
ccatgataac cttttttcttt gtaatttatg ctttcatata tccttggtcc cagagatgtt   1800
tagacaattt taggctcaaa aattaaagct aacacaggaa aaggaactgt actggctatt   1860
acataagaaa caatggaccc aagagaagaa aaggaagaaa gaaaggtttt ttggtttttg   1920
ttttgttttg ttttgttttt tgtttttttg agatggagtc tcactctttc gcccaggctg   1980
gagtgcagtg gtatgatctc agctcactgc aagctccacc tcccgggttc acgccattct   2040
cctgcctcag cctcctgagt agctgggact acaggcgccc gccaccacac ccggctaatt   2100
ttttgtattt tttgtagaga cggggtttca ccatgttagc caagatggtc tcgatctcct   2160
gacctcgtga tccacctgcc tcggcctccc aaagtgctgg gattacgggt gtgagccacc   2220
gtgcccagcc ttttttttttt taatagaaaa aataatccga ctcccactac atcaagacta   2280
atcttgtttt gtgtgttttt cacatgtatt atagaatgct tttgcatgga ctatcctctt   2340
gttttttatta aaacaaatg attttttttaa aagtcacaaa aacaattcac taaaaataaa   2400
tatgtcattg tgctttaaaa aaataaccctc ttgtagttat aaaataaaac gtttgacttc   2460
taaactctg                                                          2469
```

<210> SEQ ID NO 58
<211> LENGTH: 1715
<212> TYPE: DNA
<213> ORGANISM: Homo sapien

<400> SEQUENCE: 58

```
agacagtacc tcctccctag gactacacaa ggactgaacc agaaggaaga ggacagagca     60
aagccatgaa catcatccta gaaatccttc tgcttctgat caccatcatc tactcctact    120
tggagtcgtt ggtgaagttt ttcattcctc agaggagaaa atctgtggct ggggagattg    180
```

```
ttctcattac tggagctggg catggaatag gcaggcagac tacttatgaa tttgcaaaac      240
gacagagcat attggttctg tgggatatta ataagcgcgg tgtggaggaa actgcagctg      300
agtgccgaaa actaggcgtc actgcgcatg cgtatgtggt agactgcagc aacagagaag      360
agatctatcg ctctctaaat caggtgaaga agaagtgggg tgatgtaaca atcgtggtga      420
ataatgctgg gacagtatat ccagccgatc ttctcagcac caaggatgaa gagattacca      480
agacatttga ggtcaacatc ctaggacatt ttttggatcac aaaagcactt cttccatcga      540
tgatggagag aaatcatggc cacatcgtca cagtggcttc agtgtgcggc cacgaaggga      600
ttccttacct catcccatat tgttccagca aatttgccgc tgttggcttt cacagaggtc      660
tgacatcaga acttcaggcc ttgggaaaaa ctggtatcaa aacctcatgt ctctgcccag      720
tttttgtgaa tactgggttc accaaaaatc caagcacaag attatggcct gtattggaga      780
cagatgaagt cgtaagaagt ctgatagatg aatacttac caataagaaa atgattttg       840 ttccatcgta tatcaatatc tttctgagac tacagaagtt aagtacagca cagaacaccc      900
aaatactaaa acaccaatag agcttttttt tttgcttttt tttttttag acagagtctc     960 actctgtcac cctggctgga ttgcggtggt tgcagtggca tgatcttggc tcactgcaac     1020
ctccgcctcc tgggttcaag caattctcat gcctcagacc cccaagtaac tgggattata     1080
ggtgtgtgct gccacactac acccagctaa ttttttgtatt ttttgataga acaggtttc     1140 cccatgttgg ccaggctgga ctcgaactcc tgacctcaag ttatcctcct gtctcggcct     1200
cccaaagtgc tgggattaca gtcatgagcc accatgcctg gcccaataga gctattatta    1260
tggagcatct ttcagttgtg aaaattggca tggaaactct ccatccctgg ggagaacagt     1320
tatttcctct gttattttcc tacccagtct ataaaaagag agtgattcat tttctctacc     1380
aaatctactg tctctgccca aactttgctg aagactattc taactaaagg aaacacagtt    1440
taaaaagaat gcaatatagt gaagtagtta ataataaaga ctccattttt aaaagtctgc     1500
tggaagtttg gttgggattg cactgaatct atagagcaat tggggagtat tgacatatca    1560
acaatattga gttttctaat ccaagaacat aatatctatt tttaaaatct tcttcaaaat     1620
ctttaaatct ttaaattgta ttttgtagtt tttggtgttt aagtcttgca catattttgt    1680
cagatttatt ccaaagtatt tcacgggttc ttttt                                1715

<210> SEQ ID NO 59
<211> LENGTH: 2290
<212> TYPE: DNA
<213> ORGANISM: Homo sapien

<400> SEQUENCE: 59
agacagtacc tcctccctag gactacacaa ggactgaacc agaaggaaga ggacagagca       60
aagccatgaa catcatccta gaaatccttc tgcttctgat caccatcatc tactcctact      120
tggagtcgtt ggtgaagttt ttcattcctc agaggagaaa atctgtggct ggggagattg      180
ttctcattac tggagctggg catggaatag gcaggcagac tacttatgaa tttgcaaaac      240
gacagagcat attggttctg tgggatatta ataaggtgaa gaaagaagtg ggtgatgtaa      300
caatcgtggt gaataatgct gggacagtat atccagccga tcttctcagc accaaggatg      360
aagagattac caagacattt gaggtcaaca tcctaggaca ttttttggatc acaaaagcac     420 ttcttccatc gatgatggag agaaatcatg gccacatcgt cacagtggct tcagtgtgcg     480
gccacgaagg gattccttac ctcatcccat attgttccag caaatttgcc gctgttggct     540
```

| | | |
|---|---|---|
| ttcacagagg tctgacatca gaacttcagg ccttgggaaa aactggtatc aaaacctcat | 600 | |
| gtctctgccc agttttttgtg aatactgggt tcaccaaaaa tccaagcaca agattatggc | 660 | |
| ctgtattgga gacagatgaa gtcgtaagaa gtctgataga tggaatactt accaataaga | 720 | |
| aaatgatttt tgttccatcg tatatcaata tctttctgag actacagaag gtttcttcct | 780 | |
| gaacgcgcct cagcgatttt aaatcgtatg cagaatattc aatttgaagc agtggttggc | 840 | |
| cacaaaatca aaatgaaatg aataaataag ctccagccag agatgtatgc atgataatga | 900 | |
| tatgaatagt ttcgaatcaa tgctgcaaag ctttatttca catttttca gtcctgataa | 960 | |
| tattaaaaac attggtttgg cactagcagc agtcaaacga acaagattaa ttacctgtct | 1020 | |
| tcctgttct caagaatatt tacgtagttt ttcataggtc tgttttcct ttcatgcctc | 1080 | |
| ttaaaaactt ctgtgcttac ataaacatac ttaaaaggtt ttctttaaga tattttattt | 1140 | |
| ttccatttaa aggtggacaa aagctacctc cctaaaagta aatacaaaga gaacttattt | 1200 | |
| acacagggaa ggtttaagac tgttcaagta gcattccaat ctgtagccat gccacagaat | 1260 | |
| atcaacaaga acacagaatg agtgcacagc taagagatca agtttcagca ggcagcttta | 1320 | |
| tctcaacctg gacatatttt aagattcagc atttgaaaga tttccctagc ctcttccttt | 1380 | |
| ttcattagcc caaaacggtg caactctatt ctggacttta ttacttgatt ctgtcttctg | 1440 | |
| tataactctg aagtccacca aaagtggacc ctctatattt cctcccttt tatagtctta | 1500 | |
| taagatacat tatgaaaggt gaccgactct atttaaatc tcagaatttt aagttctagc | 1560 | |
| cccatgataa ccttttctt tgtaatttat gctttcatat atccttggtc ccagagatgt | 1620 | |
| ttagacaatt ttaggctcaa aaattaaagc taacacagga aaaggaactg tactggctat | 1680 | |
| tacataagaa acaatggacc caagagaaga aaaggaagaa agaaaggttt tttggttttt | 1740 | |
| gttttgtttt gttttgtttt ttgttttttt gagatggagt ctcactcttt cgcccaggct | 1800 | |
| ggagtgcagt ggtatgatct cagctcactg caagctccac ctcccgggtt cacgccattc | 1860 | |
| tcctgcctca gcctcctgag tagctgggac tacaggcgcc cgccaccaca cccggctaat | 1920 | |
| tttttgtatt ttttgtagag acggggtttc accatgttag ccaagatggt ctcgatctcc | 1980 | |
| tgacctcgtg atccacctgc ctcggcctcc caaagtgctg ggattacggg tgtgagccac | 2040 | |
| cgtgcccagc cttttttttt ttaatagaaa aaataatccg actcccacta catcaagact | 2100 | |
| aatcttgttt tgtgtgtttt tcacatgtat tatagaatgc ttttgcatgg actatcctct | 2160 | |
| tgttttatt aaaaacaaat gatttttta aaagtcacaa aaacaattca ctaaaaataa | 2220 | |
| atatgtcatt gtgctttaaa aaataaacct cttgtagtta taaaataaaa cgtttgactt | 2280 | |
| ctaaactctg | 2290 | |

<210> SEQ ID NO 60
<211> LENGTH: 2470
<212> TYPE: DNA
<213> ORGANISM: Homo sapien

<400> SEQUENCE: 60

| | | |
|---|---|---|
| agacagtacc tcctccctag gactacacaa ggactgaacc agaaggaaga ggacagagca | 60 | |
| aagccatgaa catcatccta gaaatccttc tgcttctgat caccatcatc tactcctact | 120 | |
| tggagtcgtt ggtgaagttt ttcattcctc agaggagaaa atctgtggct ggggagattg | 180 | |
| ttctcattac tggagctggg catggaatag gcaggcagac tacttatgaa tttgcaaaac | 240 | |
| gacagagcat attggttctg tgggatatta ataagcgcgg tgtggaggaa actgcagctg | 300 | |
| agtgccgaaa actaggcgtc actgcgcatg cgtatgtggt agactgcagc aacagagaag | 360 | |

```
agatctatcg ctctctaaat caggtgaaga agaagtgggg tgatgtaaca atcgtggtga      420
ataatgctgg gacagtatat ccagccgatc ttctcagcac caaggatgaa gagattacca      480
agacatttga ggtcaacatc ctaggacatt tttggaatgg aaaggacatc agaagtaatt      540
acttggatgt atataggatc gaggacactt ttggacgaga ctctgagatc acaaaagcac      600
ttcttccatc gatgatggag agaaatcatg gccacatcgt cacagtggct tcagtgtgcg      660
gccacgaagg gattccttac ctcatcccat attgttccag caaatttgcc gctgttggct      720
ttcacagagg tctgacatca gaacttcagg ccttgggaaa actggtatc aaaacctcat       780 gtctctgccc agttttttgtg aatactgggt tcaccaaaaa tccaagcaca agattatggc     840
ctgtattgga gacagatgaa gtcgtaagaa gtctgataga tggaatactt accaataaga     900
aaatgatttt tgttccatcg tatatcaata tctttctgag actacagaag gtttcttcct      960
gaacgcgcct cagcgatttt aaatcgtatg cagaatattc aatttgaagc agtggttggc     1020
cacaaaatca aaatgaaatg aataaataag ctccagccag agatgtatgc atgataatga    1080
tatgaatagt ttcgaatcaa tgctgcaaag ctttatttca cattttttca gtcctgataa     1140
tattaaaaac attggtttgg cactagcagc agtcaaacga acaagattaa ttacctgtct    1200
tcctgtttct caagaatatt tacgtagttt tcataggtc tgttttttcct ttcatgcctc     1260 ttaaaaactt ctgtgcttac ataaacatac ttaaaaggtt ttctttaaga tatttttattt    1320 ttccatttaa aggtggacaa aagctacctc cctaaaagta aatacaaaga gaacttattt     1380
acacagggaa ggtttaagac tgttcaagta gcattccaat ctgtagccat gcccacagaat   1440 atcaacaaga acacagaatg agtgcacagc taagagatca agtttcagca ggcagcttta     1500
tctcaacctg gacatatttt aagattcagc atttgaaaga tttccctagc ctcttccttt      1560
ttcattagcc caaaacggtg caactctatt ctggacttta ttacttgatt ctgtcttctg      1620
tataactctg aagtccacca aagtggacc ctctatattt cctcccttttt tatagtctta      1680 taagatacat tatgaaaggt gaccgactct attttaaatc tcagaatttt aagttctagc     1740
cccatgataa ccttttttctt tgtaatttat gctttcatat atccttggtc ccagagatgt   1800
ttagacaatt ttaggctcaa aaattaaagc taacacagga aaaggaactg tactggctat     1860
tacataagaa acaatggacc caagagaaga aaggaagaa agaaaggttt tttggttttt     1920
gttttgtttt gttttgtttt tgttttttt gagatggagt ctcactcttt cgcccaggct     1980
ggagtgcagt ggtatgatct cagctcactg caagctccac ctcccgggtt cacgccattc    2040
tcctgcctca gcctcctgag tagctgggac tacaggcgcc cgccaccaca cccggctaat    2100
tttttgtatt ttttgtagag acggggtttc accatgttag ccagatggt ctcgatctcc     2160 tgacctcgtg atccacctgc ctcggcctcc caaagtgctg ggattacggg tgtgagccac    2220
cgtgcccagc cttttttttt ttaatagaaa aaataatccg actcccacta catcaagact    2280
aatcttgttt tgtgtgttttt tcacatgtat tatagaatgc ttttgcatgg actatccctct   2340 tgtttttatt aaaaacaaat gatttttta aaagtcacaa aacaattca ctaaaaataa      2400 atatgtcatt gtgctttaaa aaataaacct cttgtagtta taaaataaaa cgtttgactt    2460
ctaaactctg                                                            2470
```

<210> SEQ ID NO 61
<211> LENGTH: 1714
<212> TYPE: DNA
<213> ORGANISM: Homo sapien

<400> SEQUENCE: 61

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgcgg tgtggaggaa actgcagctg   300
agtgccgaaa actaggcgtc actgcgcatg cgtatgtggt agactgcagc aacagagaag   360
agatctatcg ctctctaaat caggtgaaga agaagtgggt gatgtaaca atcgtggtga    420
ataatgctgg gacagtatat ccagccgatc ttctcagcac caaggatgaa gagattacca   480
agacatttga ggtcaacatc ctaggacatt tttggatcac aaaagcactt cttccatcga   540
tgatggagag aaatcatggc cacatcgtca cagtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgcccag   720
ttttgtgaa tactgggttc accaaaaatc caagcacaag attatggcct gtattggaga   780
cagatgaagt cgtaagaagt ctgatagatg gaatacttac caataagaaa atgattttg    840
ttccatcgta tatcaatatc tttctgagac tacagaagta agtacagcac agaacaccca   900
aatactaaaa caccaataga gctttttttt ttgctttttt ttttttaga cagagtctca    960
ctctgtcacc ctggctggat tgcggtggtt gcagtggcat gatcttggct cactgcaacc  1020
tccgcctcct gggttcaagc aattctcatg cctcagaccc ccaagtaact gggattatag  1080
gtgtgtgctg ccacactaca cccagctaat ttttgtattt tttgatagag acaggttttc  1140
ccatgttggc caggctggac tcgaactcct gacctcaagt tatcctcctg tctcggcctc  1200
ccaaagtgct gggattacag tcatgagcca ccatgcctgg cccaatagag ctattattat  1260
ggagcatctt tcagttgtga aaattggcat ggaaactctc catccctggg gagaacagtt  1320
atttcctctg ttattttcct acccagtcta taaaaagaga gtgattcatt ttctctacca  1380
aatctactgt ctctgcccaa actttgctga agactattct aactaaagga aacacagttt  1440
aaaaagaatg caatatagtg aagtagttaa taataaagac tccatttttta aaagtctgct  1500
ggaagtttgg ttgggattgc actgaatcta tagagcaatt ggggagtatt gacatatcaa  1560
caatattgag ttttctaatc caagaacata atatctattt ttaaaatctt cttcaaaatc  1620
tttaaatctt taaattgtat tttgtagttt ttggtgttta agtcttgcac atattttgtc  1680
agatttattc caaagtattt cacgggttct tttt                              1714
```

<210> SEQ ID NO 62
<211> LENGTH: 25
<212> TYPE: DNA
<213> ORGANISM: Artificial Sequence
<220> FEATURE:
<223> OTHER INFORMATION: forward primer

<400> SEQUENCE: 62

```
atgaacatca tcctagaaat ccttc                                           25
```

<210> SEQ ID NO 63
<211> LENGTH: 25
<212> TYPE: DNA
<213> ORGANISM: Artificial Sequence
<220> FEATURE:
<223> OTHER INFORMATION: reverse primer

```
<400> SEQUENCE: 63
atcatgcata catctctggc tggag                                    25

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
atcagaactt caggccttgg                                          20

<210> SEQ ID NO 65
<211> LENGTH: 21
<212> TYPE: DNA
<213> ORGANISM: Artificial Sequence
<220> FEATURE:
<223> OTHER INFORMATION: first exon

<400> SEQUENCE: 65
gcaaagccat gaacatcatc c                                        21

<210> SEQ ID NO 66
<211> LENGTH: 24
<212> TYPE: DNA
<213> ORGANISM: Artificial Sequence
<220> FEATURE:
<223> OTHER INFORMATION: last exon

<400> SEQUENCE: 66
tcttgatgta gtgggagtcg gatt                                     24
```

INHIBITION OF HSD17B13 IN THE TREATMENT OF LIVER DISEASE IN PATIENTS EXPRESSING THE PNPLA3 I148M VARIATION

REFERENCE TO A SEQUENCE LISTING

This application includes a Sequence Listing submitted electronically as a text file named 18923801001SEQ, created on Oct. 9, 2018, with a size of 238 kilobytes. The Sequence Listing is incorporated by reference herein.

FIELD

The disclosure relates generally to the field of precision medicine. More particularly, the disclosure relates to methods of identifying subjects who are patatin like phospholipase domain containing 3 (PNPLA3) Ile148Met positive and have a liver disease or susceptibility to liver disease, and treating such subjects with an inhibitor of hydroxysteroid 17-beta dehydrogenase 13 (HSD17B13).

BACKGROUND

Various references, including patents, patent applications, accession numbers, technical articles, and scholarly articles are cited throughout the specification. Each reference is incorporated by reference herein, in its entirety and for all purposes.

Chronic liver disease and cirrhosis are leading causes of morbidity and mortality in the United States, accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

Previous genome wide association studies (GWAS) have identified sequence variations associated with increased risk of chronic liver disease. The most robustly validated association is with a common missense variant in patatin-like phospholipase domain-containing 3, encoded by the gene PNPLA3. This variant (rs738409, p.Ile148Met) was initially found to be associated with an increase in hepatic triglyceride levels (Romeo et al., Nat. Genet., 2008, 40, 1461-5), and subsequently associated with nonalcoholic steatohepatitis (NASH) (Rotman et al., Hepatology, 2010, 52, 894-903; Sookoian et al., J. Lipid Res., 2009, 50, 2111-2116) and cirrhosis (Shen et al., J. Lipid Res., 2015, 56, 167-175). A missense variant in TM6SF2, encoding transmembrane 6 superfamily member 2, also confers increased risk of non-alcoholic fatty liver disease (NAFLD)(Kozlitina et al., Nat. Genet., 2014, 46, 352-6; Liu et al., Nat. Commun., 2014, 5, 4309; and Sookoian et al., Hepatology, 2015, 61, 515-25). Exactly how the variants in PNPLA3 and TM6SF2 contribute to liver disease has yet to be fully elucidated (Smagris et al., J. Biol. Chem., 2016, 291, 10659-76; Mandessian et al., Proc. Natl. Acad. Sci. USA, 2014, 111, 8913-8; Huang et al., J. Biol. Chem., 2011, 286, 37085-93; and Pirazzi et al., J. Hepatol., 2012, 57, 1276-82). To date, no genetic variants that protect from chronic liver disease have been identified.

SUMMARY

The present disclosure provides methods for identifying a human subject as a candidate for treating or inhibiting a liver disease, the method comprising: determining whether or not a sample from the subject comprises: i) a first nucleic acid encoding a patatin like phospholipase domain containing 3 (PNPLA3) protein comprising an I148M variation and a second nucleic acid encoding a functional HSD17B13 protein; and/or ii) a PNPLA3 protein comprising an I148M variation and a functional HSD17B13 protein; and identifying the subject as a candidate for treating or inhibiting a liver disease by inhibiting HSD17B13 when both the first and second nucleic acids as defined in i) and/or both of the proteins as defined in ii) are detected.

In some embodiments, the first nucleic acid molecule comprises genomic DNA, mRNA, or a cDNA obtained from mRNA.

In some embodiments, the genomic DNA comprises an ATG codon at the positions corresponding to positions 5107 to 5109 according to SEQ ID NO:31; the mRNA comprises an AUG codon at the positions corresponding to positions 442 to 444 according to SEQ ID NO:34; the mRNA comprises an AUG codon at the positions corresponding to positions 430 to 432 according to SEQ ID NO:35; the cDNA comprises an ATG codon at the positions corresponding to positions 442 to 444 according to SEQ ID NO:38; or the cDNA comprises an ATG codon at the positions corresponding to positions 430 to 432 according to SEQ ID NO:39.

In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation; the mRNA comprises the nucleotide sequence according to SEQ ID NO:34, or a nucleotide sequence having at least 90% sequence identity to SEQ ID NO:34 and encoding a PNPLA3 protein which comprises the I148M variation; the mRNA comprises the nucleotide sequence according to SEQ ID NO:35, or a nucleotide sequence having at least 90% sequence identity to SEQ ID NO:35 and encoding a PNPLA3 protein which comprises the I148M variation; the cDNA comprises the nucleotide sequence according to SEQ ID NO:38, or a nucleotide sequence having at least 90% sequence identity to SEQ ID NO:38 and encoding a PNPLA3 protein which comprises the I148M variation; or the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, detecting the first nucleic acid comprises: sequencing at least a portion of the first nucleic acid, wherein the portion comprises the codon which encodes the I148M variation; or hybridizing the first nucleic acid with a probe or primer that specifically hybridizes to a portion of the first nucleic acid, wherein the portion comprises the codon encoding the I148M variation.

In some embodiments, the probe or primer is an allele-specific probe or primer, and wherein the probe or primer optionally comprises a label.

In some embodiments, the methods further comprise determining whether the subject is homozygous or heterozygous for the I148M variation.

In some embodiments, the second nucleic acid comprises genomic DNA, mRNA, or a cDNA obtained from mRNA.

In some embodiments, the genomic DNA comprises an adenine at the position corresponding to position 12,667 according to SEQ ID NO:1; the genomic DNA comprises the nucleotide sequence according to SEQ ID NO:1, or a nucleotide sequence having at least 90% sequence identity to SEQ ID NO:1 and encoding a functional HSD17B13 protein; the mRNA comprises the nucleotide sequence according to SEQ ID NO:3, or a nucleotide sequence having at least 90% sequence identity to SEQ ID NO:3 and encoding a functional HSD17B13 protein; the mRNA comprises the nucleotide sequence according to SEQ ID NO:4 or a nucleotide sequence having at least 90% sequence identity to SEQ ID NO:4 and encoding a functional HSD17B13 protein; the mRNA comprises the nucleotide sequence according to SEQ ID NO:7 or a nucleotide sequence having at least 90% sequence identity to SEQ ID NO:7 and encoding a functional HSD17B13 protein; the mRNA comprises the nucleotide sequence according to SEQ ID NO:11 or a nucleotide sequence having at least 90% sequence identity to SEQ ID NO:11 and encoding a functional HSD17B13 protein; the cDNA comprises the nucleotide sequence according to SEQ ID NO:12 or a nucleotide sequence having at least 90% sequence identity to SEQ ID NO:12 and encoding a functional HSD17B13 protein; the cDNA comprises the nucleotide sequence according to SEQ ID NO:13 or a nucleotide sequence having at least 90% sequence identity to SEQ ID NO:13 and encoding a functional HSD17B13 protein; the cDNA comprises the nucleotide sequence according to SEQ ID NO:16 or a nucleotide sequence having at least 90% sequence identity to SEQ ID NO:16 and encoding a functional HSD17B13 protein; or the cDNA comprises the nucleotide sequence according to SEQ ID NO:20 or a nucleotide sequence having at least 90% sequence identity to SEQ ID NO:20 and encoding a functional HSD17B13 protein.

In some embodiments, detecting the second nucleic acid comprises: sequencing the second nucleic acid; or hybridizing the second nucleic acid with a probe or primer that specifically hybridizes to a portion of the second nucleic acid, wherein the portion comprises the adenine at the position corresponding to position 12,667 according to SEQ ID NO:1.

In some embodiments, the probe or primer is an allele-specific probe or primer, and wherein the probe or primer optionally comprises a label.

In some embodiments, the methods further comprise determining whether the subject is homozygous or heterozygous for the second nucleic acid encoding a functional HSD17B13 protein in the sample.

In some embodiments, the methods further comprise administering an inhibitor of HSD17B13 to the subject.

In some embodiments, the liver disease is an alcoholic liver disease. In some embodiments, the alcoholic liver disease comprises one or more of cirrhosis, steatosis, or hepatocellular carcinoma resulting from alcohol consumption.

In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

BRIEF DESCRIPTION OF THE FIGURES

The accompanying figures, which are incorporated in and constitute a part of this specification, illustrate several aspects and together with the description serve to explain the principles of the present disclosure.

FIG. 1 shows baseline characteristics of sequenced European-ancestry individuals from the discovery and replication cohorts.

FIG. 2 shows single nucleotide variants associated with serum transaminase levels at $P<1.0\times10^{-7}$ in the discovery cohort.

FIG. 3 shows replication and joint meta-analysis of 35 exome-wide significant single nucleotide variants from the discovery cohort in three separate European-ancestry cohorts.

FIG. 4 shows association of thirteen exome-wide significant and replicating single nucleotide variants with liver disease phenotypes in the discovery cohort.

FIG. 5 shows baseline characteristics of genotyped multi-ethnic cases and controls from the Dallas Liver and Pediatric Liver Studies.

FIG. 9 shows an analysis of the genetic interaction between PNPLA3 rs738409 (p.I148M) and HSD17B13 rs72613567.

Figure 6:
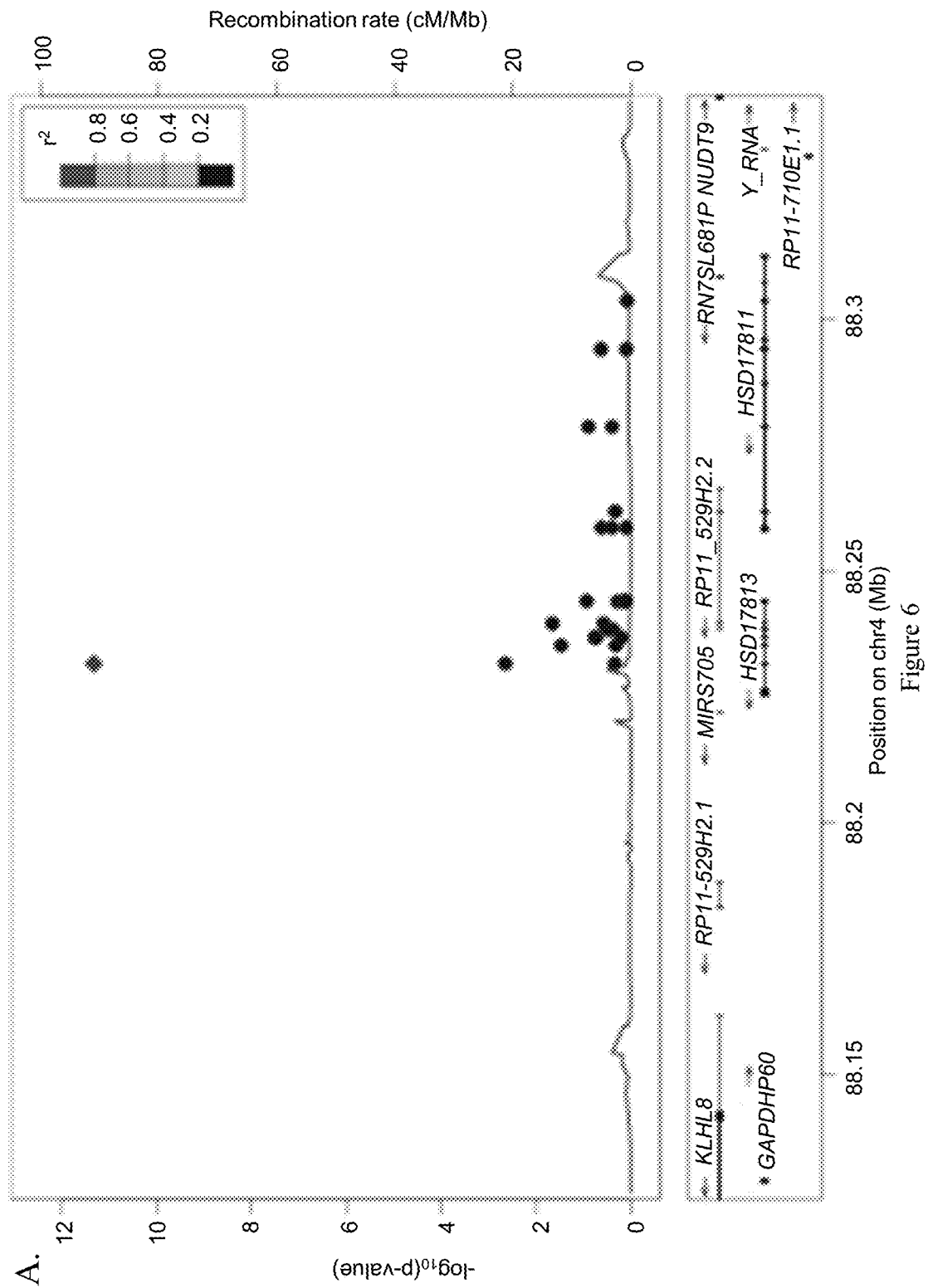
FIG. 6 (panels A and B) shows regional association plots for alanine aminotransferase (ALT; A) and aspartate aminotransferase (AST; B) levels in the GHS discovery cohort in the region around HSD17B13.

Additional advantages of the disclosure will be set forth in part in the description which follows, and in part will be apparent from the description, or can be learned by practice of the embodiments disclosed herein. The advantages of the disclosure will be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION

Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, without limitation, farm animals (e.g., horse, cow, pig), companion animals (e.g., dog, cat), laboratory animals (e.g., mouse, rat, rabbits), and non-human primates. In some embodiments, the subject is a human being.

As used herein, a "nucleic acid," a "nucleic acid molecule," a "nucleic acid sequence," "polynucleotide," or "oligonucleotide" can comprise a polymeric form of nucleotides of any length, may comprise DNA and/or RNA, and can be single-stranded, double-stranded, or multiple stranded. One strand of a nucleic acid also refers to its complement.

As used herein, the phrase "corresponding to" or grammatical variations thereof when used in the context of the numbering of a given amino acid or nucleic acid sequence or position refers to the numbering of a specified reference sequence when the given amino acid or nucleic acid sequence is compared to the reference sequence (e.g., with the reference sequence herein being the nucleic acid molecule or polypeptide of (functional or transcript behaving as a functional) HSD17B13, for example). In other words, the residue (e.g., amino acid or nucleotide) number or residue (e.g., amino acid or nucleotide) position of a given polymer is designated with respect to the reference sequence rather than by the actual numerical position of the residue within the given amino acid or nucleic acid sequence. For example, a given amino acid sequence can be aligned to a reference sequence by introducing gaps to optimize residue matches between the two sequences. In these cases, although the gaps are present, the numbering of the residue in the given amino acid or nucleic acid sequence is made with respect to the reference sequence to which it has been aligned.

For example, the phrase "nucleic acid molecule encoding an HSD17B13 loss-of-function variant protein which comprises a thymine at the position corresponding to position 12,667 according to SEQ ID NO:2" (and similar phrases) means that, if the nucleic acid sequence of the HSD17B13 genomic DNA being examined is aligned to the nucleotide sequence according to SEQ ID NO:2, the HSD17B13 genomic DNA being examined comprises a thymine at the position that corresponds to position 12,667 of SEQ ID NO:2.

A nucleic acid molecule encoding an HSD17B13 loss-of-function variant protein which comprises a thymine at the position corresponding to position 12,667 according to SEQ ID NO:2, for example, can easily be identified by performing a sequence alignment between the given HSD17B13 protein and the nucleic acid sequence of SEQ ID NO:2. Likewise, a PNPLA3 Ile148Met protein having a methionine at a position corresponding to position 148 according to SEQ ID NO:42, or at a position corresponding to position 144 according to SEQ ID NO:43 can easily be identified by performing a sequence alignment between the given PNPLA3 protein and the amino acid sequence of SEQ ID NO:42 or SEQ ID NO:43. A variety of computational algorithms exist that can be used for performing a sequence alignment in order to identify particular nucleic acid molecules and proteins having particular nucleotides or amino acids at the particular position that corresponds to a position of a particular SEQ ID NOs. For example, programs for identifying percent sequence identity can be used to perform a sequence alignment. Percent identity (or percent complementarity) between particular stretches of nucleic acid sequences within nucleic acids or amino acid sequences within polypeptides can be determined using BLAST programs (basic local alignment search tools) and Power-BLAST programs (Altschul et al., J. Mol. Biol., 1990, 215, 403-410; Zhang and Madden, Genome Res., 1997, 7, 649-656) or CLUSTALW software (Sievers et al., 2014, Methods Mol. Biol., 1079, 105-116) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). However, sequences can also be aligned manually. Herein, if reference is made to percent sequence identity, the higher percentages of sequence identity are preferred over the lower ones.

The present disclosure provides methods of identifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of identifying a subject having a protective effect against liver disease; and inhibitors of HSD17B13 for use in the treatment of a liver disease.

The present disclosure provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

It has been observed in accordance with the disclosure that a splice variant (rs72613567:TA) in HSD17B13, which encodes 17-beta hydroxysteroid dehydrogenase 13, a hepatic lipid droplet protein, was reproducibly associated with reduced ALT ($P=4.2\times10^{-12}$) and AST ($P=6.2\times10^{-10}$) levels. It was also observed that this variant was associated with reduced risk of alcoholic and nonalcoholic liver disease (by 38%, 95% confidence interval (CI) 19%-52%; and by 16%, 95% CI 9%-22%, respectively, for each rs72613567:TA allele) and cirrhosis (by 44%, 95% CI 22-59%; and by 26%, 95% CI 12%-38% for alcoholic and nonalcoholic cirrhosis, respectively, for each rs72613567:TA allele) in an allele dosage-dependent manner. The associations were confirmed in two independent cohorts. rs72613567:TA was associated with decreased severity of histological features of nonalcoholic steatohepatitis (NASH) (23% reduction, 95% CI 10%-34% in nonalcoholic steatohepatitis (NASH) for each rs72613567:TA allele among individuals with fatty liver disease), and mitigated liver injury associated with PNPLA3 p.I148M. rs72613567:TA results in a truncated isoform deficient in enzymatic activity against steroid substrates. Thus, a loss-of-function variant in HSD17B13 was associated with reduced risk of alcoholic and nonalcoholic liver disease, and progression from steatosis to NASH. U.S. Patent Application Publication No. US2018/0216084 (corresponding to PCT Publication No. WO 2018/136702) is incorporated herein by reference in its entirety.

The present disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected.

The present disclosure also provides methods of classifying a human subject as a candidate for treating or inhibiting a liver disease by inhibiting HSD17B13; methods of treating or inhibiting liver disease comprising administering an inhibitor of HSD17B13; methods of detecting PNPLA3 Ile148Met (also referred to herein as "I148M") and functional HSD17B13 in a subject; methods of classifying a subject having a protective effect against liver disease; and inhibitors of HSD17B13 for use in the treatment of a liver disease.

The present disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient.

In the methods described herein, various PNPLA3 and HSD17B13 proteins, and nucleic acid molecules (e.g., genomic DNA, mRNA, and cDNA derived from the mRNA) encoding the same are detected, expressed, or employed. These PNPLA3 and HSD17B13 proteins and nucleic acid molecules encoding the same are described in more detail.

The amino acid sequences for two wild type PNPLA3 proteins are set forth in SEQ ID NO:40 and SEQ ID NO:41. The wild type PNPLA3 protein having SEQ ID NO:40 is 481 amino acids in length, whereas the wild type PNPLA3 protein having SEQ ID NO:41 is 477 amino acids in length. The wild type PNPLA3 protein having SEQ ID NO:40 has an isoleucine at position 148. The wild type PNPLA3 protein having SEQ ID NO:41 has an isoleucine at position 144.

In some embodiments, a variant PNPLA3 Ile148Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises an amino acid sequence that has at least about 95%, at least about 96%, at least about 97%, at least about 98%, or at least about 99% sequence identity to the amino acid sequence according to SEQ ID NO:42, and comprises a methionine at a position corresponding to position 148 according to SEQ ID NO:42. In some embodiments, the variant PNPLA3 Ile148Met protein comprises or consists of the amino acid sequence according to SEQ ID NO:42.

In some embodiments, a variant PNPLA3 Ile144Met protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises an amino acid sequence that has at least about 95%, at least about 96%, at least about 97%, at least about 98%, or at least about 99% sequence identity to the amino acid sequence according to SEQ ID NO:43, and comprises a methionine at a position corresponding to position 144 according to SEQ ID NO:43. In some embodiments, the variant PNPLA3 Ile144Met protein comprises or consists of the amino acid sequence according to SEQ ID NO:43.

In some embodiments, the variant PNPLA3 Ile148Met and variant PNPLA3 Ile144Met proteins are fragments of the proteins described above, wherein the fragments comprise a methionine at a position corresponding to position 148 according to SEQ ID NO:42, or comprise a methionine at a position corresponding to position 144 according to SEQ ID NO:43. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptide having the amino acid sequence of SEQ ID NO:42 or SEQ ID NO:43). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

The nucleic acid sequence for a genomic DNA molecule encoding wild type PNPLA3 protein is set forth in SEQ ID NO:30. The wild type PNPLA3 genomic DNA molecule having SEQ ID NO:30 comprises a cytosine at position 5109. The wild type PNPLA3 genomic DNA molecule having SEQ ID NO:30 comprises the codon ATC at the positions 5107 to 5109.

In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 genomic DNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 genomic DNA molecule encoding the variant PNPLA3 Ile148Met protein or the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of a nucleic acid sequence that has at least about 95%, at least about 96%, at least about 97%, at least about 98%, or at least about 99% sequence identity to SEQ ID NO:31, and comprises a guanine at a position corresponding to position 5109 according to SEQ ID NO:31, or comprises the codon ATG at the positions corresponding to positions 5107 to 5109 according to SEQ ID NO:31. In some embodiments, the variant PNPLA3 genomic DNA molecule encoding the variant PNPLA3 Ile148Met protein or the variant PNPLA3 Ile144Met protein comprises or consists of the nucleotide sequence according to SEQ ID NO:31.

In some embodiments, the variant PNPLA3 genomic DNA molecules comprise less than the entire genomic DNA sequence. In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:31. In some embodiments, the variant PNPLA3 genomic DNA molecules comprise or consist of at least about 1000 to at least about 2000 contiguous nucleotides of SEQ ID NO:31.

In some embodiments, the variant PNPLA3 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:31.

The nucleic acid sequences of two wild type PNPLA3 mRNA molecules are set forth in SEQ ID NO:32 and SEQ ID NO:33. The wild type PNPLA3 mRNA molecule having SEQ ID NO:32 comprises a cytosine at position 444. The wild type PNPLA3 mRNA molecule having SEQ ID NO:32 comprises the codon AUC at the positions 442 to 444. The wild type PNPLA3 mRNA molecule having SEQ ID NO:33 comprises a cytosine at position 432. The wild type PNPLA3 mRNA molecule having SEQ ID NO:33 comprises the codon AUC at the positions 430 to 432.

In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 mRNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 mRNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:34, and comprises a guanine at a position corresponding to position 444 according to SEQ ID NO:34, or comprises the codon AUG at the positions corresponding to positions 442 to 444 according to SEQ ID NO:34. In some embodiments, the variant PNPLA3 mRNA molecule encoding the variant PNPLA3 Ile148Met protein comprises or consists of the nucleotide sequence according to SEQ ID NO:34.

In some embodiments, the variant PNPLA3 mRNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:35, and comprises a guanine at a position corresponding to position 432 according to SEQ ID NO:35, or comprises the codon AUG at the positions corresponding to positions 430 to 432 according to SEQ ID NO:35. In some embodiments, the variant PNPLA3 mRNA molecule encoding the variant PNPLA3 Ile144Met protein comprises or consists of the nucleotide sequence according to SEQ ID NO:35.

In some embodiments, the variant PNPLA3 mRNA molecule comprises less nucleotides than the entire variant PNPLA3 mRNA sequence. In some embodiments, the variant PNPLA3 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:34 or SEQ ID NO:35. In some embodiments, the variant PNPLA3 mRNA molecules comprise or consist of at least about 200 to at least about 500 contiguous nucleotides of SEQ ID NO:34 or SEQ ID NO:35. In this regard, the longer mRNA molecules are preferred over the shorter ones. In some embodiments, the variant PNPLA3 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:34 or SEQ ID NO:35. In this regard, the longer mRNA molecules are preferred over the shorter ones. In some embodiments, such variant PNPLA3 mRNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 mRNA molecules include the guanine at the position corresponding to position 444 according to SEQ ID NO:34 or the guanine at the position corresponding to position 432 according to SEQ ID NO:35. In some embodiments, such variant PNPLA3 mRNA molecules include the codon AUG at the positions corresponding to positions 442 to 444 according to SEQ ID NO:34, or the codon AUG at the positions corresponding to positions 430 to 432 according to SEQ ID NO:35.

The nucleic acid sequences of two wild type PNPLA3 cDNA molecules are set forth in SEQ ID NO:36 and SEQ ID NO:37. The wild type PNPLA3 cDNA molecule having SEQ ID NO:36 comprises a cytosine at position 444. The wild type PNPLA3 cDNA molecule having SEQ ID NO:36 comprises the codon ATC at positions 442 to 444. The wild type PNPLA3 cDNA molecule having SEQ ID NO:37 comprises a cytosine at position 432. The wild type PNPLA3 cDNA molecule having SEQ ID NO:37 comprises the codon ATC at positions 430 to 432.

In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists of a nucleic acid sequence that encodes a PNPLA3 Ile148Met protein or a PNPLA3 Ile144Met protein that comprises an amino acid sequence that has at least about 95%, at least about 96%, at least about 97%, at least about 98%, or at least about 99% sequence identity to SEQ ID NO:42 or SEQ ID NO:43, respectively, and comprises a methionine at a position corresponding to position 148 according to SEQ ID NO:42 or comprises a methionine at a position corresponding to position 144 according to SEQ ID NO:43. In some embodiments, the variant PNPLA3 cDNA molecule comprises or consists a nucleic acid sequence that encodes a PNPLA3 Ile148Met protein or a PNPLA3 Ile144Met protein that comprises or consists of an amino acid sequence according to SEQ ID NO:42 or SEQ ID NO:43, respectively.

In some embodiments, the variant PNPLA3 cDNA molecule encoding the variant PNPLA3 Ile148Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of a nucleic acid sequence that has at least about 95%, at least about 96%, at least about 97%, at least about 98%, or at least about 99% sequence identity to SEQ ID NO:38, and comprises a guanine at a position corresponding to position 444 according to SEQ ID NO:38, or comprises the codon ATG at the positions corresponding to positions 442 to 444 according to SEQ ID NO:38. In some embodiments, the variant PNPLA3 cDNA molecule encoding the variant PNPLA3 Ile148Met protein comprises or consists of the nucleotide sequence according to SEQ ID NO:38.

In some embodiments, the variant PNPLA3 cDNA molecule encoding the variant PNPLA3 Ile144Met protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of a nucleic acid sequence that has at least about 95%, at least about 96%, at least about 97%, at least about 98%, or at least about 99% sequence identity to SEQ ID NO:39, and comprises a guanine at a position corresponding to position 432 according to SEQ ID NO:39, or comprises the codon ATG at the positions corresponding to positions 430 to 432 according to SEQ ID NO:39. In some embodiments, the variant PNPLA3 cDNA molecule encoding the variant PNPLA3 Ile144Met protein comprises or consists of the nucleotide sequence according to SEQ ID NO:39.

In some embodiments, the variant PNPLA3 cDNA molecule comprises less nucleotides than the entire variant PNPLA3 cDNA sequence. In some embodiments, the variant PNPLA3 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of SEQ ID NO:38 or SEQ ID NO:39. In some embodiments, the variant PNPLA3 cDNA molecules comprise or consist of at least about 200 to at least about 500 contiguous nucleotides of SEQ ID NO:38 or SEQ ID NO:39. In this regard, the longer cDNA molecules are preferred over the shorter ones. In some embodiments, the variant PNPLA3 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:38 or SEQ ID NO:39. In this regard, the longer cDNA molecules are preferred over the shorter ones. In some embodiments, such variant PNPLA3 cDNA molecules include the codon that encodes the methionine at the position that corresponds to position 148 according to SEQ ID NO:42 or the codon that encodes the methionine at the position that corresponds to position 144 according to SEQ ID NO:43. In some embodiments, such variant PNPLA3 cDNA molecules include the guanine at the position corresponding to position 444 according to SEQ ID NO:38 or the guanine at the position corresponding to position 432 according to SEQ ID NO:39. In some embodiments, such variant PNPLA3 cDNA molecules include the codon ATG at the positions corresponding to positions 442 to 444 according to SEQ ID NO:38, or the codon ATG at the positions corresponding to positions 430 to 432 according to SEQ ID NO:39.

The amino acid sequences for four HSD17B13 isoform proteins associated with the functional HSD17B13 protein are set forth in SEQ ID NO:21 (Isoform A), SEQ ID NO:22 (Isoform B), SEQ ID NO:25 (Isoform E), and SEQ ID NO:29 (Isoform I). The HSD17B13 protein having SEQ ID NO:21 (Isoform A) is 300 amino acids in length. The HSD17B13 protein having SEQ ID NO:22 (Isoform B) is 264 amino acids in length. The HSD17B13 protein having SEQ ID NO:25 (Isoform E) is 324 amino acids in length. The HSD17B13 protein having SEQ ID NO:29 (Isoform I) is 271 amino acids in length.

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:21 (Isoform A). In some embodiments, the HSD17B13 isoform protein associated with the functional HSD17B13 protein comprises or consists of the amino acid sequence according to SEQ ID NO:21 (Isoform A).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:22 (Isoform B). In some embodiments, the HSD17B13 isoform protein associated with the functional HSD17B13 protein comprises or consists of the amino acid sequence according to SEQ ID NO:22 (Isoform B).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:25 (Isoform E). In some embodiments, the HSD17B13 isoform protein associated with the functional HSD17B13 protein comprises or consists of the amino acid sequence according to SEQ ID NO:25 (Isoform E).

In some embodiments, an HSD17B13 isoform protein associated with the functional HSD17B13 protein comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises an amino acid sequence that has at least about 95%, at least about 96%, at least about 97%, at least about 98%, or at least about 99% sequence identity to the amino acid sequence according to SEQ ID NO:29 (Isoform I). In some embodiments, the HSD17B13 isoform protein associated with the functional HSD17B13 protein comprises or consists of the amino acid sequence according to SEQ ID NO:29 (Isoform I).

The amino acid sequences for five HSD17B13 isoform proteins associated with the loss-of-function rs72613567 HSD17B13 protein (SEQ ID NO:2) are set forth in SEQ ID NO:23 (Isoform C), SEQ ID NO:24 (Isoform D), SEQ ID NO:26 (Isoform F), SEQ ID NO:27 (Isoform G), and SEQ ID NO:28 (Isoform H). The HSD17B13 protein having SEQ ID NO:23 (Isoform C) is 261 amino acids in length. The HSD17B13 protein having SEQ ID NO:24 (Isoform D) is 274 amino acids in length. The HSD17B13 protein having SEQ ID NO:26 (Isoform F) is 284 amino acids in length. The HSD17B13 protein having SEQ ID NO:27 (Isoform G) is 238 amino acids in length. The HSD17B13 protein having SEQ ID NO:28 (Isoform H) is 298 amino acids in length.

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:23 (Isoform C). In some embodiments, the HSD17B13 variant protein associated with a loss-of-function comprises or consists of the amino acid sequence according to SEQ ID NO:23 (Isoform C).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:24 (Isoform D). In some embodiments, the HSD17B13 variant protein associated with a loss-of-function comprises an amino acid sequence that comprises or consists of the amino acid sequence according to SEQ ID NO:24 (Isoform D).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:26 (Isoform F). In some embodiments, the HSD17B13 variant protein associated with a loss-of-function comprises or consists of the amino acid sequence according to SEQ ID NO:26 (Isoform F).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:27 (Isoform G). In some embodiments, the HSD17B13 variant protein associated with a loss-of-function comprises or consists of the amino acid sequence according to SEQ ID NO:27 (Isoform G).

In some embodiments, an HSD17B13 variant protein associated with a loss-of-function comprises an amino acid sequence that has at least about 90%, at least about 91%, at least about 92%, at least about 93%, at least about 94%, at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises an amino acid sequence that has at least about 95%, at least about 96%, at least about 97%, at least about 98%, or at least about 99% sequence identity to the amino acid sequence according to SEQ ID NO:28 (Isoform H). In some embodiments, the HSD17B13 variant protein associated with a loss-of-function comprises or consists of the amino acid sequence according to SEQ ID NO:28 (Isoform H).

In some embodiments, the HSD17B13 isoform proteins associated with the functional HSD17B13 protein and the HSD17B13 variant proteins associated with a loss-of-function are fragments of the proteins described above. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, or at least about 200 contiguous amino acid residues of the encoded polypeptide (such as the polypeptides having the amino acid sequence of SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29). In this regard, the longer fragments are preferred over the shorter ones. In some embodiments, the fragments comprise at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous amino acid residues of the encoded polypeptide. In this regard, the longer fragments are preferred over the shorter ones.

A nucleic acid sequence for the functional HSD17B13 genomic DNA molecule is set forth in SEQ ID NO:1. The functional HSD17B13 genomic DNA molecule having SEQ ID NO:1 comprises an adenine at position 12,667.

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the functional HSD17B13 genomic DNA molecule comprises or consists a nucleic acid sequence that encodes an HSD17B13 isoform protein that comprises or consists of an amino acid sequence according to SEQ ID NO:21 (Isoform A).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the functional HSD17B13 genomic DNA molecule comprises or consists a nucleic acid sequence that encodes an HSD17B13 isoform protein that comprises or consists of an amino acid sequence according to SEQ ID NO:22 (Isoform B).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the functional HSD17B13 genomic DNA molecule comprises or consists a nucleic acid sequence that encodes an HSD17B13 isoform protein that comprises or consists of an amino acid sequence according to SEQ ID NO:25 (Isoform E).

In some embodiments, the functional HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the functional HSD17B13 genomic DNA molecule comprises or consists a nucleic acid sequence that encodes an HSD17B13 isoform protein that comprises or consists of an amino acid sequence according to SEQ ID NO:29 (Isoform I).

In some embodiments, the functional HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:1. In some embodiments, the functional HSD17B13 genomic DNA molecule comprises or consists of a nucleic acid sequence that has at least about 95%, at least about 96%, at least about 97%, at least about 98%, or at least about 99% sequence identity to SEQ ID NO:1. In some embodiments, the functional HSD17B13 genomic DNA molecule comprises or consists a nucleic acid sequence according to SEQ ID NO:21.

A nucleic acid sequence for the variant HSD17B13 genomic DNA molecule encoding an HSD17B13 variant protein associated with a loss-of-function is set forth in SEQ ID NO:2. The variant HSD17B13 genomic DNA molecule having SEQ ID NO:2 comprises a thymine at position 12,667.

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the variant HSD17B13 genomic DNA molecule comprises or consists a nucleic acid sequence that encodes an HSD17B13 isoform protein that comprises or consists of an amino acid sequence according to SEQ ID NO:23 (Isoform C).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the variant HSD17B13 genomic DNA molecule comprises or consists a nucleic acid sequence that encodes an HSD17B13 isoform protein that comprises or consists of an amino acid sequence according to SEQ ID NO:24 (Isoform D).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the variant HSD17B13 genomic DNA molecule comprises or consists a nucleic acid sequence that encodes an HSD17B13 isoform protein that comprises or consists of an amino acid sequence according to SEQ ID NO:26 (Isoform F).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the variant HSD17B13 genomic DNA molecule comprises or consists a nucleic acid sequence that encodes an HSD17B13 isoform protein that comprises or consists of an amino acid sequence according to SEQ ID NO:27 (Isoform G).

In some embodiments, the variant HSD17B13 genomic DNA molecule comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the variant HSD17B13 genomic DNA molecule comprises or consists a nucleic acid sequence that encodes an HSD17B13 isoform protein that comprises or consists of an amino acid sequence according to SEQ ID NO:28 (Isoform H).

In some embodiments, the variant HSD17B13 genomic DNA molecule comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2. In some embodiments, the variant HSD17B13 genomic DNA molecule comprises or consists of a nucleic acid sequence that has at least about 95%, at least about 96%, at least about 97%, at least about 98%, or at least about 99% sequence identity to SEQ ID NO:2. In some embodiments, the variant HSD17B13 genomic DNA molecule comprises or consists a nucleic acid sequence according to SEQ ID NO:2.

In some embodiments, the functional HSD17B13 genomic DNA and variant HSD17B13 genomic DNA molecules comprise less than the entire genomic DNA sequence. In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500 contiguous nucleotides of SEQ ID NO:1 (functional HSD17B13 genomic DNA) or SEQ ID NO:2 (variant HSD17B13 genomic DNA). In some embodiments, the functional HSD17B13 genomic DNA and variant HSD17B13 genomic DNA molecules comprise or consist of at least about 1000 to at least about 2000 contiguous nucleotides of SEQ ID NO:1 (functional HSD17B13 genomic DNA) or SEQ ID NO:2 (variant HSD17B13 genomic DNA).

In some embodiments, the functional HSD17B13 genomic DNA and variant HSD17B13 genomic DNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, or at least about 2500 contiguous nucleotides of SEQ ID NO:1 (functional HSD17B13 genomic DNA) or SEQ ID NO:2 (variant HSD17B13 genomic DNA).

The nucleic acid sequences for four HSD17B13 RNA transcripts encoding isoform proteins associated with the functional HSD17B13 protein are set forth in SEQ ID NO:44 (Transcript A), SEQ ID NO:45 (Transcript B), SEQ ID NO:48 (Transcript E), and SEQ ID NO:52 (Transcript I).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 RNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 RNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 RNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:44 (Transcript A). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:44 (Transcript A). In some embodiments, the HSD17B13 RNA transcript encoding the isoform protein associated with the functional HSD17B13 protein comprises or consists of a nucleic acid sequence according to SEQ ID NO:44 (Transcript A).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:45 (Transcript B). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:45 (Transcript B). In some embodiments, the HSD17B13 RNA transcript encoding the isoform protein associated with the functional HSD17B13 protein comprises or consists of a nucleic acid sequence according to SEQ ID NO:45 (Transcript B).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:48 (Transcript E). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:48 (Transcript E). In some embodiments, the HSD17B13 RNA transcript encoding the isoform protein associated with the functional HSD17B13 protein comprises or consists of a nucleic acid sequence according to SEQ ID NO:48 (Transcript E).

In some embodiments, an HSD17B13 RNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:52 (Transcript I). In some embodiments, the HSD17B13 RNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:52 (Transcript I). In some embodiments, the HSD17B13 RNA transcript encoding the isoform protein associated with the functional HSD17B13 protein comprises or consists of a nucleic acid sequence according to SEQ ID NO:52 (Transcript I).

The nucleic acid sequences for five HSD17B13 RNA transcripts encoding isoform proteins associated with a loss-of-function are set forth in SEQ ID NO:46 (Transcript C), SEQ ID NO:47 (Transcript D), SEQ ID NO:49 (Transcript F), SEQ ID NO:50 (Transcript G), and SEQ ID NO:51 (Transcript H).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 RNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 RNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 RNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:46 (Transcript C). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:46 (Transcript C). In some embodiments, the HSD17B13 RNA transcript encoding the isoform protein associated with a loss-of-function comprises or consists of a nucleic acid sequence according to SEQ ID NO:46 (Transcript C).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:47 (Transcript D). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:47 (Transcript D). In some embodiments, the HSD17B13 RNA transcript encoding the isoform protein associated with a loss-of-function comprises or consists of a nucleic acid sequence according to SEQ ID NO:47 (Transcript D).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:49 (Transcript F). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:49 (Transcript F). In some embodiments, the HSD17B13 RNA transcript encoding the isoform protein associated with a loss-of-function comprises or consists of a nucleic acid sequence according to SEQ ID NO:49 (Transcript F).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:50 (Transcript G). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:50 (Transcript G). In some embodiments, the HSD17B13 RNA transcript encoding the isoform protein associated with a loss-of-function comprises or consists of a nucleic acid sequence according to SEQ ID NO:50 (Transcript G).

In some embodiments, an HSD17B13 RNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:51 (Transcript H). In some embodiments, the HSD17B13 RNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:51 (Transcript H). In some embodiments, the HSD17B13 RNA transcript encoding the isoform protein associated with a loss-of-function comprises or consists of a nucleic acid sequence according to SEQ ID NO:51 (Transcript H).

In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise less than the RNA transcript sequence. In some embodiments, the functional HSD17B13 RNA transcripts and variant HSD17B13 RNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts). In some embodiments, the functional HSD17B13 RNA transcripts and variant HSD17B13 RNA transcripts comprise or consist of at least about 1000 to at least about 2000 contiguous nucleotides of SEQ ID NO:44, SEQ ID NO:45, SEQ ID NO:48, or SEQ ID NO:52 (functional HSD17B13 RNA transcripts) or SEQ ID NO:46, SEQ ID NO:47, SEQ ID NO:49, SEQ ID NO:50, or SEQ ID NO:51 (variant HSD17B13 RNA transcripts).

The nucleic acid sequences for four HSD17B13 cDNA transcripts encoding isoform proteins associated with the functional HSD17B13 protein are set forth in SEQ ID NO:53 (Transcript A), SEQ ID NO:54 (Transcript B), SEQ ID NO:57 (Transcript E), and SEQ ID NO:61 (Transcript I).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA transcript encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA transcript encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:53 (Transcript A). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:53 (Transcript A). In some embodiments, the HSD17B13 cDNA transcript encoding the isoform protein associated with the functional HSD17B13 protein comprises or consists of a nucleic acid sequence according to SEQ ID NO:53 (Transcript A).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:54 (Transcript B). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:54 (Transcript B). In some embodiments, the HSD17B13 cDNA transcript encoding the isoform protein associated with the functional HSD17B13 protein comprises or consists of a nucleic acid sequence according to SEQ ID NO:54 (Transcript B).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:57 (Transcript E). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:57 (Transcript E). In some embodiments, the HSD17B13 cDNA transcript encoding the isoform protein associated with the functional HSD17B13 protein comprises or consists of a nucleic acid sequence according to SEQ ID NO:57 (Transcript E).

In some embodiments, an HSD17B13 cDNA transcript encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:61 (Transcript I). In some embodiments, the HSD17B13 cDNA transcript encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:61 (Transcript I). In some embodiments, the HSD17B13 cDNA transcript encoding the isoform protein associated with the functional HSD17B13 protein comprises or consists of a nucleic acid sequence according to SEQ ID NO:61 (Transcript I).

The nucleic acid sequences for five HSD17B13 cDNA transcripts encoding isoform proteins associated with a loss-of-function are set forth in SEQ ID NO:55 (Transcript C), SEQ ID NO:56 (Transcript D), SEQ ID NO:58 (Transcript F), SEQ ID NO:59 (Transcript G), and SEQ ID NO:60 (Transcript H).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA transcript encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA transcript encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA transcript encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:55 (Transcript C). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:55 (Transcript C). In some embodiments, the HSD17B13 cDNA transcript encoding the isoform protein associated with a loss-of-function comprises or consists of a nucleic acid sequence according to SEQ ID NO:55 (Transcript C).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:56 (Transcript D). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:56 (Transcript D). In some embodiments, the HSD17B13 cDNA transcript encoding the isoform protein associated with a loss-of-function comprises or consists of a nucleic acid sequence according to SEQ ID NO:56 (Transcript D).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:58 (Transcript F). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:58 (Transcript F). In some embodiments, the HSD17B13 cDNA transcript encoding the isoform protein associated with a loss-of-function comprises or consists of a nucleic acid sequence according to SEQ ID NO:58 (Transcript F).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:59 (Transcript G). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:59 (Transcript G). In some embodiments, the HSD17B13 cDNA transcript encoding the isoform protein associated with a loss-of-function comprises or consists of a nucleic acid sequence according to SEQ ID NO:59 (Transcript G).

In some embodiments, an HSD17B13 cDNA transcript encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:60 (Transcript H). In some embodiments, the HSD17B13 cDNA transcript encoding an isoform protein associated with a loss-of-function comprises or consists of a nucleic acid sequence that has at least about 95%, at least about 96%, at least about 97%, at least about 98%, or at least about 99% sequence identity to SEQ ID NO:60 (Transcript H). In some embodiments, the HSD17B13 cDNA transcript encoding the isoform protein associated with a loss-of-function comprises or consists of a nucleic acid sequence according to SEQ ID NO:60 (Transcript H).

In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, or at least about 2500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise less than the cDNA transcript sequence. In some embodiments, the HSD17B13 cDNA transcripts comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60. In some embodiments, the HSD17B13 cDNA transcripts comprise or consist of at least about 1000 to at least about 2000 contiguous nucleotides of SEQ ID NO:53, SEQ ID NO:54, SEQ ID NO:57, or SEQ ID NO:61 or SEQ ID NO:55, SEQ ID NO:56, SEQ ID NO:58, SEQ ID NO:59, or SEQ ID NO:60.

The nucleic acid sequences for four HSD17B13 mRNA molecules encoding isoform proteins associated with the functional HSD17B13 protein are set forth in SEQ ID NO:3 (Transcript A), SEQ ID NO:4 (Transcript B), SEQ ID NO:7 (Transcript E), and SEQ ID NO:11 (Transcript I).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 mRNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 mRNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:3 (Transcript A). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:3 (Transcript A). In some embodiments, the HSD17B13 mRNA molecule encoding the isoform protein associated with the functional HSD17B13 protein comprises or consists of a nucleic acid sequence according to SEQ ID NO:3 (Transcript A).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:4 (Transcript B). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:4 (Transcript B). In some embodiments, the HSD17B13 mRNA molecule encoding the isoform protein associated with the functional HSD17B13 protein comprises or consists of a nucleic acid sequence according to SEQ ID NO:4 (Transcript B).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:7 (Transcript E). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:7 (Transcript E). In some embodiments, the HSD17B13 mRNA molecule encoding the isoform protein associated with the functional HSD17B13 protein comprises or consists of a nucleic acid sequence according to SEQ ID NO:7 (Transcript E).

In some embodiments, an HSD17B13 mRNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:11 (Transcript I). In some embodiments, the HSD17B13 mRNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:11 (Transcript I). In some embodiments, the HSD17B13 mRNA molecule encoding the isoform protein associated with the functional HSD17B13 protein comprises or consists of a nucleic acid sequence according to SEQ ID NO:11 (Transcript I).

The nucleic acid sequences for five HSD17B13 mRNA molecules encoding isoform proteins associated with a loss-of-function are set forth in SEQ ID NO:5 (Transcript C), SEQ ID NO:6 (Transcript D), SEQ ID NO:8 (Transcript F), SEQ ID NO:9 (Transcript G), and SEQ ID NO:10 (Transcript H).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 mRNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 mRNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 mRNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5 (Transcript C). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:5 (Transcript C). In some embodiments, the HSD17B13 mRNA molecule encoding the isoform protein associated with a loss-of-function comprises or consists of a nucleic acid sequence according to SEQ ID NO:5 (Transcript C).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6 (Transcript D). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:6 (Transcript D). In some embodiments, the HSD17B13 mRNA molecule encoding the isoform protein associated with a loss-of-function comprises or consists of a nucleic acid sequence according to SEQ ID NO:6 (Transcript D).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8 (Transcript F). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:8 (Transcript F). In some embodiments, the HSD17B13 mRNA molecule encoding the isoform protein associated with a loss-of-function comprises or consists of a nucleic acid sequence according to SEQ ID NO:8 (Transcript F).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:9 (Transcript G). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:9 (Transcript G). In some embodiments, the HSD17B13 mRNA molecule encoding the isoform protein associated with a loss-of-function comprises or consists of a nucleic acid sequence according to SEQ ID NO:9 (Transcript G).

In some embodiments, an HSD17B13 mRNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:10 (Transcript H). In some embodiments, the HSD17B13 mRNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:10 (Transcript H). In some embodiments, the HSD17B13 mRNA molecule encoding the isoform protein associated with a loss-of-function comprises or consists of a nucleic acid sequence according to SEQ ID NO:10 (Transcript H).

In some embodiments, the HSD17B13 mRNA molecules comprise less nucleotides than the entire mRNA sequence. In some embodiments, the HSD17B13 mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In some embodiments, the HSD17B13 mRNA molecules comprise or consist of at least about 200 to at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones. In some embodiments, the HSD17B13 mRNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:3, SEQ ID NO:4, SEQ ID NO:7, or SEQ ID NO:11, or SEQ ID NO:5, SEQ ID NO:6, SEQ ID NO:8, SEQ ID NO:9, or SEQ ID NO:10. In this regard, the longer mRNA molecules are preferred over the shorter ones.

The nucleic acid sequences for four HSD17B13 cDNA molecules encoding isoform proteins associated with the functional HSD17B13 protein are set forth in SEQ ID NO:12 (Transcript A), SEQ ID NO:13 (Transcript B), SEQ ID NO:16 (Transcript E), and SEQ ID NO:20 (Transcript I).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21 (Isoform A). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:21 (Isoform A). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:21 (Isoform A).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:22 (Isoform B). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:22 (Isoform B). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:22 (Isoform B).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25 (Isoform E). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:25 (Isoform E). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:25 (Isoform E).

In some embodiments, an HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29 (Isoform I). In some embodiments, the HSD17B13 cDNA molecule encoding an isoform protein associated with the functional HSD17B13 protein comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:29 (Isoform I). In some embodiments, the HSD17B13 cDNA molecule encoding the isoform protein associated with the functional HSD17B13 protein comprises or consists of a nucleic acid sequence that encodes an HSD17B13 isoform protein that comprises or consists of an amino acid sequence according to SEQ ID NO:29 (Isoform I).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:12 (Transcript A). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:12 (Transcript A). In some embodiments, the HSD17B13 cDNA molecule encoding the isoform protein associated with the functional HSD17B13 protein comprises or consists of a nucleic acid sequence according to SEQ ID NO:12 (Transcript A).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:13 (Transcript B). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:13 (Transcript B). In some embodiments, the HSD17B13 cDNA molecule encoding the isoform protein associated with the functional HSD17B13 protein comprises or consists of a nucleic acid sequence according to SEQ ID NO:13 (Transcript B).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:16 (Transcript E). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:16 (Transcript E). In some embodiments, the HSD17B13 cDNA molecule encoding the isoform protein associated with the functional HSD17B13 protein comprises or consists of a nucleic acid sequence according to SEQ ID NO:16 (Transcript E).

In some embodiments, an HSD17B13 cDNA molecule encoding an isoform protein associated with the functional HSD17B13 protein comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:20 (Transcript I). In some embodiments, the HSD17B13 cDNA molecule encoding an isoform protein associated with the functional HSD17B13 protein comprises or consists of a nucleic acid sequence that has at least about 95%, at least about 96%, at least about 97%, at least about 98%, or at least about 99% sequence identity to SEQ ID NO:20 (Transcript I). In some embodiments, the HSD17B13 cDNA molecule encoding the isoform protein associated with the functional HSD17B13 protein comprises or consists of a nucleic acid sequence according to SEQ ID NO:20 (Transcript I).

The nucleic acid sequences for five HSD17B13 cDNA molecules encoding isoform proteins associated with a loss-of-function are set forth in SEQ ID NO:14 (Transcript C), SEQ ID NO:15 (Transcript D), SEQ ID NO:17 (Transcript F), SEQ ID NO:18 (Transcript G), and SEQ ID NO:19 (Transcript H).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:23 (Isoform C). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:23 (Isoform C). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:23 (Isoform C).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24 (Isoform D). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:24 (Isoform D). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:24 (Isoform D).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26 (Isoform F). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:26 (Isoform F). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:26 (Isoform F).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:27 (Isoform G). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:27 (Isoform G). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:27 (Isoform G).

In some embodiments, an HSD17B13 cDNA molecule encoding an isoform protein associated with a loss-of-function comprises or consists of a nucleic acid sequence that encodes an HSD17B13 isoform protein that comprises an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:28 (Isoform H). In some embodiments, the HSD17B13 cDNA molecule encoding an isoform protein associated with a loss-of-function comprises or consists of a nucleic acid sequence that encodes an HSD17B13 isoform protein that comprises an amino acid sequence that has at least about 95%, at least about 96%, at least about 97%, at least about 98%, or at least about 99% sequence identity to SEQ ID NO:28 (Isoform H). In some embodiments, the HSD17B13 cDNA molecule encoding the isoform protein associated with a loss-of-function comprises or consists of a nucleic acid sequence that encodes an HSD17B13 isoform protein that comprises or consists of an amino acid sequence according to SEQ ID NO:28 (Isoform H).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:14 (Transcript C). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:14 (Transcript C). In some embodiments, the HSD17B13 cDNA molecule encoding the isoform protein associated with a loss-of-function comprises or consists of a nucleic acid sequence according to SEQ ID NO:14 (Transcript C).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:15 (Transcript D). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:15 (Transcript D). In some embodiments, the HSD17B13 cDNA molecule encoding the isoform protein associated with a loss-of-function comprises or consists of a nucleic acid sequence according to SEQ ID NO:15 (Transcript D).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:17 (Transcript F). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:17 (Transcript F). In some embodiments, the HSD17B13 cDNA molecule encoding the isoform protein associated with a loss-of-function comprises or consists of a nucleic acid sequence according to SEQ ID NO:17 (Transcript F).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:18 (Transcript G). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:18 (Transcript G). In some embodiments, the HSD17B13 cDNA molecule encoding the isoform protein associated with a loss-of-function comprises or consists of a nucleic acid sequence according to SEQ ID NO:18 (Transcript G).

In some embodiments, an HSD17B13 cDNA molecule encoding an isoform protein associated with a loss-of-function comprises or consists of a nucleic acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:19 (Transcript H). In some embodiments, the HSD17B13 cDNA molecule encoding an isoform protein associated with a loss-of-function comprises or consists of a nucleic acid sequence that has at least about 95%, at least about 96%, at least about 97%, at least about 98%, or at least about 99% sequence identity to SEQ ID NO:19 (Transcript H). In some embodiments, the HSD17B13 cDNA molecule encoding the isoform protein associated with a loss-of-function comprises or consists of a nucleic acid sequence according to SEQ ID NO:19 (Transcript H).

In some embodiments, the HSD17B13 cDNA molecules comprise less nucleotides than the entire cDNA sequence. In some embodiments, the HSD17B13 cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, or at least about 900 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In some embodiments, the HSD17B13 cDNA molecules comprise or consist of at least about 200 to at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones. In some embodiments, the HSD17B13 cDNA molecules comprise or consist of at least about 50, at least about 60, at least about 70, at least about 80, at least about 90, at least about 100, at least about 200, at least about 300, at least about 400, or at least about 500 contiguous nucleotides of SEQ ID NO:12, SEQ ID NO:13, SEQ ID NO:16, or SEQ ID NO:20 or SEQ ID NO:14, SEQ ID NO:15, SEQ ID NO:17, SEQ ID NO:18, or SEQ ID NO:19. In this regard, the longer cDNA molecules are preferred over the shorter ones.

The probes and primers described herein can be used to hybridize to any of the functional or variant PNPLA3 genomic DNA molecules, mRNA molecules, or cDNA molecules derived from mRNA molecules described herein. The primers can be used, for example, to amplify portions of any of the functional or variant PNPLA3 genomic DNA molecules, mRNA molecules, or cDNA molecules derived from mRNA molecules described herein, so that the amplifications products can be, for example, detected or sequenced.

For example, the probes and primers can be used to hybridize to any of the wild type PNPLA3 genomic DNA molecules described herein, including the wild type PNPLA3 genomic DNA molecule comprising SEQ ID NO:30. The probes and primers can also be used to hybridize to any of the wild type PNPLA3 mRNA molecules described herein, including the wild type PNPLA3 mRNA molecules comprising SEQ ID NO:32 or SEQ ID NO:33. The probes and primers can also be used to hybridize to any of the wild type PNPLA3 cDNA molecules described herein, including the wild type PNPLA3 cDNA molecules comprising SEQ ID NO:36 or SEQ ID NO:37.

The probes and primers can also be used to hybridize to any of the variant PNPLA3 genomic DNA molecules described herein, including the variant PNPLA3 genomic DNA molecule comprising SEQ ID NO:31. The probes and primers can also be used to hybridize to any of the variant PNPLA3 mRNA molecules described herein, including the variant PNPLA3 mRNA molecules comprising SEQ ID NO:34 or SEQ ID NO:35. The probes and primers can also be used to hybridize to any of the variant PNPLA3 cDNA molecules described herein, including the variant PNPLA3 cDNA molecules comprising SEQ ID NO:38 or SEQ ID NO:39.

The probes can be used, for example, to detect any of the functional or variant HSD17B13 genomic DNA molecules, mRNA molecules, or cDNA molecules derived from mRNA molecules described herein. The primers can be used, for example, to amplify portions of any of the functional or variant HSD17B13 genomic DNA molecules, mRNA molecules, or cDNA molecules derived from mRNA molecules described herein, so that the amplifications products can be, for example, detected or sequenced.

For example, the probes and primers can be used to hybridize to any of the functional HSD17B13 genomic DNA molecules described herein, including the functional HSD17B13 genomic DNA molecule comprising SEQ ID NO:1. The probes and primers can also be used to hybridize to any of the functional HSD17B13 RNA transcripts described herein, including the functional HSD17B13 RNA transcripts comprising SEQ ID NO:44, SEQ ID NO:45, SEQ ID NO:48, or SEQ ID NO:52. The probes and primers can also be used to hybridize to any of the functional HSD17B13 DNA transcripts described herein, including the functional HSD17B13 DNA transcripts comprising SEQ ID NO:53, SEQ ID NO:54, SEQ ID NO:57, or SEQ ID NO:61. The probes and primers can also be used to hybridize to any of the functional HSD17B13 mRNA molecules described herein, including the functional HSD17B13 mRNA molecules comprising SEQ ID NO:3, SEQ ID NO:4, SEQ ID NO:7, or SEQ ID NO:11. The probes and primers can also be used to hybridize to any of the functional HSD17B13 cDNA molecules described herein, including the functional HSD17B13 cDNA molecules comprising SEQ ID NO:12, SEQ ID NO:13, SEQ ID NO:16, or SEQ ID NO:20.

The probes and primers can also be used to hybridize to any of the variant HSD17B13 genomic DNA molecules described herein, including the variant HSD17B13 genomic DNA molecule comprising SEQ ID NO:2. The probes and primers can also be used to hybridize to any of the variant HSD17B13 RNA transcripts described herein, including the variant HSD17B13 RNA transcripts comprising SEQ ID NO:46, SEQ ID NO:47, SEQ ID NO:49, SEQ ID NO:50, or SEQ ID NO:51. The probes and primers can also be used to hybridize to any of the variant HSD17B13 DNA transcripts described herein, including the variant HSD17B13 DNA transcripts comprising SEQ ID NO:55, SEQ ID NO:56, SEQ ID NO:58, SEQ ID NO:59, or SEQ ID NO:60. The probes and primers can also be used to hybridize to any of the variant HSD17B13 mRNA molecules described herein, including the variant HSD17B13 mRNA molecules comprising SEQ ID NO:5, SEQ ID NO:6, SEQ ID NO:8, SEQ ID NO:9, or SEQ ID NO:10. The probes and primers can also be used to hybridize to any of the HSD17B13 cDNA molecules described herein, including the HSD17B13 cDNA molecules comprising SEQ ID NO:14, SEQ ID NO:15, SEQ ID NO:17, SEQ ID NO:18, or SEQ ID NO:19.

In some embodiments, the probes and/or primers described herein comprise a nucleic acid sequence that specifically hybridizes to any of the nucleic acid molecules disclosed herein, or the complement thereof. In some embodiments, the probe or primer specifically hybridizes to any of the nucleic acid molecules disclosed herein under stringent conditions. The present disclosure also provides nucleic acid molecules having nucleic acid sequences that hybridize under moderate conditions to any of the nucleic acid molecules disclosed herein, or the complement thereof.

Appropriate stringency conditions which promote DNA hybridization include, for example, 6× sodium chloride/sodium citrate (SSC) at about 45° C., followed by a wash of 2×SSC at 50° C. (see, also *Current Protocols in Molecular Biology*, John Wiley & Sons, N.Y. (1989), 6.3.1-6.3.6). Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 1984, 138, 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7°

C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used.

The probes described herein can be linked or fused to a label to aid in detection. The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The probe or primer can comprise any suitable length, non-limiting examples of which include at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. In some embodiments, the probe or primer comprises at least about 18 nucleotides in length to about 25 nucleotides in length. The probe or primer can comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides in length. In some embodiments, the probe or primer is from about 18 to about 30 nucleotides in length. Alternately, in some embodiments, the probe comprises or consists of at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides.

In some embodiments, the probes and/or primers can hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to any of the wild type PNPLA3 or HSD17B13 nucleic acid molecules or variant PNPLA3 or HSD17B13 nucleic acid molecules described herein.

In some embodiments, the probe or primer comprises DNA. In some embodiments, the probe or primer comprises RNA.

The probes and primers described herein can also be alteration-specific probes and alteration-specific primers. The alteration-specific probe or alteration-specific primer can comprise a nucleic acid sequence which is complementary to and/or hybridizes, or specifically hybridizes, to a nucleic acid sequence encoding a variant PNPLA3 protein but which is not complementary to and/or hybridizes, or specifically hybridizes, to a nucleic acid sequence encoding a wild type PNPLA3 protein. In this context, "specifically hybridizes" means that the probe or primer (e.g., the alteration-specific probe or alteration-specific primer) does not hybridize to a nucleic acid molecule encoding a wild type PNPLA3 protein. Herein, the term "specifically hybridizes" means that the probe or primer exclusively hybridizes to the indicated nucleic acid molecule and not to another nucleic acid molecule. Accordingly, a probe or primer which specifically hybridizes to a nucleic acid molecule encoding a PNPLA3 protein comprising the 1148M variation does not hybridize to a nucleic acid molecule encoding a PNPLA3 protein which does not comprise the 1148M variation. The alteration-specific probe or alteration-specific primer can also comprise a nucleic acid sequence which is complementary to and/or hybridizes, or specifically hybridizes, to a nucleic acid sequence encoding a wild type PNPLA3 protein but which is not complementary to and/or hybridizes, or specifically hybridizes, to a nucleic acid sequence encoding a variant PNPLA3 protein. In this context, "specifically hybridizes" means that the probe or primer (e.g., the alteration-specific probe or alteration-specific primer) does not hybridize to a nucleic acid molecule encoding a variant PNPLA3 protein.

The alteration-specific probe or alteration-specific primer can also comprise a nucleic acid sequence which is complementary to and/or hybridizes, or specifically hybridizes, to a nucleic acid sequence encoding a variant HSD17B13 protein but which is not complementary to and/or hybridizes, or specifically hybridizes, to a nucleic acid sequence encoding a functional HSD17B13 protein. In this context, "specifically hybridizes" means that the probe or primer (e.g., the alteration-specific probe or alteration-specific primer) does not hybridize to a nucleic acid molecule encoding a functional HSD17B13 protein. For example, in this context "specifically hybridizes" means that the probe or primer does not hybridize to a nucleic acid molecule encoding a non-active/loss of function HSD17B13 protein. The alteration-specific probe or alteration-specific primer can also comprise a nucleic acid sequence which is complementary to and/or hybridizes, or specifically hybridizes, to a nucleic acid sequence encoding a functional HSD17B13 protein but which is not complementary to and/or hybridizes, or specifically hybridizes, to a nucleic acid sequence encoding a variant HSD17B13 protein. In this context, "specifically hybridizes" means that the probe or primer (e.g., the alteration-specific probe or alteration-specific primer) does not hybridize to a nucleic acid molecule encoding a variant HSD17B13 protein.

In some embodiments, the alteration-specific probe or alteration-specific primer comprises a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the alteration-specific probe or alteration-specific primer comprises a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34. In some embodiments, the alteration-specific probe or alteration-specific primer comprises a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38. In some embodiments, the alteration-specific probe or alteration-specific primer comprises a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39.

In some embodiments, the alteration-specific probe or alteration-specific primer comprises a nucleic acid sequence which is complementary to and/or hybridizes, or specifically hybridizes, to the portion of the HSD17B13 genomic DNA that comprises an adenine at a position corresponding to position 12,667 according to SEQ ID NO:1. In some embodiments, the alteration-specific probe or alteration-specific primer comprises a nucleic acid sequence which is complementary to and/or hybridizes, or specifically hybridizes, to the portion of the HSD17B13 genomic DNA that comprises a thymine at a position corresponding to position 12,667 according to SEQ ID NO:2.

In some embodiments, the portion of the nucleic acid molecule to which the probe or primer is hybridized comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule to which the probe or primer is hybridized comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

The kits described herein can comprise detection and/or amplification assay reagents that can be used for detecting and/or amplifying any of the wild type PNPLA3 and/or HSD17B13 nucleic acid molecules described herein and/or any of the variant PNPLA3 and/or HSD17B13 nucleic acid molecules described herein. In some embodiments, the kits for such detection and/or amplification can contain any of the reagents (e.g., probes and primers) described herein. In some embodiments, a basic kit can comprise a container having at least one probe or primer or at least two probes or primers, such as alteration-specific probes or alteration-specific primers, for a locus in any of the nucleic acid molecules disclosed herein. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers. In some embodiments, the kits comprise at least one labeled probe (e.g., alteration-specific probe) for detection. In some embodiments, any of the kits disclosed herein can further comprise products and reagents required to carry out an annealing reaction, and instructions.

The present disclosure provides methods for detecting the presence of any of the wild type PNPLA3 proteins described herein. The present disclosure also provides methods for detecting the presence of any of the variant PNPLA3 proteins described herein. The present disclosure also provides methods for detecting the presence of any of the wild type PNPLA3 nucleic acid molecules described herein (e.g., genomic DNA molecules, mRNA molecules, and cDNA molecules) described herein. The present disclosure also provides methods for detecting the presence of any of the variant PNPLA3 nucleic acid molecules described herein (e.g., genomic DNA molecules, mRNA molecules, and cDNA molecules) described herein.

The present disclosure also provides methods for detecting the presence of any of the functional HSD17B13 proteins described herein. The present disclosure also provides methods for detecting the presence of any of the variant HSD17B13 proteins described herein. The present disclosure also provides methods for detecting the presence of any of the functional HSD17B13 nucleic acid molecules described herein (e.g., genomic DNA molecules, RNA transcripts, cDNA transcripts, mRNA molecules, and cDNA molecules) described herein. The present disclosure also provides methods for detecting the presence of any of the variant HSD17B13 nucleic acid molecules described herein (e.g., genomic DNA molecules, RNA transcripts, cDNA transcripts, mRNA molecules, and cDNA molecules) described herein.

In some embodiments of any of the methods described herein, a functional HSD17B13 protein, or nucleic acid molecule encoding the same, is detected or sought to be detected in a subject or patient. In some embodiments, the subject or patient comprises a functional HSD17B13 protein. In some embodiments, the functional HSD17B13 protein is one of the functional HSD17B13 proteins described herein (which can be encoded by any of the nucleic acid molecules described herein encoding the same). In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of the HSD17B13 protein having the amino acid sequence according to SEQ ID NO:40. In some embodiments, a functional HSD17B13 protein has at least 90%, at least 80%, at least 70%, at least 60%, or at least 50% of the biological activity of the HSD17B13 protein having the amino acid sequence according to SEQ ID NO:40. In some embodiments, a functional HSD17B13 protein has at least 90%, at least 80%, at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 70%, at least 60%, at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 50%, at least 40%, at least 30%, at least 20%, at least 10%, at least 5%, or at least 1% of the biological activity of HSD17B13 protein having SEQ ID NO:40. In some embodiments, a functional HSD17B13 protein has at least 30%, at least 20%, at least 10%, at least 5%, or at least 1% of the biological activity of HSD17B13 protein having SEQ ID NO:40. In some embodiments, a functional HSD17B13 protein has at least 90% of the biological activity of HSD17B13 protein having SEQ ID NO:40. In some embodiments, a functional HSD17B13 protein has at least 80% of the biological activity of HSD17B13 protein having SEQ ID NO:40. In some embodiments, a functional HSD17B13 protein has at least 70% of the biological activity of HSD17B13 protein having SEQ ID NO:40. In some embodiments, a functional HSD17B13 protein has at least 60% of the biological activity of HSD17B13 protein having SEQ ID NO:40. In some embodiments, a functional HSD17B13 protein has at least 50% of the biological activity of HSD17B13 protein having SEQ ID NO:40. In some embodiments, a functional HSD17B13 protein has at least 40% of the biological activity of HSD17B13 protein having SEQ ID NO:40. In some embodiments, a functional HSD17B13 protein has at least 30% of the biological activity of HSD17B13 protein having SEQ ID NO:40. In some embodiments, a functional HSD17B13 protein has at least 20% of the biological activity of HSD17B13 protein having SEQ ID NO:40. In some embodiments, a functional HSD17B13 protein has at least 10% of the biological activity of HSD17B13 protein having SEQ ID NO:40. In some embodiments, a functional HSD17B13 protein has at least 5% of the biological activity of HSD17B13 protein having SEQ ID NO:40. In some embodiments, a functional HSD17B13 protein has at least 1% of the biological activity of HSD17B13 protein having SEQ ID NO:40. In some embodiments, the activity of an HSD17B13 protein (e.g., functionality) can be determined by, for example, performing an oxidoreductase activity assay.

It is understood that gene sequences within a population and mRNAs and proteins encoded by such genes can vary due to polymorphisms such as single-nucleotide polymorphisms. The sequences provided herein are only exemplary sequences. Other sequences for the variant PNPLA3 and HSD17B13 genomic DNA, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant PNPLA3 nucleic acid molecule, preliminary processing designed to isolate or enrich the sample for the genomic DNA can be employed. A variety of techniques can be used for this purpose. When detecting the level of variant PNPLA3 mRNA, different techniques can be used to enrich the biological sample with mRNA. Various methods to detect the presence or level of an mRNA or the presence of a particular variant genomic DNA locus can be used.

In some embodiments, the presence or absence of a particular PNPLA3 protein or HSD17B13 protein (e.g., functional or variant) is detected by sequencing at least a portion of the protein to determine whether the protein comprises an amino acid sequence encoding any of the variant PNPLA3 proteins or HSD17B13 proteins (e.g., functional or variant) described herein. In some embodiments, the presence or absence of a particular PNPLA3 protein or HSD17B13 protein (e.g., functional or variant) is detected by performing an immunoassay, such as an ELISA, to determine whether any of the variant PNPLA3 proteins or HSD17B13 proteins (e.g., functional or variant) described herein are present in the sample.

In some embodiments, the portion of the protein sequenced comprises from about 5 to about 100, from about 5 to about 50, from about 5 to about 40, from about 5 to about 30, from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein). In some preferred embodiments, the portion of the protein sequenced comprises from about 5 to about 20, or from about 5 to about 10 amino acids, and comprises the position corresponding to the position containing the variation (e.g., I148M of PNPLA3 or the portion of the variant HSD17B13 protein that is different from the corresponding wild type HSD17B13 protein).

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various techniques (e.g., calorimetric, fluorescent, chemiluminescent, or radioactive) are suitable for use in the immunoassays.

In some embodiments, the presence or absence of a particular PNPLA3 nucleic acid molecule or HSD17B13 nucleic acid molecule (e.g., functional or variant genomic DNA, mRNA, cDNA, RNA transcript, or cDNA transcript) is detected by sequencing at least a portion of the nucleic acid molecule to determine whether the nucleic acid molecule comprises a nucleic acid sequence according to any of the variant PNPLA3 nucleic acid molecules or HSD17B13 nucleic acid molecules (e.g., functional or variant) described herein.

In some embodiments, the portion of the nucleic acid molecule sequenced comprises from about 10 to about 200, from about 10 to about 150, from about 10 to about 100, from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein). In some preferred embodiments, the portion of the nucleic acid molecule sequenced comprises from about 10 to about 50, from about 10 to about 40, from about 10 to about 30, or from about 10 to about 20 nucleotides, and comprises the codon corresponding to the position containing codon encoding the particular variation (e.g., I148M of PNPLA3 or the portion of the variant HSD17B13 protein that is different from the corresponding wild type HSD17B13 protein).

In some embodiments, the methods of detecting the presence or absence of any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein in a subject, comprise: performing an assay on a biological sample obtained from the subject, which assay determines whether a nucleic acid molecule in the biological sample comprises any of the particular PNPLA3 nucleic acid molecules or HSD17B13 nucleic acid molecules (e.g., any of the functional or variant genomic DNA molecules, mRNA molecules, cDNA molecules, RNA transcripts, or cDNA transcripts) described herein. In some embodiments, the biological sample comprises a cell or cell lysate. Such methods can further comprise, for example, obtaining a biological sample from the subject, optionally reverse transcribing the mRNA into cDNA, and performing the assay. Such assays can comprise, for example, determining the identity of particular positions of the particular nucleic acid molecules described herein.

For example, the assay can comprise the use of alteration-specific probes or alteration-specific primers that comprise a nucleic acid sequence which is complementary to and/or hybridizes, or specifically hybridizes, to a portion of a PNPLA3 nucleic acid sequence that comprises a methionine at a position corresponding to position 148 according to SEQ ID NO:42, or comprises a methionine at a position corresponding to position 144 according to SEQ ID NO:43, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 genomic DNA that comprises an ATG codon at the positions corresponding to positions 5107 to 5109 according to SEQ ID NO:31, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 442 to 444 according to SEQ ID NO:34, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 mRNA that comprises an AUG codon at the positions corresponding to positions 430 to 432 according to SEQ ID NO:35, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 442 to 444 according to SEQ ID NO:38, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the variant PNPLA3 cDNA that comprises an ATG codon at the positions corresponding to positions 430 to 432 according to SEQ ID NO:39, or a portion adjacent thereto.

In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises an adenine at a position corresponding to position 12,667 according to SEQ ID NO:1, or a portion adjacent thereto. In some embodiments, the assay can comprise the use of alteration-specific probes or alteration-specific primers that comprise a nucleic acid sequence which is complementary to and/or hybridizes, or specifically hybridizes, to the portion of the HSD17B13 genomic DNA that comprises a thymine at a position corresponding to position 12,667 according to SEQ ID NO:2, or a portion adjacent thereto.

In some embodiments, the assay comprises: sequencing at least a portion of the nucleic acid molecules described herein present in the biological sample from the subject, wherein the portion sequenced includes the positions disclosed herein. For example, the portion sequenced can be a portion of a PNPLA3 nucleic acid sequence that comprises a methionine at a position corresponding to position 148 according to SEQ ID NO:42, or comprises a methionine at a position corresponding to position 144 according to SEQ ID NO:43. In some embodiments, the portion sequenced can be portion of the variant PNPLA3 genomic DNA that comprises an ATG codon at the positions corresponding to positions 5107 to 5109 according to SEQ ID NO:31. In some embodiments, the portion sequenced can be a portion of the variant PNPLA3 mRNA that comprises an AUG codon at the positions corresponding to positions 442 to 444 according to SEQ ID NO:34. In some embodiments, the portion sequenced can be a portion of the variant PNPLA3 mRNA that comprises an AUG codon at the positions corresponding to positions 430 to 432 according to SEQ ID NO:35. In some embodiments, the portion sequenced can be a portion of the variant PNPLA3 cDNA that comprises an ATG codon at the positions corresponding to positions 442 to 444 according to SEQ ID NO:38. In some embodiments, the portion sequenced can be a portion of the variant PNPLA3 cDNA that comprises an ATG codon at the positions corresponding to positions 430 to 432 according to SEQ ID NO:39.

In some embodiments, the portion sequenced can be a portion of the HSD17B13 genomic DNA that comprises an adenine at a position corresponding to position 12,667 according to SEQ ID NO:1. In some embodiments, the portion sequenced can be a portion of the HSD17B13 genomic DNA that comprises a thymine at a position corresponding to position 12,667 according to SEQ ID NO:2.

In some embodiments, the assay comprises: a) contacting the biological sample with a primer (or alteration-specific primer) hybridizing to the regions adjacent to the portions of the nucleic acid molecules identified herein (e.g., adjacent to a portion of a PNPLA3 nucleic acid sequence that comprises a methionine at a position corresponding to position 148 according to SEQ ID NO:42, or comprises a methionine at a position corresponding to position 144 according to SEQ ID NO:43; adjacent to a portion of the variant PNPLA3 genomic DNA that comprises an ATG codon at the positions corresponding to positions 5107 to 5109 according to SEQ ID NO:31; adjacent to a portion of the variant PNPLA3 mRNA that comprises an AUG codon at the positions corresponding to positions 442 to 444 according to SEQ ID NO:34; adjacent to a portion of the variant PNPLA3 mRNA that comprises an AUG codon at the positions corresponding to positions 430 to 432 according to SEQ ID NO:35; adjacent to a portion of the variant PNPLA3 cDNA that comprises an ATG codon at the positions corresponding to positions 442 to 444 according to SEQ ID NO:38; adjacent to a portion of the variant PNPLA3 cDNA that comprises an ATG codon at the positions corresponding to positions 430 to 432 according to SEQ ID NO:39; adjacent to a portion of the HSD17B13 genomic DNA that comprises an adenine at a position corresponding to position 12,667 according to SEQ ID NO:1; or adjacent to a portion of the HSD17B13 genomic DNA that comprises a thymine at a position corresponding to position 12,667 according to SEQ ID NO:2); b) extending the primer at least through the position of the nucleic acid molecules corresponding to nucleotide positions beyond the altered site (e.g., the portion of a PNPLA3 nucleic acid sequence that comprises a methionine at a position corresponding to position 148 according to SEQ ID NO:42, or comprises a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2); and c) determining whether the extension product of the primer comprises the nucleic acid sequence of any of the variant or wild type PNPLA3 or HSD17B13 nucleic acid molecules described herein.

In some embodiments, only PNPLA3 genomic DNA is analyzed. In some embodiments, only PNPLA3 mRNA is analyzed. In some embodiments, only PNPLA3 cDNA obtained from PNPLA3 mRNA is analyzed. In some embodiments, only HSD17B13 genomic DNA is analyzed. In some embodiments, only HSD17B13 mRNA is analyzed. In some embodiments, only HSD17B13 cDNA obtained from HSD17B13 mRNA is analyzed. In some embodiments, only HSD17B13 RNA transcripts is analyzed. In some embodiments, only HSD17B13 cDNA obtained from HSD17B13 RNA transcripts is analyzed.

In some embodiments, the assay comprises contacting the biological sample with a primer or probe that specifically hybridizes to any of the particular variant PNPLA3 nucleic acid molecules or variant HSD17B13 nucleic acid molecules (e.g., any of the variant genomic DNA molecules, mRNA molecules, cDNA molecules, RNA transcripts, or cDNA transcripts) described herein and not the corresponding functional nucleic acid molecules under stringent conditions, and determining whether hybridization has occurred.

In some embodiments, the assay comprises contacting the biological sample with a primer or probe that specifically hybridizes to any of the particular variant PNPLA3 nucleic acid molecules (e.g., any of the variant genomic DNA molecules, mRNA molecules, cDNA molecules, RNA transcripts, or cDNA transcripts) or nucleic acid molecules encoding a functional HSD17B13 protein (e.g., any of the genomic DNA molecules, mRNA molecules, cDNA molecules, RNA transcripts, or cDNA transcripts encoding a functional HSD17B13 protein) described herein and not to the corresponding nucleic acid molecules encoding wild type PNPLA3 or variant HSD17B13, respectively, under stringent conditions, and determining whether hybridization has occurred.

In some embodiments, the assay comprises RNA sequencing (RNA-Seq). In some embodiments, the assays also comprise reverse transcribing mRNA into cDNA via the reverse transcriptase polymerase chain reaction (RT-PCR).

Such probes and primers can hybridize specifically to a target sequence under high stringency hybridization conditions. Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity or complementarity to the target nucleic acid molecule.

When a probe is hybridized with a nucleic acid molecule in a biological sample under conditions that allow for the binding of the probe to the nucleic acid molecule, this binding can be detected and allow for an indication of the presence of the particular variant or wild type PNPLA3 or variant or functional HSD17B13 locus or the presence or the level of the particular variant or wild type PNPLA3 or variant or functional HSD17B13 mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 gene. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 mRNA. The specific probe may comprise a sequence of at least about 80%, from about 80% to about 85%, from about 85% to about 90%, from about 90% to about 95%, and from about 95% to about 100% identical (or complementary) to a specific region of a variant or wild type PNPLA3 or variant or functional HSD17B13 cDNA.

In some embodiments, to determine whether a particular nucleic acid complement of a biological sample comprises a nucleic acid sequence encoding a particular functional or variant PNPLA3 protein or HSD17B13 protein, the biological sample may be subjected to a nucleic acid amplification method using a primer pair that includes a first primer derived from the 5' flanking sequence adjacent to positions encoding a site of interest (e.g., any of the positions described herein), and a second primer derived from the 3' flanking sequence adjacent to positions encoding the same site of interest, to produce an amplicon that is diagnostic for the presence of the particular functional or variant PNPLA3 protein or HSD17B13 protein. For example, with regard to PNPLA3 the amplicon may comprise a nucleotide sequence encoding the position which corresponds to position 148 according to SEQ ID NO: 42. With regard to HSD17B13 the amplicon may comprise a nucleotide sequence which corresponds to positions 5107 to 5109 according to SEQ ID NO: 31. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding the site of interest and at least 1, 2, 3, 4, 5, 6, 7, 8, 9, 10, or more nucleotides on each side of positions encoding the site of interest. Similar amplicons can be generated from the mRNA and/or cDNA sequences.

Representative methods for preparing and using probes and primers are described, for example, in *Molecular Cloning: A Laboratory Manual,* 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using guidelines.

Any nucleic acid hybridization or amplification or sequencing method can be used to specifically detect the presence of the functional or variant PNPLA3 or HSD17B13 gene locus and/or the level of functional or variant PNPLA3 or HSD17B13 mRNA or cDNA produced from mRNA. In some embodiments, the nucleic acid molecule can be used either as a primer to amplify a region of the functional or variant PNPLA3 or HSD17B13 nucleic acid or the nucleic acid molecule can be used as a probe that specifically hybridizes, for example, under stringent conditions, to a nucleic acid molecule comprising the functional or variant PNPLA3 or HSD17B13 gene locus or a nucleic acid molecule comprising a functional or variant PNPLA3 or HSD17B13 mRNA or cDNA produced from mRNA.

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, the methods of Southern (DNA: DNA) blot hybridizations, in situ hybridization (ISH), and fluorescence in situ hybridization (FISH) of chromosomal material. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected. In any such methods, the process can include hybridization using any of the probes described or exemplified herein.

In hybridization techniques, stringent conditions can be employed such that a probe or primer will specifically hybridize to its target. In some embodiments, a polynucleotide primer or probe under stringent conditions will hybridize to its target sequence (e.g., the functional or variant PNPLA3 or HSD17B13 locus, functional or variant PNPLA3 or HSD17B13 mRNA, or functional or variant PNPLA3 or HSD17B13 cDNA) to a detectably greater degree than to other sequences (e.g., the corresponding functional or variant PNPLA3 or HSD17B13 locus, functional or variant PNPLA3 or HSD17B13 mRNA, or functional or variant PNPLA3 or HSD17B13 cDNA), such as, at least 2-fold, at least 3-fold, at least 4-fold, or more over background, including over 10-fold over background. In some embodiments, a polynucleotide primer or probe under stringent conditions will hybridize to its target sequence to a detectably greater degree than to other sequences by at least 2-fold. In some embodiments, a polynucleotide primer or probe under stringent conditions will hybridize to its target sequence to a detectably greater degree than to other sequences by at least 3-fold. In some embodiments, a polynucleotide primer or probe under stringent conditions will hybridize to its target sequence to a detectably greater degree than to other sequences by at least 4-fold. In some embodiments, a polynucleotide primer or probe under stringent conditions will hybridize to its target sequence to a detectably greater degree than to other sequences by over 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing).

In some embodiments, the detecting step comprises: amplifying at least a portion of the nucleic acid molecule that encodes a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding the a site of interest (e.g., any of the positions described herein); and detecting the detectable label.

In some embodiments, the detecting step comprises: amplifying at least a portion of the nucleic acid molecule that encodes a PNPLA3 or HSD17B13 protein, wherein the amplified nucleic acid molecule encodes an amino acid sequence which comprises a site of interest (e.g., any of the positions described herein); labeling the nucleic acid molecule with a detectable label; contacting the labeled nucleic acid with a support comprising a probe, wherein the probe comprises a nucleic acid sequence which hybridizes under stringent conditions to a nucleic acid sequence encoding a site of interest (e.g., any of the positions described herein); and detecting the detectable label. Any of the nucleic acid molecules disclosed herein can be amplified. For example, any of the genomic DNA, cDNA, or mRNA molecules disclosed herein can be amplified. In some embodiments, the nucleic acid molecule is mRNA and the method further comprises reverse-transcribing the mRNA into a cDNA prior to the amplifying step.

In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding the variant PNPLA3 or HSD17B13 protein, and detecting the detectable label. In some embodiments, the detecting step comprises: contacting the nucleic acid molecule that encodes a PNPLA3 or HSD17B13 protein with a probe comprising a detectable label, wherein the probe comprises a nucleic acid sequence which hybridizes under stringent conditions to a nucleic acid sequence encoding a site of interest (e.g., any of the positions described herein), and detecting the detectable label. In some embodiments, the nucleic acid molecule is present within a cell obtained from the human subject, such that the detection is according to an in situ hybridization technique.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by detection of the presence and quantity of variant mRNA or cDNA in the biological sample.

In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding the particular PNPLA3 or HSD17B13 protein, and detecting the detectable label. In some embodiments, the detecting step comprises amplifying at least a portion of the nucleic acid molecule that encodes a particular PNPLA3 or HSD17B13 protein, labeling the amplified nucleic acid molecule with a detectable label, contacting the labeled nucleic acid molecule with a support comprising a probe, wherein the probe comprises a nucleic acid sequence which specifically hybridizes, including, for example, under stringent conditions, to a nucleic acid sequence encoding a site of interest (e.g., the portion of a PNPLA3 nucleic acid sequence that encodes a methionine at a position corresponding to position 148 according to SEQ ID NO:42, or encodes a methionine at a position corresponding to position 144 according to SEQ ID NO:43; the portion of the variant PNPLA3 genomic DNA that comprises an ATG codon at the positions corresponding to positions 5107 to 5109 according to SEQ ID NO:31; the portion of the variant PNPLA3 mRNA that comprises an AUG codon at the positions corresponding to positions 442 to 444 according to SEQ ID NO:34; the portion of the variant PNPLA3 mRNA that comprises an AUG codon at the positions corresponding to positions 430 to 432 according to SEQ ID NO:35; the portion of the variant PNPLA3 cDNA that comprises an ATG codon at the positions corresponding to positions 442 to 444 according to SEQ ID NO:38; the portion of the variant PNPLA3 cDNA that comprises an ATG codon at the positions corresponding to positions 430 to 432 according to SEQ ID NO:39; the portion of the HSD17B13 genomic DNA that comprises an adenine at a position corresponding to position 12,667 according to SEQ ID NO:1; or the portion of the HSD17B13 genomic DNA that comprises a thymine at a position corresponding to position 12,667 according to SEQ ID NO:2), and detecting the detectable label. If the nucleic acid includes mRNA, the method may further comprise reverse-transcribing the mRNA into a cDNA prior to the amplifying step. In some embodiments, the determining step comprises contacting the nucleic acid molecule that encodes a particular PNPLA3 or HSD17B13 protein with a probe comprising a detectable label and detecting the detectable label.

The disclosure provides methods for identifying a human subject as a candidate for treating or inhibiting a liver disease by inhibiting hydroxysteroid 17-beta dehydrogenase 13 (HSD17B13), the method comprising determining whether or not a sample from the subject comprises a first nucleic acid encoding a patatin like phospholipase domain containing 3 (PNPLA3) protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or both of the proteins are detected. In some embodiments, the subject is obese. In some embodiments, the subject has a fatty liver. In some embodiments, the first nucleic acid molecule comprises genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the first nucleic acid molecule comprises mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the first nucleic acid molecule comprises a cDNA obtained from mRNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, detecting the first nucleic acid comprises sequencing at least a portion of the first nucleic acid and the portion comprises the codon which encodes the I148M variation. In some embodiments, detecting the first nucleic acid comprises hybridizing the first nucleic acid with a probe or primer that specifically hybridizes to a portion of the first nucleic acid, wherein the portion comprises the codon encoding the I148M variation. In some embodiments, the probe or primer is an allele-specific probe or primer. In some embodiments, the probe or primer comprises a label. In some embodiments, the methods further comprise determining whether the subject is homozygous or heterozygous for the I148M variation.

In some embodiments, the second nucleic acid comprises genomic DNA. In some embodiments, the genomic DNA comprises an adenine at a position corresponding to position 12,667 according to SEQ ID NO:1. In some embodiments, the genomic DNA comprises SEQ ID NO:1. In some embodiments, the second nucleic acid molecule comprises mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the second nucleic acid molecule comprises cDNA obtained from mRNA. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, detecting the second nucleic acid comprises sequencing the second nucleic acid. In some embodiments, detecting the second nucleic acid comprises hybridizing the second nucleic acid with a probe or primer that specifically hybridizes to the second nucleic acid. In some embodiments, the probe or primer is an allele-specific probe or primer. In some embodiments, the probe or primer comprises a label. In some embodiments, the methods further comprise determining whether the subject is homozygous or heterozygous for the second nucleic acid encoding a functional HSD17B13 protein in the sample.

The present disclosure provides methods of identifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for identifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and identifying the subject as a candidate for treating or inhibiting a liver disease by inhibiting HSD17B13 when both the first and second nucleic acids are detected and/or when both proteins are detected.

The present disclosure also provides methods of classifying a subject who is a candidate for HSD17B13 inhibition, the method comprising determining whether or not a sample from the subject comprises a nucleic acid encoding a PNPLA3 Ile148Met variant or PNPLA3 Ile144Met variant. The present disclosure also provides methods for classifying a human subject as a candidate for treating or inhibiting a liver disease by inhibiting HSD17B13, the method comprising determining whether or not a sample from the subject comprises a first nucleic acid encoding a PNPLA3 protein comprising an I148M variation and a second nucleic acid encoding a functional HSD17B13 protein, and/or a PNPLA3 protein comprising an I148M variation and a functional HSD17B13 protein, and classifying the subject as a candidate for treating or inhibiting a liver disease by inhibiting HSD17B13 when both the first and second nucleic acids are detected and/or when both proteins are detected.

The variant PNPLA3 Ile148Met variant or PNPLA3 Ile144Met variant can be any of the variant PNPLA3 Ile148Met variants and PNPLA3 Ile144Met variants described herein. The variant PNPLA3 Ile148Met variant or PNPLA3 Ile144Met variant can be detected by any of the methods described herein. In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In preferred embodiments, the subject does not comprise any genes encoding loss of function variations in the HSD17B13 protein. It is believed that loss of function variations in the HSD17B13 protein, including those described or exemplified herein, confer a liver disease-protective effect and it is further believed that this protective effect is enhanced in the presence of the variant PNPLA3 Ile148M variation. Thus, it is believed that subjects (e.g., subjects comprising the I148M variation in PNPLA3) in whom both copies of the genes (from each chromosome) encoding the HSD17B13 protein encode a loss of function variation are unlikely to benefit from HSD17B13 inhibition therapy. Nevertheless, it is believed that subjects who express at least a partially functional HSD17B13 protein will benefit from HSD17B13 inhibition therapy. Thus, the methods may comprise classifying the status of the gene (in one or both chromosomes) encoding HSD17B13, including whether the gene encodes a loss of function variation in the HSD17B13 protein, as well as whether the subject is homozygous or heterozygous.

In some embodiments, the methods further comprise detecting the presence of a nucleic acid molecule or gene encoding a functional HSD17B13 protein in a sample from the subject. The nucleic acid molecule can encode any of the functional HSD17B13 proteins described herein. The HSD17B13 nucleic acid molecule can be detected by any of the methods described herein. In some embodiments, the methods further comprise determining whether the subject is homozygous or heterozygous for a gene encoding a functional HSD17B13 protein. In some embodiments, the subject is homozygous for a gene encoding a functional HSD17B13 protein. In some embodiments, the subject is heterozygous for a gene encoding a functional HSD17B13.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A form for a solid-state substrate is a microtiter dish, such as a standard 96-well type. In some embodiments, a multi-well glass slide can be employed that normally contain one array per well. This feature allows for greater control of assay reproducibility, increased throughput and sample handling, and ease of automation. In some embodiments, the support is a microarray.

In some embodiments, the methods further comprises determining whether the subject is obese. In some embodiments, a subject is obese if their body mass index (BMI) is over 30 kg/m$^2$. Obesity is can be a characteristic of a subject having or at risk of developing a liver disease. In some embodiments, the methods further comprises determining whether the subject has a fatty liver. A fatty liver can be a characteristic of a subject having or at risk of developing a liver disease. In some embodiments, the methods further comprises determining whether the subject is obese and has a fatty liver.

In some embodiments, the methods further comprise administering an inhibitor of HSD17B13 to the subject. Methods of administering an inhibitor of HSD17B13 to the subject are described herein.

In some embodiments, the nucleic acid molecule encoding the variant PNPLA3 Ile148Met protein or PNPLA3 Ile144Met protein is any of the nucleic acid molecules described herein. In some embodiments, the nucleic acid molecule encoding the variant PNPLA3 Ile148Met protein or PNPLA3 Ile144Met protein is genomic DNA. In some embodiments, the genomic DNA encoding the variant PNPLA3 Ile148Met protein or PNPLA3 Ile144Met protein is any of the genomic DNA molecules described herein. In some embodiments, the nucleic acid molecule encoding the variant PNPLA3 Ile148Met protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein is detected by nucleic acid sequencing or hybridization of a probe, as described herein. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding the variant PNPLA3 Ile148Met protein or PNPLA3 Ile144Met protein is mRNA. In some embodiments, the mRNA encoding the variant PNPLA3 Ile148Met protein or PNPLA3 Ile144Met protein is any of the mRNA molecules described herein. In some embodiments, the nucleic acid molecule encoding the variant PNPLA3 Ile148Met protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein is detected by nucleic acid sequencing or hybridization of a probe, as described herein. In some embodiments, the mRNA encoding the variant PNPLA3 protein that comprises the AUG codon is identified by nucleic acid sequencing or hybridization of a probe, as described herein.

In some embodiments, the nucleic acid molecule encoding the variant PNPLA3 Ile148Met protein or PNPLA3 Ile144Met protein is cDNA. In some embodiments, the cDNA encoding the variant PNPLA3 Ile148Met protein or PNPLA3 Ile144Met protein is any of the cDNA molecules described herein. In some embodiments, the nucleic acid molecule encoding a PNPLA3 Ile148Met protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein is identified by nucleic acid sequencing or hybridization of a probe. In some embodiments, the cDNA encoding the variant PNPLA3 protein that comprises the ATG codon is identified by nucleic acid sequencing or hybridization of a probe, as described herein.

In some embodiments, the nucleic acid molecule encoding the functional HSD17B13 protein is any of the nucleic acid molecules described herein. In some embodiments, the nucleic acid molecule encoding the functional HSD17B13 protein is genomic DNA. In some embodiments, the genomic DNA encoding the functional HSD17B13 protein is any of the genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the presence of the functional HSD17B13 genomic DNA is determined by nucleic acid sequencing or hybridization of a probe, as described herein.

In some embodiments, the nucleic acid molecule encoding the functional HSD17B13 protein is mRNA. In some embodiments, the mRNA encoding the functional HSD17B13 protein is any of the mRNA molecules described herein. In some embodiments, the functional HSD17B13 nucleic acid molecule is mRNA. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the presence of the functional HSD17B13 mRNA is determined by nucleic acid sequencing or hybridization of a probe, as described herein.

In some embodiments, the nucleic acid molecule encoding the functional HSD17B13 protein is cDNA. In some embodiments, the cDNA encoding the functional HSD17B13 protein is any of the cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the presence of the functional HSD17B13 cDNA is determined by nucleic acid sequencing or hybridization of a probe, as described herein.

In some embodiments, the methods further comprising obtaining the sample from the subject. In some embodiments, the subject who is a candidate for HSD17B13 inhibition has a liver disease or is susceptible to developing a liver disease. In some embodiments, the liver disease is a chronic liver disease. In some preferred embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some preferred embodiments, the chronic liver disease is nonalcoholic fatty liver disease (NAFLD), alcoholic liver disease (ALD), non-alcoholic steatohepatitis (NASH), cirrhosis, or steatosis. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods of detecting a PNPLA3 Ile148Met variant, or a PNPLA3 Ile144Met variant, and functional HSD17B13 in a subject comprising: detecting the presence of a PNPLA3 Ile148Met protein, or a nucleic acid molecule encoding a PNPLA3 Ile148Met protein, in a sample from the subject, or detecting the presence of a PNPLA3 Ile144Met protein, or a nucleic acid molecule encoding a PNPLA3 Ile144Met protein, in a sample from the subject; and detecting the presence of a functional HSD17B13 protein, or a nucleic acid molecule encoding a functional HSD17B13 protein, in a sample from the subject. The variant PNPLA3 Ile148Met variant protein or nucleic acid molecule can be any of the variant PNPLA3 Ile148Met variant proteins or nucleic acid molecules described herein. The variant PNPLA3 Ile144Met variant protein or nucleic acid molecule can be any of the variant PNPLA3 Ile144Met variant proteins or nucleic acid molecules described herein. The functional HSD17B13 protein or nucleic acid molecule can be any of the functional HSD17B13 proteins or nucleic acid molecules described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the presence of a functional HSD17B13 protein is detected in the sample. The functional HSD17B13 protein can be any of the functional HSD17B13 proteins described herein. In some embodiments, the functional HSD17B13 protein comprises an amino acid sequence according to SEQ ID NO:21, SEQ ID NO:22, SEQ ID NO:25, or SEQ ID NO:29. In some embodiments, the functional HSD17B13 protein is detected by amino acid sequencing or immunoassay, as described herein.

In some embodiments, the presence of a functional HSD17B13 nucleic acid molecule is detected in the sample. The functional HSD17B13 nucleic acid molecule can be any of the functional HSD17B13 nucleic acid molecules described herein. In some embodiments, the functional HSD17B13 nucleic acid molecule is genomic DNA. The functional HSD17B13 genomic DNA molecule can be any of the functional HSD17B13 genomic DNA molecules described herein. In some embodiments, the genomic DNA comprises an adenine at a position corresponding to position 12,667 according to SEQ ID NO:1. In some embodiments, the genomic DNA comprises SEQ ID NO:1. In some embodiments, the genomic DNA is detected by nucleic acid sequencing or hybridization of a probe, as described herein.

In some embodiments, the functional HSD17B13 nucleic acid molecule is mRNA. The functional HSD17B13 mRNA molecule can be any of the functional HSD17B13 mRNA molecules described herein. In some embodiments, the mRNA comprises SEQ ID NO:3. In some embodiments, the mRNA comprises SEQ ID NO:4. In some embodiments, the mRNA comprises SEQ ID NO:7. In some embodiments, the mRNA comprises SEQ ID NO:11. In some embodiments, the mRNA is detected by nucleic acid sequencing or hybridization of a probe, as described herein.

In some embodiments, the functional HSD17B13 nucleic acid molecule is cDNA. The functional HSD17B13 cDNA molecule can be any of the functional HSD17B13 cDNA molecules described herein. In some embodiments, the cDNA comprises SEQ ID NO:12. In some embodiments, the cDNA comprises SEQ ID NO:13. In some embodiments, the cDNA comprises SEQ ID NO:16. In some embodiments, the cDNA comprises SEQ ID NO:20. In some embodiments, the cDNA is detected by nucleic acid sequencing or hybridization of a probe, as described herein.

In some embodiments, the presence of a PNPLA3 Ile148Met protein or PNPLA3 Ile144Met protein is detected in the sample. The variant PNPLA3 Ile148Met protein or PNPLA3 Ile144Met protein can be any of the variant PNPLA3 Ile148Met proteins or PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein or PNPLA3 Ile144Met protein is detected by amino acid sequencing or immunoassay, as described herein.

In some embodiments, the presence of a nucleic acid molecule encoding a PNPLA3 Ile148Met protein or PNPLA3 Ile148Met protein is detected in the sample. The nucleic acid molecule encoding a PNPLA3 Ile148Met protein or PNPLA3 Ile148Met protein can be any of the nucleic acid molecules encoding a PNPLA3 Ile148Met protein or PNPLA3 Ile148Met protein described herein.

In some embodiments, the nucleic acid molecule encoding a PNPLA3 Ile148Met protein or PNPLA3 Ile144Met protein is genomic DNA. The genomic DNA encoding a PNPLA3 Ile148Met protein or PNPLA3 Ile144Met protein can be any of the genomic DNA molecules described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe, as described herein.

In some embodiments, the nucleic acid molecule encoding a PNPLA3 Ile148Met protein or PNPLA3 Ile148Met protein is mRNA. The mRNA molecule encoding a PNPLA3 Ile148Met protein or PNPLA3 Ile148Met protein can be any of the mRNA molecules described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, nucleic acid molecule encoding a PNPLA3 Ile148Met protein or PNPLA3 Ile144Met protein is cDNA. The cDNA encoding a PNPLA3 Ile148Met protein or PNPLA3 Ile144Met protein can be any of the cDNA molecules described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the method further comprises obtaining the sample from the subject.

The present disclosure also provides methods of identifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The present disclosure also provides methods of classifying a subject having a protective effect against liver disease, comprising: detecting the presence of a PNPLA3 Ile148Met variant or PNPLA3 Ile144Met variant in a sample from the subject; and detecting the presence of an HSD17B13 loss-of-function variant in a sample from the subject. The variant PNPLA3 Ile148Met variant and PNPLA3 Ile144Met variant can be any of the variant PNPLA3 Ile148Met variants and PNPLA3 Ile144Met variants described herein. The HSD17B13 loss-of-function variant can be any of the HSD17B13 loss-of-function variants described herein.

In some embodiments, the methods further comprise determining whether the subject is homozygous or heterozygous for the variant PNPLA3 Ile148Met variant or PNPLA3 Ile144Met variant. In some embodiments, the subject is homozygous for the variant PNPLA3 Ile148Met variant or PNPLA3 Ile144Met variant. In some embodiments, the subject is heterozygous for the variant PNPLA3 Ile148Met variant or PNPLA3 Ile144Met variant. In some embodiments, the subject is homozygous for the variant PNPLA3 Ile148Met variant. In some embodiments, the subject is heterozygous for the variant PNPLA3 Ile148Met variant. In some embodiments, the subject is homozygous for the variant PNPLA3 Ile144Met variant. In some embodiments, the subject is heterozygous for the variant PNPLA3 Ile144Met variant.

In some embodiments, the methods further comprise determining whether the subject is homozygous or heterozygous for functional HSD17B13. In some embodiments, the subject is homozygous for functional HSD17B13. In some embodiments, the subject is heterozygous for functional HSD17B13.

In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject, or detecting a PNPLA3 Ile144Met protein, or a nucleic acid molecule encoding a PNPLA3 Ile144Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject. In some embodiments, the variant PNPLA3 Ile148Met variant or PNPLA3 Ile144Met variant is detected in the subject by detecting a PNPLA3 Ile148Met protein, or a nucleic acid molecule encoding a PNPLA3 Ile148Met protein, in a sample from the subject; and the HSD17B13 loss-of-function is detected in the subject by detecting an HSD17B13 loss-of-function variant protein, or a nucleic acid molecule encoding an HSD17B13 loss-of-function variant protein, in a sample from the subject.

In some embodiments, the presence of a PNPLA3 Ile148Met protein or PNPLA3 Ile144Met protein is detected in the sample. The variant PNPLA3 Ile148Met protein and PNPLA3 Ile144Met protein can be any of the variant PNPLA3 Ile148Met proteins and PNPLA3 Ile144Met proteins described herein. In some embodiments, the variant PNPLA3 Ile148Met protein comprises a methionine at a position corresponding to position 148 according to SEQ ID NO:42, or comprises a methionine at a position corresponding to position 144 according to SEQ ID NO:43. In some embodiments, the variant PNPLA3 Ile148Met protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 Ile148Met protein comprises a methionine at a position corresponding to position 144 according to SEQ ID NO:43. In some embodiments, the variant PNPLA3 protein in the sample comprises the amino acid sequence according to SEQ ID NO:43. In some embodiments, the variant PNPLA3 Ile148Met protein is detected by amino acid sequencing or immunoassay, as described herein.

In some embodiments, the presence of a nucleic acid molecule encoding a PNPLA3 Ile148Met protein or PNPLA3 Ile144Met protein is detected in the sample. The nucleic acid molecule encoding the variant PNPLA3 Ile148Met protein or PNPLA3 Ile144Met protein can be any of the nucleic acid molecules encoding the variant PNPLA3 Ile148Met proteins and PNPLA3 Ile144Met proteins described herein.

In some embodiments, wherein the nucleic acid molecule encoding a PNPLA3 Ile148Met protein or PNPLA3 Ile144Met protein is genomic DNA. The genomic DNA encoding the variant PNPLA3 Ile148Met protein or PNPLA3 Ile144Met protein can be any of the variant PNPLA3 Ile148Met proteins and PNPLA3 Ile144Met proteins described herein. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is detected by nucleic acid sequencing or hybridization of a probe.

In some embodiments, the nucleic acid molecule encoding the variant PNPLA3 Ile148Met protein or PNPLA3 Ile144Met protein is mRNA. The mRNA molecule encoding the variant PNPLA3 Ile148Met proteins and PNPLA3 Ile144Met proteins can be any of the variant PNPLA3 Ile148Met proteins and PNPLA3 Ile144Met proteins described herein. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the nucleic acid molecule encoding a PNPLA3 Ile148Met protein or PNPLA3 Ile148Met protein is cDNA. The cDNA encoding the variant PNPLA3 Ile148Met protein and PNPLA3 Ile148Met protein can be any of the variant PNPLA3 Ile148Met proteins and PNPLA3 Ile148Met proteins described herein. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

In some embodiments, the presence of an HSD17B13 loss-of-function variant protein is detected in the sample. The HSD17B13 loss-of-function variant can be any of the HSD17B13 loss-of-function variant proteins described herein. In some embodiments, the HSD17B13 loss-of-function variant protein comprises an amino acid sequence according to SEQ ID NO:23. In some embodiments, the HSD17B13 loss-of-function variant protein comprises an amino acid sequence according to SEQ ID NO:24. In some embodiments, the HSD17B13 loss-of-function variant protein comprises an amino acid sequence according to SEQ ID NO:26. In some embodiments, the HSD17B13 loss-of-function variant protein comprises an amino acid sequence according to SEQ ID NO:27. In some embodiments, the HSD17B13 loss-of-function variant protein comprises an amino acid sequence according to SEQ ID NO:28. In some embodiments, the HSD17B13 loss-of-function variant protein is detected by amino acid sequencing or immunoassay, as described herein.

In some embodiments, the presence of a nucleic acid molecule encoding an HSD17B13 loss-of-function variant protein is detected in the sample. The nucleic acid molecule encoding an HSD17B13 loss-of-function variant protein can be any of the nucleic acid molecules encoding the HSD17B13 loss-of-function variant protein described herein.

In some embodiments, the nucleic acid molecule encoding the HSD17B13 loss-of-function variant protein is genomic DNA. The genomic DNA molecule encoding the HSD17B13 loss-of-function variant protein can be any of the HSD17B13 loss-of-function variant proteins described herein. In some embodiments, the genomic DNA encoding an HSD17B13 loss-of-function variant protein which comprises a thymine at a position corresponding to position 12,667 according to SEQ ID NO:2. In some embodiments, the genomic DNA encoding an HSD17B13 loss-of-function variant protein comprises SEQ ID NO:2. In some embodiments, the genomic DNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is mRNA. The mRNA molecule encoding the HSD17B13 loss-of-function variant protein can be any of the mRNA molecules encoding the HSD17B13 loss-of-function variant proteins described herein. In some embodiments, the mRNA encoding an HSD17B13 loss-of-function variant protein comprises SEQ ID NO:5. In some embodiments, the mRNA encoding an HSD17B13 loss-of-function variant protein comprises SEQ ID NO:6. In some embodiments, the mRNA encoding an HSD17B13 loss-of-function variant protein comprises SEQ ID NO:8. In some embodiments, the mRNA encoding an HSD17B13 loss-of-function variant protein comprises SEQ ID NO:9. In some embodiments, the mRNA encoding an HSD17B13 loss-of-function variant protein comprises SEQ ID NO:10. In some embodiments, the mRNA encoding the HSD17B13 loss-of-function variant protein is detected by nucleic acid sequencing or hybridization of a probe, as described herein.

In some embodiments, the nucleic acid molecule encoding the HSD17B13 loss-of-function variant protein is cDNA. The cDNA molecules encoding the HSD17B13 loss-of-function variant protein can be any of the cDNA molecules encoding the HSD17B13 loss-of-function variant protein described herein. In some embodiments, the cDNA encoding an HSD17B13 loss-of-function variant protein comprises SEQ ID NO:5. In some embodiments, the cDNA encoding an HSD17B13 loss-of-function variant protein comprises SEQ ID NO:6. In some embodiments, the cDNA encoding an HSD17B13 loss-of-function variant protein comprises SEQ ID NO:8. In some embodiments, the cDNA encoding an HSD17B13 loss-of-function variant protein comprises SEQ ID NO:9. In some embodiments, the cDNA encoding an HSD17B13 loss-of-function variant protein comprises SEQ ID NO:10. In some embodiments, the cDNA encoding the HSD17B13 loss-of-function variant protein is detected by nucleic acid sequencing or hybridization of a probe, as described herein.

In some embodiments, the methods further comprises obtaining the sample from the subject. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides any of the methods described herein further comprising administering to the subject an inhibitor of HSD17B13. In some embodiments, the inhibitor of HSD17B13 comprises a functional polypeptide, an antisense DNA, RNA, an siRNA, or an shRNA that hybridizes to the endogenous HSD17B13 genomic DNA or mRNA and decreases expression of HSD17B13 polypeptide in a cell in the subject. In some embodiments, the HSD17B13 inhibitor can also inhibit one or more additional members of the short-chain dehydrogenases/reductases (SDR) family, of which HSD17B13 is a member. Such other members include, but are not limited to, HSD17B1, HSD17B2, HSD17B3, HSD17B4, HSD17B6, HSD17B7, HSD17B8, HSD17B10, HSD17B11, HSD17B12, HSD17B13, HSD17B14, HSD11B1, HSD11B2, HSD3B1, HSD3B2, and HSD3B7, as well as close homologs dehydrogenase/reductase 3 (DHRS3) and retinol dehydrogenase 10 (RDH10). In some embodiments, the inhibitor of HSD17B13 is administered to inhibit liver disease in the subject. In some embodiments, the inhibitor of HSD17B13 is administered to treat liver disease in the subject. In some embodiments, the liver disease is a chronic liver disease. In some embodiments, the chronic liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the subject is homozygous for the gene encoding the I148M variation. In some embodiments, the subject is heterozygous for the gene encoding the I148M variation. In some embodiments, the subject further is homozygous for the gene encoding the functional HSD17B13 protein. In some embodiments, the subject further is heterozygous for the gene encoding the functional HSD17B13 protein and a gene encoding a loss of function variant of HSD17B13.

The disclosure also provides methods of treating or inhibiting liver disease, comprising administering an inhibitor of hydroxysteroid 17-beta dehydrogenase 13 (HSD17B13) to a human liver disease patient expressing a patatin like phospholipase domain containing 3 (PNPLA3) protein comprising an I148M variation such that liver disease is treated or inhibited in the patient. In some embodiments, the liver disease is a chronic liver disease. In some embodiments, the liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the patient is obese. In some embodiments, the patient has a fatty liver. In some embodiments, the patient has been determined to express the variant PNPLA3 protein (e.g., a PNPLA3 protein comprising the I148M or I144M variation) by detection of the variant PNPLA3 protein in a sample from the subject. In some embodiments, the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42. In some embodiments, the variant PNPLA3 protein is detected by amino acid sequencing or by an immunoassay. In some embodiments, the subject has been determined to express the variant PNPLA3 protein by detection of a nucleic acid molecule encoding the variant PNPLA3 protein (e.g., a variant PNPLA3 nucleic acid molecule encoding a PNPLA3 protein comprising the I148M or I144M variation) in a sample from the subject. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the nucleic acid molecule encoding the variant PNPLA3 protein comprises genomic DNA, mRNA, or cDNA obtained from mRNA. In some embodiments, the nucleic acid molecule comprises genomic DNA comprising an ATG codon at the positions corresponding to positions 5107 to 5109 according to SEQ ID NO:31. In some embodiments, the genomic DNA comprises the nucleotide sequence according to SEQ ID NO:31. In some embodiments, the nucleic acid molecule comprises mRNA comprising an AUG codon at the positions corresponding to positions 442 to 444 according to SEQ ID NO:34. In some embodiments, the mRNA comprises the nucleotide sequence according to SEQ ID NO:34. In some embodiments, the nucleic acid molecule comprises mRNA comprising an AUG codon at the positions corresponding to positions 430 to 432 according to SEQ ID NO:35. In some embodiments, the mRNA comprises the nucleotide sequence according to SEQ ID NO:35. In some embodiments, the nucleic acid molecule comprises cDNA obtained from mRNA, the cDNA comprising an ATG codon at the positions corresponding to positions 442 to 444 according to SEQ ID NO:38. In some embodiments, the cDNA comprises the nucleotide sequence according to SEQ ID NO:38. In some embodiments, the nucleic acid molecule comprises cDNA obtained from mRNA, the cDNA comprising an ATG codon at the positions corresponding to positions 430 to 432 according to SEQ ID NO:39. In some embodiments, the cDNA comprises the nucleotide sequence according to SEQ ID NO:39. In some embodiments, the nucleic acid is detected by sequencing at least a portion of the nucleic acid, the portion encoding the I148M variation. In some embodiments, the nucleic acid is detected by hybridization of a probe or primer that specifically hybridizes to a portion of the nucleic acid, wherein the portion comprises the codon encoding the I148M variation. In some embodiments, the probe or primer is an allele-specific probe or primer. In some embodiments, the probe or primer comprises a label. In some embodiments, the patient is homozygous for a gene encoding the variant PNPLA3 protein. In some embodiments, the patient is heterozygous for a gene encoding the variant PNPLA3 protein. In some embodiments, patient is homozygous for a gene encoding a functional HSD17B13 protein. In some embodiments, the patient is heterozygous for a gene encoding a functional HSD17B13 protein. In some embodiments, the patient is heterozygous for the gene encoding the functional HSD17B13 protein and a gene encoding a loss of function variant of HSD17B13.

Inhibitors of HSD17B13 can be used as described herein for treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the method as defined herein. In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the variant PNPLA3 protein comprises a methionine at the position corresponding to position 144 according to SEQ ID NO:43. In some embodiments, the variant PNPLA3 protein comprises the amino acid sequence according to SEQ ID NO:43, or an amino acid sequence having at least 90% sequence identity to SEQ ID NO:43 and comprising the I144M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the I144M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the I144M variation. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or nonalcoholic steatohepatitis (NASH). In some embodiments, the non-alcoholic liver disease comprises one or more of cirrhosis, steatosis, or hepatocellular carcinoma not caused by alcohol consumption. In some embodiments, the human subject is homozygous or heterozygous for functional HSD17B13.

In some embodiments, inhibitors of HSD17B13 reduce or inhibit HSD17B13 gene expression or the function of HSD17B13 protein. Inhibitors of HSD17B13 include, but are not limited to, naturally occurring and synthetic ligands, antagonists, agonists, antibodies, peptides, cyclic peptides, nucleic acids, functional polynucleotides, small organic molecules, and the like. Functional polynucleotides are nucleic acid molecules that have a specific function, such as binding a target molecule or catalyzing a specific reaction. Examples of functional polynucleotides include, but are not limited to, antisense molecules, aptamers, ribozymes, and triplex forming molecules. The functional polynucleotides can act as inhibitors of a specific activity possessed by a target molecule. Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant (kd) less than or equal to about 10-6, less than or equal to about 10-8, less than or equal to about 10-10, or less than or equal to about 10-12. A representative sample of methods and techniques which aid in the design and use of antisense molecules, and antisense molecules, can be found in the following non-limiting list of U.S. Patents and applications: U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; 6,057,437; and U.S. Ser. No. 62/645,941 filed Mar. 21, 2018, each of which is incorporated herein by reference in its entirety. Examples of antisense molecules include, but are not limited to, antisense RNAs, small interfering RNAs (siRNAs), and short hairpin RNAs (shRNAs). For example, the antisense RNAs, siRNAs, or shRNAs can be designed to target a region unique of the HSD17B13 genomic DNA or mRNA. In some embodiments, the inhibitor of HSD17B13 is an antisense molecule. In some embodiments, the inhibitor of HSD17B13 is an shRNA molecule. In some embodiments, the inhibitor of HSD17B13 is an siRNA molecule.

In any of the methods described herein, administration of an inhibitor of HSD17B13 can result in the reduction or elimination of particular characteristics of liver disease. In some embodiments, the characteristics of liver disease include, but are not limited to inflammation and fibrosis.

The present disclosure also provides methods of treating a subject who is PNPLA3 Ile148Met positive (i.e., "PNPLA3 Ile148Met+") or PNPLA3 Ile144Met positive (i.e., "PNPLA3 Ile144Met+"), comprising administering an inhibitor of HSD17B13 to the subject. The present disclosure also provides methods of treating or inhibiting liver disease comprising administering an inhibitor of HSD17B13 to a human liver disease patient expressing a PNPLA3 protein comprising an I148M variation such that liver disease is treated or inhibited in the patient.

The variant PNPLA3 Ile148Met positive or PNPLA3 Ile144Met positive subject can have any of the variant PNPLA3 proteins described herein. In some embodiments, the subject is also homozygous or heterozygous for functional HSD17B13. In some embodiments, the subject is homozygous for functional HSD17B13. In some embodiments, the subject is heterozygous for functional HSD17B13. In some embodiments, the subject is homozygous for the HSD17B13 loss-of-function variant. The subject can have any of the functional HSD17B13 proteins described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 proteins described herein.

In some embodiments, the subject who is PNPLA3 Ile148Met+ has been determined to be PNPLA3 Ile148Met+ by detection of a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the variant PNPLA3 protein that comprises the methionine at the position corresponding to position 148 according to SEQ ID NO:42, or that comprises the methionine at the position corresponding to position 144 according to SEQ ID NO:43 is identified by amino acid sequencing or immunoassay as described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a nucleic acid molecule encoding a PNPLA3 protein in a sample from the subject, wherein the variant PNPLA3 protein comprises a methionine at a position corresponding to position 148 according to SEQ ID NO:42, or comprises a methionine at a position corresponding to position 144 according to SEQ ID NO:43. The variant PNPLA3 Ile148Met positive or PNPLA3 Ile144Met positive subject can have any of the variant PNPLA3 nucleic acid molecules described herein.

In some embodiments, the subject who is PNPLA3 Ile148Met+ has been determined to be PNPLA3 Ile148Met+ by detection of a nucleic acid molecule encoding a PNPLA3 protein in a sample from the subject, wherein the variant PNPLA3 protein comprises a methionine at a position corresponding to position 148 according to SEQ ID NO:42. In some embodiments, the variant PNPLA3 protein in the sample comprises the amino acid sequence according to SEQ ID NO:42.

In some embodiments, the subject who is PNPLA3 Ile144Met+ has been determined to be PNPLA3 Ile144Met+ by detection of a nucleic acid molecule encoding PNPLA3 protein in a sample from the subject, wherein the variant PNPLA3 protein comprises a methionine at a position corresponding to position 144 according to SEQ ID NO:43. In some embodiments, the variant PNPLA3 protein in the sample comprises the amino acid sequence according to SEQ ID NO:43.

In some embodiments, the nucleic acid molecule encoding the variant PNPLA3 protein is genomic DNA, mRNA, or cDNA derived from mRNA.

In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31. In some embodiments, the genomic DNA encoding the variant PNPLA3 protein that comprises the ATG codon is identified by nucleic acid sequencing or hybridization of a probe, as described herein.

In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35. In some embodiments, the mRNA encoding the variant PNPLA3 protein that comprises the AUG codon is identified by nucleic acid sequencing or hybridization of a probe, as described herein.

In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39. In some embodiments, the cDNA encoding the variant PNPLA3 protein that comprises the ATG codon is identified by nucleic acid sequencing or hybridization of a probe, as described herein.

Administration of the inhibitor of HSD17B13 can be by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In some embodiments, the subject has a liver disease or is susceptible to developing a liver disease. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods for treating a patient with a liver disease therapeutic agent, wherein the patient is suffering from a liver disease. The methods comprise determining whether or not a sample from the subject comprises: i) a first nucleic acid encoding a PNPLA3 protein comprising an I148M variation and a second nucleic acid encoding a functional HSD17B13 protein, and/or ii) a PNPLA3 protein comprising an I148M variation and a functional HSD17B13 protein. In some embodiments, the methods comprise determining whether or not a sample from the subject comprises a first nucleic acid encoding a PNPLA3 protein comprising an I148M variation and a second nucleic acid encoding a functional HSD17B13 protein. In some embodiments, the methods comprise determining whether or not a sample from the subject comprises a PNPLA3 protein comprising an I148M variation and a functional HSD17B13 protein.

In some embodiments, this determination is carried out by obtaining or having obtained a biological sample from the patient. In some embodiments, the methods further comprise performing or having performed a genotyping assay on the biological sample to determine if the patient has a first nucleic acid encoding a PNPLA3 protein comprising an I148M variation and a second nucleic acid encoding a functional HSD17B13 protein. In some embodiments, the methods further comprise performing or having performed an assay on the biological sample to determine if the patient has a PNPLA3 protein comprising an I148M variation and a functional HSD17B13 protein.

In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient. In some embodiments, when the patient has a nucleic acid encoding a PNPLA3 protein comprising an I148M variation and/or has a PNPLA3 protein comprising an I148M variation, and has a nucleic acid encoding a functional HSD17B13 protein and/or has a functional HSD17B13 protein, then the method further comprises administering an inhibitor of HSD17B13 to the patient and administering a liver disease therapeutic agent to the patient. In some embodiments, when the patient has a nucleic acid encoding a PNPLA3 protein comprising an I148M variation and/or has a PNPLA3 protein comprising an I148M variation, but does not have a nucleic acid encoding a functional HSD17B13 protein and/or has a functional HSD17B13 protein, then the method further comprises administering a liver disease therapeutic agent to the patient.

Examples of liver disease therapeutic agents include, but are not limited to, Disulfiram, Naltrexone, Acamprosate, Prednisone, Prednisone, Azathioprine, Penicillamine, Trientine, Deferoxamine, Ciprofloxacin, Norofloxacin, Ceftriaxone, Ofloxacin, Amoxicillin-clavulanate, Phytonadione, Bumetanide, Furosemide, Hydrochlorothiazide, Chlorothiazide, Amiloride, Triamterene, Spironolactone, Octreotide, Atenolol, Metoprolol, Nadolol, Propranolol, Timolol, and Carvedilol.

Additional examples of liver disease therapeutic agents (e.g., for use in chronic hepatitis C treatment) include, but are not limited to, ribavirin, paritaprevir, simeprevir (Olysio), grazoprevir, ledipasvir, ombitasvir, elbasvir, daclatasvir (Daklinza), dasabuvir, ritonavir, sofosbuvir, velpatasvir, voxilaprevir, glecaprevir, pibrentasvir, peginterferon alfa-2a, peginterferon alfa-2b, and interferon alfa-2b.

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; atioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA). Other suitable treatments include ACE inhibitors/ARBs, oligofructose, and Incretin analogs.

Additional examples of liver disease therapeutic agents (e.g., for use in NASH) include, but are not limited to, obeticholic acid (Ocaliva®), Selonsertib, Elafibranor, Ceniciviroc, GR_MD_02, MGL_3196, IMM124E, arachidyl amido cholanoic acid (Aramchol™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

The present disclosure also provides inhibitors of HSD17B13 for use in the manufacture of a medicament for the treatment of liver disease in a human subject who is PNPLA3 Ile148Met positive or PNPLA3 Ile144Met positive and who is also homozygous or heterozygous for functional HSD17B13. In some embodiments, the subject is homozygous for PNPLA3 Ile148Met variant or PNPLA3 Ile144Met variant. In some embodiments, the subject is heterozygous for PNPLA3 Ile148Met variant or PNPLA3 Ile144Met variant. In some embodiments, the subject is homozygous for functional HSD17B13. In some embodiments, the subject is heterozygous for functional HSD17B13.

In some embodiments, the inhibitor of HSD17B13 is for use in the treatment of a liver disease in a human subject having a PNPLA3 protein comprising a methionine at a position corresponding to position 148 according to SEQ ID NO:42, or a nucleic acid molecule encoding a PNPLA3 protein comprising a methionine at a position corresponding to position 148 according to SEQ ID NO:42, or comprising a methionine at a position corresponding to position 144 according to SEQ ID NO:43, or a nucleic acid molecule encoding a PNPLA3 protein comprising a methionine at a position corresponding to position 148 according to SEQ ID NO:43. In some embodiments, the variant PNPLA3 protein comprises a methionine at a position corresponding to position 148 according to SEQ ID NO:42. In some embodiments, the variant PNPLA3 protein comprises the amino acid sequence according to SEQ ID NO:42. In some embodiments, the variant PNPLA3 protein comprises a methionine at a position corresponding to position 144 according to SEQ ID NO:43. In some embodiments, the variant PNPLA3 protein comprises the amino acid sequence according to SEQ ID NO:43.

In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31.

In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34. In some embodiments, the mRNA comprises an AUG codon at the positions corresponding to positions 430 to 432 according to SEQ ID NO:35. In some embodiments, the mRNA comprises the nucleotide sequence according to SEQ ID NO:35.

In some embodiments, nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38. In some embodiments, the cDNA comprises an ATG codon at the positions corresponding to positions 430 to 432 according to SEQ ID NO:39. In some embodiments, the cDNA comprises the nucleotide sequence according to SEQ ID NO:39.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13. In some embodiments, the subject is homozygous for functional HSD17B13. In some embodiments, the subject is heterozygous for functional HSD17B13.

In any of the methods described herein, a probe or primer or an alteration-specific probe or an alteration-specific primer can be specifically complementary to or specifically hybridize with a single nucleic acid species. For example, a probe or primer or an alteration-specific probe or an alteration-specific primer specifically complementary to or specifically hybridizing with a nucleic acid molecule for HSD17B13 transcript A, transcript B, transcript E, or transcript I (e.g., any of the mRNA, cDNA, RNA transcript, or cDNA transcript for functional HSD17B13 described herein) is not complementary to or does not hybridize with any of the nucleic acid molecules for a variant HSD17B13 (e.g., any of the mRNA, cDNA, RNA transcripts, or cDNA transcripts for variants C, D, F, G, H of HSD17B13).

The present disclosure also provides an inhibitor of HSD17B13 for use in the treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether or not the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the methods as defined herein.

In some embodiments, the variant PNPLA3 protein comprises a methionine at the position corresponding to position 148 according to SEQ ID NO:42. In some embodiments, the variant PNPLA3 protein comprises the amino acid sequence according to SEQ ID NO:42, or an amino acid sequence having at least 90% sequence identity to SEQ ID NO:42 and comprising the I148M variation. In some embodiments, the nucleic acid molecule encoding the variant PNPLA3 protein is genomic DNA. In some embodiments, the genomic DNA comprises an ATG codon at the positions corresponding to positions 5107 to 5109 according to SEQ ID NO:31. In some embodiments, the genomic DNA comprises the nucleotide sequence according to SEQ ID NO:31, or a nucleotide sequence having at least 90% sequence identity to SEQ ID NO:31 and encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444 according to SEQ ID NO:34. In some embodiments, the mRNA comprises the nucleotide sequence according to SEQ ID NO:34, or a nucleotide sequence having at least 90% sequence identity to SEQ ID NO:34 and encoding a PNPLA3 protein which comprises the I148M variation. In some embodiments, the mRNA comprises an AUG codon at the positions corresponding to positions 430 to 432 according to SEQ ID NO:35. In some embodiments, the mRNA comprises the nucleotide sequence according to SEQ ID NO:35, or a nucleotide sequence having at least 90% sequence identity to SEQ ID NO:35 and encoding a PNPLA3 protein which comprises the I148M variation. In some embodiments, the nucleic acid molecule encoding the variant PNPLA3 protein is cDNA. In some embodiments, the cDNA comprises an ATG codon at the positions corresponding to positions 442 to 444 according to SEQ ID NO:38. In some embodiments, the cDNA comprises the nucleotide sequence according to SEQ ID NO:38, or a nucleotide sequence having at least 90% sequence identity to SEQ ID NO:38 and encoding a PNPLA3 protein which comprises the I148M variation. In some embodiments, the cDNA comprises an ATG codon at the positions corresponding to positions 430 to 432 according to SEQ ID NO:39. In some embodiments, the cDNA comprises the nucleotide sequence according to SEQ ID NO:39, or a nucleotide sequence having at least 90% sequence identity to SEQ ID NO:39 and encoding a PNPLA3 protein which comprises the I148M variation.

In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

In some embodiments, the human subject is homozygous or heterozygous for functional HSD17B13.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their subject matter. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Genetic Interaction Between PNPLA3 rs738409 (p.I148M) and HSD17B13 rs72613567—Study Design In this study, exome sequencing was used to identify variants associated with serum alanine aminotransferase (ALT) and aspartate aminotransferase (AST) levels, which are markers of hepatocyte injury, in the DiscovEHR human genetics study, a cohort that links exome sequence data to electronic health records (EHR), and in three additional studies. The associations between implicated genetic variants and clinical diagnoses of chronic liver disease in DiscovEHR and two independent cohorts was also studied. The association between one of these variants and the histopathological severity of liver disease in an independent cohort of bariatric surgery patients who underwent liver biopsy was also studied.

Study Design and Participants

Human genetics studies were conducted using genomic DNA samples and data from six cohorts. These studies included two Regeneron Genetics Center and the Geisinger Health System (GHS) DiscovEHR study populations originating from the first 50,726 adult consented participants from the MyCode® Community Health Initiative of GHS20. The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery. Replication studies of associations with liver transaminases were performed in the Dallas Heart Study and the Penn Medicine Biobank, which included 1,357 and 8,527 individuals of European ancestry, respectively. Replication studies of the associations with chronic liver disease included 517 individuals from the Dallas Liver Study (DLS) and 439 individuals from the Dallas Pediatric Liver Study (DPLS). Full study descriptions and clinical phenotype and disease definitions are described the Methods section in the Supplementary Appendix.

Baseline characteristics of genotyped multi-ethnic cases and controls from the Dallas Liver and Pediatric Liver Studies are shown in FIG. 5.

Sample Preparation, Sequencing, and Genotyping

DNA sample preparation and whole exome sequencing for the participants in the DiscovEHR study, the Dallas Heart Study, and the Penn Medicine Biobank were performed at the Regeneron Genetics as previously described (Dewey et al., Science, 2016, In Press). HSD17B13 rs72613567 was genotyped by Taqman assay (and verified by Sanger sequencing in 5 individuals of each genotype) in the Dallas Liver Study and Dallas Pediatric Liver Study.

Clinical Measurements and Chronic Liver Disease Definitions in the Discovery Cohort Clinical laboratory measurements for alanine aminotransferase (ALT) and aspartate aminotransferase (AST) were extracted from EHRs of participants from the GHS discovery cohort and bariatric surgery cohort. Median ALT and AST values were calculated for all participants with two or more measurements, and were $\log_{10}$-transformed to normalize the distribution prior to association analyses.

International Classification of Diseases, Ninth Revision (ICD-9) disease diagnosis codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease ("no liver disease") was defined as participants with no case criteria or single-encounter or problem-list diagnosis code indicating any type of liver disease.

Regional association plots for alanine aminotransferase (ALT; A) and aspartate aminotransferase (AST; B) levels in the GHS discovery cohort in the region around HSD17B13 are shown in FIG. 6 (panels A and B). Purple diamonds indicate the splice variant rs72613567. Each circle indicates a single nucleotide variant with the color of the circle indicating the linkage disequilibrium (r2 calculated in the DiscovEHR cohort) between that variant and rs72613567. Blue lines indicate estimated recombination rates in HapMap. The bottom portion of the panels show the relative position and the transcribed strand of each gene in the locus. There were no significant associations between AST or ALT and coding or splice region variants in the neighboring gene HSD17B11 (most significant P-values $1.4 \times 10^{-1}$ and $4.3 \times 10^{-2}$ for ALT and AST, respectively).

Liver Histopathologic Phenotype Definitions in the Bariatric Surgery Cohort

The GHS bariatric surgery cohort consisted of 2,644 individuals of European descent, with intra-operative liver biopsy specimens available from 2,391 of these individuals. Liver biopsy specimens were formalin-fixed and stained with hematoxylin and eosin for histology, and Masson's trichrome stain for assessment of fibrosis, as previously described (Gerhard et al., Patient Saf. Surg., 2011, 5, 1). Histologic diagnoses were determined by hepatopathologists using previously established criteria (Brunt et al., Am. J. Gastroenterol., 1999, 94, 2467-74). Histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage).

Baseline characteristics of sequenced European-ancestry individuals from the discovery and replication cohorts are shown in FIG. 1. Single nucleotide variants associated with serum transaminase levels at $P<1.0\times10^{-7}$ in the discovery cohort are shown in FIG. 2.

DNA Sample Preparation and Sequencing

In brief, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20× haploid read depth of over 85% of targeted bases in 96% of samples (approximately 80× mean haploid read depth of targeted bases). Raw sequence data from each Illumina Hiseq 2500 run were uploaded to the DNAnexus platform (Reid et al., BMC Bioinformatics, 2014, 15, 30) for sequence read alignment and variant identification. In brief, raw sequence data were converted from BCL files to sample-specific FASTQ-files, which were aligned to the human reference build GRCh37.p13 with BWA-mem (Li et al., Bioinformatics, 2009, 25, 1754-60). Single nucleotide variants (SNV) and insertion/deletion (indel) sequence variants were identified using the Genome Analysis Toolkit (McKenna et al., Genome Res., 2010, 20, 1297-303).

Exome-Wide Association Analysis of Liver Enzymes and Chronic Liver Disease Phenotypes 502,219 biallelic variants with missing data rate <1%, Hardy-Weinberg equilibrium P-value $>1.0\times10^{-6}$, and minor allele frequency >0.1%, were examined for association with transaminase levels. $Log_{10}$-transformed median ALT and AST were adjusted for age, $age^2$, sex, BMI, and the first four principal components of ancestry. To account for relatedness among study participants, a genetic relatedness matrix was fit as a random-effects covariate. Both principal components and the genetic relatedness matrix were constructed from 39,858 non-MHC markers in approximate linkage equilibrium and with minor allele frequency >0.1%. A linear mixed models was used as implemented in the GCTA package (Yang et al., Am. J. Hum. Genet., 2011, 88, 76-82) to test for association between trait residuals and single nucleotide variants. All P-values reported in the text correspond to the allelic model.

Replication of associations in the GHS discovery cohort was attempted in three separate European-ancestry cohorts: the GHS bariatric surgery cohort, the Dallas Heart Study, and the Penn Medicine Biobank (described above). ALT and AST measures from the GHS bariatric surgery cohort and from Penn Medicine Biobank were $log_{10}$-transformed and adjusted for age, $age^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, $age^2$, sex, BMI, and the first ten principal components of ancestry, and analysis was performed using linear regression implemented in PLINK. Summary statistics for the three replication cohorts were meta-analyzed using METAL (Willer et al., Bioinformatics, 2010, 26, 2190-1) (replication meta-analysis). Summary statistics for the discovery cohort and the three replication cohorts were meta-analyzed similarly (joint meta-analysis).

Replication and joint meta-analysis of 35 exome-wide significant single nucleotide variants from the discovery cohort in three separate European-ancestry cohorts is shown in FIG. 3.

For variants with exome wide significant associations with transaminases ($p<1\times10^{-7}$) in the GHS discovery cohort, association analyses and meta-analysis were performed, as described herein, in the European-ancestry replication studies described herein. A Bonferroni significance threshold determined by the number of variants tested was used to define replicated associations. Meta-analysis of discovery and replication studies was also performed. All P-values reported in the text correspond to the allelic model.

Transaminase-associated single nucleotide variants was also examined for associations with chronic liver disease phenotypes (defined and analyzed as described herein). A Bonferroni significance threshold determined by the number of variants and broad chronic liver disease categories tested was used to determine significance of associations. Replicated novel variants were also examined for association with histopathologically defined liver phenotypes from the GHS bariatric surgery cohort.

Association Analysis with Chronic Liver Disease Phenotypes

Thirteen significant and replicated single nucleotide variants from the liver enzyme ExWAS were analyzed for associations with chronic liver disease phenotypes defined from the GHS discovery cohort, as described above. A Bonferroni significance threshold of P<0.05/26 ($P<1.92\times10^{-3}$) was used to account for the thirteen variants and two broad chronic liver disease categories (alcoholic and non-alcoholic) tested. The HSD17B13 rs72613567 variant was further tested for association with histopathologically defined liver phenotypes from the GHS bariatric surgery cohort, as described above. Odds ratios were estimated with the use of Firth's penalized likelihood method of logistic regression after adjustment for age, $age^2$, sex, BMI, and the first four principal components of ancestry. Genotypic odds ratios were estimated for HSD17B13 rs72613567 using the same covariates.

Odds ratios for liver disease in the DLS were estimated by logistic regression, adjusted for age, $age^2$, sex, BMI, and self-reported ethnicity. Participants from the Dallas Heart Study with available rs72613567 genotypes were used as normal controls (n=4,279). Odds ratios in the DPLS were estimated by logistic regression.

Association of thirteen exome-wide significant and replicating single nucleotide variants with liver disease phenotypes in the discovery cohort is shown in FIG. 4.

Genetic Interaction Between PNPLA3 rs738409 (p.I148M) And HSD17B13 rs72613567—Analysis To evaluate the combined effect of PNPLA3 rs738409 and HSD17B13 rs72613567, association analyses for quantitative (ALT and AST) and binary (nonalcoholic liver disease and alcoholic liver disease) traits were conducted using linear and logistic regression, respectively, modeling main effects for both genetic variants as well as an interaction term, assuming an additive genetic model. All models were adjusted for age, $age^2$, sex, BMI, and the first four principal components of ancestry. Statistical analyses were performed using the glm function in base R.

Software

Genetic association analyses were performed using GCTA software, version 1.25.0 (Yang et al., Am. J. Hum. Genet., 2011, 88, 76-82) and PLINK, version 1.9.0. Quantile-quantile and Manhattan plots were generated using R software, version 3.2.1 (R Project for Statistical Computing). Regional association plots were generated using LocusZoom (Pruim et al., Bioinformatics, 2010, 26, 2336-7).

RNA Sequencing Studies

RNA quality and concentration was evaluated by running total RNA on an Agilent RNA Nano Bioanalyzer chip; all samples had an RNA integrity number (RIN) greater than 8. Polyadenylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to the standard DNA library preparation method referenced above for exomes with the addition of a uracil DNA-glycosylase step to generate strand-specific sequencing libraries. Samples were pooled and sequenced using 75 bp paired-end sequencing on an Illumina v4 HiSeq 2500.

Identification and Validation of Novel HSD17B13 Transcripts

Reads were mapped to the Human.B38 using ArrayStudio® software (OmicSoft®, Cary, N.C.) allowing two mismatches. Two approaches were employed to identify novel HSD17B13 transcripts. Novel exon junctions were discovered based on Gencode v24 using ArrayStudio. De novo transcript assembly was performed using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms was determined. RT-PCR was performed on total RNA from human liver samples using the SuperScript™ One-Step RT-PCR System with Platinum™ Taq DNA Polymerase (Thermofisher). Each 50 µL RT-PCR reaction contained 1× Reaction Mix, 500 nM each forward and reverse primers (PST516: ATGAACATCATCCTAGAAATCCTTC; SEQ ID NO:62) and PST517: ATCATGCATACATCTCTGGCT GGAG; SEQ ID NO:63), 1 µL of RT/Platinum Taq, and 75 ng RNA. Cycling conditions were: one cycle of 45° C. for 30 minutes; one cycle of 94° C. for 2 minutes; 40 cycles of 94° C. for 20 seconds, 53° C. for 30 seconds, and 72° C. for 90 seconds; one cycle of 72° C. for 5 minutes; then a 10° C. hold. Products were purified using the QIAquick PCR Purification Kit (Qiagen) and submitted for direct Sanger sequencing using the primer DE002 (ATCAGAACTTC AGGCCTTGG; SEQ ID NO:64). To identify the B and C transcripts, the RT-PCR products were run out on a 2% agarose gel stained with SYBR GoldSYBR® Gold Nucleic Acid Gel Stain (Thermofisher), and bands of the expected molecular weight were excised and purified using the QIAquick Gel Extraction Kit (Qiagen), then subjected to cloning with the TOPO® TA Cloning Kit (Thermofisher). Sequencing of the TOPO clones was performed using, M13F and M13R sequencing primers. Sequence analysis was performed using the Sequencher DNA analysis software (Gene Codes Corporation).

Full-length HSD17B13 transcripts were amplified directly from 50 ng of total RNA with the SuperScript III One-step RT-PCR System with Platinum Taq High Fidelity (Thermo Fisher Scientific) using gene-specific primers in the first (GCAAAGCCATGAACATCATCC; SEQ ID NO:65) and last exons (TCTTGATGTAGTGGGAGTCGGATT; SEQ ID NO:66) to generate an amplicon of about 2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 minutes on the PacBio RSII platform. The data was demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD17B13 Isoforms

HepG2 cells were infected with lentivirus carrying the HSD17B13 A and D transcripts, stable cell lines were selected, and HSD17B13 isoforms, lipid droplets, and endoplasmic reticulum were visualized using immunofluorescence. Briefly, HepG2 cells were cultured in Eagle's Minimum Essential Medium supplemented with 10% fetal bovine serum. HSD17B13 transcripts A and D were subcloned into Myc-DDK backbone lentivirus constructs, and lentivirus were generated. HepG2 cells were infected with lentivirus carrying the HSD17B13 transcripts. Stable cell lines expressing each HSD17B13 transcript were selected with 1-3 mg/ml Geneticin G-418 sulfate in complete culture medium for two weeks. Following fixation, HSD17B13 isoforms were detected with mouse anti-Myc antibody. Lipid droplets were labeled with BODIPY FL dye (Sigma). Lipid coat protein and endoplasmic reticulum were labeled with rabbit anti-PLIN antibody (Sigma) and rabbit anti-calnexin antibody (Cell Signaling Technology). Secondary antibodies for immunofluorescence were Alexa Fluor 488 donkey anti-rabbit IgG and Alexa Fluor 594 donkey anti-mouse IgG (Jackson ImmunoResearch).

Quantification of HSD171B3 Protein Expression in Human Liver Biopsy Tissue

Human liver and cell pellet samples were homogenized in ice-cold 1×RIPA lysis buffer (EMD Millipore) in the presence of protease and phosphatase inhibitor mixtures (Thermo-Fisher). Supernatant was collected and used for protein concentration using BCA protein assay (Thermo-Fisher). Human tissue lysates were loaded at 30 µg/well and stable cell lines were loaded 9 µg/well and separated on SDS/PAGE gels (Bio-Rad) and transferred to PVDF membranes (Bio-Rad). The membranes were blocked for 1 hour with 5% (wt/vol) milk in 1×TBS supplemented with 0.1% Tween20 (Bio-Rad). Membranes were incubated with antibody at CC overnight against HSD17B13 (1:200, Thermo-Fisher) and B-Actin (1:500, Cell Signaling Technology). Bound antibody was detected using HRP-conjugated anti-rabbit antibody (1:10,000, Jackson ImmunoResearch) and enhanced using chemiluminescence reagent (Thermo-Fisher). Band intensities were quantified using Image J software.

In Vitro and Cellular Characterization of HSD17B13 Enzymatic Activity

Recombinant human HSD17B13 protein was purified from E. coli (Genscript) transformed with plasmid DNA harboring HSD17B13 transcript A or transcript D. The HSD17B13 variants contained a 10×His tag at the C terminus and were purified from soluble fraction using a $Ni^{2+}$ affinity purification. Enzymatic activity was determined through measurement of NADH production using the NAD(P)H-Glo Detection System (Promega). Reactions were performed for 3 hours at 25° C. in 0.2 M tris-HCl, pH 7.5, 0.5 mM $NAD^+$, 75 µM of substrate (Sigma) and 500 ng purified enzyme in a final volume of 100 µL. After incubation, 20 µL of the reaction was combined with 20 µl luciferase reagent (Promega), incubated at room temperature for 1 hour and read on an Envision Plate Reader (Perkin Elmer).

HEK293 cells overexpressing HSD17B13 transcript A, transcript D or green fluorescent protein (GFP, control) were used to investigate the activity of HSD17B13 against estradiol in a cell-based assay. Estradiol was fed to each cell type. After 48 hours, the media was collected and the concentration of estradiol and its converted product estrone were identified and quantified by LC-MS. Hydroxyestradiol (metabolite from estradiol) and hydroxyestrone (metablolite from estrone) were identified by LC-MS.

Example 2: Gene Expression Analysis of HSD17B13 and PNPLA3 in 66 Human Liver Samples Gene expression of HSD17B13 and PNPLA3 were analyzed with 66 human liver samples. All the samples were from control donors without steatosis, lobular inflammation, or fibrosis. The distribution of HSD17B13 rs72613567 (T/T, T/TA, and TA/TA) and PNPLA3 rs738409 (C/C, C/G, and G/G) genotypes is shown in Table 1.

| Genotype | C/C | C/G | G/G | ND |
|---|---|---|---|---|
| T/T | 12 | 8 | 1 | 0 |
| T/TA | 15 | 12 | 0 | 2 |
| TA/TA | 12 | 4 | 0 | 0 |

Figure 7:
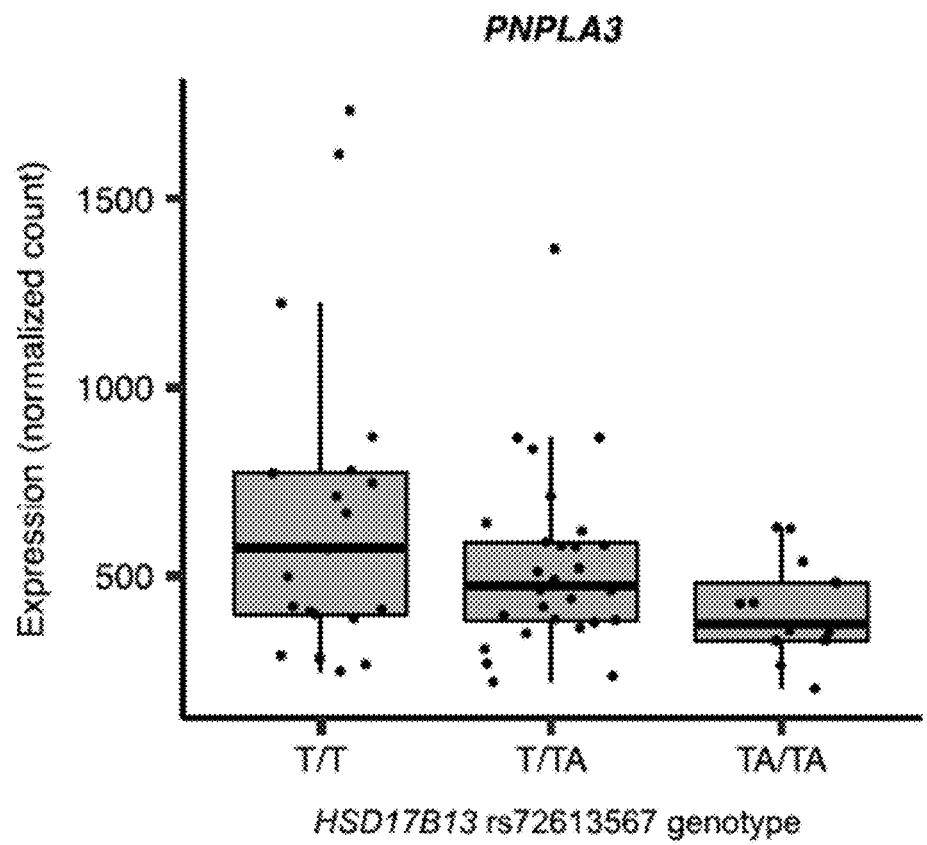
FIG. 7 shows the expression of PNPLA3 in homozygous reference (T/T), heterozygous (T/TA), and homozygous alternate (TA/TA) carriers of the HSD17B13 rs72613567 splice variant.
Figure 8:
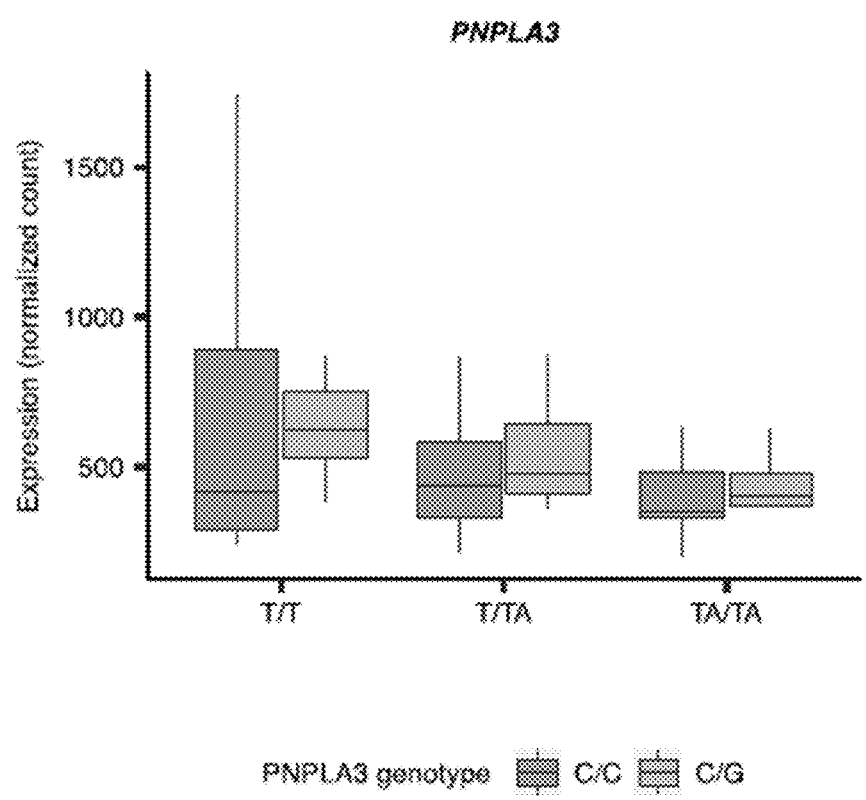
FIG. 8 shows the expression difference of the 63 PNPLA3 rs738409 carriers (C/C and C/G) in the three HSD17B13 rs72613567 genotypes (T/T, T/TA, TA/TA).

The expression of PNPLA3 was significantly reduced in homozygous alternate carriers of the HSD17B13 rs72613567 splice variant (see, FIG. 7). mRNA expression is displayed in FPKM units. A 1.6-fold decrease compared to T/T with FDR 0.0071 was observed. The variant PNPLA3 C/C carries with the HSD17B13 TA/TA genotype had significantly decreased expression when compared with HSD17B13 T/T carries: 1.7-fold (FDR 0.017) decrease. The variant PNPLA3 C/G carriers with TA/TA genotype showed decrease in expression but not statistically significant (1.4-fold, FDR 1). FIG. 8 shows the expression difference of the 63 PNPLA3 rs738409 carriers (C/C and C/G, see Table 1) in the three HSD17B13 rs72613567 genotypes (T/T, T/TA, TA/TA).

Figure 10:
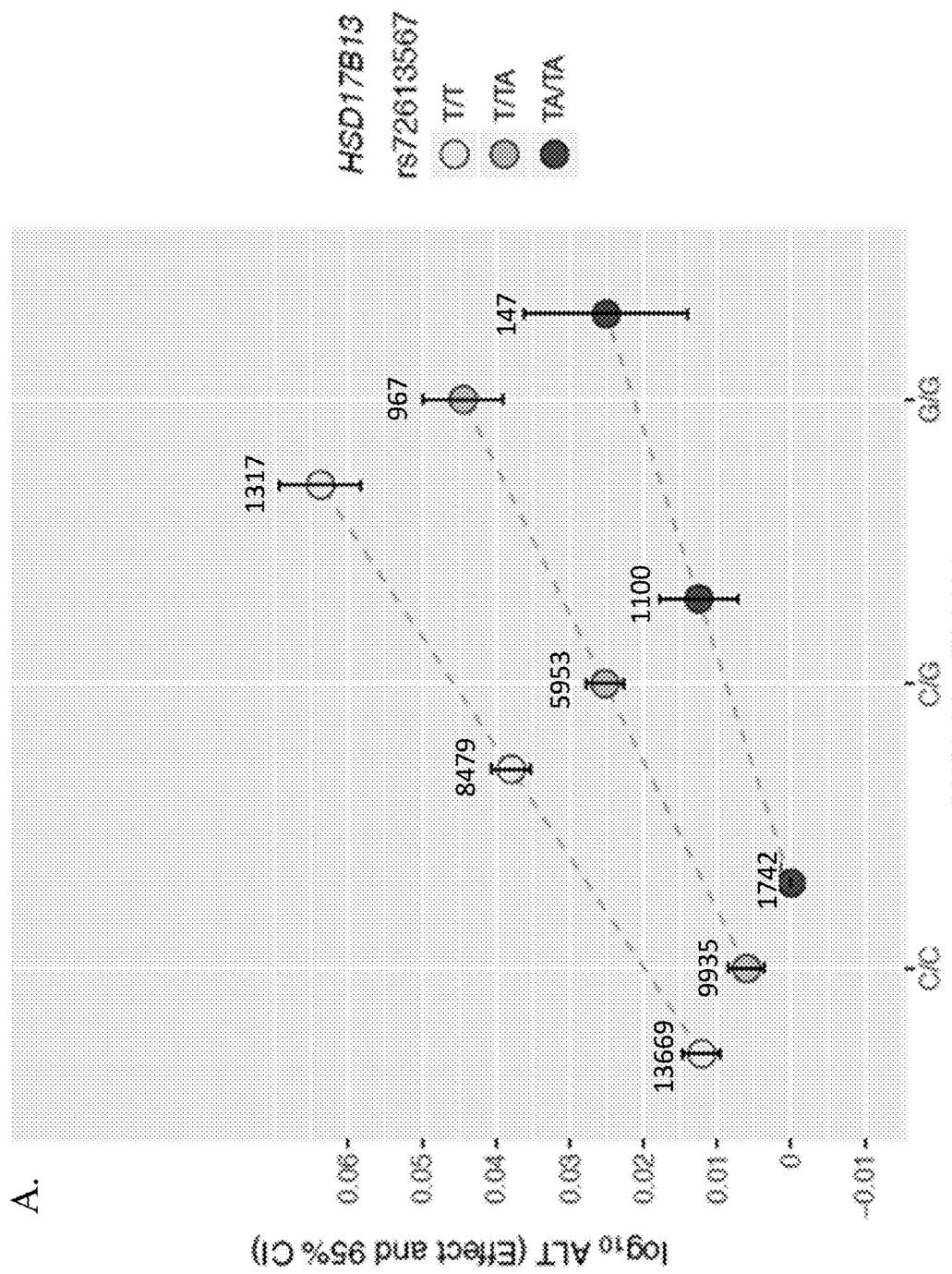
FIG. 10 (panels A and B) shows HSD17B13 rs72613567: TA mitigates the risk of liver injury associated with PNPLA3 p.I148M.
Figure 10:
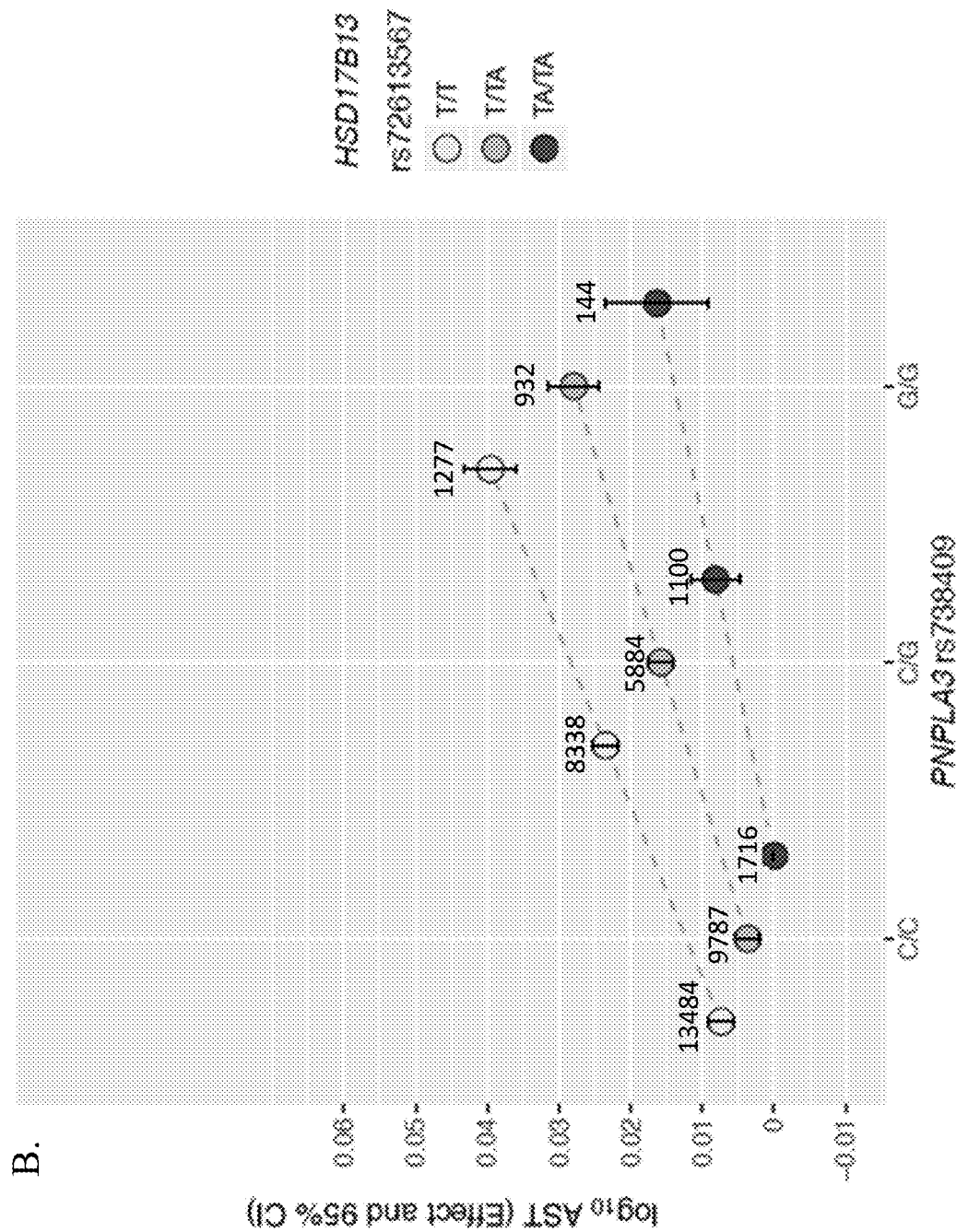
Figure 11:
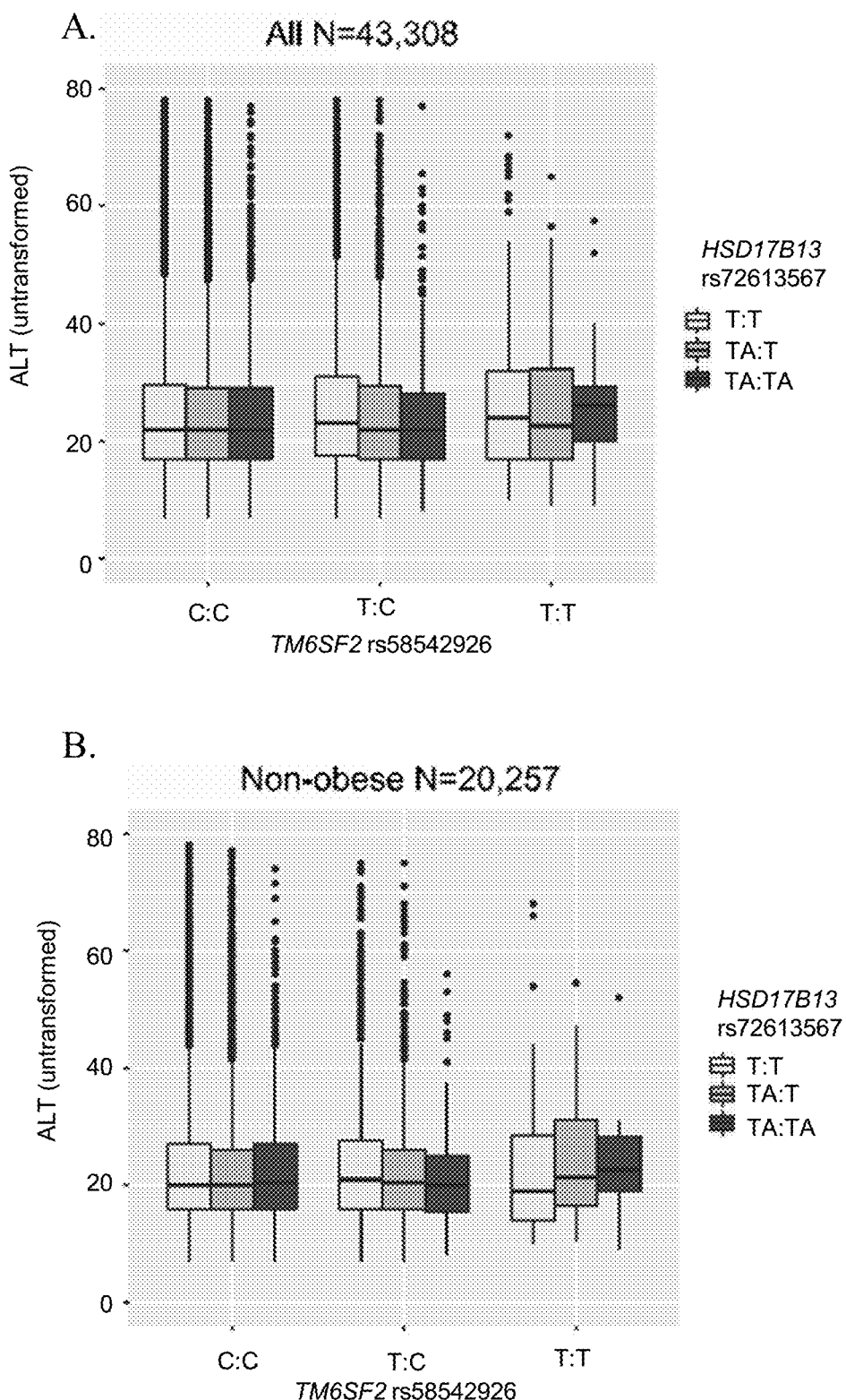
FIG. 11 (panels A through F) shows raw and residualized ALT levels by PNPLA3 rs738409 (p.I148M) and HSD17B13 rs72613567 genotype.
Figure 11:
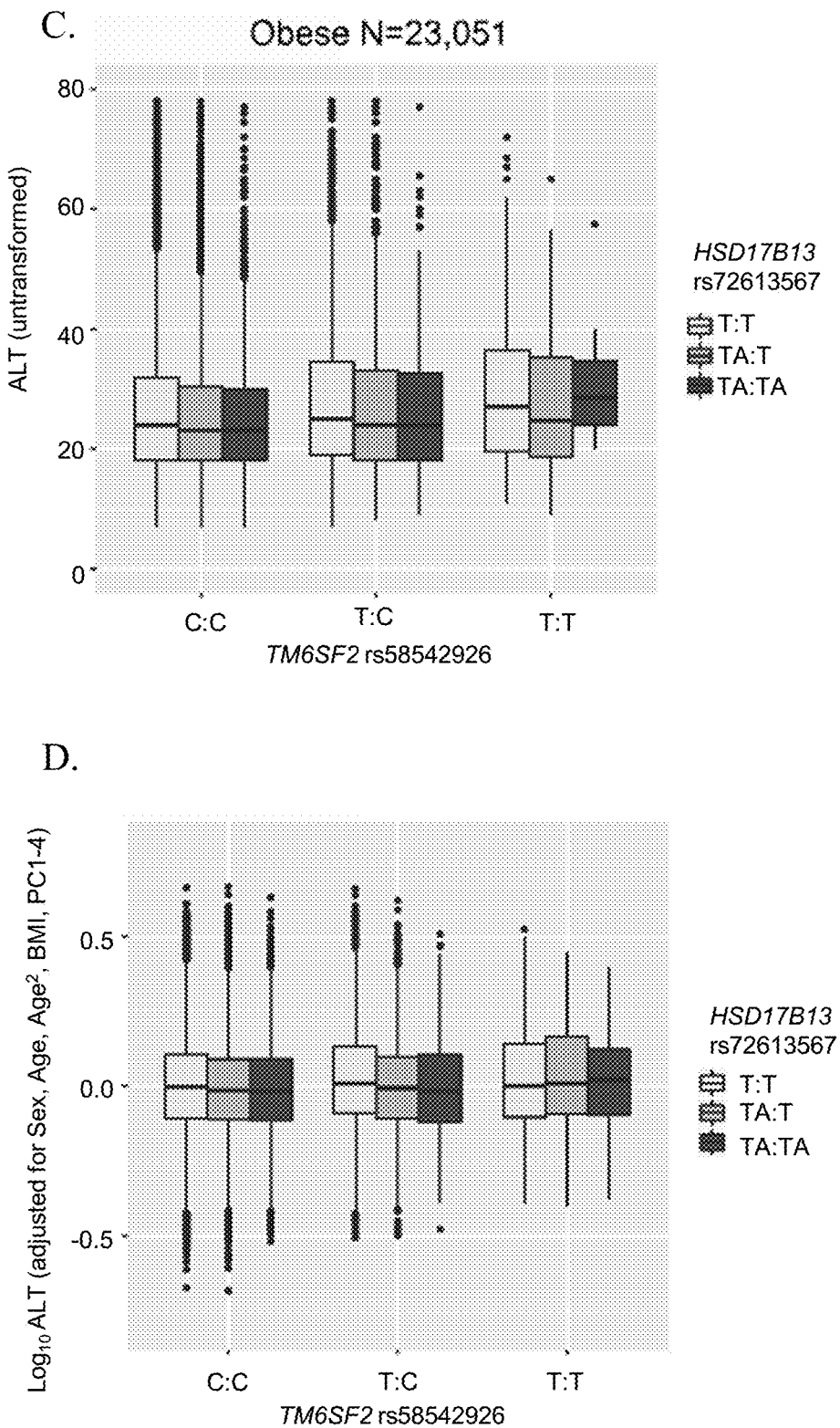
Figure 12:
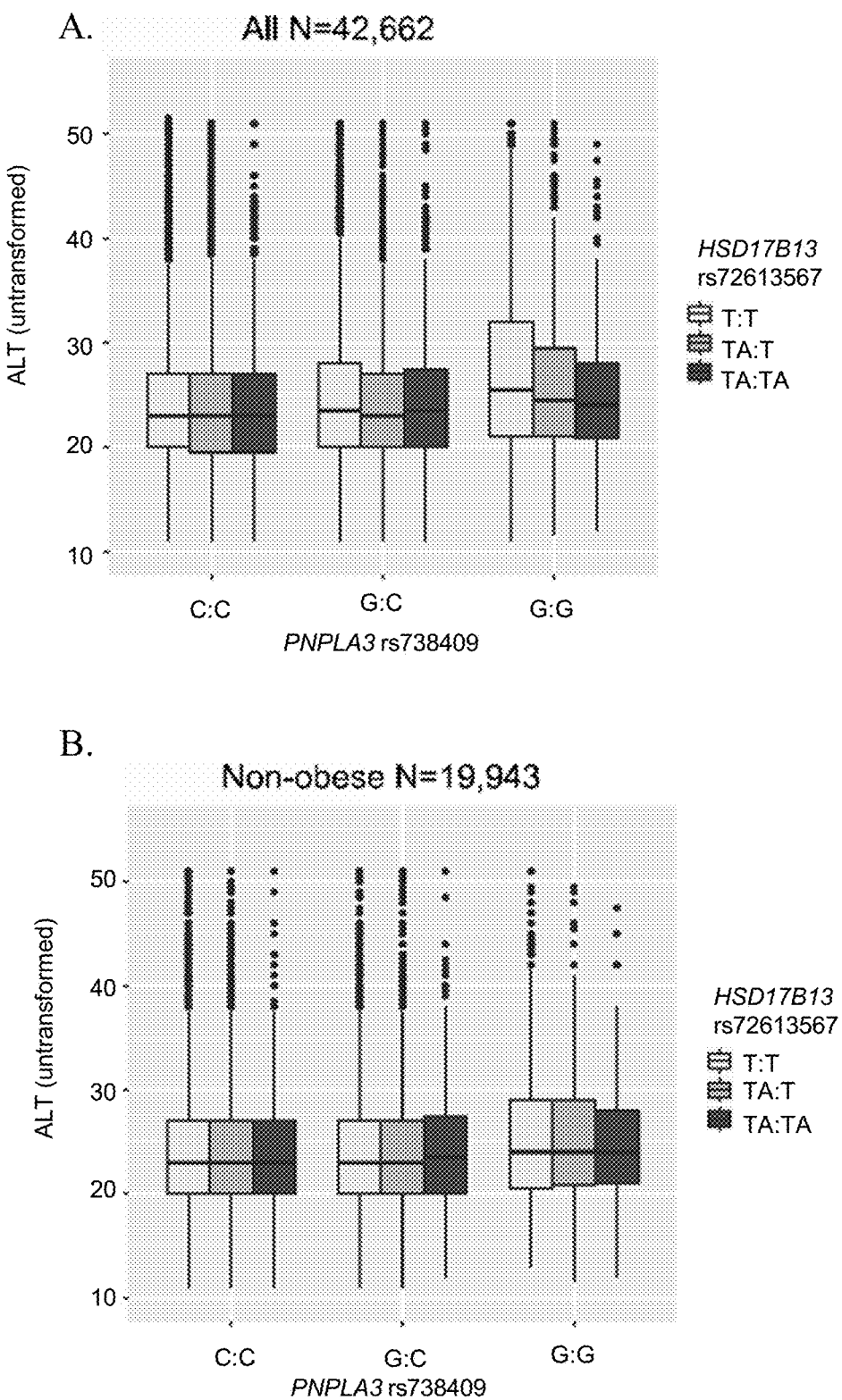
FIG. 12 (panels A through F) shows raw and residualized AST levels by PNPLA3 rs738409 (p.I148M) and HSD17B13 rs72613567 genotype.
Figure 13:
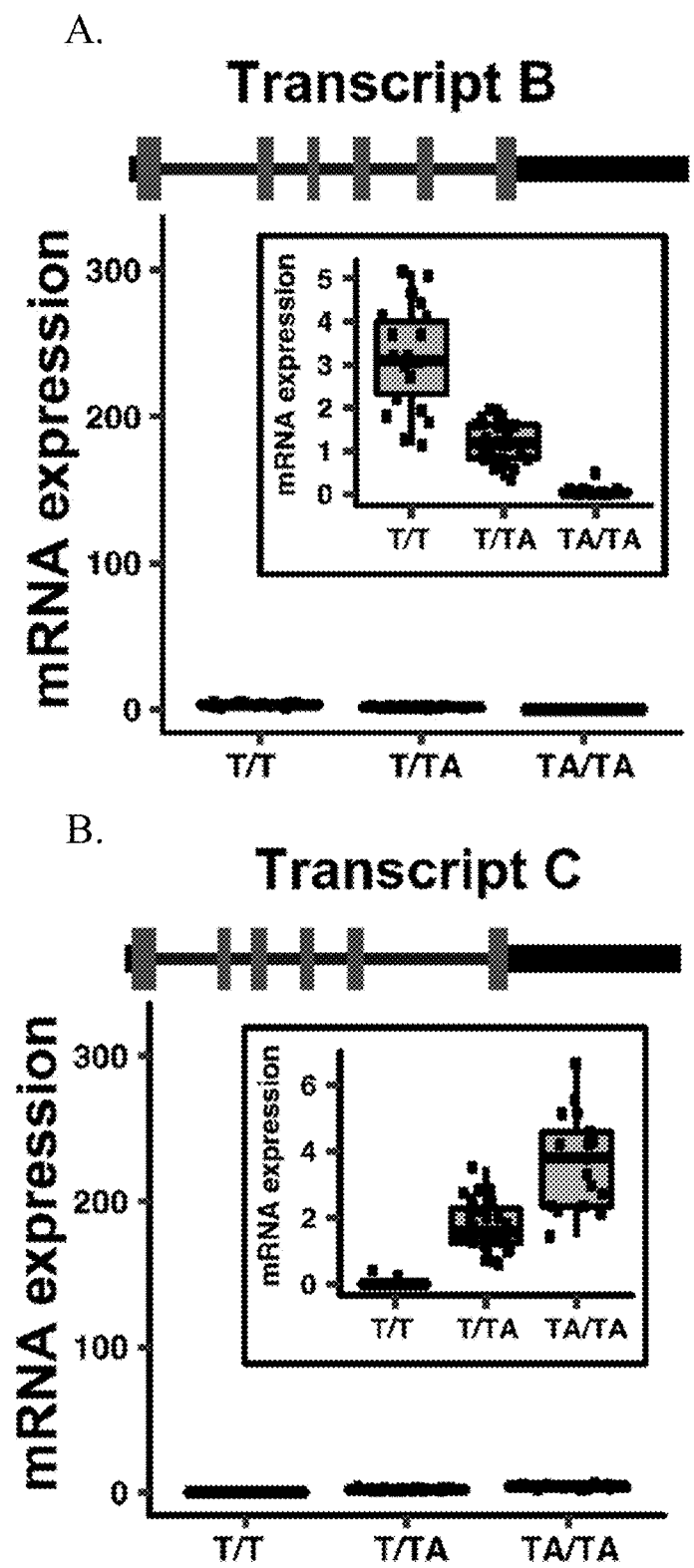
FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant.

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index (BMI)>30 kg/m$^2$) and non-obese (BMI 30 kg/m$^2$) subpopulations. There was nominally significant interaction between HSD17B13 rs72613567:TA and PNPLA3 p.I148M in association analyses of ALT ($P=1.8\times10^{-3}$ for interaction) and AST ($P=4.5\times10^{-3}$ for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 10). Referring to FIG. 10, panel A shows the association of HSD17B13 rs72613567 with ALT in individuals with each PNPLA3 p.I148M genotype, and panel B shows the association of HSD17B13 rs72613567 with AST in individuals with each PNPLA3 p.I148M genotype. Effect estimates (beta and 95% CI) were calculated using linear regression, with adjustment for age, age$^2$, sex, BMI, and four principal components of ancestry. FIG. 11 (panels A through F) show raw and residualized ALT levels by PNPLA3 rs738409 (p.I148M) and HSD17B13 rs72613567 genotype. Residuals were calculated by linear regression adjusted for age, age$^2$, sex, BMI, and four principal components 1-4. FIG. 12 (panels A through F) show raw and residualized AST levels by PNPLA3 rs738409 (p.I148M) and HSD17B13 rs72613567 genotype. Residuals were calculated by linear regression adjusted for age, age$^2$, sex, BMI, and four principal components 1-4. FIG. 13 (panels A through F) show mRNA expression of four additional novel HSD17B13 transcripts (E-H) in homozygous reference (T/T), heterozygous (T/TA), and homozygous alternate (TA/TA) carriers of the HSD17B13 splice variant. Coding regions in gene models are indicated in red and untranslated regions in black. Transcripts E and H contain an additional exon between exons 3 and 4. Transcript F involves read-through from exon 6 to intron 6. The blue arrow indicates the A insertion from rs72613567. Transcript G lacks exon 2. The asterisk in transcripts G and H illustrates insertion of G at the 3'-end of exon 6, which leads to premature truncation of the protein (similar to transcript D). Transcripts are differentially expressed according to HSD17B13 genotype, as shown in the box plots. mRNA expression is displayed in FPKM units.

These data suggest the HSD17B13 rs72613567:TA variant mitigates the risk of liver injury in individuals genetically predisposed to steatotic liver disease by the variant PNPLA3 p.I148M variant. This finding may suggest an important subpopulation for therapeutic modulation of HSD17B13—individuals heterozygous or homozygous for the variant PNPLA3 148M allele.

Figure 14:
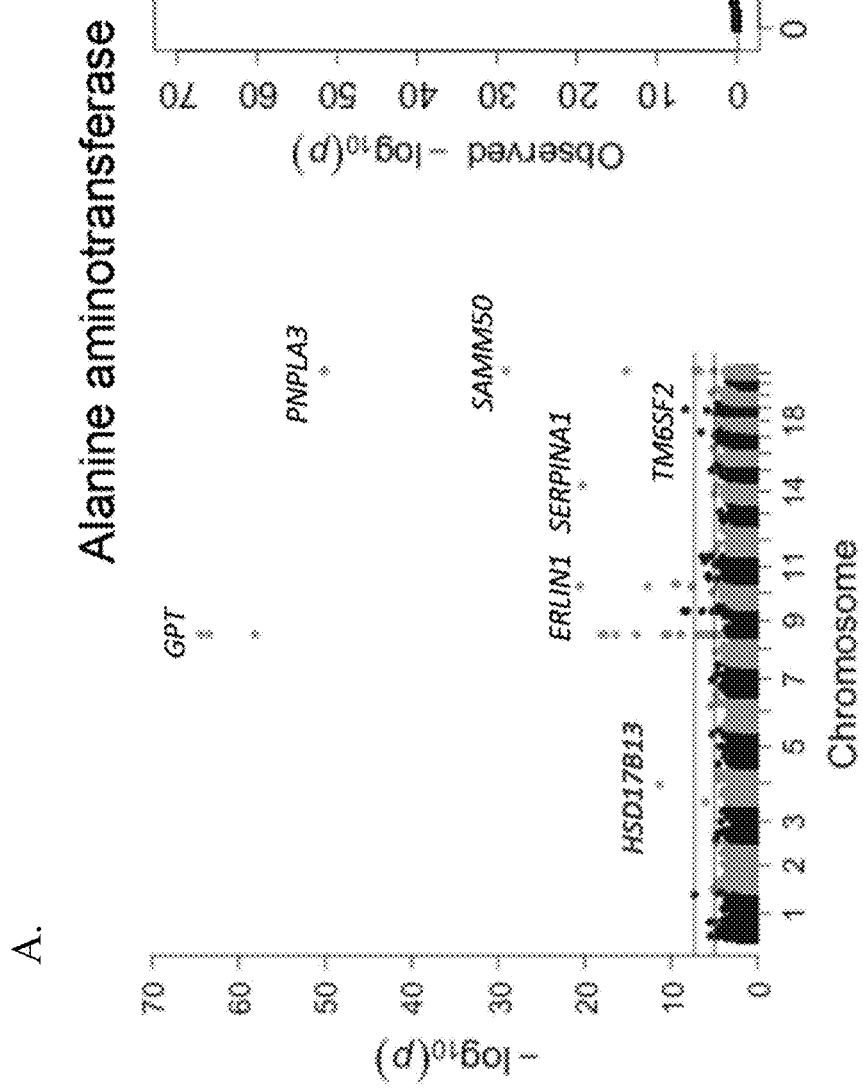
FIG. 14 (panels A and B) shows Manhattan plots (left) and quantile-quantile plots (right) of single nucleotide variant associations with serum transaminase levels in the GHS discovery cohort.
Figure 14:
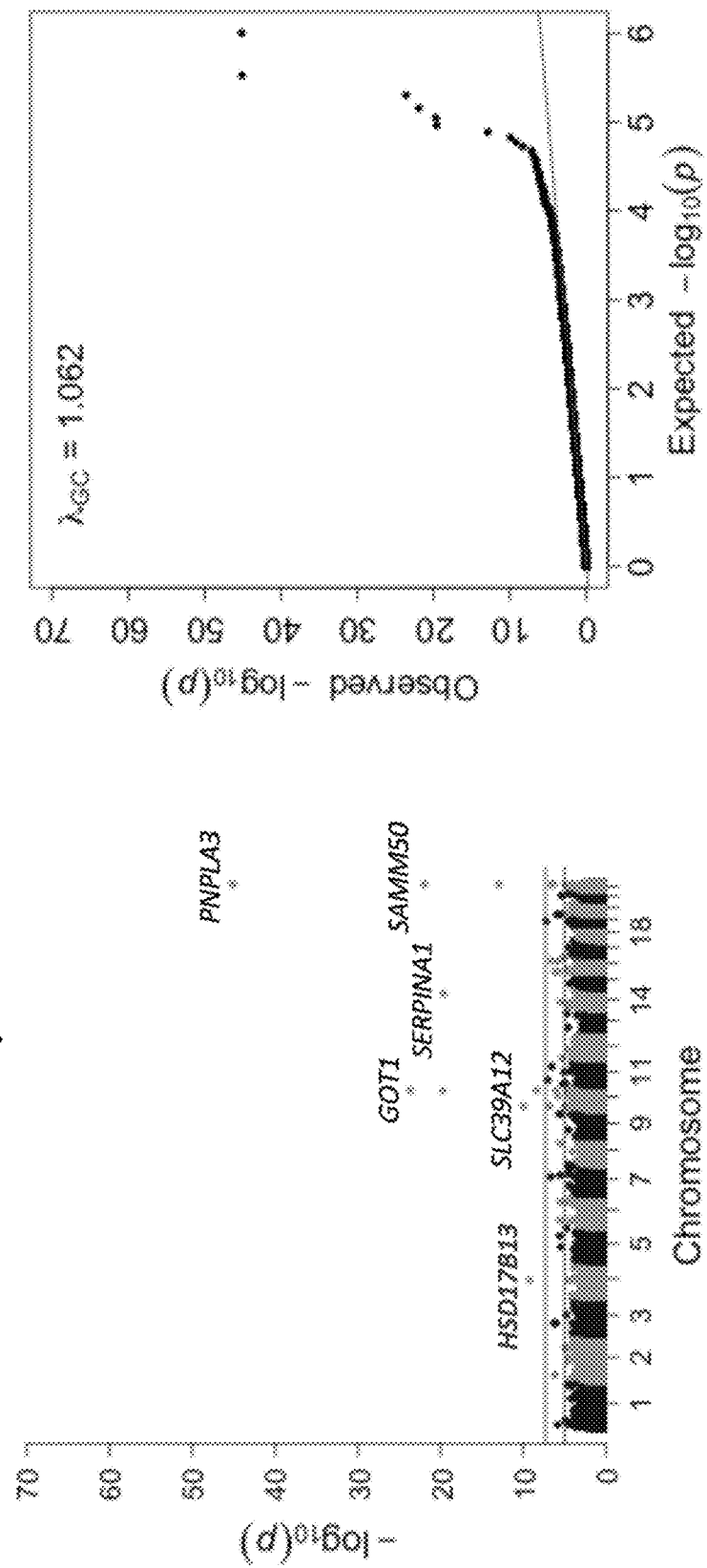

Example 3: Gene Expression Analysis of HSD17B13 and PNPLA3 in 66 Human Liver Samples Association of Exonic Variants with Asparatate and Alanine Aminotransferases 502,219 biallelic single genetic variants were examined for association with serum ALT or AST levels in 46,544 individuals of European descent from the DiscovEHR study ("GHS discovery cohort"; basic demographics in FIG. 1). A total of 35 variants in 19 genes were found to be associated with ALT or AST at $P<1.0\times10^{-7}$ (see, FIG. 14 and FIG. 2). Referring to FIG. 14, Manhattan plots (left) and quantile-quantile plots (right) of single nucleotide variant associations with serum transaminase levels in the GHS discovery cohort are shown. There were 31 variants in 16 genes significantly associated with alanine aminotransferase (ALT) levels at $P<1.0\times10^{-7}$ (see, Panel A). There were 12 variants in 10 genes significantly associated with aspartate aminotransferase (AST) levels at $P<1.0\times10^{-7}$ (see, Panel B). All significant associations are shown in FIG. 2. There were thirteen variants in nine genes (indicated here by their gene name), including HSD17B13, that remained significantly associated with ALT or AST in a replication meta-analysis of three separate European-ancestry cohorts (see, FIG. 3). The association tests were well calibrated, as shown by exome-wide quantile-quantile plots and genomic control lambda values.

Replication studies were performed in three cohorts of European-ancestry individuals: 1) bariatric surgery patients (n=2,644) from DiscovEHR ("GHS bariatric surgery cohort"); 2) 1,357 individuals from the Dallas Heart Study; and 3) 8,526 individuals from the Penn Medicine Biobank. In meta-analysis of the replication cohorts, thirteen variants in nine genes were significantly associated with serum levels of ALT or AST (Bonferroni significance threshold of $P<1.43\times10^{-3}$ for 35 variants tested (see, FIG. 3). These included variants that were previously reported to be associated with elevated transaminase levels, such as PNPLA3 (Romeo et al., Nat. Genet., 2008, 40, 1461-5), TM6SF2 (Kozlitina et al., Nat. Genet. 2014, 46, 352-6), SERPINA1 (Brantly et al., Am. J. Med., 1988, 84, 13-31), SAMM50 (Kitamoto et al., Hum. Genet., 2013, 132, 783-92), and ERLIN1 (Feitosa et al., Atherosclerosis, 2013, 228, 175-80). SERPINA1 encodes alpha-1-antitrypsin, whose functional deficiency causes liver disease; the association with SAMM50 is mediated via linkage disequilibrium with variation in PNPLA3, and ERLIN1 has been implicated in liver fat deposition. Variants that were not previously reported to be associated with liver disease were also identified. These included several variants in GPT and GOT1, the genes encoding ALT and AST, respectively, and SLC39A12, which encodes solute carrier family 39 member 12.

A reproducible association between a variant in HSD17B13, the gene encoding hydroxysteroid 17-beta dehydrogenase 13, an uncharacterized member of the 17-beta hydroxysteroid dehydrogenase family, and decreased levels of ALT (discovery P=$4.2 \times 10^{-12}$, replication P=$1.7 \times 10^{-4}$) and AST (discovery P=$6.2 \times 10^{-10}$, replication P=$1.7 \times 10^{-4}$, see, FIG. 3) was also identified. The associated variant, rs72613567, is an insertion of an adenine adjacent to the donor splice site of exon six (TA allele), and had an allele frequency of 26.0% in the GHS discovery cohort. Previously, Chambers, et al identified a nearby locus at 4q22 (rs6834314) associated with ALT levels (Chambers et al., Nat. Genet., 2011, 43, 1131-8); rs72613567 has not heretofore been reported to be associated with transaminase levels. HSD17B13 is 30 kb upstream of HSD17B11, another member of the same gene family. No exome-wide significant associations were observed between coding or splice variants in HSD17B11 and transaminase levels in the discovery cohort (see, FIG. 6) or in the joint meta-analysis of the discovery cohort and three replication cohorts. Furthermore, linkage disequilibrium of rs72613567 with variants in HSD17B11 was modest across all ancestry groups ($r^2<0.4$ with all ascertained variants in HSD17B11 in all ancestry groups; data not shown). Collectively, these findings suggest HSD17B13 as the gene in the genomic region that is most likely to be functionally related to transaminase levels.

Association of Exonic Variants with Clinical Diagnoses of Chronic Liver Disease

The relationship between the thirteen transaminase-associated variants in the nine genes found in the discovery and replication cohorts and chronic liver disease, including alcoholic and nonalcoholic (non-viral) liver disease, as well as the most advanced forms of chronic liver disease: alcoholic cirrhosis, nonalcoholic cirrhosis, and hepatocellular carcinoma (HCC), was also analyzed. Using a Bonferroni significance threshold of P<$1.92 \times 10^{-3}$ for the thirteen variants tested, significant associations were found between six variants in five genes (HSD17B13, SERPINA1, TM6SF2, PNPLA3, and SAMM50) and chronic liver disease phenotypes (see, FIG. 4). The SERPINA1, TM6SF2, PNPLA3, and SAMM50 associations confirm previously reported associations. In the discovery cohort, HSD17B13 rs72613567:TA was associated with lower odds of all EHR-derived categories of both alcoholic and nonalcoholic liver disease in an allele dosage-dependent manner (see, FIG. 15, panel A): all categories of alcoholic liver disease, heterozygous odds ratio ($OR_{het}$) (95% confidence interval) 0.58 (0.42-0.80), homozygous OR ($OR_{hom}$) 0.47 (0.23-0.97), allelic OR ($OR_{allelic}$) 0.62 (0.48-0.81), P=$1.8 \times 10^{-4}$; all categories of nonalcoholic liver disease, $OR_{het}$ 0.83 (0.75-0.92), $OR_{hom}$ 0.70 (0.57-0.87), $OR_{allelic}$ 0.84 (0.78-0.91), P=$1.3 \times 10^{-5}$. HSD17B13 rs72613567:TA was also associated with lower odds alcoholic and nonalcoholic cirrhosis, with 42% and 73% lower odds of alcoholic cirrhosis for heterozygotes and homozygotes, respectively, ($OR_{het}$ 0.58 (0.39-0.86), $OR_{hom}$ 0.27 (0.09-0.85), $OR_{allelic}$ 0.56 (0.41-0.78), P=$3.4 \times 10^{-4}$) and 26% and 49% lower odds of nonalcoholic cirrhosis for heterozygotes and homozygotes, respectively ($OR_{het}$ 0.74 (0.60-0.93), $OR_{hom}$ 0.51 (0.31-0.85), $OR_{allelic}$ 0.74 (0.62-0.88), P=$4.5 \times 10^{-4}$). HSD17B13 rs72613567:TA was also nominally associated with lower odds of HCC.

These findings were confirmed and extended in the multiethnic Dallas Liver Study (DLS) and the Dallas Pediatric Liver Study (DPLS) (see, FIG. 5). In the DLS, the TA allele was associated with lower odds of any liver disease in an allele-dosage dependent manner ($OR_{het}$ 0.74 (0.57-0.97), $OR_{hom}$ 0.41 (0.21-0.83), $OR_{allelic}$ 0.70 (0.5-0.88), P=$1.8 \times 10^{-3}$, see FIG. 15, panel B). Similar effects were observed across EHR-derived liver disease subtypes, including protective associations with advanced, cirrhotic forms of alcoholic ($OR_{allelic}$ 0.72 (0.53-0.99), P=$4.4 \times 10^{-2}$) and nonalcoholic ($OR_{allelic}$ 0.65 (0.40-1.07), P=$9.0 \times 10^{-2}$) liver disease. In subset analyses of individuals grouped by self-reported ethnicity, the association with liver disease was significant in Hispanic Americans (n=326 cases and 722 controls, $OR_{allelic}$ 0.51 (0.35-0.74), P=$4.0 \times 10^{-4}$); similar numerical trends, which did not achieve statistical significance, were also noted in the African American (n=33 cases and 2,291 controls, $OR_{allelic}$ 0.74 (0.25-2.47), P=0.67) and European American (n=158 cases and 1,266 controls, $OR_{allelic}$ 0.87 (0.65-1.15), P=0.32) subsets of the DLS. In the DPLS, a separate study of Hispanic American pediatric liver disease patients and obese controls, the TA allele was also associated with lower odds of liver disease ($OR_{allelic}$ 0.61 (0.37-0.99), P=$4.6 \times 10^{-2}$). Thus, HSD17B13 rs72613567:TA was associated with reduced odds of multiple forms of chronic liver disease, including cirrhosis, in adults and children in three independent populations.

Figure 15:
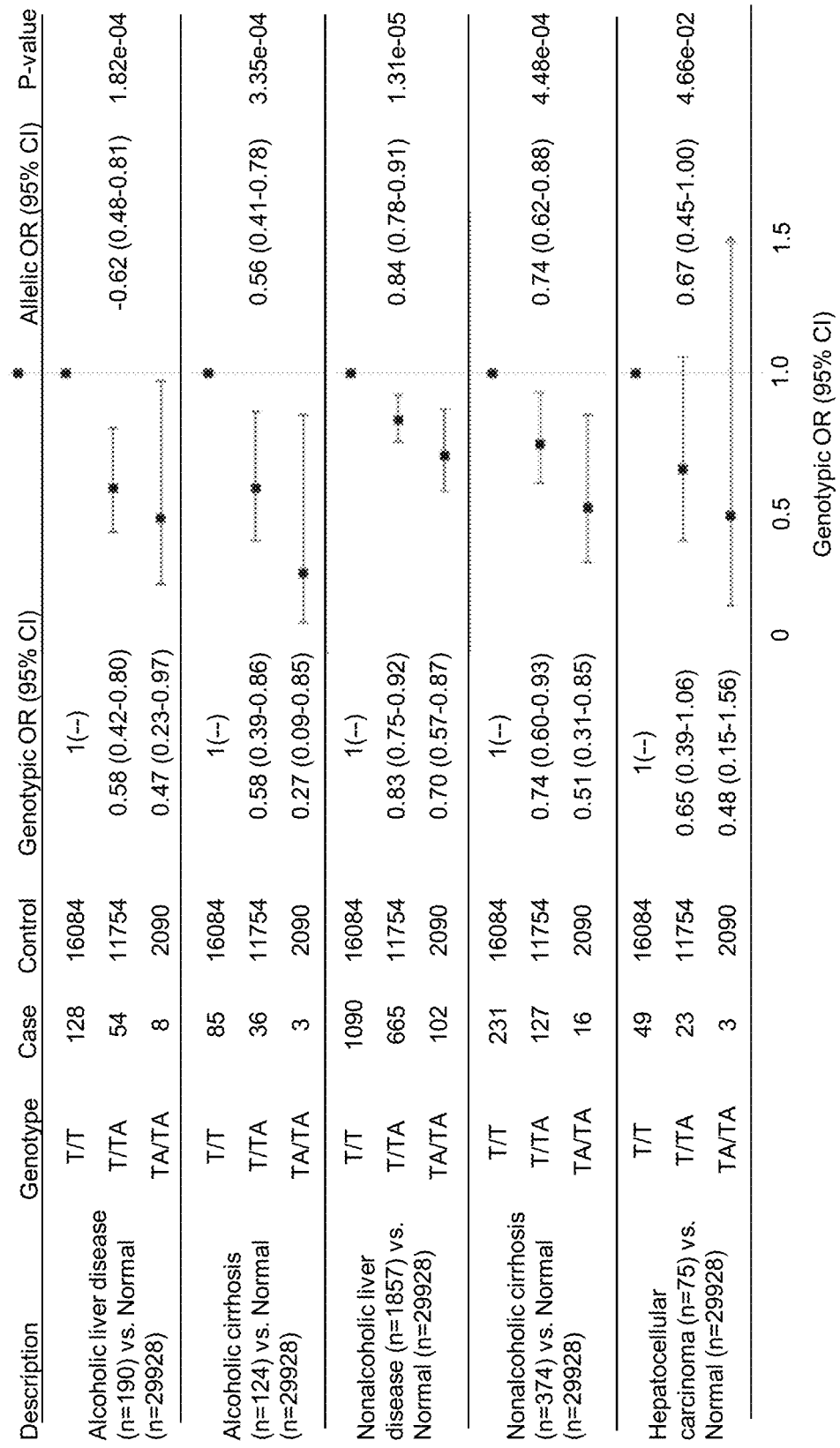
FIG. 15 (panels A and B) shows HSD17B13 rs72613567: TA is associated with reduced risk of alcoholic and nonalcoholic liver disease phenotypes.
Figure 15:
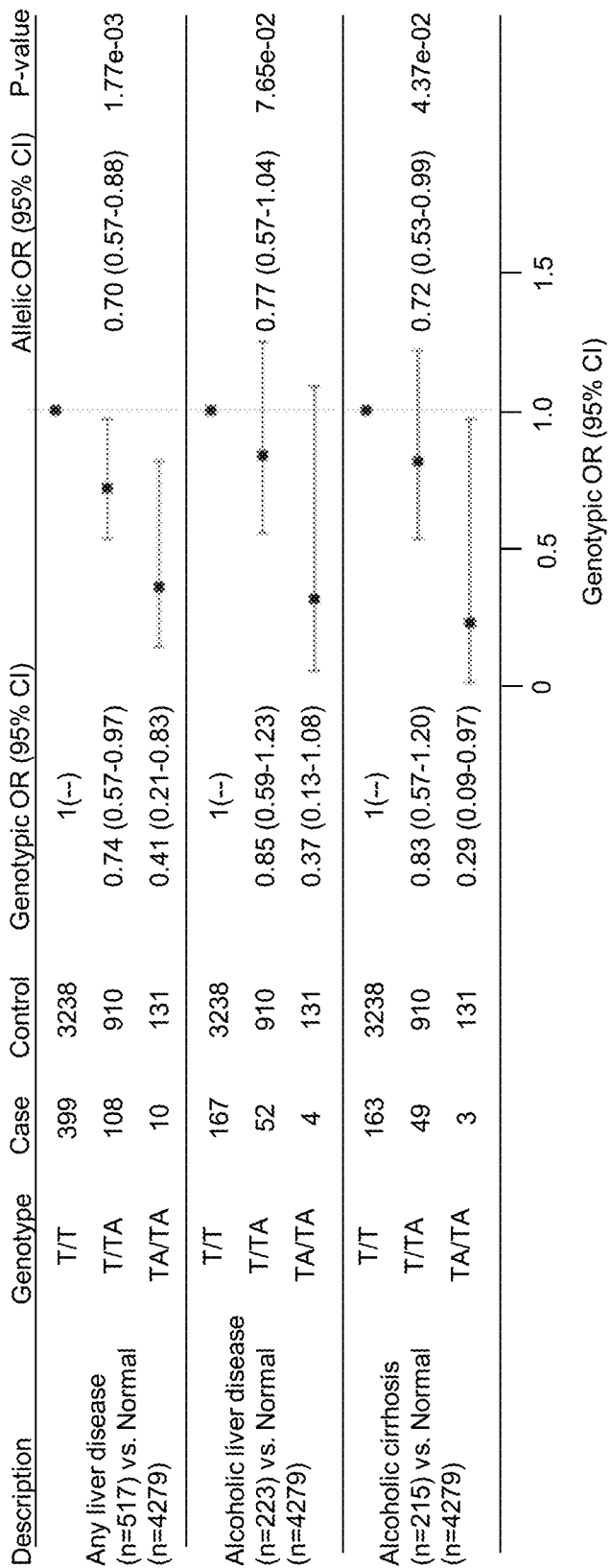
Figure 15:
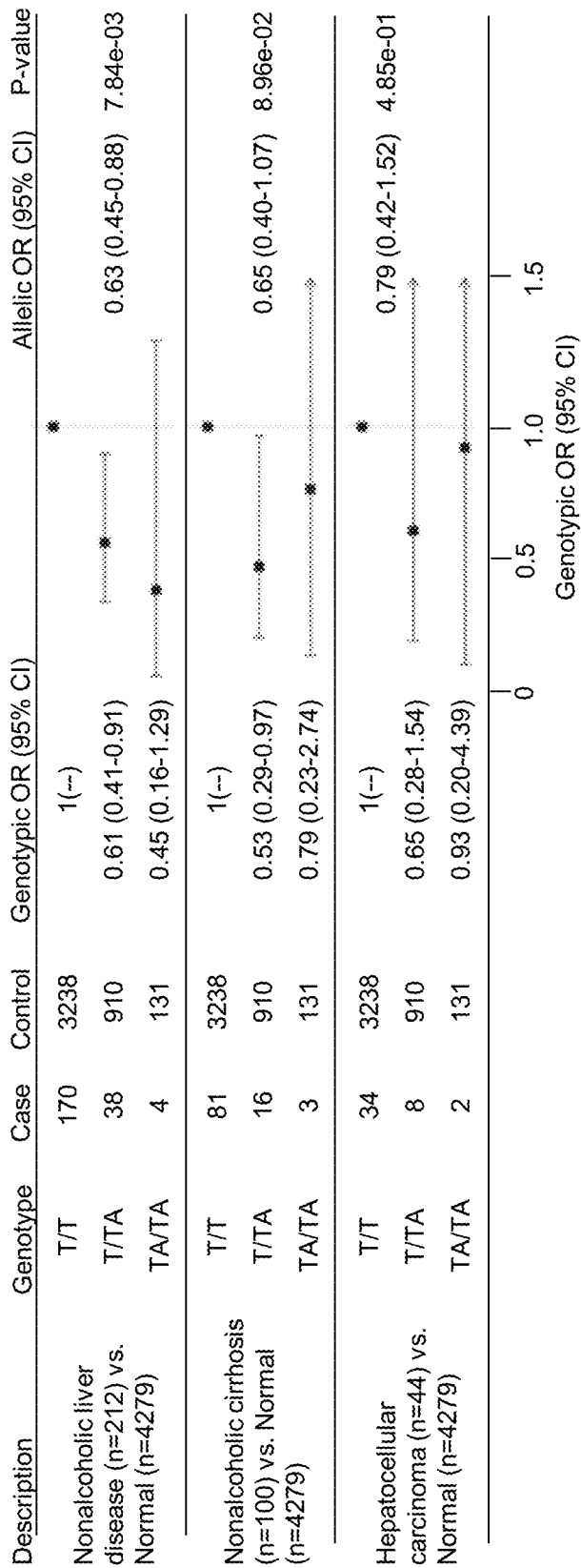

Referring to FIG. 15, HSD17B13 rs72613567:TA is associated with reduced risk of alcoholic and nonalcoholic liver disease phenotypes is shown. In the GHS discovery cohort, HSD17B13 rs72613567 was associated with lower odds of nonalcoholic and alcoholic liver disease, cirrhosis, and hepatocellular carcinoma in an allele dosage-dependent manner (see, Panel A). Odds ratios were calculated using logistic regression, with adjustment for age, $age^2$, sex, BMI, and principal components of ancestry. Genotypic odds ratios for heterozygous (Het OR) and homozygous (Hom OR) carriers are also shown. In the Dallas Liver Study, HSD17B13 rs72613567 was associated with lower odds of any liver disease in an allele dosage-dependent manner (see, Panel B). Similar allele dosage-dependent effects were observed across liver disease subtypes. Odds ratios were calculated using logistic regression, with adjustment for age, $age^2$, sex, BMI, and self-reported ethnicity.

Genetic Interaction Between PNPLA3 rs738409 (p.I148M) and HSD17B13 rs72613567

The variant PNPLA3 p.I148M variant is the most well validated genetic risk factor for NAFLD, and the 148M allele exists in homozygous state in 5-25% of individuals, depending on ancestry. To understand whether the HSD17B13 rs72613567:TA modifies the risk of liver injury associated with PNPLA3 p.I148M, analyses of interaction between the two variants in association with ALT, AST, and chronic liver disease phenotypes in DiscovEHR was performed. These analyses were performed in all participants, as well as in obese (body mass index [BMI]≥30 kg/m$^2$) and non-obese (BMI<30 kg/m$^2$) subpopulations. There was nominally significant interaction between HSD17B13 rs72613567:TA and PNPLA3 p.I148M in association analyses of ALT (P=$1.8 \times 10^{-3}$ for interaction) and AST (P=$4.5 \times 10^{-3}$ for interaction) levels; these associations were primarily driven by associations in obese individuals (see, FIG. 9). In these analyses, the rs72613567:TA allele mitigated the allele dosage-dependent associations of PNPLA3 148M allele with increased ALT and AST (see, FIG. 16, FIG. 11, and FIG. 12). RNA sequencing-based expression analysis revealed that HSD17B13 rs72613567:TA was associated with decreased PNPLA3 mRNA expression in an allele dosage-dependent manner (see, FIG. 7). These data suggest the HSD17B13 rs72613567:TA variant mitigates the risk of liver injury in individuals genetically predisposed to steatotic liver disease by the variant PNPLA3 p.I148M variant.

Figure 16:
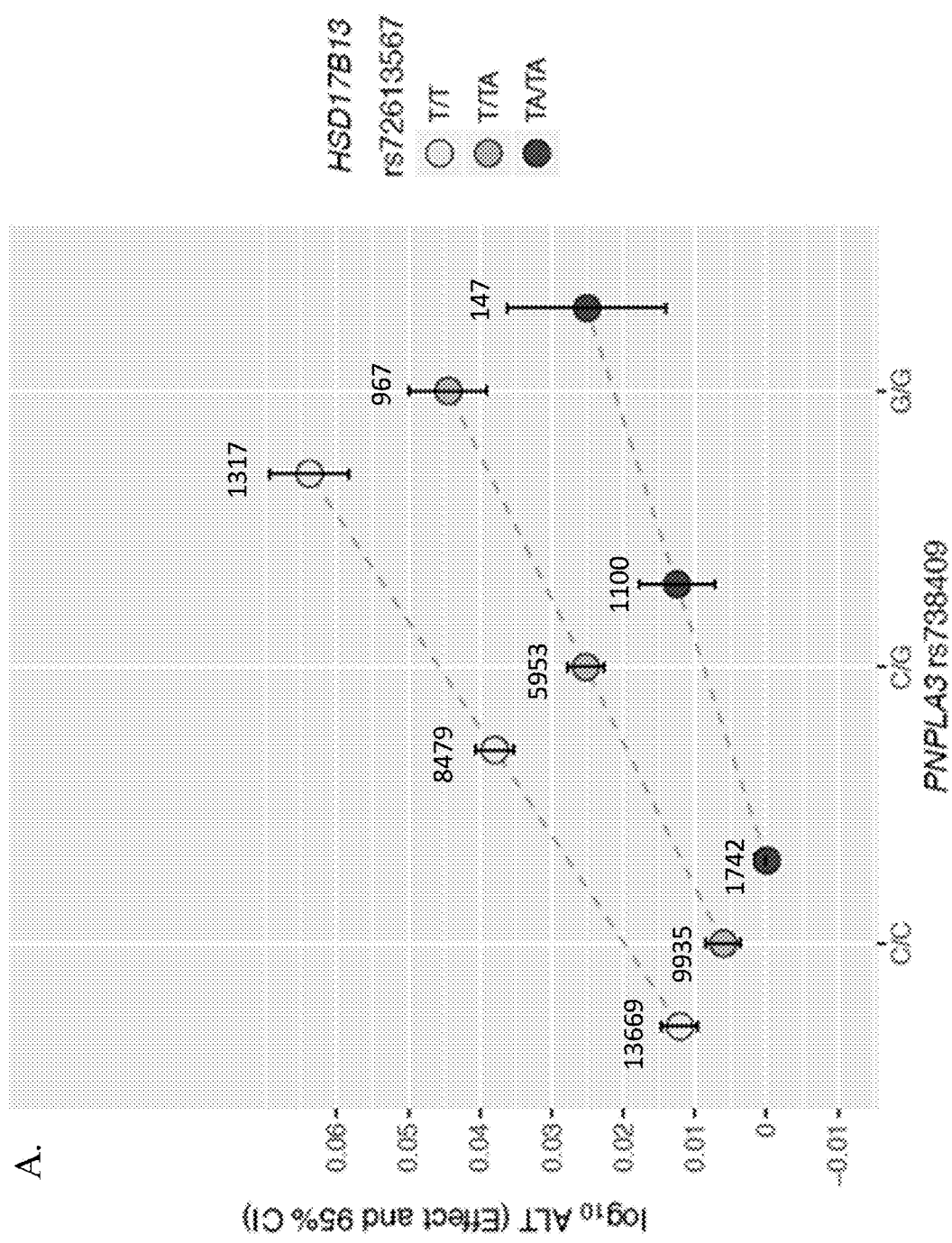
FIG. 16 (panels A and B) shows HSD17B13 rs72613567: TA mitigates the risk of liver injury associated with PNPLA3 p.I148M.
Figure 16:
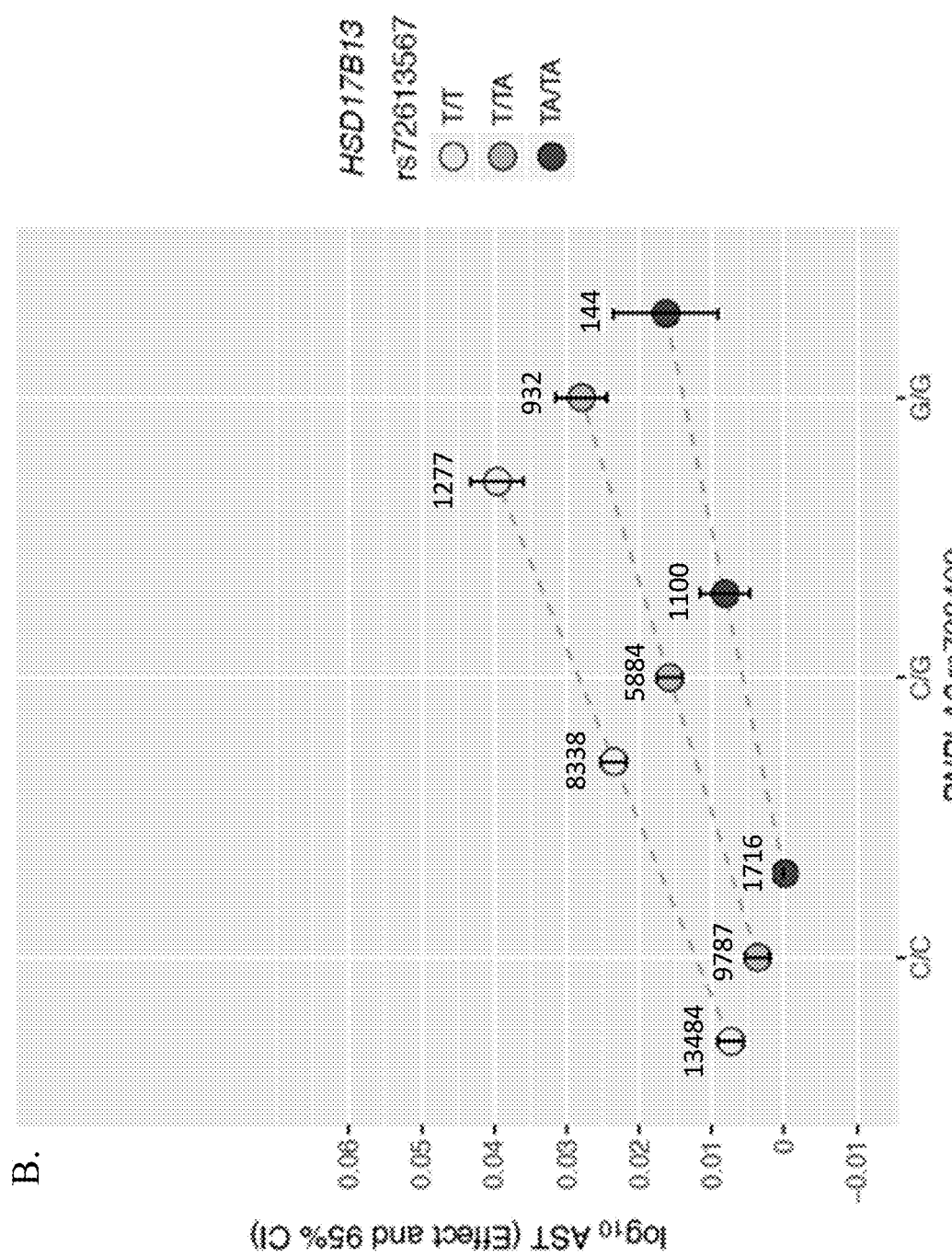

Referring to FIG. 16, HSD17B13 rs72613567:TA mitigates the risk of liver injury associated with PNPLA3 p.I148M is shown. Association of HSD17B13 rs72613567 with ALT in individuals with each PNPLA3 p.I148M genotype (see, Panel A). Association of HSD17B13 rs72613567 with AST in individuals with each PNPLA3 p.I148M genotype (see, Panel B). Effect estimates (beta and 95% CI) were calculated using linear regression, with adjustment for age, $age^2$, sex, BMI, and four principal components of ancestry. The P values for interaction between HSD17B13 rs72613567:TA and PNPLA3 p.I148M in association analyses of ALT and AST levels were $P=1.8\times10^{-3}$ and $P=4.5\times10^{-3}$, respectively.

Association of HSD17B13 rs72613567:TA with Liver Pathology

NAFLD describes a disease spectrum ranging from liver fat accumulation without evidence of significant inflammation (simple steatosis), to more clinically impactful NASH. To confirm the association between the HSD17B13 rs72613567:TA and EHR-derived liver disease diagnoses codes, and to further understand its association with histopathological progression of steatosis to NASH, tests of association in the GHS bariatric surgery cohort were performed. In this cohort of 2,391 of the whole exome sequenced individuals assessed by liver biopsy at the time of bariatric surgery, a total of 555 (23%) individuals had no evidence of steatosis, steatohepatitis, or fibrosis ("normal"), 830 (35%) had simple steatosis, and 1006 (42%) had NASH. When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T, T/TA, and TA/TA carriers, respectively, $P=1.6\times10^{-4}$) and that of simple steatosis increased (33%, 35%, and 47% for T/T, T/TA, and TA/TA carriers, respectively, $P=1.1\times10^{-3}$) with each TA allele (see, FIG. 17, Panel A). Among individuals with steatosis, the TA allele was associated with statistically significantly lower odds of NASH, as compared to simple steatosis, in an allele dosage-dependent manner ($OR_{het}$ 0.87 (0.71-1.06), $OR_{hom}$ 0.48 (0.33-0.70), $OR_{allelic}$ 0.77 (0.66-0.90), $P=6.5\times10^{-4}$) (see, FIG. 17, Panel B). Altogether, these data suggest a role for HSD17B13 in mediating NAFLD progression from simple steatosis to more advanced stages of NASH and fibrosis.

Figure 17:
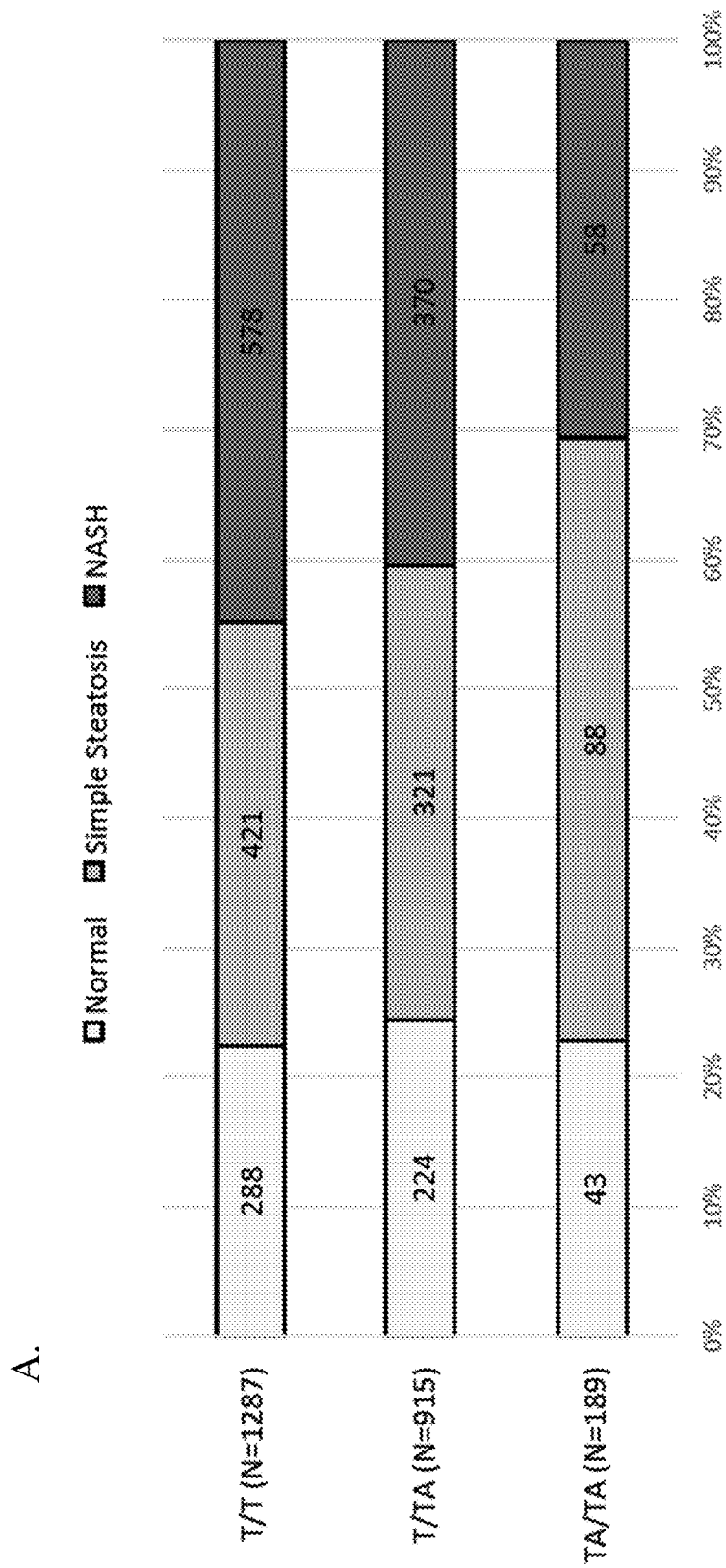
FIG. 17 (panels A and B) shows HSD17B13 rs72613567: TA is associated with reduced risk of progression from simple steatosis to steatohepatitis and fibrosis.
Figure 17:
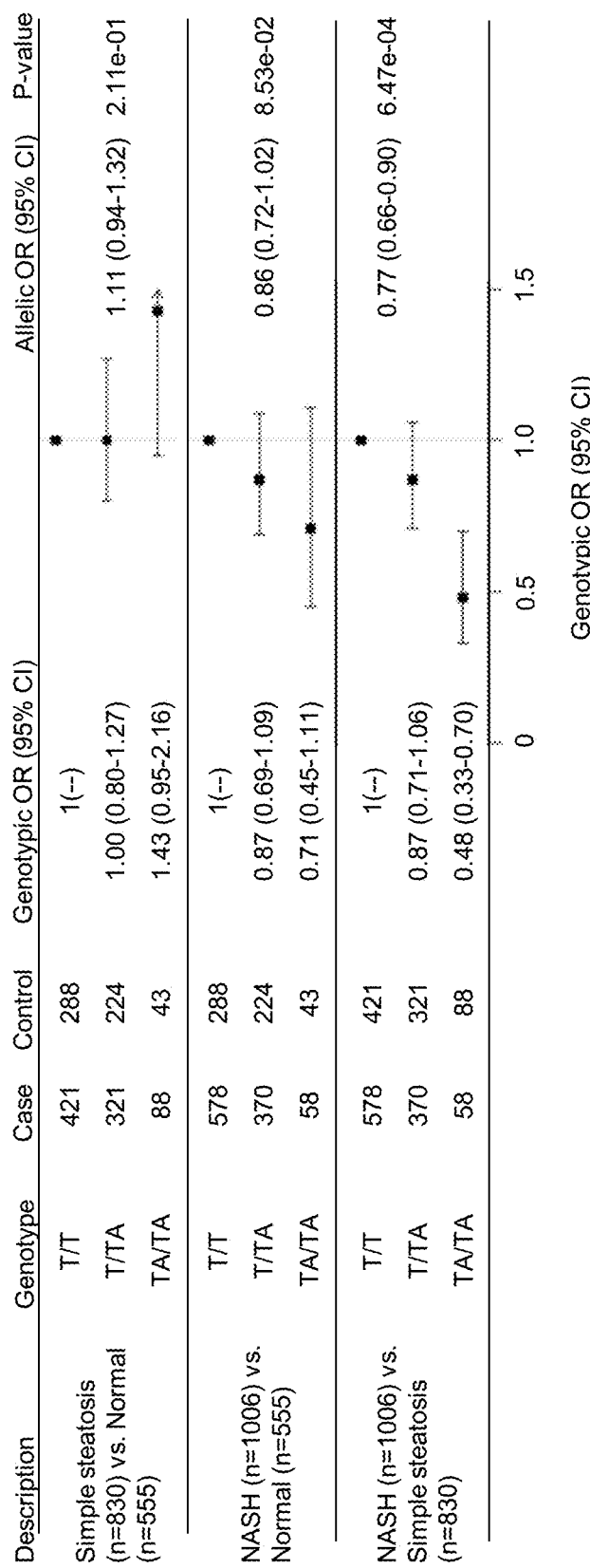

Referring to FIG. 17, HSD17B13 rs72613567:TA is associated with reduced risk of progression from simple steatosis to steatohepatitis and fibrosis is shown. Prevalence of histopathologically-characterized liver disease according to HSD17B13 rs72613567 genotype in 2,391 individuals with liver biopsies from the GHS bariatric surgery cohort (see, Panel A). The prevalence of normal liver did not appear to differ by genotype (P=0.5 by Chi-squared test for trend in proportions), but the prevalence of NASH decreased ($P=1.6\times10^{-4}$) and that of simple steatosis increased ($P=1.1\times10^{-3}$) with each TA allele. In the GHS bariatric surgery cohort, HSD17B13 rs72613567 was associated with 13% and 52% lower odds of NASH in heterozygous and homozygous TA carriers, respectively (see, Panel B). Odds ratios were calculated using logistic regression, with adjustment for age, $age^2$, sex, BMI, and principal components of ancestry. Genotypic odds ratios for heterozygous (Het OR) and homozygous (Hom OR) carriers are also shown.

Effect of rs72613567:TA on HSD17B13 mRNA and HSD17B13 Protein Expression

The effect of the HSD17B13 rs72613567:TA allele on expression of known and novel transcripts of the gene was examined. RNA sequencing was used to assess HSD17B13 mRNA expression in histologically normal liver samples from 22 T/T homozygous, 30 T/TA heterozygous, and 17 TA/TA homozygous carriers of the HSD17B13 rs72613567 splice variant. In addition to the two HSD17B13 transcripts, A and B, two novel transcripts were identified: transcript C, which lacked exon 6, and transcript D which contained an insertion of a guanine nucleotide at the 3' end of exon 6, which would be predicted to result in premature truncation of the protein. Four additional transcripts (E-H) were expressed at very low levels (see, FIG. 13). The transcripts were validated by RT-PCR and Sanger sequencing (data not shown). The D transcript was also validated using long read cDNA sequencing. The expression levels of these transcripts varied according to HSD17B13 rs72613567 genotype; levels of transcripts A and B decreased, while those of transcripts C and D increased in an allele dosage-dependent manner with each TA allele (see, FIG. 18, Panels A and B). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (see, FIG. 18, Panels C and D). These data are consistent with HSD17B13 rs72613567 altering mRNA splicing, resulting in the synthesis of a truncated form of the protein with substantially reduced expression in human liver.

Figure 18:
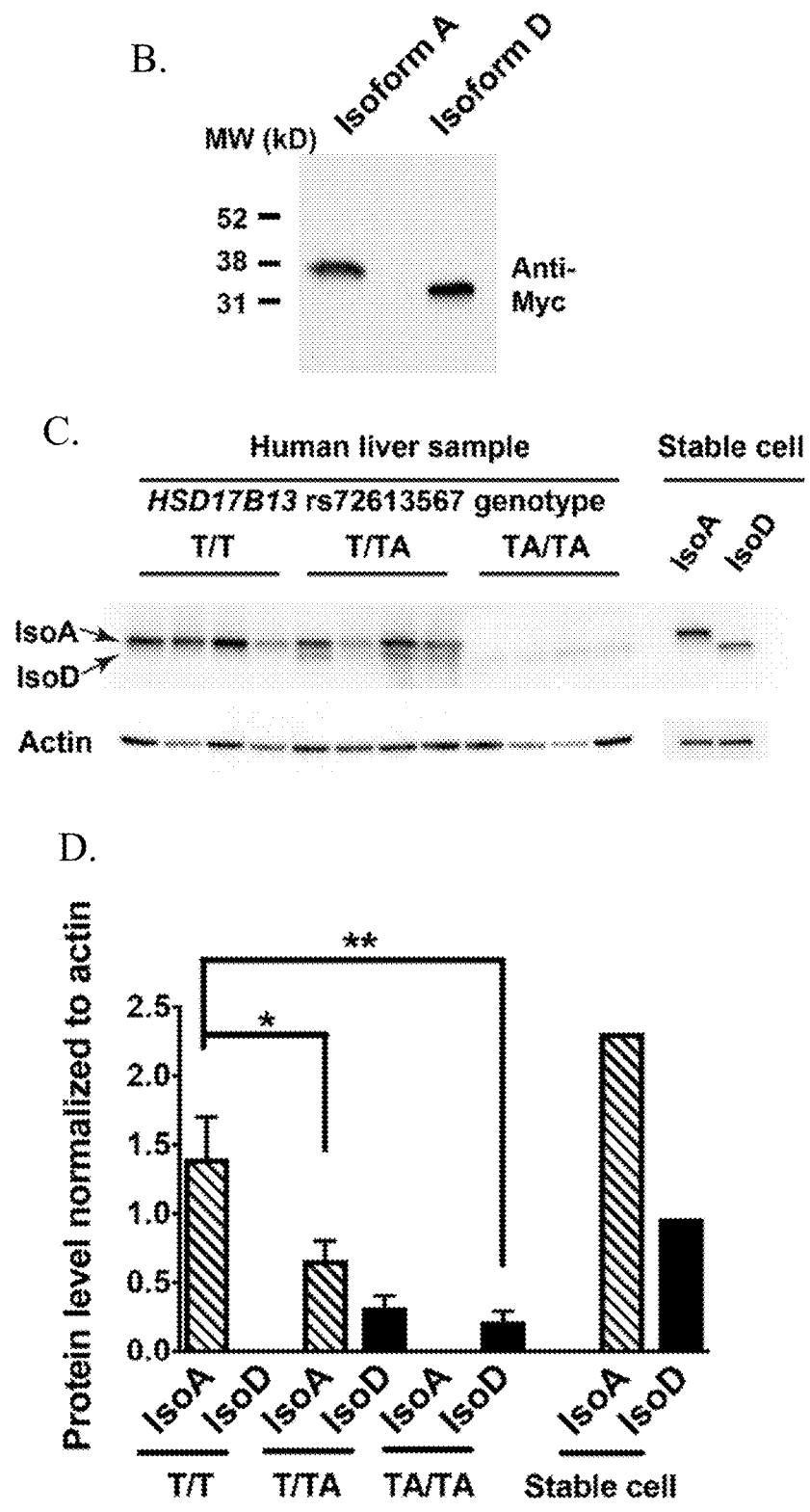
FIG. 18 (panels A through G) shows Expression, subcellular localization, and enzymatic activity of a novel HSD17B13 transcript.
Figure 18:
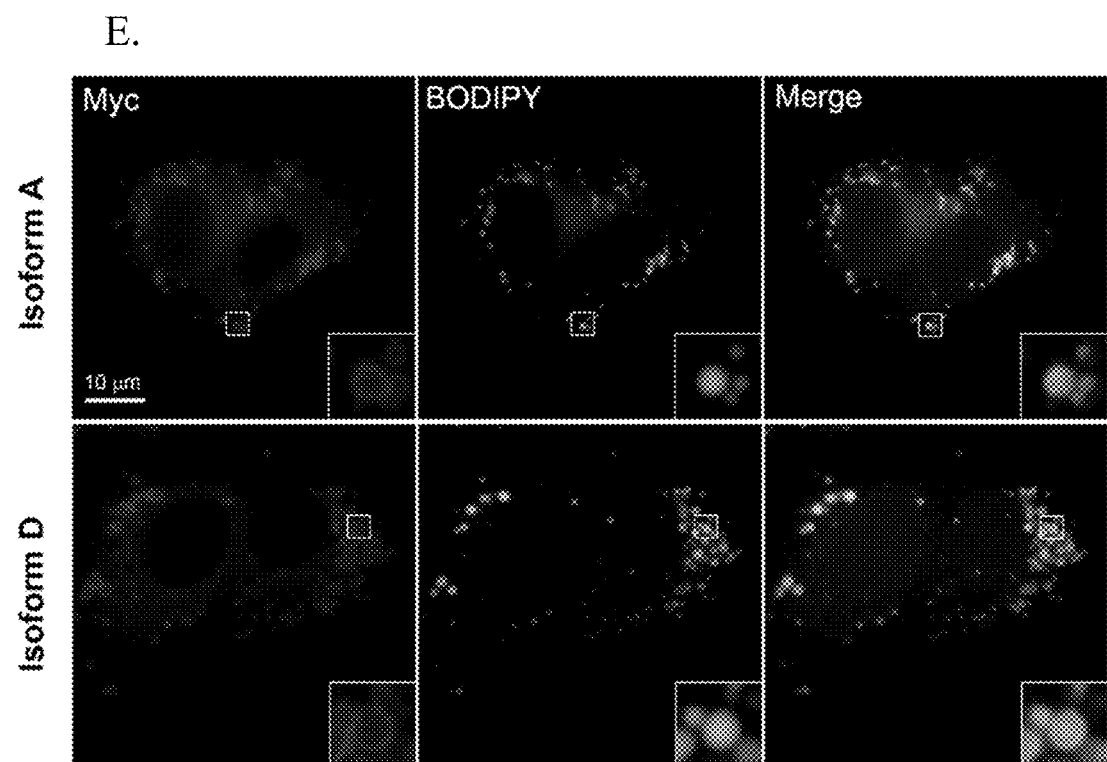

Referring to FIG. 18, expression, subcellular localization, and enzymatic activity of a novel HSD17B13 transcript is shown. Expression of HSD17B13 transcripts A and D in homozygous reference (T/T), heterozygous (T/TA), and homozyous alternate (TA/TA) carriers of the HSD17B13 rs72613567 splice variant (see, Panel A). Coding regions in HSD17B13 gene are indicated in red, untranslated regions as thick black lines, and introns as thin black lines. The asterisk in transcript D indicates the A insertion from rs72613567. mRNA expression is displayed in FPKM units (Fragments Per Kilobase of transcript per Million mapped reads). Western blot from HepG2 cells overexpressing HSD17B13 transcripts A and D. HSD17B13 transcript D was translated to a truncated protein with lower molecular weight compared to HSD17B13 transcript A (see, Panel B). HSD17B13 western blot from fresh frozen human liver and HEK293 cell samples (see, Panel C). Human liver samples are from homozygous reference (T/T), heterozygous (T/TA), and homozygous alternate (TA/TA) carriers of the HSD17B13 rs72613567 splice variant. Cell samples are from HEK293 cells overexpressing non-tagged HSD17B13 transcripts A and D. HSD17B13 transcript D was translated to a truncated protein IsoD with lower molecular weight than HSD17B13 IsoA. HSD17B13 IsoD protein levels were lower than IsoA protein levels from both human liver (left) and cell (right) samples (see, Panel D). Protein level normalized to Actin was shown in the bar columns; **P<0.001, *P<0.05. Both HSD17B13 isoforms A and D were localized on lipid droplet membrane (see, Panel E). HepG2 stably overexpressing HSD17B13 transcripts A or D were labelled with BODIPY to show lipid droplets and anti-Myc to show HSD17B13 localization. All figures are magnified to the same extent. Scale bar indicates 10 µm. Insets represent 4× amplification of the original images. Enzymatic activity of HSD17B13 isoforms A and D to 17-beta estradiol (estradiol), leukotriene B4 (LTB4), and 13-Hydroxyoctadecadienoic acid (13(S)-HODE (see, Panel F). HSD17B13 isoform D show <10% enzymatic activity of the corresponding values for isoform A. G, HSD17B13 isoform D when overexpressed in HEK293 cells did not show much conversion of estradiol (substrate) to estrone (product) when measured in the culture media, while overexpressed HSD17B13 isoform A showed robust conversion.

Expression of HSD17B13 in Human Liver Cells

HSD17B13 is expressed primarily in the liver (Liu et al., Acta Biochim. Pol., 2007, 54, 213-8), where it localizes to lipid droplets (Su et al., Proc. Natl. Acad. Sci. USA, 2014, 111, 11437-42), consistent with a role in the pathogenesis of fatty liver disease. The expression of HSD171B3 and its localization was evaluated in an immortalized human liver cell line stably transduced with lentivirus expressing HSD17B13 transcripts A and D. HSD17B13 isoform A was mainly detected on membranes surrounding BODIPY-labeled lipid droplets (see, FIG. 18, Panel E). Similar subcellular localization was observed for HSD17B13 isoform D at the lipid droplet surface (see, FIG. 18, Panel F).

Effect of rs72613567:TA on HSD17B13 Activity In Vitro and in Cellular Models

To understand the functional consequences of premature truncation of HSD17B13 protein due to rs72613567:TA, the enzymatic activity of isoforms A and D was evaluated in vitro using recombinant protein. Greater than 300 putative substrates were examined, of which estradiol, leukotriene B4, and 13-Hydroxyoctadecadienoic acid were enzymatically converted by HSD17B13, resulting in oxidation of a hydroxyl to a ketone group. HSD17B13 isoform D showed greatly reduced activity towards the 3 substrates (see, FIG. 18, Panel F).

Compared to GFP control, HSD17B13 transcript A overexpressing cells had lower concentration of estradiol as well as higher concentration of estrone in the cell culture medium, suggesting enzyme activity against estradiol (see, FIG. 18, Panel G). HSD17B13 transcript D overexpressing cells had similar ratio of estrone/estadiol to GFP control cells, suggesting that HSD17B13 transcript D has significant loss of function. The mass spec analysis revealed rapid conversion of estrone into hydroxyestrone and other products accounting for the low accumulation of estrone compared to consumed estradiol.

Through large-scale exome sequencing, a novel association was identified between a splice variant in HSD17B13 and decreased serum transaminase levels, as well as reduced risk of nonalcoholic and alcoholic forms of liver disease, including advanced cirrhotic forms of liver disease and HCC. To our knowledge, this is the first report of a protein-altering variant that has a protective association with liver disease. The HSD17B13 rs72613567:TA allele was not associated with simple steatosis, but reduced the risk of progression to NASH. The consistency of the dosage-dependent protective associations in four independent cohorts (DiscovEHR, an independent bariatric surgery cohort in DiscovEHR, DLS, and DPLS) across several different liver disease categories and ethnicities support the notion that the reported HSD17B13 variant protects from progression to more clinically advanced stages of chronic liver disease. The observed allele dosage-dependence also argues that more profound regulation of HSD17B13 function may result in more profound effects on disease risk and progression. The HSD17B13 rs72613567:TA allele also mitigated the risk of liver injury in individuals genetically predisposed to steatotic liver disease by the variant PNPLA3 p.I148M variant. This finding may suggest an important subpopulation for therapeutic modulation of HSD17B13—individuals heterozygous or homozygous for the variant PNPLA3 148M allele.

The association findings described herein were primarily based on observations in European and Hispanic Americans who have elevated BMI. HSD17B13 is in close proximity with HSD17B11, a member of the same gene family with high sequence similarity to HSD17B13 but broader tissue distribution. Overall, the data presented herein support the position that HSD17B13 is a potential therapeutic target for prevention and treatment of fatty liver disease in humans. The data presented herein indicate that targeting of HSD17B13 could reduce progression of liver disease from steatosis to later stages of NASH, fibrosis, and cirrhosis, which are associated with significant morbidity and mortality, and for which there are currently no effective treatments.

Figure 19:
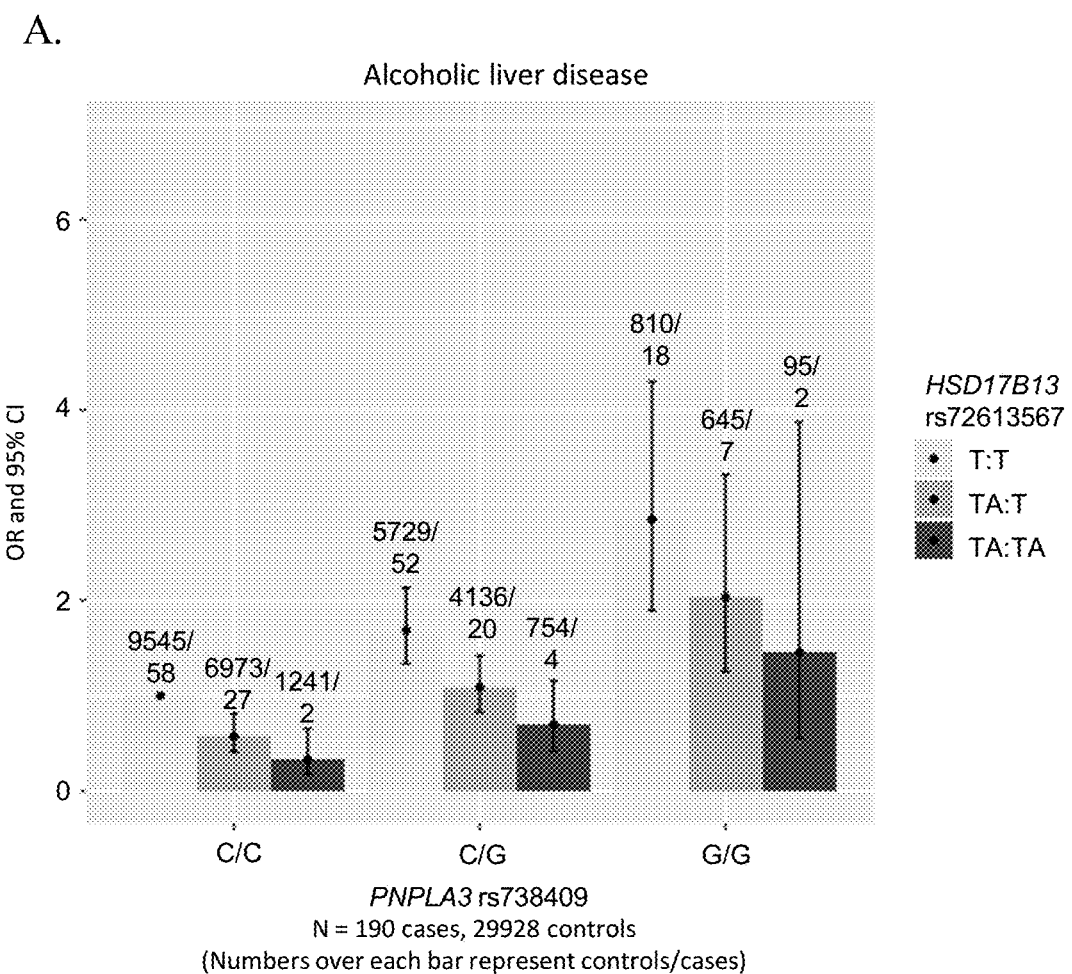
FIG. 19 (panels A and B) shows HSD17B13 rs72613567:TA mitigates the risk of alcoholic and nonalcoholic liver disease associated with PNPLA3 I148M. The numbers over each bar represent controls/cases.
Figure 19:
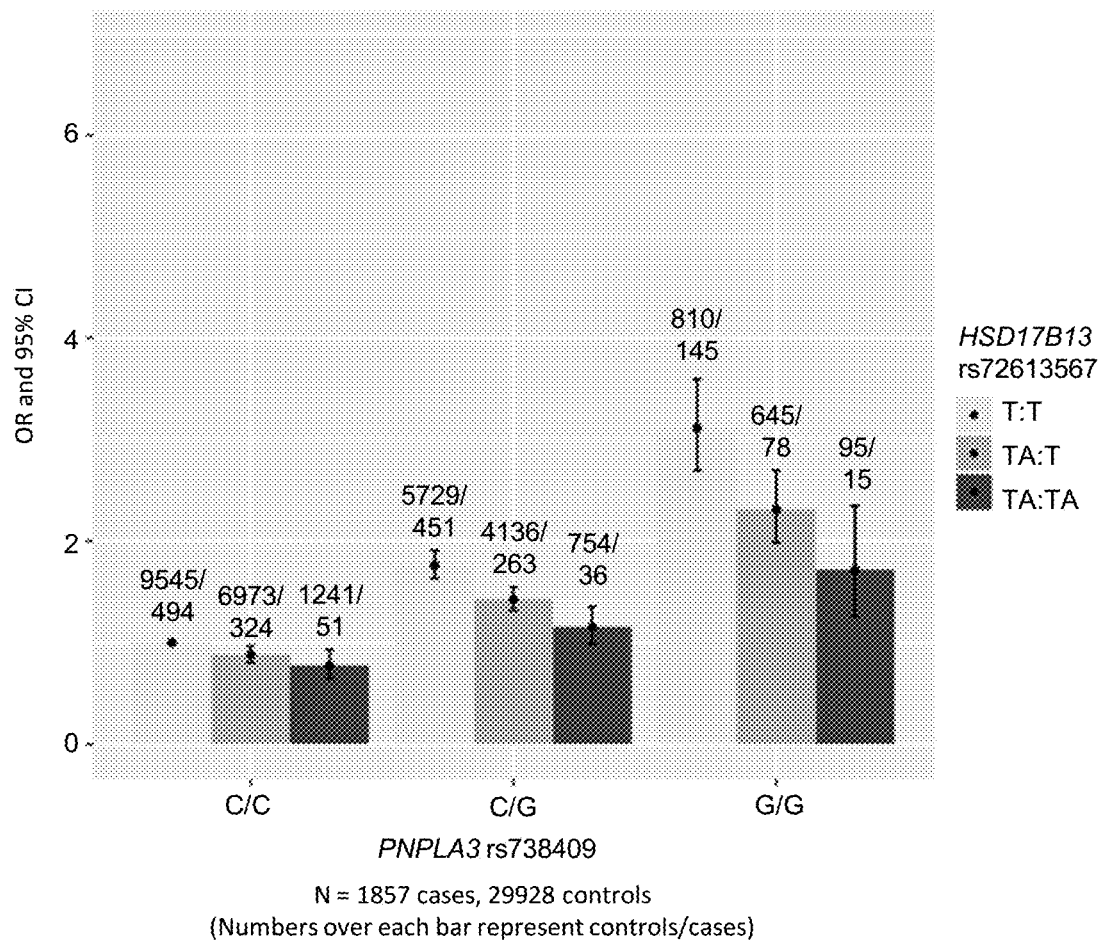

Example 4: HSD17B13 rs72613567:TA Mitigates the Risk of Alcoholic and Nonalcoholic Liver Disease Associated with PNPLA3 I148M Association of HSD17B13 and PNPLA3 genotypes with liver disease was analyzed by comparing HSD17B13 and PNPLA3 genotypes of 29,928 human liver samples from control donors without steatosis, lobular inflammation, or fibrosis with either 190 samples from patients having alcoholic liver disease, or with 1857 patients having nonalcoholic liver disease. The odds ratio was calculated by the equation of (incidence rate of a group having disease)/ (incidence rate of the control group) for each combination of HSD17B13 and PNPLA3 genotype with 95% confidence intervals. Referring to FIG. 19, panel A shows the association of HSD17B13 rs72613567 with alcoholic liver disease in individuals with each PNPLA3 p.I148M genotype, and panel B shows the association of HSD17B13 rs72613567 with nonalcoholic liver disease in individuals with each PNPLA3 p.I148M genotype. The data demonstrate that PNPLA3 p.I148M is associated with higher incidence of both alcoholic and nonalcoholic liver disease in a dosage-dependent manner. The HSD17B13 rs72613567:TA genotype was associated with a reduced risk for both alcoholic and nonalcoholic liver disease in an allele dosage-dependent manner.

What is claimed:

1. A method for treating a subject having a non-alcoholic liver disease, the method comprising administering an inhibitor of hydroxysteroid 17-beta dehydrogenase 13 (HSD17B13) to the subject;

wherein the subject has been determined to have a first nucleic acid molecule encoding a patatin like phospholipase domain containing 3 (PNPLA3) protein comprising an I148M variation and a second nucleic acid molecule encoding a functional HSD17B13 protein having oxidoreductase activity;

wherein the non-alcoholic liver disease is nonalcoholic fatty liver disease (NAFLD) or non-alcoholic steatohepatitis (NASH); and wherein the inhibitor of HSD17B13 is an inhibitory nucleic acid molecule.

2. The method according to claim 1, wherein the inhibitory nucleic acid molecule comprises an antisense RNA.

3. The method according to claim 1, wherein the inhibitory nucleic acid molecule comprises a small interfering RNA (siRNA).

4. The method according to claim 1, wherein the inhibitory nucleic acid molecule comprises a short hairpin RNA (shRNA).

5. The method according to claim 1, wherein the first nucleic acid molecule is:

genomic DNA that comprises an ATG codon at the positions corresponding to positions 5107 to 5109 according to SEQ ID NO:31;

mRNA that comprises an AUG codon at the positions corresponding to positions 442 to 444 according to SEQ ID NO:34; or mRNA that comprises an AUG codon at the positions corresponding to positions 430 to 432 according to SEQ ID NO:35.

6. The method according to claim 1, wherein the first nucleic acid molecule is:

genomic DNA that comprises the nucleotide sequence according to SEQ ID NO:31, or a nucleotide sequence having at least 90% sequence identity to SEQ ID NO:31 and encoding a PNPLA3 protein which comprises the I148M variation;

mRNA that comprises the nucleotide sequence according to SEQ ID NO:34, or a nucleotide sequence having at least 90% sequence identity to SEQ ID NO:34 and encoding a PNPLA3 protein which comprises the I148M variation; or mRNA that comprises the nucleotide sequence according to SEQ ID NO:35, or a nucleotide sequence having at least 90% sequence identity to SEQ ID NO:35 and encoding a PNPLA3 protein which comprises the I148M variation.

7. The method according to claim 1, wherein the subject is heterozygous for the first nucleic acid molecule.

8. The method according to claim 1, wherein the second nucleic acid molecule is:

genomic DNA that comprises an adenine at the position corresponding to position 12,667 according to SEQ ID NO:1;

genomic DNA that comprises the nucleotide sequence according to SEQ ID NO:1, or a nucleotide sequence having at least 90% sequence identity to SEQ ID NO:1 and encoding a functional HSD17B13 protein;

mRNA that comprises the nucleotide sequence according to SEQ ID NO:3, or a nucleotide sequence having at least 90% sequence identity to SEQ ID NO:3 and encoding a functional HSD17B13 protein;

mRNA that comprises the nucleotide sequence according to SEQ ID NO:4 or a nucleotide sequence having at least 90% sequence identity to SEQ ID NO:4 and encoding a functional HSD17B13 protein;

mRNA that comprises the nucleotide sequence according to SEQ ID NO:7 or a nucleotide sequence having at least 90% sequence identity to SEQ ID NO:7 and encoding a functional HSD17B13 protein; or mRNA that comprises the nucleotide sequence according to SEQ ID NO:11 or a nucleotide sequence having at least 90% sequence identity to SEQ ID NO:11 and encoding a functional HSD17B13 protein.

9. The method according to claim 1, wherein the subject is heterozygous for the second nucleic acid molecule.

10. A method for treating a subject having nonalcoholic fatty liver disease (NAFLD), the method comprising administering an inhibitor of hydroxysteroid 17-beta dehydrogenase 13 (HSD17B13) to the subject;
wherein the subject has been determined to have a first nucleic acid molecule encoding a patatin like phospholipase domain containing 3 (PNPLA3) protein comprising an I148M variation and a second nucleic acid molecule encoding a functional HSD17B13 protein having oxidoreductase activity; and
wherein the inhibitor of HSD17B13 is an inhibitory nucleic acid molecule.

11. The method according to claim 10, wherein the inhibitory nucleic acid molecule comprises an antisense RNA.

12. The method according to claim 10, wherein the inhibitory nucleic acid molecule comprises a small interfering RNA (siRNA).

13. The method according to claim 10, wherein the inhibitory nucleic acid molecule comprises a short hairpin RNA (shRNA).

14. The method according to claim 10, wherein the first nucleic acid molecule is:
genomic DNA that comprises an ATG codon at the positions corresponding to positions 5107 to 5109 according to SEQ ID NO:31;
mRNA that comprises an AUG codon at the positions corresponding to positions 442 to 444 according to SEQ ID NO:34; or
mRNA that comprises an AUG codon at the positions corresponding to positions 430 to 432 according to SEQ ID NO:35.

15. The method according to claim 10, wherein the first nucleic acid molecule is:
genomic DNA that comprises the nucleotide sequence according to SEQ ID NO:31, or a nucleotide sequence having at least 90% sequence identity to SEQ ID NO:31 and encoding a PNPLA3 protein which comprises the I148M variation;
mRNA that comprises the nucleotide sequence according to SEQ ID NO:34, or a nucleotide sequence having at least 90% sequence identity to SEQ ID NO:34 and encoding a PNPLA3 protein which comprises the I148M variation; or
mRNA that comprises the nucleotide sequence according to SEQ ID NO:35, or a nucleotide sequence having at least 90% sequence identity to SEQ ID NO:35 and encoding a PNPLA3 protein which comprises the I148M variation.

16. The method according to claim 10, wherein the subject is heterozygous for the first nucleic acid molecule.

17. The method according to claim 10, wherein the second nucleic acid molecule is:
genomic DNA that comprises an adenine at the position corresponding to position 12,667 according to SEQ ID NO:1;
genomic DNA that comprises the nucleotide sequence according to SEQ ID NO:1, or a nucleotide sequence having at least 90% sequence identity to SEQ ID NO:1 and encoding a functional HSD17B13 protein mRNA that comprises the nucleotide sequence according to SEQ ID NO:3, or a nucleotide sequence having at least 90% sequence identity to SEQ ID NO:3 and encoding a functional HSD17B13 protein;

mRNA that comprises the nucleotide sequence according to SEQ ID NO:4 or a nucleotide sequence having at least 90% sequence identity to SEQ ID NO:4 and encoding a functional HSD17B13 protein;

mRNA that comprises the nucleotide sequence according to SEQ ID NO:7 or a nucleotide sequence having at least 90% sequence identity to SEQ ID NO:7 and encoding a functional HSD17B13 protein; or mRNA that comprises the nucleotide sequence according to SEQ ID NO:11 or a nucleotide sequence having at least 90% sequence identity to SEQ ID NO:11 and encoding a functional HSD17B13 protein.

18. The method according to claim 10, wherein the subject is heterozygous for the second nucleic acid molecule.

19. A method for treating a subject having non-alcoholic steatohepatitis (NASH), the method comprising administering an inhibitor of hydroxysteroid 17-beta dehydrogenase 13 (HSD17B13) to the subject;
wherein the subject has been determined to have a first nucleic acid molecule encoding a patatin like phospholipase domain containing 3 (PNPLA3) protein comprising an I148M variation and a second nucleic acid molecule encoding a functional HSD17B13 protein having oxidoreductase activity; and
wherein the inhibitor of HSD17B13 is an inhibitory nucleic acid molecule.

20. The method according to claim 19, wherein the inhibitory nucleic acid molecule comprises an antisense RNA.

21. The method according to claim 19, wherein the inhibitory nucleic acid molecule comprises a small interfering RNA (siRNA).

22. The method according to claim 19, wherein the inhibitory nucleic acid molecule comprises a short hairpin RNA (shRNA).

23. The method according to claim 19, wherein the first nucleic acid molecule is:
genomic DNA that comprises an ATG codon at the positions corresponding to positions 5107 to 5109 according to SEQ ID NO:31;
mRNA that comprises an AUG codon at the positions corresponding to positions 442 to 444 according to SEQ ID NO:34; or
mRNA that comprises an AUG codon at the positions corresponding to positions 430 to 432 according to SEQ ID NO:35.

24. The method according to claim 19, wherein the first nucleic acid molecule is:
genomic DNA that comprises the nucleotide sequence according to SEQ ID NO:31, or a nucleotide sequence having at least 90% sequence identity to SEQ ID NO:31 and encoding a PNPLA3 protein which comprises the I148M variation;

mRNA that comprises the nucleotide sequence according to SEQ ID NO:34, or a nucleotide sequence having at least 90% sequence identity to SEQ ID NO:34 and encoding a PNPLA3 protein which comprises the I148M variation; or mRNA that comprises the nucleotide sequence according to SEQ ID NO:35, or a nucleotide sequence having at least 90% sequence identity to SEQ ID NO:35 and encoding a PNPLA3 protein which comprises the I148M variation.

25. The method according to claim 19, wherein the subject is heterozygous for the first nucleic acid molecule.

26. The method according to claim 19, wherein the second nucleic acid molecule is:

genomic DNA that comprises an adenine at the position corresponding to position 12,667 according to SEQ ID NO:1;

genomic DNA that comprises the nucleotide sequence according to SEQ ID NO:1, or a nucleotide sequence having at least 90% sequence identity to SEQ ID NO:1 and encoding a functional HSD17B13 protein mRNA that comprises the nucleotide sequence according to SEQ ID NO:3, or a nucleotide sequence having at least 90% sequence identity to SEQ ID NO:3 and encoding a functional HSD17B13 protein;

mRNA that comprises the nucleotide sequence according to SEQ ID NO:4 or a nucleotide sequence having at least 90% sequence identity to SEQ ID NO:4 and encoding a functional HSD17B13 protein;

mRNA that comprises the nucleotide sequence according to SEQ ID NO:7 or a nucleotide sequence having at least 90% sequence identity to SEQ ID NO:7 and encoding a functional HSD17B13 protein; or mRNA that comprises the nucleotide sequence according to SEQ ID NO:11 or a nucleotide sequence having at least 90% sequence identity to SEQ ID NO:11 and encoding a functional HSD17B13 protein.

27. The method according to claim 19, wherein the subject is heterozygous for the second nucleic acid molecule.

* * * * *